United States Patent
Claremon et al.

(10) Patent No.: US 10,144,715 B2
(45) Date of Patent: Dec. 4, 2018

(54) PIPERAZINE DERIVATIVES AS LIVER X RECEPTOR MODULATORS

(71) Applicant: Vitae Pharmaceuticals, Inc., Fort Washington, PA (US)

(72) Inventors: David A. Claremon, Maple Glen, PA (US); Chengguo Dong, Staten Island, NY (US); Yi Fan, Doylestown, PA (US); Katerina Leftheris, San Diego, CA (US); Stephen D. Lotesta, Burlington, NJ (US); Suresh B. Singh, Kendall Park, NJ (US); Colin M. Tice, Maple Glen, PA (US); Wei Zhao, North Potomac, MD (US); Yajun Zheng, Hockessin, DE (US); Linghang Zhuang, Chalfont, PA (US)

(73) Assignee: Vitae Pharmaceuticals, Inc., Madison, NJ (US)

( * ) Notice: Subject to any disclaimer, the term of this patent is extended or adjusted under 35 U.S.C. 154(b) by 0 days.

(21) Appl. No.: 15/502,356

(22) PCT Filed: Aug. 4, 2015

(86) PCT No.: PCT/US2015/043538
§ 371 (c)(1),
(2) Date: Feb. 7, 2017

(87) PCT Pub. No.: WO2016/022521
PCT Pub. Date: Feb. 11, 2016

(65) Prior Publication Data
US 2017/0226067 A1    Aug. 10, 2017

Related U.S. Application Data

(60) Provisional application No. 62/034,274, filed on Aug. 7, 2014.

(51) Int. Cl.

| | | |
|---|---|---|
| *C07D 241/04* | (2006.01) | |
| *C07D 403/04* | (2006.01) | |
| *C07D 413/14* | (2006.01) | |
| *C07D 401/04* | (2006.01) | |
| *C07D 401/06* | (2006.01) | |
| *C07D 403/14* | (2006.01) | |
| *C07D 405/06* | (2006.01) | |
| *C07D 413/04* | (2006.01) | |
| *C07D 417/04* | (2006.01) | |
| *C07D 417/14* | (2006.01) | |
| *C07D 497/04* | (2006.01) | |
| *C07D 513/04* | (2006.01) | |

(52) U.S. Cl.
CPC ......... *C07D 241/04* (2013.01); *C07D 401/04* (2013.01); *C07D 401/06* (2013.01); *C07D 403/04* (2013.01); *C07D 403/14* (2013.01); *C07D 405/06* (2013.01); *C07D 413/04* (2013.01); *C07D 413/14* (2013.01); *C07D 417/04* (2013.01); *C07D 417/14* (2013.01); *C07D 497/04* (2013.01); *C07D 513/04* (2013.01)

(58) Field of Classification Search
None
See application file for complete search history.

(56) References Cited

FOREIGN PATENT DOCUMENTS

| | | |
|---|---|---|
| WO | 2013/138565 A1 | 9/2013 |
| WO | 2013/138568 A1 | 9/2013 |
| WO | 2014/101113 A1 | 7/2014 |

*Primary Examiner* — Deepak R Rao
*Assistant Examiner* — Laura M Daniel
(74) *Attorney, Agent, or Firm* — McCarter & English, LLP; Steven G. Davis; Michael J. DeGrazia

(57) ABSTRACT

Provided are novel compounds of Formula (I): pharmaceutically acceptable salts thereof, and pharmaceutical compositions thereof, which are liver X receptor modulators, and which are useful in the treatment of diseases and disorders associated with the liver X receptor. Also provided are the compounds of Formula (I) and pharmaceutical compositions thereof for treating atherosclerosis, cardiovascular disease, Alzheimer's disease, dermatitis, dyslipidemia, cancer and other diseases or disorders.

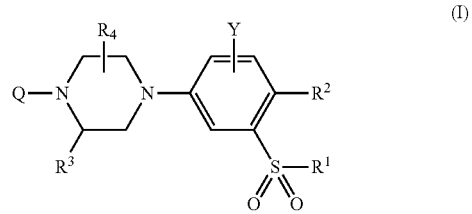

23 Claims, No Drawings

PIPERAZINE DERIVATIVES AS LIVER X RECEPTOR MODULATORS

RELATED APPLICATIONS

This application is a 35 U.S.C. § 371 national stage filing of International Application No. PCT/US2015/043538, filed Aug. 4, 2015, which claims the benefit of the filing date of U.S. Provisional Application No. 62/034,274, filed Aug. 7, 2014. The entire content of each of the aforementioned applications are incorporated by reference herein.

FIELD OF THE INVENTION

The present invention relates to compounds that modulate the activity of liver X receptors.

BACKGROUND OF THE INVENTION

Atherosclerosis is the leading cause of death in the developed world, and atherosclerosis is predicted to be the leading cause of death in the developing world in the 21st century. Liver X receptors (LXRs) are ligand-activated transcription factors that play a crucial role in regulating the expression of genes involved in lipid metabolism and cellular cholesterol homeostasis. LXR agonists have been shown to enhance reverse cholesterol transport (RCT), facilitating cholesterol trafficking from the periphery back to the liver for processing and excretion. RCT occurs via upregulation of cholesterol transporters (ATP-Binding Cassettes: ABCA1 and ABCG1) in peripheral macrophages. Active RCT has the potential to inhibit the progression of atherosclerosis.

There are two isoforms of LXR, LXRα (NR1H3) and LXRβ (NR1H2), encoded by separate genes. LXRα expression is tissue-selective, detectable in liver, intestine, kidney, adipose tissue and adrenal glands, all of which are important for lipid homeostasis, whereas LXRβ is expressed ubiquitously. Both LXRs require the retinoid X receptor (RXR) as an obligate heterodimer partner to recognize and bind cooperatively to LXR response elements (LXREs) consisting of two direct repeats of a core hexameric sequence spaced by four nucleotides (DR4). The ligand binding domains of the two LXRs are fairly well conserved (~78% amino acid homology) and respond to endogenous ligands consisting of oxidized derivatives of cholesterol (oxysterols) that serve as intermediates in steroid hormone and bile acid synthesis. The most potent of such endogenous ligands are 22(R)-hydroxycholesterol, 24(S)-hydroxycholesterol and 24(S), 25-epoxycholesterol. These data suggested an important role for LXRs in cholesterol regulation, which was later confirmed through gene knock-out studies in mice. Non-steroidal ligands have also been identified, and, using these as chemical probes many LXR-regulated genes have been discovered. Several LXRE-containing genes are involved in cholesterol metabolism, reverse cholesterol transport (RCT) and lipogenesis. Other genes involved in inflammation and carbohydrate metabolism lack LXREs, but are repressed by LXRs in a ligand-dependent manner. Based on these discoveries, the liver X receptors have recently emerged as unprecedented targets acting as intracellular cholesterol sensors, providing the basis for the treatment of a variety of diseases, including atherosclerosis, diabetes, Alzheimer's disease, skin disorders, reproductive disorders and cancer (Viennois et al., 2011, Expert Opin. Ther. Targets, 15 (2): 219-232; Hong et al., 2014, Nature Reviews Drug Discovery, 13:433-444). Additionally, it has been determined that LXR agonists modulate intestinal and renal sodium phosphate (NaPi) transporters and, in turn, serum phosphate levels (Caldas et al., 2011, Kidney International, 80:535-544). Thus, LXR is also a target for kidney disorders, and particularly for the prevention of hyperphosphatemia and associated cardiovascular complications. Recently, LXRs have been identified as targets in the treatment of osteoporosis and related diseases (Kleyer et al., 2012, J. Bone Miner. Res., 27 (12):2442-51).

Alzheimer's disease is one of the most common forms of dementia, characterized by the accumulation and deposition of amyloid-beta (Aβ) peptides in the brain, leading to the perturbation of synaptic function and neuronal loss in the brains of affected individuals. Neurons in the brain produce Aβ peptides via cleavage of amyloid precursor protein (APP), and Aβ peptides are normally cleared through efflux into the peripheral circulation and by degradation by proteinases within the brain.

Apolipoprotein E (apoE) is associated with age-related risk for Alzheimer's disease and plays critical roles in Aβ homeostasis. LXR increases the expression of apoE and increases the lipidation of apoE. Degradation of Aβ both intra- and extracellularly is enhanced by lipidated apoE. LXR agonist treatment stimulated proteolytic degradation of Aβ, reduced plaque pathology, and improved memory in APP-expressing transgenic mice (Jiang et al., 2008, Neuron, 58:681-693).

In skin, keratinocytes are a critical component of the epidermis. The outer layer, stratum corneum, is primarily responsible for the permeability barrier to water and electrolyte transit. Keratinocytes in the epidermis undergo differentiation which culminates in keratinocyte cornification ("the bricks") and in formation of the extracellular lipid-enriched lamellar membranes ("the mortar") in the stratum corneum. Both LXRα and LXRβ are expressed in keratinocytes, and LXR expression and activation promotes epidermis barrier function. Activation of LXR is involved in keratinocyte differentiation, formation of the lamellar membrane and overall improvement of epidermal barrier function. Thus, LXR activation is expected to result in increased keratinocyte differentiation, increased lipid secretion (via ABCA1, ABCA12), and increased lamellar body formation, leading to a healthy epidermis (smooth skin).

The potential therapeutic utility of LXR agonists has led to the development of several high affinity LXR ligands with potent agonism for both receptor subtypes. The therapeutic utility of LXR agonists is constrained by their potential to induce lipogenic genes including sterol response element binding protein-1c (SREBP1c) and fatty acid synthase (FAS). Preclinical studies have demonstrated that synthetic modulators of LXRs reduce lesion progression in murine models of atherosclerosis with limited increase in hepatic lipogenesis. There is a clear need for new LXR chemotypes that retain the anti-atherosclerotic efficacy of current LXR agonists but are devoid of lipogenic activity. Compounds exhibiting a pharmacological profile with positive effects on RCT while being neutral or suppressive on lipogenic genes will be valuable therapeutic agents in patients with atherosclerotic dyslipidemia.

Rett Syndrome (RTT) is an X-linked neurological disorder presenting with autistic features that afflicts approximately 1 in 10,000 females. Mutations in the X-linked gene, methyl CpG binding protein 2 (MECP2), are the primary cause of RTT. Hemizygous males with truncating or loss-of-function mutations typically die of encephalopathy, whereas mild mutations in either sex are associated with a variety of intellectual disabilities. Approximately 80% of RTT clinical cases show a typical clinical picture, characterized by loss of acquired cognitive, social, and motor skills in a typical four-stage neurological regression, together with development of autistic behavior. Recently, researchers showed that cholesterol metabolism is perturbed in brains and livers of Mecp2-null male mice, and inhibitors of cholesterol biosynthesis (statins) ameliorate the systemic imbalance of lipid profile, alleviate motor symptoms and confer increased longevity in Mecp2 mutant mice, suggesting that cholesterol homeostasis maintenance could be altered in patients affected by RTT (Buchovecky et al., 2013, Nat. Genet., 45:1013). These findings suggest that the disease may be ameliorated or even reversed by genetic or pharmacological means after symptom onset. Since LXR agonists have the capacity to actively remove cholesterol from peripheral tissues, leading to elimination of cholesterol from the body, LXR agonists are useful for the treatment of patients suffering from RTT.

Suppression of LXR activity in liver has been proposed for the treatment of hepatic diseases, such as fatty liver, cirrhosis, nonalcoholic fatty liver disease (NAFLD), and non-alcoholic hepatosteatosis (NASH) (Ducheix et al., 2013, Biochem. Pharmacol., 86:96-105). LXR antagonists have been shown to down regulate lipogenic genes in liver, limit hepatic accumulation of lipids, and reduce plasma cholesterol levels in a mouse model of NASH (Griffett, et al., 2013, ACS Chem. Biol., 8:559-567), and to reduce plasma levels of total cholesterol, triglycerides, and free fatty acids in mice fed a high fat diet (Jwa et al., 2012, Biochem. Pharmacol., 84:1501-1510). Therefore, liver-specific LXR antagonists are expected to be useful in the treatment of metabolic disorders associated with fat accumulation in the liver. Activation of LXRα has been shown to induce lipid synthesis and sebum secretion in sebocytes (Hong et al., 2008, J. Invest. Dermatol., 128:1266-1272). Given that excess sebum production is a major cause of acne, LXR antagonists are expected to have therapeutic potential in the treatment of sebaceous gland-associated disorders such as seborrhea and acne. Thus, antagonism of LXR has therapeutic potential in the treatment of diseases such as seborrhea and acne, as well as hepatic diseases such as cirrhosis, NASH, and NAFLD, and there is a need for new LXR modulators that antagonize LXR.

SUMMARY OF THE INVENTION

It has now been found that the compounds described herein, and pharmaceutically acceptable salts, are useful LXR modulators (see e.g., Tables 1 and 2). Such compounds include those of Formula (I):

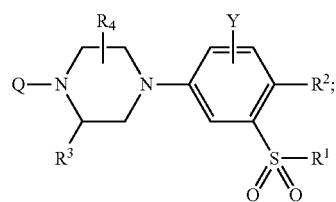

or a pharmaceutically acceptable salt thereof, wherein the variables Q, Y, $R^1$, $R^2$, $R^3$, and $R^4$ are as defined herein.

The provided compounds, and pharmaceutically acceptable compositions thereof, modulate LXR, e.g., by acting as an agonist, partial agonist, or antagonist, and are useful as therapeutic agents for the promotion of reverse cholesterol transport and the suppression of hepatic lipogenesis, and for the prevention, amelioration or treatment of diseases or disorders including atherosclerosis, cardiovascular disease, Alzheimer's disease, dermatitis, dyslipidemia and cancer.

DETAILED DESCRIPTION OF CERTAIN EMBODIMENTS

I. General Description of Compounds of the Invention

In one embodiment, the present invention provides a compound represented by structural Formula I:

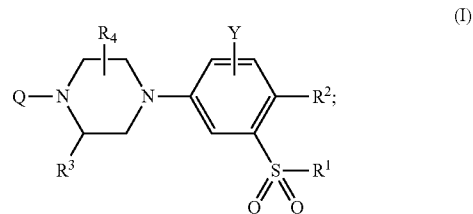

or a pharmaceutically acceptable salt thereof; wherein
Q is 1) $R^{10}OC(=O)-$; 2) a heteroaryl ring optionally substituted with 1 to 3 groups independently selected from $R^{21}$; 3) a group of formula $R^{30}$-L, wherein $R^{30}$ is optionally substituted with 1 to 3 groups independently selected from $R^{31}$; or 4) a group of formula $R^{40}$-L, wherein $R^{40}$ is optionally substituted with 1 to 3 groups independently selected from $R^{41}$;
$R^1$ is selected from $(C_1-C_6)$alkyl, $(C_3-C_6)$cycloalkyl, $(C_3-C_6)$cycloalkylalkyl$(C_1-C_3)$alkyl; aryl$(C_1-C_3)$alkyl, halo$(C_1-C_6)$alkyl, halo$(C_3-C_6)$cycloalkyl, halo$(C_3-C_6)$cycloalkyl$(C_1-C_3)$alkyl, amino, $(C_1-C_6)$alkylamino, di$(C_1-C_6)$alkylamino, aryl$(C_1-C_3)$alkylamino and {aryl$(C_1-C_3)$alkyl}{$(C_1-C_6)$ alkyl}amino, wherein the aryl groups are optionally substituted with 1 to 3 groups independently selected from halogen, cyano, $CONH_2$, $(C_1-C_3)$alkyl, halo$(C_1-C_3)$alkyl, $(C_1-C_3)$alkoxy and halo$(C_1-C_3)$alkoxy;
$R^2$ is selected from hydrogen, halogen, cyano, $CONH_2$, hydroxy$(C_1-C_3)$alkyl, amino$(C_1-C_3)$alkyl, $(C_1-C_3)$alkoxy$(C_1-C_3)$alkyl, $(C_1-C_3)$alkylcarbonyl$(C_1-C_3)$alkyl and $(C_1-C_3)$alkylcarbonylamino$(C_1-C_3)$alkyl; or $R^2$ is a 5-membered heteroaryl, optionally substituted with 1 or 2 groups independently selected from halogen, cyano, methyl, $CF_3$, methoxy, methoxycarbonyl, ethoxycarbonyl and $CONH_2$;
$R^3$ is (1) $(C_1-C_6)$alkyl, halo$(C_1-C_6)$alkyl, $(C_3-C_6)$cycloalkyl, halo$(C_3-C_6)$cycloalkyl, $(C_1-C_3)$alkoxy$(C_1-C_3)$alkyl, hydroxy$(C_1-C_6)$alkyl, $(C_1-C_6)$alkoxycarbonyl or $(C_1-C_6)$alkoxycarbonyl$(C_1-C_3)$alkyl, or cyano$(C_1-C_6)$alkyl; or (2) aryl, heteroaryl, aryl$(C_1-C_3)$alkyl or heteroaryl$(C_1-C_3)$alkyl, each optionally substituted with 1 to 3 substituents selected from halogen, cyano, $(C_1-C_3)$alkyl, $CF_3$, methoxy and $CONH_2$;
$R^4$ is hydrogen or $(C_1-C_6)$alkyl;
$R^{10}$ is selected from $(C_1-C_8)$alkyl, aryl$(C_1-C_3)$alkyl, halo$(C_1-C_6)$alkyl, $(C_3-C_7)$cycloalkyl, $(C_3-C_6)$cycloalkyl$(C_1-C_3)$alkyl, halo$(C_3-C_7)$cycloalkyl and halo$(C_3-C_6)$cycloalkyl$(C_1-C_3)$alkyl;
$R^{30}$ is an aryl or heteroaryl ring;
$R^{40}$ is $(C_4-C_7)$cycloalkyl or heterocyclyl;

$R^{21}$, $R^{31}$, and $R^{41}$ are each independently selected from halogen, hydroxy, amino, nitro, $(C_1-C_6)$alkyl, halo$(C_1-C_6)$alkyl, $(C_3-C_6)$cyclo alkyl, $(C_1-C_6)$alkenyl, $(C_1-C_6)$alkoxy, halo$(C_1-C_6)$alkoxy, hydroxy$(C_1-C_6)$alkyl, hydroxy$(C_1-C_6)$haloalkyl, $(C_1-C_3)$alkoxy$(C_1-C_3)$alkyl, halo$(C_1-C_3)$alkoxy$(C_1-C_3)$alkyl, $(C_1-C_3)$alkoxy$(C_1-C_3)$haloalkyl, $(C_1-C_6)$alkylthio, halo$(C_1-C_6)$alkylthio, $(C_1-C_3)$alkylthio$(C_1-C_3)$alkyl, halo$(C_1-C_3)$alkylthio$(C_1-C_3)$alkyl, cyano$(C_1-C_6)$alkyl, $CO_2H$, $(C_1-C_6)$alkoxycarbonyl, $(C_1-C_6)$alkylsulfonyl, $(C_1-C_6)$haloalkylsulfonyl, $(C_1-C_3)$alkylsulfonyl$(C_1-C_3)$alkyl, halo$(C_1-C_3)$alkylsulfonyl$(C_1-C_3)$alkyl, heterocyclyl, $R^{22}R^{23}NCO$, $R^{22}R^{23}NCO(C_1-C_3)$alkyl, $R^{22}CONH$, $R^{22}CONH(C_1-C_3)$alkyl, $R^{22}SO_2NH$, $R^{22}SO_2NH(C_1-C_3)$alkyl, $R^{22}R^{23}N$, $R^{22}R^{23}N(C_1-C_3)$alkyl and aryl$(C_1-C_3)$alkyl, wherein aryl$(C_1-C_3)$alkyl is optionally substituted by $R^{25}$;

$R^{22}$ is selected from H, $(C_1-C_6)$alkyl, halo$(C_1-C_6)$alkyl, hydroxy$(C_1-C_6)$alkyl, $(C_1-C_6)$alkoxy$(C_1-C_6)$alkyl, $(C_1-C_6)$alkoxycarbonyl$(C_1-C_6)$alkyl, $(C_1-C_6)$alkoxycarbonylamino$(C_1-C_6)$alkyl and heterocyclyl, wherein the heterocyclyl is optionally substituted with 1 or 2 groups independently selected from $R^{24}$;

$R^{23}$ is hydrogen, $(C_1-C_6)$alkyl, $(C_1-C_6)$alkoxy or halo$(C_1-C_6)$alkyl; or $R^{22}$ and $R^{23}$, together with the nitrogen to which they are attached, form an azetidine, pyrrolidine, piperidine, piperazine or morpholine ring, each optionally substituted by 1 or 2 groups independently selected from $R^{24}$;

$R^{24}$ is selected from halogen, hydroxy, amino $(C_1-C_3)$alkyl, halo$(C_1-C_3)$alkyl, $(C_1-C_3)$alkoxy and $(C_1-C_6)$alkoxycarbonyl;

$R^{25}$ is hydroxy$(C_1-C_6)$alkyl or $CO_2H$;

L is $CH_2$, $CHCH_3$ or $C(CH_3)_2$; and

Y is hydrogen, halogen, cyano, $(C_1-C_3)$alkyl, methyl, haloalkyl, or methoxy.

Another aspect of the invention is a pharmaceutical composition comprising a compound of the invention and a pharmaceutically acceptable carrier or diluent.

A further aspect of the present invention also provides for a method of treating a subject with a disease or disorder that is treatable by upregulating LXR activity. The method comprises administering an effective amount of a compound of the invention or a pharmaceutically acceptable salt thereof to the subject in need thereof.

Also provided in the invention is the use of a compound of the invention for the manufacture of a medicament for treating a subject with a disease or disorder that is treatable by downregulating LXR activity in a subject in need thereof.

Disclosed herein is also a compound of the invention for use in treating a disease or disorder that is treatable by downregulating LXR activity in a subject in need thereof.

A further aspect of the present invention also provides for a method of treating a subject with a disease or disorder that is treatable by downregulating LXR activity. The method comprises administering an effective amount of a compound of the invention or a pharmaceutically acceptable salt thereof to the subject in need thereof.

Also provided in the invention is the use of a compound of the invention for the manufacture of a medicament for treating a subject with a disease or disorder that is treatable by downregulating LXR activity in a subject in need thereof.

Disclosed herein is also a compound of the invention for use in treating a disease or disorder that is treatable by downregulating LXR activity in a subject in need thereof.

2. Compounds and Definitions

"Halo" or "halogen" means chloro, bromo, fluoro, or iodo. In one embodiment, halo is fluoro.

"Alkyl" means a straight or branched hydrocarbon group having 1 to 15 carbon atoms in the chain. In one embodiment, alkyl groups have 1 to 12 carbon atoms in the chain. In another embodiment, alkyl groups have 1 to 6 carbon atoms. Exemplary alkyl groups include, but are not limited to, methyl, ethyl, n-propyl, isopropyl, n-butyl, tert-butyl, sec-butyl, n-pentyl, 3-pentyl, heptyl, octyl, nonyl, decyl, and dodecyl.

"Cycloalkyl" means a monocyclic, bicyclic or tricyclic, saturated hydrocarbon ring of 3 to 10 carbon atoms. In one embodiment, the cycloalkyl group has 3 to 6 carbon atoms. Exemplary cycloalkyl rings include cyclopropyl (c-Pr), cyclobutyl, cyclopentyl, cyclohexyl, cycloheptyl, cyclooctyl, bicyclo[2.2.2]octyl, bicyclo[2.2.1]heptyl, spiro[4.4]nonane, adamantyl and the like.

"Alkoxy" is an alkyl group which is attached to another moiety via an oxygen linker (—O(alkyl)). Non-limiting examples include methoxy, ethoxy, propoxy, and butoxy.

"Haloalkyl" or "halogenated alkyl" means an alkyl group in which one or more, including all, of the hydrogen radicals are replaced by a halo group, wherein each halo group is independently selected from —F, —Cl, —Br, and —I, and includes mono, di, tri, poly and per halogenated groups. For example, the term "halomethyl" or "halogenated methyl" means a methyl in which one to three hydrogen radical(s) have been replaced by a halo group. Representative haloalkyl groups include fluoromethyl, difluoromethyl, trifluoromethyl, bromomethyl, 1,2-dichloroethyl, 4-iodobutyl, 2-fluoropentyl, and the like. Other examples include groups such as but are not limited to —$CH_2CF_3$, —$CH(CH_2F)_2$, —$CH(CHF_2)_2$, —$CH(CF_3)_2$, —$CF(CH_3)_2$, —$CF_3$.

"Aryl" means an aromatic radical that is a phenyl group, a naphthyl group, an indanyl group or a tetrahydronaphthalene group. An aryl group is optionally substituted with 1-4 substituents. Exemplary substituents include alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido.

"Heteroaryl" means a 5- or 6-membered heteroaromatic radical containing 1-4 heteroatoms independently selected from N, O, and S, and which is optionally fused to a saturated or unsaturated ring containing 0-4 heteroatoms selected from N, O, and S and includes, for example, heteroaromatic radicals such as 2- or 3-thienyl, 2- or 3-furanyl, 2- or 3-pyrrolyl, 2-, 3-, or 4-pyridyl, 2-pyrazinyl, 2-, 4-, or 5-pyrimidinyl, 3- or 4-pyridazinyl, 1H-indol-6-yl, 1H-indol-5-yl, 1H-benzimidazol-6-yl, 1H-benzimidazol-5-yl, 2-, 4-, 5-, 6-, 7- or 8-quinazolinyl, 2-, 3-, 5-, 6-, 7- or 8-quinoxalinyl, 2-, 3-, 4-, 5-, 6-, 7- or 8-quinolinyl, 1-, 3-, 4-, 5-, 6-, 7- or 8-isoquinolinyl, 2-, 4-, or 5-thiazolyl, 2-, 3-, 4-, or 5-pyrazolyl, 2-, 3-, 4-, or 5-imidazolyl. A heteroaryl is optionally substituted. Exemplary substituents include alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido, or by oxo to form an N-oxide.

"Heterocyclyl" means a 4-, 5-, 6- and 7-membered saturated or partially unsaturated heterocyclic ring containing 1 to 4 heteroatoms independently selected from N, O, and S. Exemplary heterocyclyls include pyrrolidine, pyrrolidin-2-one, 1-methylpyrrolidin-2-one, piperidine, piperidin-2-one, dihydropyridine, tetrahydropyridine, piperazine, 1-(2,2,2-trifluoroethyl)piperazine, 1,2-dihydro-2-oxopyridine, 1,4-dihydro-4-oxopyridine, piperazin-2-one, 3,4,5,6-tetrahydro-4-oxopyrimidine, 3,4-dihydro-4-oxopyrimidine, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, oxazolidin-2-one, imidazolidin-2-one, imidazolidine-2,4-dione, tetrahydropyrimidin-2(1H)-one, morpholine, N-methylmorpholine, morpholin-3-one, 1,3-oxazinan-2-one, thiomorpholine, thiomorpholine 1,1-dioxide, tetrahydro-1,2,5-thiaoxazole 1,1-dioxide, tetrahydro-2H-1,2-thiazine 1,1-dioxide, hexahydro-1,2,6-thiadiazine 1,1-dioxide, tetrahydro-1,2,5-thiadiazole 1,1-dioxide isothiazolidine 1,1-dioxide, 6-oxo-1,6-dihydropyridazin-3-yl, 6-oxo-1,6-dihydropyridazin-4-yl, 5-oxo-4,5-dihydro-1H-1,2,4-triazol-3-yl and 5-oxo-4,5-dihydro-1H-imidazol-2-yl. A heterocyclyl can be optionally substituted with 1-4 substituents. Exemplary substituents include alkyl, haloalkyl, halogen and oxo.

"Spirocycloalkyl" means a cycloalkyl group which shares one ring carbon with another alkyl or cycloalkyl group. The compound(s) of the invention provided herein include both the neutral form and a pharmaceutically acceptable salt thereof.

Certain disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms.

When a compound is designated by a name or structure that indicates a single enantiomer, unless indicated otherwise, the compound is at least 50%, 60%, 70%, 80%, 90%, 95%, 99%, 99.5% or 99.9% optically pure (also referred to as "enantiomerically pure"). Optical purity is the weight in the mixture of the named or depicted enantiomer divided by the total weight in the mixture of both enantiomers.

"Subject", "patient" and "mammal" are used interchangeably herein. In one embodiment, the subject is a non-human animal such as a non-human primate (e.g., a monkey, chimpanzee), a farm animal (e.g., a horse, cow, pig, chicken, or sheep), a laboratory animal (e.g., a rat or mouse), or a companion animal (e.g., dog, cat, guinea pig or rabbit). In a preferred embodiment, the subject is a human.

"Compound(s) of the invention" refers to compounds represented by Structural Formula I, Ia, Ib, Ic, Id, Ie, If, Ig, Ih, Ii, Ij, Ik, Il, Im, In, Io, Ip; a compound named in Table 1; a compound depicted in Table 2; a compound named or depicted in the examples herein as the final compound(s) of the examples; or a pharmaceutically acceptable salt thereof. "Compound(s) of the invention" also includes the neutral form of the compounds as depicted herein.

"Pharmaceutically acceptable" refers to a component that is, within the scope of sound medical judgment, suitable for use in contact with the tissues of the subject, such as humans and other mammals, without undue toxicity, irritation, allergic response and the like, and are commensurate with a reasonable benefit/risk ratio.

Included in the invention are pharmaceutically acceptable salts of the compounds disclosed herein. The disclosed compounds have basic amine groups and therefore can form pharmaceutically acceptable salts with pharmaceutically acceptable acid(s). Suitable pharmaceutically acceptable acid addition salts of the compounds of the invention include salts of inorganic acids (such as hydrochloric acid, hydrobromic, phosphoric, metaphosphoric, nitric, and sulfuric acids) and of organic acids (such as, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, and tartaric acids). Compounds of the invention with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts). Lists of suitable salts are found in Remington's Pharmaceutical Sciences, 18th ed., Mack Publishing Company, Easton, Pa., 1990, p 1445, the disclosure of which is hereby incorporated by reference.

"Liver X receptors or LXRs" includes both the α and β subtypes of the liver X receptor. In one embodiment, the disclosed compounds selectively bind and upregulate the activity of the LXRβ subtype over the LXRα subtype. To "modulate" a receptor means that there is a change or alteration in the activity of a molecule of interest, e.g., the biological activity of liver X receptor. Modulation may be an upregulation (increase) or a downregulation (decrease) in the magnitude of a certain activity or function of the molecule of interest. Exemplary activities and functions of a molecule include, but are not limited to, binding characteristics, enzymatic activity, cell receptor activation, transcriptional activity, and signal transduction. In an embodiment, the compounds of the invention are LXR agonists that, for example, upregulate or downregulate genes which are transcriptional targets of LXR (i.e., "LXR target genes"). In another embodiment, the compounds of the invention are partial agonists. In another embodiment, the compounds of the invention are antagonists.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to prevent or delay their recurrence.

"Disease" or "disorder" means any condition that is modulated or otherwise affected by LXR activity or in which LXR activity is implicated. The diseases or disorders include those which are associated with, or symptoms arising from the complications of, altered cholesterol transport, cholesterol reverse transport, fatty acid metabolism, cholesterol absorption, cholesterol re-absorption, cholesterol secretion, cholesterol excretion, or cholesterol metabolism.

"Effective amount" is the quantity of the compound which is sufficient to treat (therapeutically or prophylactically) the target disorder or in which a beneficial clinical outcome is achieved when the compound is administered to a subject in a proper dosing regimen. Effective doses will also vary, as recognized by one of ordinary skill in the art, depending on the disease being treated, the severity of the disease, the route of administration, the sex, age and general health condition of the patient, excipient usage, the possibility of co-usage with other therapeutic treatments such as use of other agents and the judgment of the treating physician or other medical provider. For example, an effective amount is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy. For example, when a compound of the invention is administered to a subject with a cancer, a "beneficial clinical outcome" includes a reduction in tumor mass, a reduction in metastasis, a reduction in the severity of the symptoms associated with the cancer and/or an increase in the longevity of the subject compared with the absence of the treatment.

When a compound of the invention is administered to a subject with a disorder such as atherosclerosis, a "beneficial clinical outcome" includes reduction in the severity or number of symptoms associated with the disorder, lower cholesterol, or increase in the longevity of the subject compared with the absence of the treatment. The recommended dosages of agents currently used for the treatment of a disorder can be obtained from various references in the art including, but not limited to, Hardman et al., eds., 1996, Goodman & Gilman's The Pharmacological Basis Of Basis Of Therapeutics $9^{th}$ Ed, Mc-Graw-Hill, N.Y.; Physician's Desk Reference (PDR) $57^{th}$ Ed., 2003, Medical Economics Co., Inc., Montvale, N.J., each of which is incorporated herein by reference in its entirety. In certain embodiments, an effective amount of a compound of this invention is in the range of from 0.5 mg to 2000 mg, or from 0.5 mg to 1000 mg, or from 0.5 mg to 500 mg, or from 0.5 mg to 100 mg, or from 100 mg to 1000 mg, or from 20 mg to 2000 mg per treatment. Treatment typically is administered from one to three times daily.

3. Description of Exemplary Compounds

In a first embodiment, the present invention provides a compound of Formula (I):

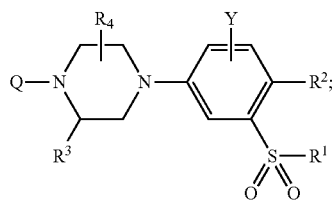

(I)

or a pharmaceutically acceptable salt thereof, wherein the variables are as described above.

In a second embodiment, the compounds of the present invention are represented by structural Formula (I), or a pharmaceutically acceptable salt thereof, wherein Q is 1) $R^{10}OC(=O)$—; 2) 2-pyridyl, 3-pyridyl, 4-pyridyl, 3-pyridazinyl, 2-pyrimidinyl, 4-pyrimidinyl, 2-pyrazinyl, 2-oxazolyl, 2-thiazolyl, 1,3,4-thiadiazol-2-yl, 2-pyridon-4-yl, 2-benzoxazolyl, 2-benzothiazolyl, thiazolo[4,5-b]pyridin-2-yl, thiazolo[4,5-c]pyridin-2-yl, thiazolo[5,4-c]pyridin-2-yl or thiazolo[5,4-b]pyridin-2-yl, each optionally substituted by one to three groups independently selected from $R^{21}$; 3) phenylCH$_2$, phenylCHMe, pyridylCH$_2$, furanylCH$_2$, each optionally substituted with one to three substituents independently selected from $R^{31}$; or 4) cyclohexylCH$_2$, bicyclo[3.1.0]hexylCH$_2$, spiro[2.5]octylCH$_2$, piperidinylCH$_2$, pyrrolidinylCH$_2$ and tetrahydropyranylCH$_2$, each optionally substituted with one to three substituents independently selected from $R^{41}$;

$R^1$ is selected from Me, —NH$_2$, —NHMe, and —NMe-4-methoxybenzyl;

$R^2$ is selected from (1) H, F, Cl, CN, CF$_3$, CH$_2$OH, CH$_2$NH$_2$, CONH$_2$, CH$_2$OAc, CH$_2$OMe, and CH$_2$NHAc or (2) 2-oxazolyl, 1,3,4-oxadiazol-2-yl, 1,2,4-oxadiazol-5-yl, 2-thiazolyl and 1,3,4-thiadiazol-2-yl each of which is optionally substituted with a group selected from methyl, cyano, ethoxycarbonyl and CONH$_2$;

Y is H, F or Cl;

$R^3$ is selected from i-Pr, i-Bu, t-Bu, CF$_3$, CF$_2$Me, CH$_2$CMe$_2$F, CH$_2$CF$_3$, CH(OMe)Me, c-Pr, c-hexyl, phenyl, 2-Cl-phenyl, 2-Br-phenyl, 2-Me-phenyl, 3-Cl-phenyl, 3-Me-phenyl, 4-F-phenyl, 4-Cl-phenyl, 4-Br-phenyl, benzyl, 4-methyl-2-thiazolyl, CO$_2$Me, CMe$_2$OH and CH$_2$CMe$_2$OH;

$R^4$ is H or methyl;

$R^{10}$ is selected from i-Pr, t-Bu, i-Bu, t-BuCH$_2$, benzyl, CF$_3$CH$_2$, CF$_3$CHMe, CF$_3$CMe$_2$, and 2,2,3,3-tetrafluorocyclobutyl;

$R^{21}$ is selected from F, Cl, Br, CN, NO$_2$, NH$_2$, OH, Me, i-Pr, c-Pr, C(=CH$_2$)Me, CHF$_2$, CF$_3$, CF$_2$Me, OMe, Oi-Pr, OCHF$_2$, OCH$_2$CF$_3$, CH$_2$OH, CH(OH)Me, CH(OH)Et, CH(OH)CF$_3$, CMe$_2$OH, CMe(OH)CF$_3$, CH(OMe)CF$_3$, CMe$_2$CN, C(=O)H, C(=O)Me, SO$_2$Me, CO$_2$H, CO$_2$Me, CO$_2$Et, CONR$^{22}$R$^{23}$, CH$_2$NR$^{22}$R$^{23}$, CH$_2$NHAc, CH$_2$SMe, CH$_2$NHSO$_2$Me, CH$_2$C$_6$H$_4$R$^{25}$ and 4,4-dimethyl-2-oxazolidinyl;

$R^{22}$ is selected from H, Me, Et, n-Bu, t-Bu, CH$_2$CH$_2$OH, CH$_2$CH$_2$OMe, CH$_2$CH$_2$CH$_2$OH, CH$_2$CH$_2$CMe$_2$OH, CH$_2$CH$_2$CH$_2$OMe, CH$_2$CO$_2$Et, CH$_2$CH$_2$CO$_2$Et; CH$_2$CH$_2$CH$_2$NHCO$_2$Me, CH$_2$CH$_2$CH$_2$NHCO$_2$t-Bu, and N-t-BuOC(=O)-3-azetidinyl;

$R^{23}$ is hydrogen, methyl, ethyl or methoxy; or $R^{22}$ and $R^{23}$, together with the nitrogen to which they are attached, form an azetidine or morpholine ring, each optionally substituted by one or two groups independently selected from $R^{24}$;

$R^{24}$ is F, OH, OMe, or NH$_2$;

$R^{25}$ is CO$_2$H or CMe$_2$OH;

$R^{31}$ is selected from F, Cl, Br, Me, i-Pr, CF$_3$, OCHF$_2$, OCF$_3$, CMe(OH)CF$_3$, CO$_2$Me and CMe$_2$OH; and $R^{41}$ is selected from F, OH, OMe, Me, i-Pr, CHF$_2$, CF$_3$, CH$_2$CF$_3$, CF$_2$CH$_3$, and CMe$_2$OH.

In a third embodiment, the compounds of the present invention are represented by structural Formula (I), or a pharmaceutically acceptable salt thereof, wherein Q is pyridyl or pyrimidinyl, each being substituted with one or two groups independently selected from $R^{21}$; $R^1$ is selected from methyl, NH$_2$ and NHMe; $R^2$ is H, F or CH$_2$OH; Y is H; $R^3$ is i-Pr; $R^4$ is H; wherein the remaining variables are as described in Formula (I) or the first or second embodiment.

In a fourth embodiment, the compounds of the present invention are represented by structural Formula (I), or a pharmaceutically acceptable salt thereof, wherein Q is 2-pyridyl or 2-pyrimidinyl, each being substituted with one CF$_3$ group and optionally substituted with a second group selected from $R^{21}$; $R^1$ is methyl; $R^2$ is H, F or CH$_2$OH; Y is H; $R^3$ is i-Pr; $R^4$ is H; wherein the remaining variables are as described in Formula (I) or the first, second, or third embodiment.

In a fifth embodiment, at least one $R^{21}$ is a hydroxy($C_1$-$C_4$)alkyl group and the remaining variables are as described in Formula (I) or the first, second, third, or fourth embodiment.

In a sixth embodiment, the compounds of the present invention are represented by structural Formula (I), or a pharmaceutically acceptable salt thereof, wherein Q is phenyl$CH_2$ or pyridyl$CH_2$, each being optionally substituted with one to three substituents independently selected from $R^{31}$; $R^1$ is methyl, $NH_2$ or NHMe; $R^2$ is H, F or $CH_2OH$; Y is H; $R^3$ is selected from i-Pr, phenyl and halophenyl; and $R^4$ is H, wherein the remaining variables are as described in Formula (I) or the first or second embodiment.

In a seventh embodiment, the compounds of the present invention are represented by structural Formula (I), or a pharmaceutically acceptable salt thereof, wherein Q is phenyl$CH_2$ or 3-pyridyl$CH_2$, each being substituted with one $CF_3$ group and optionally substituted with one other group selected from $R^{31}$; $R^1$ is methyl; $R^2$ is H, F or $CH_2OH$; Y is H; $R^3$ is isopropyl; and $R^4$ is H, wherein the remaining variables are as described in Formula (I) or the first or second embodiment.

In an eighth embodiment, the compounds of the present invention are represented by structural Formula (I), or a pharmaceutically acceptable salt thereof, wherein Q is cyclohexyl$CH_2$, piperidinyl$CH_2$ or tetrahydropyranyl$CH_2$, each being optionally substituted with one to three substituents independently selected from $R^{41}$; $R^1$ is methyl, $NH_2$ or NHMe; $R^2$ is H, F or $CH_2OH$; Y is H; $R^3$ is isopropyl, phenyl or halophenyl; and $R^4$ is H, wherein the remaining variables are as described in Formula (I) or the first or second embodiment.

In a ninth embodiment, the compounds of the present invention are represented by structural Formula (I), or a pharmaceutically acceptable salt thereof, wherein Q is cyclohexyl$CH_2$, 3-piperidinyl$CH_2$, or 3-tetrahydropyranyl$CH_2$, each being substituted with one $CF_3$ group and optionally substituted with one other group selected from $R^{41}$; $R^1$ is methyl; $R^2$ is H, F or $CH_2OH$; Y is H; $R^3$ is isopropyl; and $R^4$ is H, wherein the remaining variables are as described in Formula (I) or the first or second embodiment.

In a tenth embodiment, the compound of Formula (I) is represented by structural Formula Ia or Ib:

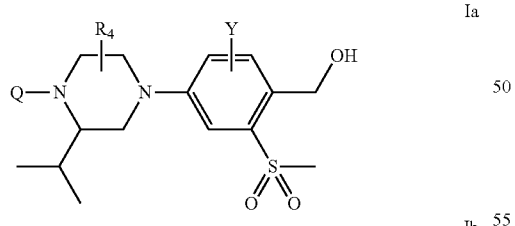

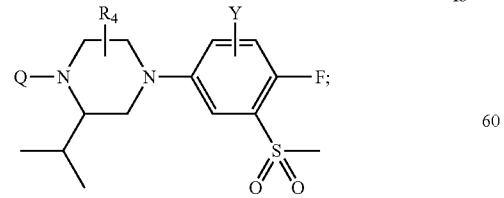

or a pharmaceutically acceptable salt thereof; wherein $R^4$, Q and Y are as defined in Formula (I) or the first or second embodiment.

In an eleventh embodiment, the compound of Formula (I) is represented by structural Formula Ic, Id, Ie, If, Ig, Ih, Ii or Ij:

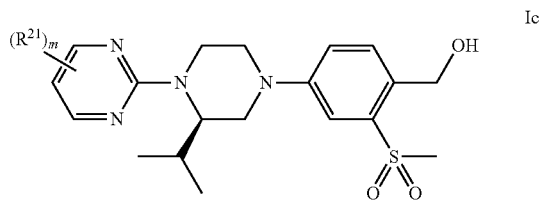

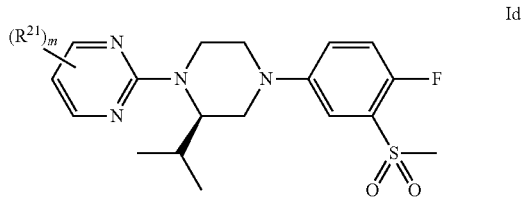

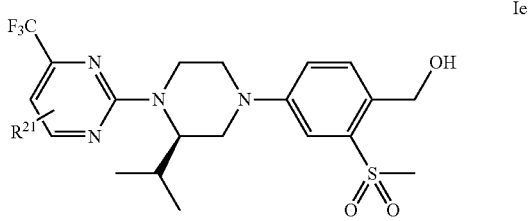

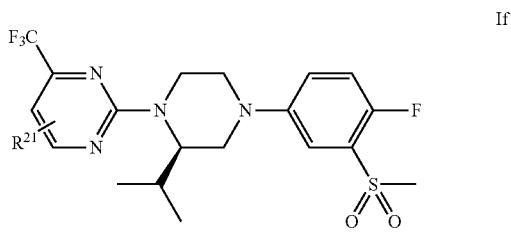

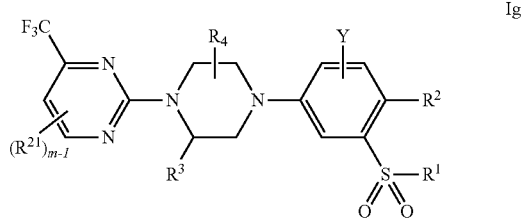

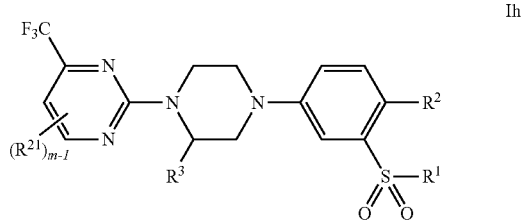

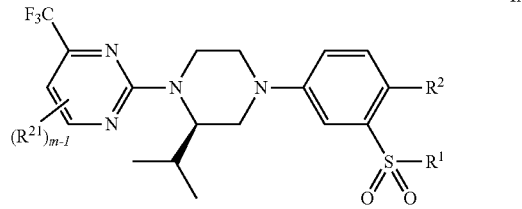

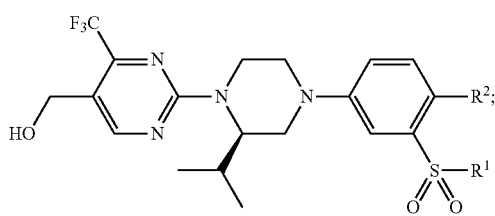

Ij or a pharmaceutically acceptable salt thereof, wherein m is 1, 2 or 3; and $R^1$, $R^2$, $R^3$, $R^4$, $R^{21}$ and Y are as defined in Formula (I) or the first, second, third, fourth, or fifth embodiments.

In a twelfth embodiment, the compound of Formula (I) is represented by structural Formula Ik, Il, Im, In, Io or Ip:

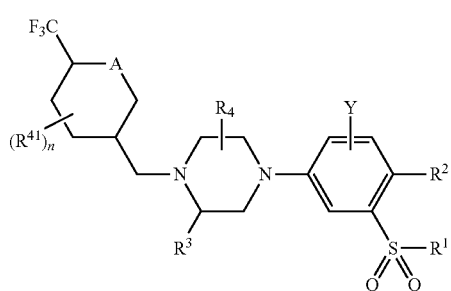

Ik

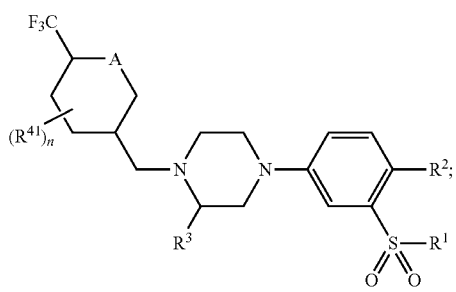

Il

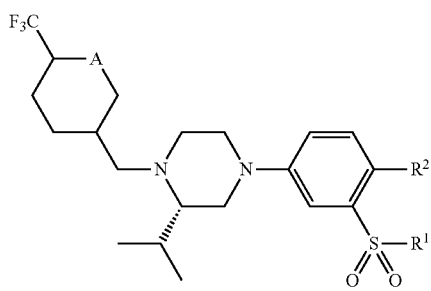

Im

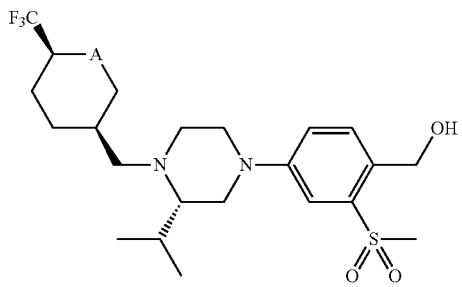

In

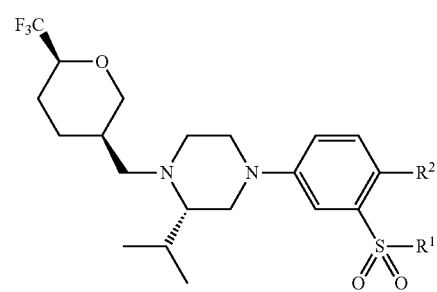

Io

Ip or a pharmaceutically acceptable salt thereof, wherein n is 0, 1 or 2; A is $CH_2$, NH, NMe or O; and $R^1$, $R^2$, $R^3$, $R^4$, $R^{41}$ and Y are as defined in Formula (I) or the first, second, eighth or ninth embodiments.

In one embodiment, a compound of the invention is a compound in Table 1 or a pharmaceutically acceptable salt thereof.

TABLE 1

| Cpd No. | Compound Name[a] |
|---|---|
| 1-1 | tert-butyl (R)-2-isopropyl-4-(3-(methylsulfonyl)phenyl)piperazine-1-carboxylate |
| 1-2 | tert-butyl (S)-2-isobutyl-4-(3-(methylsulfonyl)phenyl)piperazine-1-carboxylate |
| 1-3 | tert-butyl (R)-2-isobutyl-4-(3-(methylsulfonyl)phenyl)piperazine-1-carboxylate |
| 1-4 | 1-(tert-butyl) 2-methyl (S)-4-(3-(methylsulfonyl)phenyl)piperazine-1,2-dicarboxylate |
| 1-5 | tert-butyl 4-(3-(methylsulfonyl)phenyl)-2-phenylpiperazine-1-carboxylate |
| 1-6 | tert-butyl (S)-4-(3-(methylsulfonyl)phenyl)-2-phenylpiperazine-1-carboxylate |
| 1-7 | tert-butyl (S)-2-benzyl-4-(3-(methylsulfonyl)phenyl)piperazine-1-carboxylate |
| 1-8 | tert-butyl (R)-2-benzyl-4-(3-(methylsulfonyl)phenyl)piperazine-1-carboxylate |

TABLE 1-continued

| Cpd No. | Compound Name[a] |
|---|---|
| 1-9 | tert-butyl 2-(2-bromophenyl)-4-(3-(methylsulfonyl)phenyl)piperazine-1-carboxylate |
| 1-10 | tert-butyl 2-methyl-4-(3-(methylsulfonyl)phenyl)-2-phenylpiperazine-1-carboxylate |
| 1-11 | tert-butyl 2-cyclohexyl-4-(3-(methylsulfonyl)phenyl)piperazine-1-carboxylate |
| 1-12 | tert-butyl 2-(4-bromophenyl)-4-(3-(methylsulfonyl)phenyl)piperazine-1-carboxylate |
| 1-13 | benzyl (R)-2-isobutyl-4-(3-(methylsulfonyl)phenyl)piperazine-1-carboxylate |
| 1-14 | benzyl 4-(3-(methylsulfonyl)phenyl)-2-phenylpiperazine-1-carboxylate |
| 2-1 | tert-butyl (R)-4-(4-fluoro-3-(methylsulfonyl)phenyl)-2-isopropylpiperazine-1-carboxylate |
| 2-2 | tert-butyl (S)-2-isopropyl-4-(3-(methylsulfonyl)phenyl)piperazine-1-carboxylate |
| 2-3 | tert-butyl 4-(4-(methoxycarbonyl)-3-(methylsulfonyl)phenyl)-2-phenylpiperazine-1-carboxylate |
| 2-4 | ethyl (R)-2-(4-(4-(tert-butoxycarbonyl)-3-isopropylpiperazin-1-yl)-2-(methylsulfonyl)phenyl)thiazole-4-carboxylate |
| 2-5 | tert-butyl (R)-4-(4-fluoro-3-(N-(4-methoxybenzyl)-N-methylsulfamoyl)phenyl)-2-isopropylpiperazine-1-carboxylate |
| 3-1 | tert-butyl (R)-4-(4-cyano-3-(methylsulfonyl)phenyl)-2-isopropylpiperazine-1-carboxylate |
| 3-2 | tert-butyl (R)-2-isopropyl-4-(3-(methylsulfonyl)-4-(trifluoromethyl)phenyl)piperazine-1-carboxylate |
| 3-3 | (R)-2-(4-(4-fluoro-3-(methylsulfonyl)phenyl)-2-isopropylpiperazin-1-yl)-4-methyl-5-(methylsulfonyl)pyrimidine |
| 4-1 | tert-butyl (R)-4-(4-carbamoyl-3-(methylsulfonyl)phenyl)-2-isopropylpiperazine-1-carboxylate |
| 4-2 | (R)-4-(3-isopropyl-4-(4-(trifluoromethyl)pyrimidin-2-yl)piperazin-1-yl)-2-(methylsulfonyl)benzamide |
| 4-3 | (R)-3-chloro-4-(3-isopropyl-4-(4-(trifluoromethyl)pyrimidin-2-yl)piperazin-1-yl)-2-(methylsulfonyl)benzamide |
| 4-4 | (R)-5-chloro-4-(3-isopropyl-4-(4-(trifluoromethyl)pyrimidin-2-yl)piperazin-1-yl)-2-(methylsulfonyl)benzamide |
| 4-5 | (R)-2-(4-(4-fluoro-3-(methylsulfonyl)phenyl)-2-isopropylpiperazin-1-yl)pyrimidine-4-carboxamide |
| 4-6 | (R)-4-(4-(4-(hydroxymethyl)-3-(methylsulfonyl)phenyl)-2-isopropylpiperazin-1-yl)picolinamide |
| 4-7 | (R)-2-(4-(4-fluoro-3-(methylsulfonyl)phenyl)-2-isopropylpiperazin-1-yl)-5-(trifluoromethyl)pyrimidine-4-carboxamide |
| 4-8 | 4-((S)-3-(2-chlorophenyl)-4-(((1s,4R)-4-(trifluoromethyl)cyclohexyl)methyl)piperazin-1-yl)-2-(methylsulfonyl)benzamide |
| 4-9 | 4-((R)-3-(2-chlorophenyl)-4-(((1s,4S)-4-(trifluoromethyl)cyclohexyl)methyl)piperazin-1-yl)-2-(methylsulfonyl)benzamide |
| 5-1 | 2,2,3,3-tetrafluorocyclobutyl (2R)-4-(4-fluoro-3-(methylsulfonyl)phenyl)-2-isopropylpiperazine-1-carboxylate |
| 5-2 | 1,1,1-trifluoro-2-methylpropan-2-yl (R)-4-(4-fluoro-3-(methylsulfonyl)phenyl)-2-isopropylpiperazine-1-carboxylate |
| 5-3 | 1,1,1-trifluoropropan-2-yl (2R)-4-(4-fluoro-3-(methylsulfonyl)phenyl)-2-isopropylpiperazine-1-carboxylate |
| 5-4 | 2,2,2-trifluoroethyl (R)-4-(4-fluoro-3-(methylsulfonyl)phenyl)-2-isopropylpiperazine-1-carboxylate |
| 5-5 | isobutyl 4-(3-(methylsulfonyl)phenyl)-2-phenylpiperazine-1-carboxylate |
| 5-6 | neopentyl (R)-2-isopropyl-4-(3-(methylsulfonyl)phenyl)piperazine-1-carboxylate |
| 5-7 | isobutyl (R)-2-isopropyl-4-(3-(methylsulfonyl)phenyl)piperazine-1-carboxylate |
| 5-8 | isopropyl 4-(3-(methylsulfonyl)phenyl)-2-phenylpiperazine-1-carboxylate |
| 6-1 | tert-butyl (S)-2-(2-hydroxypropan-2-yl)-4-(3-(methylsulfonyl)phenyl)piperazine-1-carboxylate |
| 7-1 | (R)-2-(4-(4-fluoro-3-(methylsulfonyl)phenyl)-2-isopropylpiperazin-1-yl)-4-(trifluoromethyl)pyrimidine |
| 7-2 | (R)-2-(2-isopropyl-4-(3-(methylsulfonyl)phenyl)piperazin-1-yl)pyrimidine |
| 7-3 | (R)-2-(2-isopropyl-4-(3-(methylsulfonyl)phenyl)piperazin-1-yl)-4,6-dimethylpyrimidine |
| 7-4 | (R)-5-chloro-2-(2-isopropyl-4-(3-(methylsulfonyl)phenyl)piperazin-1-yl)pyrimidine |
| 7-5 | (R)-5-cyclopropyl-2-(2-isopropyl-4-(3-(methylsulfonyl)phenyl)piperazin-1-yl)pyrimidine |
| 7-6 | (R)-5-isopropyl-2-(2-isopropyl-4-(3-(methylsulfonyl)phenyl)piperazin-1-yl)pyrimidine |
| 7-7 | (R)-2-(4-(4-fluoro-3-(methylsulfonyl)phenyl)-2-isopropylpiperazin-1-yl)pyrimidine-4-carbonitrile |
| 7-8 | (R)-2-(4-(4-fluoro-3-(methylsulfonyl)phenyl)-2-isopropylpiperazin-1-yl)-6-methylpyrimidine-4-carbonitrile |
| 7-9 | methyl (R)-2-(2-isopropyl-4-(3-(methylsulfonyl)phenyl)piperazin-1-yl)pyrimidine-5-carboxylate |
| 7-10 | (R)-4-cyclopropyl-2-(4-(4-fluoro-3-(methylsulfonyl)phenyl)-2-isopropylpiperazin-1-yl)pyrimidine |
| 7-11 | (R)-5-(difluoromethoxy)-2-(2-isopropyl-4-(3-(methylsulfonyl)phenyl)piperazin-1-yl)pyrimidine |
| 7-12 | (R)-5-chloro-2-(4-(4-fluoro-3-(methylsulfonyl)phenyl)-2-isopropylpiperazin-1-yl)-4-methylpyrimidine |
| 7-13 | (R)-2-(2-isopropyl-4-(3-(methylsulfonyl)phenyl)piperazin-1-yl)-4-(trifluoromethyl)pyrimidine |

TABLE 1-continued

| Cpd No. | Compound Name[a] |
|---|---|
| 7-14 | methyl (R)-2-(4-(4-fluoro-3-(methylsulfonyl)phenyl)-2-isopropylpiperazin-1-yl)pyrimidine-5-carboxylate |
| 7-15 | methyl (R)-2-(4-(4-fluoro-3-(methylsulfonyl)phenyl)-2-isopropylpiperazin-1-yl)pyrimidine-4-carboxylate |
| 7-16 | (R)-5-bromo-2-(2-isopropyl-4-(3-(methylsulfonyl)phenyl)piperazin-1-yl)pyrimidine |
| 7-17 | (R)-4-(3-isopropyl-4-(4-(trifluoromethyl)pyrimidin-2-yl)piperazin-1-yl)-2-(methylsulfonyl)benzonitrile |
| 7-18 | (R)-2-(4-(4-fluoro-3-(methylsulfonyl)phenyl)-2-isopropylpiperazin-1-yl)-4-methyl-6-(trifluoromethyl)pyrimidine |
| 7-19 | ethyl (R)-2-(4-(4-fluoro-3-(methylsulfonyl)phenyl)-2-isopropylpiperazin-1-yl)-4-methylpyrimidine-5-carboxylate |
| 7-20 | (R)-5-bromo-2-(4-(4-fluoro-3-(methylsulfonyl)phenyl)-2-isopropylpiperazin-1-yl)-4-methylpyrimidine |
| 7-21 | (R)-2-(4-(4-fluoro-3-(methylsulfonyl)phenyl)-2-isopropylpiperazin-1-yl)-4-(trifluoromethyl)pyrimidine-5-carbonitrile |
| 7-22 | ethyl 2-(4-(4-fluoro-3-(methylsulfonyl)phenyl)-2-(2,2,2-trifluoroethyl)piperazin-1-yl)-4-methylpyrimidine-5-carboxylate |
| 7-23 | (R)-5-fluoro-2-(4-(4-fluoro-3-(methylsulfonyl)phenyl)-2-isopropylpiperazin-1-yl)-4-methylpyrimidine |
| 7-24 | (S)-2-(4-(3-(methylsulfonyl)phenyl)-1-(4-(trifluoromethyl)pyrimidin-2-yl)piperazin-2-yl)propan-2-ol |
| 7-25 | (R)-2-(2-(1,1-difluoroethyl)-4-(3-(methylsulfonyl)phenyl)piperazin-1-yl)-4-(trifluoromethyl)pyrimidine |
| 7-26 | (S)-2-(2-(1,1-difluoroethyl)-4-(3-(methylsulfonyl)phenyl)piperazin-1-yl)-4-(trifluoromethyl)pyrimidine |
| 7-27 | (R)-2-(4-(3-(methylsulfonyl)phenyl)-2-(trifluoromethyl)piperazin-1-yl)-4-(trifluoromethyl)pyrimidine |
| 7-28 | (S)-2-(4-(3-(methylsulfonyl)phenyl)-2-(trifluoromethyl)piperazin-1-yl)-4-(trifluoromethyl)pyrimidine |
| 7-29 | 2-(2-(tert-butyl)-4-(4-fluoro-3-(methylsulfonyl)phenyl)piperazin-1-yl)-4-(trifluoromethyl)pyrimidine |
| 7-30 | (S)-2-(4-(3-(methylsulfonyl)phenyl)-2-phenylpiperazin-1-yl)-4-(trifluoromethyl)pyrimidine |
| 7-31 | (R)-2-(4-(3-(methylsulfonyl)phenyl)-2-phenylpiperazin-1-yl)-4-(trifluoromethyl)pyrimidine |
| 7-32 | (R)-2-(2-(4-(4-fluoro-3-(methylsulfonyl)phenyl)-2-isopropylpiperazin-1-yl)-4-(trifluoromethyl)pyrimidin-5-yl)-4,4-dimethyl-4,5-dihydrooxazole |
| 7-33 | (R)-4-(4-fluoro-3-(methylsulfonyl)phenyl)-1-(5-fluoro-6-(trifluoromethyl)pyridin-2-yl)-2-isopropylpiperazine |
| 7-34 | (R)-1-(5-(difluoromethyl)pyridin-2-yl)-2-isopropyl-4-(3-(methylsulfonyl)phenyl)piperazine |
| 7-35 | (R)-2-isopropyl-4-(3-(methylsulfonyl)phenyl)-1-(5-(trifluoromethyl)pyridin-2-yl)piperazine |
| 7-36 | (R)-4-(4-fluoro-3-(methylsulfonyl)phenyl)-2-isopropyl-1-(5-(trifluoromethyl)pyridin-2-yl)piperazine |
| 7-37 | (R)-4-(3-isopropyl-4-(5-(trifluoromethyl)pyridin-2-yl)piperazin-1-yl)-2-(methylsulfonyl)benzonitrile |
| 7-38 | (R)-4-(3-isopropyl-4-(6-(trifluoromethyl)pyridin-2-yl)piperazin-1-yl)-2-(methylsulfonyl)benzonitrile |
| 7-39 | (R)-4-(3-isopropyl-4-(4-(trifluoromethyl)pyridin-2-yl)piperazin-1-yl)-2-(methylsulfonyl)benzonitrile |
| 7-40 | (S)-4-(3-(methylsulfonyl)phenyl)-2-phenyl-1-(5-(trifluoromethyl)pyridin-2-yl)piperazine |
| 7-41 | (R)-1-(3-chloro-5-(trifluoromethyl)pyridin-2-yl)-4-(4-fluoro-3-(methylsulfonyl)phenyl)-2-isopropylpiperazine |
| 7-42 | (R)-4-(4-fluoro-3-(methylsulfonyl)phenyl)-2-isopropyl-1-(3-nitro-5-(trifluoromethyl)pyridin-2-yl)piperazine |
| 7-43 | methyl (R)-6-(4-(4-fluoro-3-(methylsulfonyl)phenyl)-2-isopropylpiperazin-1-yl)-2-(trifluoromethyl)nicotinate |
| 7-44 | (R)-2-(4-(4-fluoro-3-(methylsulfonyl)phenyl)-2-isopropylpiperazin-1-yl)-5-(trifluoromethyl)pyrazine |
| 7-45 | (R)-2-(4-(4-fluoro-3-(methylsulfonyl)phenyl)-2-isopropylpiperazin-1-yl)-6-(trifluoromethyl)pyrazine |
| 7-46 | (R)-3-(2-isopropyl-4-(3-(methylsulfonyl)phenyl)piperazin-1-yl)-6-methylpyridazine |
| 7-47 | (R)-3-cyclopropyl-6-(2-isopropyl-4-(3-(methylsulfonyl)phenyl)piperazin-1-yl)pyridazine |
| 7-48 | (R)-3-(2-isopropyl-4-(3-(methylsulfonyl)phenyl)piperazin-1-yl)-6-(trifluoromethyl)pyridazine |
| 7-49 | (R)-3-(4-(4-fluoro-3-(methylsulfonyl)phenyl)-2-isopropylpiperazin-1-yl)-6-(trifluoromethyl)pyridazine |
| 7-50 | (R)-4-(2-isopropyl-4-(3-(methylsulfonyl)phenyl)piperazin-1-yl)-2-(trifluoromethyl)pyrimidine |
| 7-51 | (R)-2-(2-isopropyl-4-(3-(methylsulfonyl)phenyl)piperazin-1-yl)-5-(trifluoromethyl)-1,3,4-thiadiazole |

TABLE 1-continued

| Cpd No. | Compound Name[a] |
|---|---|
| 7-52 | (R)-2-(4-(4-fluoro-3-(methylsulfonyl)phenyl)-2-isopropylpiperazin-1-yl)benzo[d]oxazole |
| 7-53 | (R)-2-(4-(4-fluoro-3-(methylsulfonyl)phenyl)-2-isopropylpiperazin-1-yl)benzo[d]thiazole-6-carbonitrile |
| 7-54 | (R)-4-fluoro-2-(4-(4-fluoro-3-(methylsulfonyl)phenyl)-2-isopropylpiperazin-1-yl)benzo[d]thiazole |
| 7-55 | (R)-6-fluoro-2-(4-(4-fluoro-3-(methylsulfonyl)phenyl)-2-isopropylpiperazin-1-yl)benzo[d]thiazole |
| 7-56 | (R)-2-(4-(4-fluoro-3-(methylsulfonyl)phenyl)-2-isopropylpiperazin-1-yl)benzo[d]thiazole |
| 7-57 | (R)-2-(4-(4-fluoro-3-(methylsulfonyl)phenyl)-2-isopropylpiperazin-1-yl)thiazolo[5,4-b]pyridine |
| 7-58 | (R)-2-(4-(4-fluoro-3-(methylsulfonyl)phenyl)-2-isopropylpiperazin-1-yl)thiazolo[4,5-c]pyridine |
| 7-59 | (R)-2-(4-(4-fluoro-3-(methylsulfonyl)phenyl)-2-isopropylpiperazin-1-yl)thiazolo[4,5-b]pyridine |
| 7-60 | (R)-3-(3-isopropyl-4-(4-(trifluoromethyl)pyrimidin-2-yl)piperazin-1-yl)benzenesulfonamide |
| 8-1 | (R)-2-(2-(4-fluorophenyl)-4-(3-(methylsulfonyl)phenyl)piperazin-1-yl)-4-(trifluoromethyl)pyrimidine |
| 9-1 | ethyl (R)-2-(4-(4-fluoro-3-(methylsulfonyl)phenyl)-2-isopropylpiperazin-1-yl)-4-(trifluoromethyl)pyrimidine-5-carboxylate |
| 9-2 | methyl (R)-2-(4-(4-fluoro-3-(methylsulfonyl)phenyl)-2-isopropylpiperazin-1-yl)-4-(trifluoromethyl)pyrimidine-5-carboxylate |
| 9-3 | methyl (R)-2-(4-(4-fluoro-3-(N-(4-methoxybenzyl)-N-methylsulfamoyl)phenyl)-2-isopropylpiperazin-1-yl)-4-(trifluoromethyl)pyrimidine-5-carboxylate |
| 9-4 | ethyl (R)-2-(2-cyclopropyl-4-(4-fluoro-3-(methylsulfonyl)phenyl)piperazin-1-yl)-4-(trifluoromethyl)pyrimidine-5-carboxylate |
| 9-5 | methyl 2-(2-(tert-butyl)-4-(4-fluoro-3-(methylsulfonyl)phenyl)piperazin-1-yl)-4-(trifluoromethyl)pyrimidine-5-carboxylate |
| 9-6 | methyl (R)-2-(4-(4-fluoro-3-(N-methylsulfamoyl)phenyl)-2-isopropylpiperazin-1-yl)-4-(trifluoromethyl)pyrimidine-5-carboxylate |
| 9-7 | ethyl (R)-2-(4-(4-fluoro-3-(methylsulfonyl)phenyl)-2-isobutylpiperazin-1-yl)-4-(trifluoromethyl)pyrimidine-5-carboxylate |
| 9-8 | ethyl (S)-2-(4-(3-(methylsulfonyl)phenyl)-2-(4-methylthiazol-2-yl)piperazin-1-yl)-4-(trifluoromethyl)pyrimidine-5-carboxylate |
| 9-9 | methyl (R)-2-(4-(4-fluoro-3-(methylsulfonyl)phenyl)-2-(4-fluorophenyl)piperazin-1-yl)-4-(trifluoromethyl)pyrimidine-5-carboxylate |
| 9-10 | ethyl (R)-2-(4-(4-(acetoxymethyl)-3-(methylsulfonyl)phenyl)-2-isopropylpiperazin-1-yl)-4-(trifluoromethyl)pyrimidine-5-carboxylate |
| 9-11 | ethyl (R)-2-(2-isopropyl-4-(4-(5-methyl-1,3,4-oxadiazol-2-yl)-3-(methylsulfonyl)phenyl)piperazin-1-yl)-4-(trifluoromethyl)pyrimidine-5-carboxylate |
| 9-12 | ethyl (R)-2-(2-isopropyl-4-(4-(3-methyl-1,2,4-oxadiazol-5-yl)-3-(methylsulfonyl)phenyl)piperazin-1-yl)-4-(trifluoromethyl)pyrimidine-5-carboxylate |
| 9-13 | ethyl (R)-2-(2-isopropyl-4-(4-(5-methyl-1,3,4-thiadiazol-2-yl)-3-(methylsulfonyl)phenyl)piperazin-1-yl)-4-(trifluoromethyl)pyrimidine-5-carboxylate |
| 9-14 | ethyl (R)-2-(4-(4-carbamoylthiazol-2-yl)-3-(methylsulfonyl)phenyl)-2-isopropylpiperazin-1-yl)-4-(trifluoromethyl)pyrimidine-5-carboxylate |
| 10-1 | (R)-2-(2-(4-(4-fluoro-3-(methylsulfonyl)phenyl)-2-isopropylpiperazin-1-yl)-4-(trifluoromethyl)pyrimidin-5-yl)propan-2-ol |
| 10-2 | (R)-2-fluoro-5-(4-(5-(2-hydroxypropan-2-yl)-4-(trifluoromethyl)pyrimidin-2-yl)-3-isopropylpiperazin-1-yl)benzenesulfonamide |
| 10-3 | (R)-2-fluoro-5-(4-(5-(2-hydroxypropan-2-yl)-4-(trifluoromethyl)pyrimidin-2-yl)-3-isopropylpiperazin-1-yl)-N-methylbenzenesulfonamide |
| 10-4 | 2-(2-(2-(tert-butyl)-4-(4-fluoro-3-(methylsulfonyl)phenyl)piperazin-1-yl)-4-(trifluoromethyl)pyrimidin-5-yl)propan-2-ol |
| 10-5 | (S)-2-(2-(4-(4-(hydroxymethyl)-3-(methylsulfonyl)phenyl)-2-isopropylpiperazin-1-yl)-4-(trifluoromethyl)pyrimidin-5-yl)propan-2-ol |
| 10-6 | 2-(2-(4-(4-fluoro-3-(methylsulfonyl)phenyl)-2-(2,2,2-trifluoroethyl)piperazin-1-yl)-4-methylpyrimidin-5-yl)propan-2-ol |
| 10-7 | (R)-2-(2-(4-(4-(hydroxymethyl)-3-(methylsulfonyl)phenyl)-2-isopropylpiperazin-1-yl)-4-(trifluoromethyl)pyrimidin-5-yl)propan-2-ol |
| 10-8 | (R)-2-(2-(4-(4-fluoro-3-(methylsulfonyl)phenyl)-2-isopropylpiperazin-1-yl)-4-(trifluoromethyl)oxazol-5-yl)propan-2-ol |
| 10-9 | (R)-2-(4-(4-fluoro-3-(methylsulfonyl)phenyl)-1-(6-methyl-5-(trifluoromethyl)pyridin-2-yl)piperazin-2-yl)propan-2-ol |
| 10-10 | (S)-2-(4-(4-fluoro-3-(methylsulfonyl)phenyl)-1-(6-methyl-5-(trifluoromethyl)pyridin-2-yl)piperazin-2-yl)propan-2-ol |
| 10-11 | (R)-2-(4-((4-(3-(methylsulfonyl)phenyl)-2-phenylpiperazin-1-yl)methyl)phenyl)propan-2-ol |
| 10-12 | (S)-2-(4-((4-(3-(methylsulfonyl)phenyl)-2-phenylpiperazin-1-yl)methyl)phenyl)propan-2-ol |
| 10-13 | (S)-2-(5-((4-(3-(methylsulfonyl)phenyl)-2-phenylpiperazin-1-yl)methyl)-2-(trifluoromethyl)phenyl)propan-2-ol |

TABLE 1-continued

| Cpd No. | Compound Name[a] |
|---|---|
| 10-14 | (R)-2-(5-((4-(3-(methylsulfonyl)phenyl)-2-phenylpiperazin-1-yl)methyl)-2-(trifluoromethyl)phenyl)propan-2-ol |
| 11-1 | (R)-(2-(4-(4-fluoro-3-(methylsulfonyl)phenyl)-2-isopropylpiperazin-1-yl)-4-(trifluoromethyl)pyrimidin-5-yl)methanol |
| 11-2 | (R)-2-fluoro-5-(4-(5-(hydroxymethyl)-4-(trifluoromethyl)pyrimidin-2-yl)-3-isopropylpiperazin-1-yl)benzenesulfonamide |
| 11-3 | (R)-(2-(4-(4-chloro-3-(methylsulfonyl)phenyl)-2-isopropylpiperazin-1-yl)-4-(trifluoromethyl)pyrimidin-5-yl)methanol |
| 11-4 | (2-((S)-4-(4-(hydroxymethyl)-3-(methylsulfonyl)phenyl)-2-((S)-1-methoxyethyl)piperazin-1-yl)-4-(trifluoromethyl)pyrimidin-5-yl)methanol |
| 11-5 | (2-((S)-4-(4-(hydroxymethyl)-3-(methylsulfonyl)phenyl)-2-((R)-1-methoxyethyl)piperazin-1-yl)-4-(trifluoromethyl)pyrimidin-5-yl)methanol |
| 11-6 | (R)-(2-fluoro-4-(4-(5-(hydroxymethyl)-4-(trifluoromethyl)pyrimidin-2-yl)-3-isopropylpiperazin-1-yl)-6-(methylsulfonyl)phenyl)methanol |
| 11-7 | (R)-(2-(4-(4-fluoro-3-(methylsulfonyl)phenyl)-2-(4-fluorophenyl)piperazin-1-yl)-4-(trifluoromethyl)pyrimidin-5-yl)methanol |
| 11-8 | (R)-(2-(2-isopropyl-4-(4-(4-methyloxazol-2-yl)-3-(methylsulfonyl)phenyl)piperazin-1-yl)-4-(trifluoromethyl)pyrimidin-5-yl)methanol |
| 11-9 | (R)-(2-(2-isopropyl-4-(4-(5-methyl-1,3,4-oxadiazol-2-yl)-3-(methylsulfonyl)phenyl)piperazin-1-yl)-4-(trifluoromethyl)pyrimidin-5-yl)methanol |
| 11-10 | (R)-(2-(2-isopropyl-4-(4-(3-methyl-1,2,4-oxadiazol-5-yl)-3-(methylsulfonyl)phenyl)piperazin-1-yl)-4-(trifluoromethyl)pyrimidin-5-yl)methanol |
| 11-11 | (R)-(2-(2-isopropyl-4-(4-(5-methyl-1,3,4-thiadiazol-2-yl)-3-(methylsulfonyl)phenyl)piperazin-1-yl)-4-(trifluoromethyl)pyrimidin-5-yl)methanol |
| 11-12 | (R)-2-(4-(4-(5-(hydroxymethyl)-4-(trifluoromethyl)pyrimidin-2-yl)-3-isopropylpiperazin-1-yl)-2-(methylsulfonyl)phenyl)thiazole-4-carbonitrile |
| 11-13 | (R)-2-(4-(4-(5-(hydroxymethyl)-4-(trifluoromethyl)pyrimidin-2-yl)-3-isopropylpiperazin-1-yl)-2-(methylsulfonyl)phenyl)thiazole-4-carboxamide |
| 11-14 | (R)-(2-(4-(4-fluoro-3-(methylsulfonyl)phenyl)-2-isopropylpiperazin-1-yl)-4-methylpyrimidin-5-yl)methanol |
| 11-15 | (R)-(2-(4-(4-fluoro-3-(methylsulfonyl)phenyl)-2-isopropylpiperazin-1-yl)pyrimidin-4-yl)methanol |
| 11-16 | (R)-(2-(4-(4-(hydroxymethyl)-3-(methylsulfonyl)phenyl)-2-isopropylpiperazin-1-yl)-4-(trifluoromethyl)oxazol-5-yl)methanol |
| 11-17 | (R)-(2-(4-(4-(hydroxymethyl)-3-(methylsulfonyl)phenyl)-2-isopropylpiperazin-1-yl)-4-(trifluoromethyl)thiazol-5-yl)methanol |
| 12-1 | 1-(2-((R)-4-(4-fluoro-3-(methylsulfonyl)phenyl)-2-isopropylpiperazin-1-yl)-4-(trifluoromethyl)pyrimidin-5-yl)ethan-1-ol |
| 12-2 | (S)-1-(2-((R)-4-(4-fluoro-3-(methylsulfonyl)phenyl)-2-isopropylpiperazin-1-yl)-4-(trifluoromethyl)pyrimidin-5-yl)ethan-1-ol |
| 12-3 | (R)-1-(2-((R)-4-(4-fluoro-3-(methylsulfonyl)phenyl)-2-isopropylpiperazin-1-yl)-4-(trifluoromethyl)pyrimidin-5-yl)ethan-1-ol |
| 12-4 | 4-((R)-4-(5-((R)-1-hydroxyethyl)-4-(trifluoromethyl)pyrimidin-2-yl)-3-isopropylpiperazin-1-yl)-2-(methylsulfonyl)benzonitrile |
| 12-5 | 4-((R)-4-(5-((S)-1-hydroxyethyl)-4-(trifluoromethyl)pyrimidin-2-yl)-3-isopropylpiperazin-1-yl)-2-(methylsulfonyl)benzonitrile |
| 12-6 | (S)-1-(2-((R)-4-(4-fluoro-3-(methylsulfonyl)phenyl)-2-isopropylpiperazin-1-yl)-4-(trifluoromethyl)pyrimidin-5-yl)propan-1-ol |
| 12-7 | (R)-1-(2-((R)-4-(4-fluoro-3-(methylsulfonyl)phenyl)-2-isopropylpiperazin-1-yl)-4-(trifluoromethyl)pyrimidin-5-yl)propan-1-ol |
| 12-8 | 2-fluoro-5-((3R)-4-(5-(1-hydroxyethyl)-4-(trifluoromethyl)pyrimidin-2-yl)-3-isopropylpiperazin-1-yl)-N-methylbenzenesulfonamide |
| 12-9 | 1-(2-((R)-4-(4-fluoro-3-(methylsulfonyl)phenyl)-2-(4-fluorophenyl)piperazin-1-yl)-4-(trifluoromethyl)pyrimidin-5-yl)ethan-1-ol |
| 13-1 | (R)-1-(2-(4-(4-fluoro-3-(methylsulfonyl)phenyl)-2-isopropylpiperazin-1-yl)-4-(trifluoromethyl)pyrimidin-5-yl)ethan-1-one |
| 13-2 | (R)-5-(4-(5-acetyl-4-(trifluoromethyl)pyrimidin-2-yl)-3-isopropylpiperazin-1-yl)-2-fluoro-N-methylbenzenesulfonamide |
| 13-3 | (R)-1-(2-(4-(4-fluoro-3-(methylsulfonyl)phenyl)-2-(4-fluorophenyl)piperazin-1-yl)-4-(trifluoromethyl)pyrimidin-5-yl)ethan-1-one |
| 14-1 | (R)-2-(4-(4-fluoro-3-(methylsulfonyl)phenyl)-2-isopropylpiperazin-1-yl)-5-(prop-1-en-2-yl)-4-(trifluoromethyl)pyrimidine |
| 14-2 | (R)-(4-(3-isopropyl-4-(5-(prop-1-en-2-yl)-4-(trifluoromethyl)pyrimidin-2-yl)piperazin-1-yl)-2-(methylsulfonyl)phenyl)methanol |
| 15-1 | (R)-2-(4-(4-fluoro-3-(methylsulfonyl)phenyl)-2-isopropylpiperazin-1-yl)-5-((3-fluoroazetidin-1-yl)methyl)-4-(trifluoromethyl)pyrimidine |
| 15-2 | (R)-(2-(4-(4-fluoro-3-(methylsulfonyl)phenyl)-2-isopropylpiperazin-1-yl)-4-(trifluoromethyl)pyrimidin-5-yl)methanamine |
| 15-3 | (R)-1-(2-(4-(4-fluoro-3-(methylsulfonyl)phenyl)-2-isopropylpiperazin-1-yl)-4-(trifluoromethyl)pyrimidin-5-yl)-N,N-dimethylmethanamine |
| 15-4 | (R)-1-((2-(4-(4-fluoro-3-(methylsulfonyl)phenyl)-2-isopropylpiperazin-1-yl)-4-(trifluoromethyl)pyrimidin-5-yl)methyl)azetidin-3-ol |
| 15-5 | (R)-4-((2-(4-(4-fluoro-3-(methylsulfonyl)phenyl)-2-isopropylpiperazin-1-yl)-4-(trifluoromethyl)pyrimidin-5-yl)methyl)morpholine |
| 15-6 | (R)-N-((2-(4-(4-fluoro-3-(methylsulfonyl)phenyl)-2-isopropylpiperazin-1-yl)-4-(trifluoromethyl)pyrimidin-5-yl)methyl)-N,2-dimethylpropan-2-amine |

TABLE 1-continued

| Cpd No. | Compound Name[a] |
|---|---|
| 15-7 | (R)-N-((2-(4-(4-fluoro-3-(methylsulfonyl)phenyl)-2-isopropylpiperazin-1-yl)-4-(trifluoromethyl)pyrimidin-5-yl)methyl)methanesulfonamide |
| 15-8 | (R)-2-(4-(4-fluoro-3-(methylsulfonyl)phenyl)-2-isopropylpiperazin-1-yl)-5-((methylthio)methyl)-4-(trifluoromethyl)pyrimidine |
| 15-9 | (R)-3-(((2-(4-(4-fluoro-3-(methylsulfonyl)phenyl)-2-isopropylpiperazin-1-yl)-4-(trifluoromethyl)pyrimidin-5-yl)methyl)(methyl)amino)propan-1-ol |
| 15-10 | (R)-N-((2-(4-(4-fluoro-3-(methylsulfonyl)phenyl)-2-isopropylpiperazin-1-yl)-4-(trifluoromethyl)pyrimidin-5-yl)methyl)-2-methoxy-N-methylethan-1-amine |
| 15-11 | (R)-(4-(3-isopropyl-4-(trifluoromethyl)pyrimidin-2-yl)piperazin-1-yl)-2-(methylsulfonyl)phenyl)methanamine |
| 16-1 | (R)-2-(4-(4-fluoro-3-(methylsulfonyl)phenyl)-2-isopropylpiperazin-1-yl)-4-(trifluoromethyl)pyrimidine-5-carboxylic acid |
| 16-2 | (R)-2-(4-(4-fluoro-3-(methylsulfonyl)phenyl)-2-(4-fluorophenyl)piperazin-1-yl)-4-(trifluoromethyl)pyrimidine-5-carboxylic acid |
| 17-1 | (R)-2-(4-(4-fluoro-3-(methylsulfonyl)phenyl)-2-isopropylpiperazin-1-yl)-N,N-dimethyl-4-(trifluoromethyl)pyrimidine-5-carboxamide |
| 17-2 | (R)-2-(4-(4-fluoro-3-(methylsulfonyl)phenyl)-2-isopropylpiperazin-1-yl)-4-(trifluoromethyl)pyrimidine-5-carboxamide |
| 17-3 | (R)-2-(4-(4-fluoro-3-(methylsulfonyl)phenyl)-2-isopropylpiperazin-1-yl)-N-methyl-4-(trifluoromethyl)pyrimidine-5-carboxamide |
| 17-4 | (R)-(3-aminoazetidin-1-yl)(2-(4-(4-fluoro-3-(methylsulfonyl)phenyl)-2-isopropylpiperazin-1-yl)-4-(trifluoromethyl)pyrimidin-5-yl)methanone |
| 17-5 | (R)-(2-(4-(4-fluoro-3-(methylsulfonyl)phenyl)-2-isopropylpiperazin-1-yl)-4-(trifluoromethyl)pyrimidin-5-yl)(3-hydroxyazetidin-1-yl)methanone |
| 17-6 | (R)-2-(4-(4-fluoro-3-(methylsulfonyl)phenyl)-2-isopropylpiperazin-1-yl)-N-(2-methoxyethyl)-4-(trifluoromethyl)pyrimidine-5-carboxamide |
| 17-7 | (R)-2-(4-(4-fluoro-3-(methylsulfonyl)phenyl)-2-isopropylpiperazin-1-yl)-N-(2-hydroxyethyl)-N-methyl-4-(trifluoromethyl)pyrimidine-5-carboxamide |
| 17-8 | (R)-(2-(4-(4-fluoro-3-(methylsulfonyl)phenyl)-2-isopropylpiperazin-1-yl)-4-(trifluoromethyl)pyrimidin-5-yl)(morpholino)methanone |
| 17-9 | (R)-(2-(4-(4-fluoro-3-(methylsulfonyl)phenyl)-2-isopropylpiperazin-1-yl)-4-(trifluoromethyl)pyrimidin-5-yl)(3-methoxyazetidin-1-yl)methanone |
| 17-10 | (R)-N-butyl-2-(4-(4-fluoro-3-(methylsulfonyl)phenyl)-2-isopropylpiperazin-1-yl)-N-methyl-4-(trifluoromethyl)pyrimidine-5-carboxamide |
| 17-11 | (R)-2-(4-(4-fluoro-3-(methylsulfonyl)phenyl)-2-isopropylpiperazin-1-yl)-N-(3-hydroxypropyl)-N-methyl-4-(trifluoromethyl)pyrimidine-5-carboxamide |
| 17-12 | (R)-2-(4-(4-fluoro-3-(methylsulfonyl)phenyl)-2-isopropylpiperazin-1-yl)-N-(2-methoxyethyl)-N-methyl-4-(trifluoromethyl)pyrimidine-5-carboxamide |
| 17-13 | (R)-2-(4-(4-fluoro-3-(methylsulfonyl)phenyl)-2-isopropylpiperazin-1-yl)-N-(3-methoxypropyl)-N-methyl-4-(trifluoromethyl)pyrimidine-5-carboxamide |
| 17-14 | (R)-N-ethyl-2-(4-(4-fluoro-3-(methylsulfonyl)phenyl)-2-isopropylpiperazin-1-yl)-N-(2-methoxyethyl)-4-(trifluoromethyl)pyrimidine-5-carboxamide |
| 17-15 | (R)-N-ethyl-2-(4-(4-fluoro-3-(methylsulfonyl)phenyl)-2-isopropylpiperazin-1-yl)-N-(3-hydroxypropyl)-4-(trifluoromethyl)pyrimidine-5-carboxamide |
| 17-16 | ethyl (R)-N-(2-(4-(4-fluoro-3-(methylsulfonyl)phenyl)-2-isopropylpiperazin-1-yl)-4-(trifluoromethyl)pyrimidine-5-carbonyl)-N-methylglycinate |
| 17-17 | (R)-2-(4-(4-fluoro-3-(methylsulfonyl)phenyl)-2-isopropylpiperazin-1-yl)-N-(3-hydroxy-3-methylbutyl)-N-methyl-4-(trifluoromethyl)pyrimidine-5-carboxamide |
| 17-18 | ethyl (R)-3-(2-(4-(4-fluoro-3-(methylsulfonyl)phenyl)-2-isopropylpiperazin-1-yl)-N-methyl-4-(trifluoromethyl)pyrimidine-5-carboxamido)propanoate |
| 17-19 | methyl (R)-(3-(2-(4-(4-fluoro-3-(methylsulfonyl)phenyl)-2-isopropylpiperazin-1-yl)-N-methyl-4-(trifluoromethyl)pyrimidine-5-carboxamido)propyl)carbamate |
| 17-20 | tert-butyl (R)-3-(2-(4-(4-fluoro-3-(methylsulfonyl)phenyl)-2-isopropylpiperazin-1-yl)-4-(trifluoromethyl)pyrimidine-5-carboxamido)azetidine-1-carboxylate |
| 17-21 | tert-butyl (R)-(1-(2-(4-(4-fluoro-3-(methylsulfonyl)phenyl)-2-isopropylpiperazin-1-yl)-4-(trifluoromethyl)pyrimidine-5-carbonyl)azetidin-3-yl)carbamate |
| 17-22 | tert-butyl (R)-3-(2-(4-(4-fluoro-3-(methylsulfonyl)phenyl)-2-isopropylpiperazin-1-yl)-N-methyl-4-(trifluoromethyl)pyrimidine-5-carboxamido)azetidine-1-carboxylate |
| 17-23 | tert-butyl (R)-(3-(2-(4-(4-fluoro-3-(methylsulfonyl)phenyl)-2-isopropylpiperazin-1-yl)-N-methyl-4-(trifluoromethyl)pyrimidine-5-carboxamido)propyl)carbamate |
| 17-24 | (R)-2-(4-(4-fluoro-3-(methylsulfonyl)phenyl)-2-isopropylpiperazin-1-yl)-4-methylpyrimidine-5-carboxamide |
| 17-25 | (R)-2-(4-(hydroxymethyl)-3-(methylsulfonyl)phenyl)-2-isopropylpiperazin-1-yl)-4-(trifluoromethyl)pyrimidine-5-carboxamide |
| 17-26 | (R)-2-(4-(4-fluoro-3-(methylsulfonyl)phenyl)-2-isopropylpiperazin-1-yl)-N-(2-methoxyethyl)-N,4-dimethylpyrimidine-5-carboxamide |
| 17-27 | (R)-2-(4-(4-fluoro-3-(methylsulfonyl)phenyl)-2-isopropylpiperazin-1-yl)-N-(3-hydroxypropyl)-N,4-dimethylpyrimidine-5-carboxamide |
| 17-28 | (R)-2-(4-(3-fluoro-4-(hydroxymethyl)-5-(methylsulfonyl)phenyl)-2-isopropylpiperazin-1-yl)-4-(trifluoromethyl)pyrimidine-5-carboxamide |
| 17-29 | (R)-2-(4-(2-fluoro-4-(hydroxymethyl)-5-(methylsulfonyl)phenyl)-2-isopropylpiperazin-1-yl)-4-(trifluoromethyl)pyrimidine-5-carboxamide |
| 17-30 | (R)-N-ethyl-2-(4-(4-fluoro-3-(methylsulfonyl)phenyl)-2-isopropylpiperazin-1-yl)-N-(2-methoxyethyl)-4-methylpyrimidine-5-carboxamide |
| 17-31 | (R)-2-(4-(4-fluoro-3-(methylsulfonyl)phenyl)-2-isopropylpiperazin-1-yl)-N-(3-methoxypropyl)-N,4-dimethylpyrimidine-5-carboxamide |

TABLE 1-continued

| Cpd No. | Compound Name[a] |
|---|---|
| 17-32 | (R)-2-(4-(4-fluoro-3-(methylsulfonyl)phenyl)-2-(4-fluorophenyl)piperazin-1-yl)-N-methoxy-N-methyl-4-(trifluoromethyl)pyrimidine-5-carboxamide |
| 17-33 | (R)-2-(4-(4-fluoro-3-(methylsulfonyl)phenyl)-2-(4-fluorophenyl)piperazin-1-yl)-N,N-dimethyl-4-(trifluoromethyl)pyrimidine-5-carboxamide |
| 17-34 | (R)-2-(4-(4-(hydroxymethyl)-3-(methylsulfonyl)phenyl)-2-isopropylpiperazin-1-yl)-N,N-dimethyl-4-(trifluoromethyl)thiazole-5-carboxamide |
| 17-35 | (R)-2-(4-(4-(hydroxymethyl)-3-(methylsulfonyl)phenyl)-2-isopropylpiperazin-1-yl)-4-(trifluoromethyl)thiazole-5-carboxamide |
| 17-36 | 2-(methylsulfonyl)-4-((R)-3-phenyl-4-(((1r,4R)-4-(trifluoromethyl)cyclohexyl)methyl)piperazin-1-yl)benzamide |
| 17-37 | 2-(methylsulfonyl)-4-((S)-3-phenyl-4-(((1r,4S)-4-(trifluoromethyl)cyclohexyl)methyl)piperazin-1-yl)benzamide |
| 17-38 | 2-(methylsulfonyl)-4-((R)-3-phenyl-4-(((1s,4S)-4-(trifluoromethyl)cyclohexyl)methyl)piperazin-1-yl)benzamide |
| 17-39 | 2-(methylsulfonyl)-4-((S)-3-phenyl-4-(((1s,4R)-4-(trifluoromethyl)cyclohexyl)methyl)piperazin-1-yl)benzamide |
| 18-1 | (R)-2-fluoro-5-(3-isopropyl-4-(5-(trifluoromethyl)pyridin-2-yl)piperazin-1-yl)benzenesulfonamide |
| 19-1 | (R)-(2-(4-(4-(hydroxymethyl)-3-(methylsulfonyl)phenyl)-2-isopropylpiperazin-1-yl)-4-(trifluoromethyl)pyrimidin-5-yl)methanol |
| 19-2 | (S)-(2-(4-(4-(hydroxymethyl)-3-(methylsulfonyl)phenyl)-2-isopropylpiperazin-1-yl)-4-(trifluoromethyl)pyrimidin-5-yl)methanol |
| 20-1 | (R)-4-(4-fluoro-3-(methylsulfonyl)phenyl)-2-isopropyl-1-(5-(trifluoromethyl)pyridin-3-yl)piperazine |
| 20-2 | (R)-1-(5-(1,1-difluoroethyl)pyridin-2-yl)-2-isopropyl-4-(3-(methylsulfonyl)phenyl)piperazine |
| 20-3 | 1,1,1-trifluoro-2-(6-((R)-4-(4-fluoro-3-(methylsulfonyl)phenyl)-2-isopropylpiperazin-1-yl)pyridin-3-yl)propan-2-ol |
| 20-4 | (R)-(4-(3-isopropyl-4-(6-(trifluoromethyl)pyridin-3-yl)piperazin-1-yl)-2-(methylsulfonyl)phenyl)methanol |
| 21-1 | (R)-2-(4-(4-fluoro-3-(methylsulfonyl)phenyl)-2-isopropylpiperazin-1-yl)-5-(trifluoromethyl)pyridin-3-amine |
| 22-1 | (R)-5-chloro-4-cyclopropyl-2-(4-(4-fluoro-3-(methylsulfonyl)phenyl)-2-isopropylpiperazin-1-yl)pyrimidine |
| 22-2 | (R)-5-chloro-2-(4-(2-chloro-4-fluoro-3-(methylsulfonyl)phenyl)-2-isopropylpiperazin-1-yl)-4-cyclopropylpyrimidine |
| 22-3 | (R)-5-chloro-2-(4-(4-fluoro-3-(methylsulfonyl)phenyl)-2-isopropylpiperazin-1-yl)-4-(trifluoromethyl)pyrimidine |
| 22-4 | (R)-5-bromo-2-(4-(4-fluoro-3-(methylsulfonyl)phenyl)-2-isopropylpiperazin-1-yl)-4-(trifluoromethyl)pyrimidine |
| 23-1 | (R)-2-(4-(4-fluoro-3-(methylsulfonyl)phenyl)-2-isopropylpiperazin-1-yl)-4-isopropoxy-6-(trifluoromethyl)pyrimidine |
| 24-1 | (R)-2-(4-(4-fluoro-3-(methylsulfonyl)phenyl)-2-isopropylpiperazin-1-yl)-6-(trifluoromethyl)pyrimidin-4-ol |
| 25-1 | (R)-2-(2-(4-(4-(hydroxymethyl)-3-(methylsulfonyl)phenyl)-2-isopropylpiperazin-1-yl)-4-(trifluoromethyl)pyrimidin-5-yl)-2-methylpropanenitrile |
| 26-1 | (R)-2-(2-(4-(4-fluoro-3-(methylsulfonyl)phenyl)-2-isopropylpiperazin-1-yl)-4-(trifluoromethyl)thiazol-5-yl)propan-2-ol |
| 26-2 | (R)-2-(2-(4-(4-(hydroxymethyl)-3-(methylsulfonyl)phenyl)-2-isopropylpiperazin-1-yl)-4-(trifluoromethyl)oxazol-5-yl)propan-2-ol |
| 27-1 | (R)-2-(2-(4-(4-(hydroxymethyl)-3-(methylsulfonyl)phenyl)-2-isopropylpiperazin-1-yl)-4-(trifluoromethyl)thiazol-5-yl)propan-2-ol |
| 28-1 | (R)-(2-(2-isopropyl-4-(3-(methylsulfonyl)-4-(4-methylthiazol-2-yl)phenyl)piperazin-1-yl)-4-(trifluoromethyl)pyrimidin-5-yl)methanol |
| 29-1 | (R)-2-(4-(4-fluoro-3-(methylsulfonyl)phenyl)-2-isopropylpiperazin-1-yl)-5-methoxy-4-(trifluoromethyl)pyrimidine |
| 30-1 | (R)-2-(4-(4-fluoro-3-(methylsulfonyl)phenyl)-2-isopropylpiperazin-1-yl)-4-(trifluoromethyl)pyrimidin-5-ol |
| 31-1 | (R)-2-(4-((2-(4-(4-fluoro-3-(methylsulfonyl)phenyl)-2-isopropylpiperazin-1-yl)-4-(trifluoromethyl)pyrimidin-5-yl)methyl)phenyl)propan-2-ol |
| 32-1 | (R)-4-((2-(4-(4-fluoro-3-(methylsulfonyl)phenyl)-2-isopropylpiperazin-1-yl)-4-(trifluoromethyl)pyrimidin-5-yl)methyl)benzoic acid |
| 33-1 | (R)-4-(4-fluoro-3-(methylsulfonyl)phenyl)-2-isopropyl-1-(2-methoxypyridin-4-yl)piperazine |
| 33-1 | (R)-2-(2-isopropyl-4-(3-(methylsulfonyl)phenyl)piperazin-1-yl)-4-methoxypyrimidine |
| 34-1 | 1-(4-(4-fluoro-3-(methylsulfonyl)phenyl)-1-(5-(trifluoromethyl)pyridin-2-yl)piperazin-2-yl)-2-methylpropan-2-ol |
| 35-1 | 2-(2-fluoro-2-methylpropyl)-4-(4-fluoro-3-(methylsulfonyl)phenyl)-1-(5-(trifluoromethyl)pyridin-2-yl)piperazine |
| 36-1 | (R)-4-chloro-2-(4-(4-fluoro-3-(methylsulfonyl)phenyl)-2-isopropylpiperazin-1-yl)-5-(trifluoromethyl)pyrimidine |
| 37-1 | (R)-2-(4-(4-fluoro-3-(methylsulfonyl)phenyl)-2-isopropylpiperazin-1-yl)-4-methyl-5-(trifluoromethyl)pyrimidine |

TABLE 1-continued

| Cpd No. | Compound Name[a] |
|---|---|
| 37-2 | (R)-2-isopropyl-1-(6-methyl-5-(trifluoromethyl)pyridin-2-yl)-4-(3-(methylsulfonyl)phenyl)piperazine |
| 37-3 | (R)-2-(4-(4-fluoro-3-(methylsulfonyl)phenyl)-2-isopropylpiperazin-1-yl)-5-methyl-4-(trifluoromethyl)pyrimidine |
| 38-1 | 1-(2-((R)-4-(4-fluoro-3-(methylsulfonyl)phenyl)-2-isopropylpiperazin-1-yl)-5-(trifluoromethyl)pyrimidin-4-yl)ethan-1-ol |
| 39-1 | (R)-2-(2-(4-(4-fluoro-3-(methylsulfonyl)phenyl)-2-isopropylpiperazin-1-yl)-5-(trifluoromethyl)pyrimidin-4-yl)propan-2-ol |
| 40-1 | (R)-5-cyclopropyl-2-(4-(4-fluoro-3-(methylsulfonyl)phenyl)-2-isopropylpiperazin-1-yl)-4-(trifluoromethyl)pyrimidine |
| 40-2 | (R)-1-(6-cyclopropyl-5-methylpyridin-2-yl)-2-isopropyl-4-(3-(methylsulfonyl)phenyl)piperazine |
| 40-3 | (R)-1-(6-cyclopropyl-3-methylpyridin-2-yl)-2-isopropyl-4-(3-(methylsulfonyl)phenyl)piperazine |
| 40-4 | (R)-1-(6-cyclopropyl-5-(trifluoromethyl)pyridin-2-yl)-2-isopropyl-4-(3-(methylsulfonyl)phenyl)piperazine |
| 41-1 | 2,2,2-trifluoro-1-(2-((R)-4-(4-fluoro-3-(methylsulfonyl)phenyl)-2-isopropylpiperazin-1-yl)pyrimidin-5-yl)ethan-1-ol |
| 42-1 | 2-((R)-4-(4-fluoro-3-(methylsulfonyl)phenyl)-2-isopropylpiperazin-1-yl)-5-(2,2,2-trifluoro-1-methoxyethyl)pyrimidine |
| 43-1 | (R)-2-(4-(4-fluoro-3-(methylsulfonyl)phenyl)-2-isopropylpiperazin-1-yl)-5-(trifluoromethyl)pyrimidine-4-carbonitrile |
| 44-1 | (R)-1-(2-(difluoromethoxy)pyridin-4-yl)-4-(4-fluoro-3-(methylsulfonyl)phenyl)-2-isopropylpiperazine |
| 44-2 | (R)-4-(difluoromethoxy)-2-(2-isopropyl-4-(3-(methylsulfonyl)phenyl)piperazin-1-yl)pyrimidine |
| 44-3 | (R)-2-(4-(4-fluoro-3-(methylsulfonyl)phenyl)-2-isopropylpiperazin-1-yl)-4-(2,2,2-trifluoroethoxy)pyrimidine |
| 45-1 | (S)-2-benzyl-1-(3-chloro-4-(trifluoromethyl)benzyl)-4-(3-(methylsulfonyl)phenyl)piperazine |
| 46-1 | 1-(3-chloro-4-(trifluoromethyl)benzyl)-4-(3-(methylsulfonyl)phenyl)-2-phenylpiperazine |
| 46-2 | (R)-1-(3-chloro-4-(trifluoromethyl)benzyl)-4-(3-(methylsulfonyl)phenyl)-2-phenylpiperazine |
| 46-3 | (S)-1-(3-chloro-4-(trifluoromethyl)benzyl)-4-(3-(methylsulfonyl)phenyl)-2-phenylpiperazine |
| 46-4 | 1-benzyl-4-(3-(methylsulfonyl)phenyl)-2-phenylpiperazine |
| 46-5 | (R)-1-(4-methylbenzyl)-4-(3-(methylsulfonyl)phenyl)-2-phenylpiperazine |
| 46-6 | (S)-1-(4-methylbenzyl)-4-(3-(methylsulfonyl)phenyl)-2-phenylpiperazine |
| 46-7 | (R)-1-(4-isopropylbenzyl)-4-(3-(methylsulfonyl)phenyl)-2-phenylpiperazine |
| 46-8 | (S)-1-(4-isopropylbenzyl)-4-(3-(methylsulfonyl)phenyl)-2-phenylpiperazine |
| 46-9 | (S)-4-(3-isopropyl-4-(4-(trifluoromethyl)benzyl)piperazin-1-yl)-2-(methylsulfonyl)benzonitrile |
| 46-10 | (R)-1-(4-(difluoromethoxy)benzyl)-4-(3-(methylsulfonyl)phenyl)-2-phenylpiperazine |
| 46-11 | (S)-1-(4-(difluoromethoxy)benzyl)-4-(3-(methylsulfonyl)phenyl)-2-phenylpiperazine |
| 46-12 | 4-(3-(methylsulfonyl)phenyl)-2-phenyl-1-(2-(trifluoromethyl)benzyl)piperazine |
| 46-13 | 4-(3-(methylsulfonyl)phenyl)-2-phenyl-1-(3-(trifluoromethyl)benzyl)piperazine |
| 46-14 | (R)-4-(3-(methylsulfonyl)phenyl)-2-phenyl-1-(4-(trifluoromethyl)benzyl)piperazine |
| 46-15 | (S)-4-(3-(methylsulfonyl)phenyl)-2-phenyl-1-(4-(trifluoromethyl)benzyl)piperazine |
| 46-16 | (S)-4-(3-(methylsulfonyl)phenyl)-2-phenyl-1-((S)-1-(4-(trifluoromethyl)phenyl)ethyl)piperazine |
| 46-17 | (R)-4-(3-(methylsulfonyl)phenyl)-2-phenyl-1-((S)-1-(4-(trifluoromethyl)phenyl)ethyl)piperazine |
| 46-18 | (S)-4-(3-(methylsulfonyl)phenyl)-2-phenyl-1-((R)-1-(4-(trifluoromethyl)phenyl)ethyl)piperazine |
| 46-19 | (R)-4-(3-(methylsulfonyl)phenyl)-2-phenyl-1-((R)-1-(4-(trifluoromethyl)phenyl)ethyl)piperazine |
| 46-20 | (R)-2-methyl-4-(3-(methylsulfonyl)phenyl)-2-phenyl-1-(4-(trifluoromethyl)benzyl)piperazine |
| 46-21 | (S)-2-methyl-4-(3-(methylsulfonyl)phenyl)-2-phenyl-1-(4-(trifluoromethyl)benzyl)piperazine |
| 46-22 | (R)-4-(3-(methylsulfonyl)phenyl)-2-phenyl-1-(4-(trifluoromethoxy)benzyl)piperazine |
| 46-23 | (S)-4-(3-(methylsulfonyl)phenyl)-2-phenyl-1-(4-(trifluoromethoxy)benzyl)piperazine |
| 46-24 | (S)-2-(4-fluorophenyl)-4-(3-(methylsulfonyl)phenyl)-1-(4-(trifluoromethyl)benzyl)piperazine |
| 46-25 | (R)-1-(3-fluoro-4-(trifluoromethyl)benzyl)-4-(3-(methylsulfonyl)phenyl)-2-phenylpiperazine |
| 46-26 | (S)-1-(3-fluoro-4-(trifluoromethyl)benzyl)-4-(3-(methylsulfonyl)phenyl)-2-phenylpiperazine |
| 46-27 | 1-(3-chloro-4-(trifluoromethyl)benzyl)-2-cyclohexyl-4-(3-(methylsulfonyl)phenyl)piperazine |
| 46-28 | (S)-1,1,1-trifluoro-2-(4-(((S)-4-(3-(methylsulfonyl)phenyl)-2-phenylpiperazin-1-yl)methyl)phenyl)propan-2-ol |

TABLE 1-continued

| Cpd No. | Compound Name[a] |
|---|---|
| 46-29 | (S)-1,1,1-trifluoro-2-(4-(((R)-4-(3-(methylsulfonyl)phenyl)-2-phenylpiperazin-1-yl)methyl)phenyl)propan-2-ol |
| 46-30 | (R)-1,1,1-trifluoro-2-(4-(((R)-4-(3-(methylsulfonyl)phenyl)-2-phenylpiperazin-1-yl)methyl)phenyl)propan-2-ol |
| 46-31 | (R)-1,1,1-trifluoro-2-(4-(((S)-4-(3-(methylsulfonyl)phenyl)-2-phenylpiperazin-1-yl)methyl)phenyl)propan-2-ol |
| 46-33 | (R)-2-benzyl-1-(3-chloro-4-(trifluoromethyl)benzyl)-4-(3-(methylsulfonyl)phenyl)piperazine |
| 46-34 | (S)-1-(3-chloro-4-(trifluoromethyl)benzyl)-2-methyl-4-(3-(methylsulfonyl)phenyl)-2-phenylpiperazine |
| 46-35 | (R)-1-(3-chloro-4-(trifluoromethyl)benzyl)-2-methyl-4-(3-(methylsulfonyl)phenyl)-2-phenylpiperazine |
| 46-36 | methyl 5-((4-(3-(methylsulfonyl)phenyl)-2-phenylpiperazin-1-yl)methyl)-2-(trifluoromethyl)benzoate |
| 46-37 | 1-(3-bromo-4-(trifluoromethyl)benzyl)-4-(3-(methylsulfonyl)phenyl)-2-phenylpiperazine |
| 46-38 | methyl 4-(4-(3-chloro-4-(trifluoromethyl)benzyl)-3-phenylpiperazin-1-yl)-2-(methylsulfonyl)benzoate |
| 46-39 | 4-(3-(methylsulfonyl)phenyl)-2-phenyl-1-(pyridin-3-ylmethyl)piperazine |
| 46-40 | 1-((6-methylpyridin-3-yl)methyl)-4-(3-(methylsulfonyl)phenyl)-2-phenylpiperazine |
| 46-41 | (S)-2-isopropyl-4-(3-(methylsulfonyl)phenyl)-1-((6-(trifluoromethyl)pyridin-3-yl)methyl)piperazine |
| 46-42 | 1-((6-isopropylpyridin-3-yl)methyl)-4-(3-(methylsulfonyl)phenyl)-2-phenylpiperazine |
| 46-43 | (S)-4-(3-(methylsulfonyl)phenyl)-2-phenyl-1-((6-(trifluoromethyl)pyridin-3-yl)methyl)piperazine |
| 46-44 | (R)-4-(3-(methylsulfonyl)phenyl)-2-phenyl-1-((6-(trifluoromethyl)pyridin-3-yl)methyl)piperazine |
| 46-45 | (R)-4-(3-(methylsulfonyl)phenyl)-2-(o-tolyl)-1-((6-(trifluoromethyl)pyridin-3-yl)methyl)piperazine |
| 46-46 | (S)-4-(3-(methylsulfonyl)phenyl)-2-(o-tolyl)-1-((6-(trifluoromethyl)pyridin-3-yl)methyl)piperazine |
| 46-47 | 1-((2-methyl-6-(trifluoromethyl)pyridin-3-yl)methyl)-4-(3-(methylsulfonyl)phenyl)-2-phenylpiperazine |
| 46-48 | 1-((5-methyl-6-(trifluoromethyl)pyridin-3-yl)methyl)-4-(3-(methylsulfonyl)phenyl)-2-phenylpiperazine |
| 46-49 | 2-methyl-4-(3-(methylsulfonyl)phenyl)-2-phenyl-1-((6-(trifluoromethyl)pyridin-3-yl)methyl)piperazine |
| 46-50 | 4-(2-fluoro-5-(methylsulfonyl)phenyl)-2-phenyl-1-((6-(trifluoromethyl)pyridin-3-yl)methyl)piperazine |
| 46-51 | 2-(4-fluorophenyl)-4-(3-(methylsulfonyl)phenyl)-1-((6-(trifluoromethyl)pyridin-3-yl)methyl)piperazine |
| 46-52 | 4-(4-fluoro-3-(methylsulfonyl)phenyl)-2-phenyl-1-((6-(trifluoromethyl)pyridin-3-yl)methyl)piperazine |
| 46-53 | 4-(3-fluoro-5-(methylsulfonyl)phenyl)-2-phenyl-1-((6-(trifluoromethyl)pyridin-3-yl)methyl)piperazine |
| 46-54 | 2-(4-chlorophenyl)-4-(3-(methylsulfonyl)phenyl)-1-((6-(trifluoromethyl)pyridin-3-yl)methyl)piperazine |
| 46-55 | 2-(3-chlorophenyl)-4-(3-(methylsulfonyl)phenyl)-1-((6-(trifluoromethyl)pyridin-3-yl)methyl)piperazine |
| 46-56 | (R)-2-(2-chlorophenyl)-4-(3-(methylsulfonyl)phenyl)-1-((6-(trifluoromethyl)pyridin-3-yl)methyl)piperazine |
| 46-57 | (S)-2-(2-chlorophenyl)-4-(3-(methylsulfonyl)phenyl)-1-((6-(trifluoromethyl)pyridin-3-yl)methyl)piperazine |
| 46-58 | 2-(methylsulfonyl)-4-(3-phenyl-4-((6-(trifluoromethyl)pyridin-3-yl)methyl)piperazin-1-yl)benzamide |
| 46-59 | methyl 2-(methylsulfonyl)-4-(3-phenyl-4-((6-(trifluoromethyl)pyridin-3-yl)methyl)piperazin-1-yl)benzoate |
| 46-60 | 2-(2-bromophenyl)-4-(3-(methylsulfonyl)phenyl)-1-((6-(trifluoromethyl)pyridin-3-yl)methyl)piperazine |
| 46-61 | 2-(4-bromophenyl)-4-(3-(methylsulfonyl)phenyl)-1-((6-(trifluoromethyl)pyridin-3-yl)methyl)piperazine |
| 46-62 | 4-(3-(methylsulfonyl)phenyl)-2-(m-tolyl)-1-((6-(trifluoromethyl)pyridin-3-yl)methyl)piperazine |
| 46-63 | (R)-4-(3-(methylsulfonyl)phenyl)-2-phenyl-1-((5-(trifluoromethyl)pyridin-2-yl)methyl)piperazine |
| 46-64 | (S)-4-(3-(methylsulfonyl)phenyl)-2-phenyl-1-((5-(trifluoromethyl)pyridin-2-yl)methyl)piperazine |
| 46-65 | (R)-4-(3-(methylsulfonyl)phenyl)-2-phenyl-1-((5-(trifluoromethyl)furan-2-yl)methyl)piperazine |
| 46-66 | (S)-4-(3-(methylsulfonyl)phenyl)-2-phenyl-1-((5-(trifluoromethyl)furan-2-yl)methyl)piperazine |
| 47-1 | (2-(methylsulfonyl)-4-(3-phenyl-4-((6-(trifluoromethyl)pyridin-3-yl)methyl)piperazin-1-yl)phenyl)methanol |
| 47-2 | (S)-(4-(3-isopropyl-4-(4-(trifluoromethyl)benzyl)piperazin-1-yl)-2-(methylsulfonyl)phenyl)methanol |

TABLE 1-continued

| Cpd No. | Compound Name[a] |
|---|---|
| 47-3 | (S)-(4-(4-(3-fluoro-4-(trifluoromethyl)benzyl)-3-isopropylpiperazin-1-yl)-2-(methylsulfonyl)phenyl)methanol |
| 47-4 | (4-(4-(3-chloro-4-(trifluoromethyl)benzyl)-3-phenylpiperazin-1-yl)-2-(methylsulfonyl)phenyl)methanol |
| 47-5 | (S)-(4-(3-isopropyl-4-((5-(trifluoromethyl)furan-2-yl)methyl)piperazin-1-yl)-2-(methylsulfonyl)phenyl)methanol |
| 48-1 | (S)-4-((4-(3-(methylsulfonyl)phenyl)-2-phenylpiperazin-1-yl)methyl)-1-(trifluoromethyl)cyclohexan-1-ol |
| 48-2 | (S)-1-((4,4-dimethylcyclohexyl)methyl)-2-isopropyl-4-(3-(methylsulfonyl)phenyl)piperazine |
| 48-3 | (R)-1-((4,4-dimethylcyclohexyl)methyl)-4-(3-(methylsulfonyl)phenyl)-2-phenylpiperazine |
| 48-4 | (S)-1-((4,4-dimethylcyclohexyl)methyl)-4-(3-(methylsulfonyl)phenyl)-2-phenylpiperazine |
| 48-5 | (1R,4s)-1-methyl-4-(((S)-4-(3-(methylsulfonyl)phenyl)-2-phenylpiperazin-1-yl)methyl)cyclohexan-1-ol |
| 48-6 | (1S,4s)-1-methyl-4-(((R)-4-(3-(methylsulfonyl)phenyl)-2-phenylpiperazin-1-yl)methyl)cyclohexan-1-ol |
| 48-7 | (1S,4r)-1-methyl-4-(((S)-4-(3-(methylsulfonyl)phenyl)-2-phenylpiperazin-1-yl)methyl)cyclohexan-1-ol |
| 48-8 | (1R,4r)-1-methyl-4-(((R)-4-(3-(methylsulfonyl)phenyl)-2-phenylpiperazin-1-yl)methyl)cyclohexan-1-ol |
| 48-9 | (R)-2-isopropyl-4-(3-(methylsulfonyl)phenyl)-1-(((1s,4S)-4-(trifluoromethyl)cyclohexyl)methyl)piperazine |
| 48-10 | (R)-2-isopropyl-4-(3-(methylsulfonyl)phenyl)-1-(((1r,4R)-4-(trifluoromethyl)cyclohexyl)methyl)piperazine |
| 48-11 | (S)-2-isopropyl-4-(3-(methylsulfonyl)phenyl)-1-(((1s,4R)-4-(trifluoromethyl)cyclohexyl)methyl)piperazine |
| 48-12 | (S)-2-isopropyl-4-(3-(methylsulfonyl)phenyl)-1-(((1r,4S)-4-(trifluoromethyl)cyclohexyl)methyl)piperazine |
| 48-13 | (S)-1-((4,4-difluorocyclohexyl)methyl)-4-(3-(methylsulfonyl)phenyl)-2-phenylpiperazine |
| 48-14 | (R)-1-(((1r,4R)-4-isopropylcyclohexyl)methyl)-4-(3-(methylsulfonyl)phenyl)-2-phenylpiperazine |
| 48-15 | (S)-1-(((1r,4S)-4-isopropylcyclohexyl)methyl)-4-(3-(methylsulfonyl)phenyl)-2-phenylpiperazine |
| 48-16 | (R)-1-(((1s,4S)-4-(difluoromethyl)cyclohexyl)methyl)-4-(3-(methylsulfonyl)phenyl)-2-phenylpiperazine |
| 48-17 | (S)-1-(((1s,4R)-4-(difluoromethyl)cyclohexyl)methyl)-4-(3-(methylsulfonyl)phenyl)-2-phenylpiperazine |
| 48-18 | (R)-1-(((1r,4R)-4-(difluoromethyl)cyclohexyl)methyl)-4-(3-(methylsulfonyl)phenyl)-2-phenylpiperazine |
| 48-19 | (S)-1-(((1r,4S)-4-(difluoromethyl)cyclohexyl)methyl)-4-(3-(methylsulfonyl)phenyl)-2-phenylpiperazine |
| 48-20 | 3-((R)-4-(((1r,4R)-4-(difluoromethyl)cyclohexyl)methyl)-3-phenylpiperazin-1-yl)benzenesulfonamide |
| 48-21 | 3-((S)-4-(((1r,4S)-4-(difluoromethyl)cyclohexyl)methyl)-3-phenylpiperazin-1-yl)benzenesulfonamide |
| 48-22 | 3-((R)-4-(((1s,4S)-4-(difluoromethyl)cyclohexyl)methyl)-3-phenylpiperazin-1-yl)benzenesulfonamide |
| 48-23 | 3-((S)-4-(((1s,4R)-4-(difluoromethyl)cyclohexyl)methyl)-3-phenylpiperazin-1-yl)benzenesulfonamide |
| 48-24 | (R)-4-(4-fluoro-3-(methylsulfonyl)phenyl)-2-isopropyl-1-(((1s,4S)-4-(trifluoromethyl)cyclohexyl)methyl)piperazine |
| 48-25 | 2-((1S,3R)-3-((4-(3-(methylsulfonyl)phenyl)-2-phenylpiperazin-1-yl)methyl)cyclohexyl)propan-2-ol |
| 48-26 | (S)-(4-(4-((4,4-dimethylcyclohexyl)methyl)-3-phenylpiperazin-1-yl)-2-(methylsulfonyl)phenyl)methanol |
| 48-27 | (R)-(4-(4-((4,4-dimethylcyclohexyl)methyl)-3-phenylpiperazin-1-yl)-2-(methylsulfonyl)phenyl)methanol |
| 48-28 | (S)-1-(((1s,4R)-4-(1,1-difluoroethyl)cyclohexyl)methyl)-4-(3-(methylsulfonyl)phenyl)-2-phenylpiperazine |
| 48-29 | (R)-1-(((1s,4S)-4-(1,1-difluoroethyl)cyclohexyl)methyl)-4-(3-(methylsulfonyl)phenyl)-2-phenylpiperazine |
| 48-30 | (R)-4-(3-(methylsulfonyl)phenyl)-2-phenyl-1-(((1s,4S)-4-(trifluoromethyl)cyclohexyl)methyl)piperazine |
| 48-31 | (S)-4-(3-(methylsulfonyl)phenyl)-2-phenyl-1-(((1s,4R)-4-(trifluoromethyl)cyclohexyl)methyl)piperazine |
| 48-32 | (R)-4-(3-(methylsulfonyl)phenyl)-2-phenyl-1-(((1r,4R)-4-(trifluoromethyl)cyclohexyl)methyl)piperazine |
| 48-33 | (S)-4-(3-(methylsulfonyl)phenyl)-2-phenyl-1-(((1r,4S)-4-(trifluoromethyl)cyclohexyl)methyl)piperazine |
| 48-34 | 3-((R)-3-phenyl-4-(((1s,4S)-4-(trifluoromethyl)cyclohexyl)methyl)piperazin-1-yl)benzenesulfonamide |

TABLE 1-continued

| Cpd No. | Compound Name[a] |
|---|---|
| 48-35 | 3-((S)-3-phenyl-4-((((1s,4R)-4-(trifluoromethyl)cyclohexyl)methyl)piperazin-1-yl)benzenesulfonamide |
| 48-36 | 3-((R)-3-phenyl-4-((((1r,4R)-4-(trifluoromethyl)cyclohexyl)methyl)piperazin-1-yl)benzenesulfonamide |
| 48-37 | 3-((S)-3-phenyl-4-((((1r,4S)-4-(trifluoromethyl)cyclohexyl)methyl)piperazin-1-yl)benzenesulfonamide |
| 48-38 | (S)-4-((4-(4-(hydroxymethyl)-3-(methylsulfonyl)phenyl)-2-isopropylpiperazin-1-yl)methyl)-1-(trifluoromethyl)cyclohexan-1-ol |
| 48-39 | (S)-2-(4-fluorophenyl)-4-(3-(methylsulfonyl)phenyl)-1-((((1R,3R)-3-(trifluoromethyl)cyclohexyl)methyl)piperazine |
| 48-40 | (S)-2-(4-fluorophenyl)-4-(3-(methylsulfonyl)phenyl)-1-((((1S,3S)-3-(trifluoromethyl)cyclohexyl)methyl)piperazine |
| 48-41 | (S)-2-(4-fluorophenyl)-4-(3-(methylsulfonyl)phenyl)-1-((((1R,3S)-3-(trifluoromethyl)cyclohexyl)methyl)piperazine |
| 48-42 | (S)-2-(4-fluorophenyl)-4-(3-(methylsulfonyl)phenyl)-1-((((1S,3R)-3-(trifluoromethyl)cyclohexyl)methyl)piperazine |
| 48-43 | (S)-2-(4-fluorophenyl)-4-(3-(methylsulfonyl)phenyl)-1-((((1s,4R)-4-(trifluoromethyl)cyclohexyl)methyl)piperazine |
| 48-44 | (2-(methylsulfonyl)-4-((R)-3-phenyl-4-(((1r,4R)-4-(trifluoromethyl)cyclohexyl)methyl)piperazin-1-yl)phenyl)methanol |
| 48-45 | (2-(methylsulfonyl)-4-((S)-3-phenyl-4-(((1r,4S)-4-(trifluoromethyl)cyclohexyl)methyl)piperazin-1-yl)phenyl)methanol |
| 48-46 | (S)-2-(2-chlorophenyl)-4-(3-(methylsulfonyl)phenyl)-1-(((1r,4S)-4-(trifluoromethyl)cyclohexyl)methyl)piperazine |
| 48-47 | (R)-2-(2-chlorophenyl)-4-(3-(methylsulfonyl)phenyl)-1-(((1r,4R)-4-(trifluoromethyl)cyclohexyl)methyl)piperazine |
| 48-48 | (S)-4-(4-fluoro-3-(methylsulfonyl)phenyl)-2-(4-fluorophenyl)-1-(((1s,4R)-4-(trifluoromethyl)cyclohexyl)methyl)piperazine |
| 48-49 | (S)-4-(4-(methoxymethyl)-3-(methylsulfonyl)phenyl)-2-phenyl-1-(((1r,4S)-4-(trifluoromethyl)cyclohexyl)methyl)piperazine |
| 48-50 | (S)-(4-(3-isopropyl-4-((1-(2,2,2-trifluoroethyl)piperidin-4-yl)methyl)piperazin-1-yl)-2-(methylsulfonyl)phenyl)methanol |
| 48-51 | (R)-4-(3-(methylsulfonyl)phenyl)-2-phenyl-1-((1-(2,2,2-trifluoroethyl)piperidin-4-yl)methyl)piperazine |
| 48-52 | (S)-4-(3-(methylsulfonyl)phenyl)-2-phenyl-1-((1-(2,2,2-trifluoroethyl)piperidin-4-yl)methyl)piperazine |
| 48-53 | (S)-1-((4-fluoro-1-(2,2,2-trifluoroethyl)piperidin-4-yl)methyl)-4-(3-(methylsulfonyl)phenyl)-2-phenylpiperazine |
| 48-54 | (R)-1-((4-fluoro-1-(2,2,2-trifluoroethyl)piperidin-4-yl)methyl)-4-(3-(methylsulfonyl)phenyl)-2-phenylpiperazine |
| 48-55 | (S)-2-(2-chlorophenyl)-4-(3-(methylsulfonyl)phenyl)-1-((1-(2,2,2-trifluoroethyl)piperidin-4-yl)methyl)piperazine |
| 48-56 | (R)-2-(2-chlorophenyl)-4-(3-(methylsulfonyl)phenyl)-1-((1-(2,2,2-trifluoroethyl)piperidin-4-yl)methyl)piperazine |
| 48-57 | (S)-1-((4-fluoro-1-(2,2,2-trifluoroethyl)piperidin-4-yl)methyl)-2-(4-fluorophenyl)-4-(3-(methylsulfonyl)phenyl)piperazine |
| 48-58 | (4-((S)-3-isopropyl-4-(((S)-1-(2,2,2-trifluoroethyl)pyrrolidin-3-yl)methyl)piperazin-1-yl)-2-(methylsulfonyl)phenyl)methanol |
| 48-59 | (4-((S)-3-isopropyl-4-(((R)-1-(2,2,2-trifluoroethyl)pyrrolidin-3-yl)methyl)piperazin-1-yl)-2-(methylsulfonyl)phenyl)methanol |
| 48-60 | (R)-4-(3-(methylsulfonyl)phenyl)-2-phenyl-1-(((S)-1-(2,2,2-trifluoroethyl)pyrrolidin-3-yl)methyl)piperazine |
| 48-61 | (S)-4-(3-(methylsulfonyl)phenyl)-2-phenyl-1-(((R)-1-(2,2,2-trifluoroethyl)pyrrolidin-3-yl)methyl)piperazine |
| 48-62 | (R)-4-(3-(methylsulfonyl)phenyl)-2-phenyl-1-(((R)-1-(2,2,2-trifluoroethyl)pyrrolidin-3-yl)methyl)piperazine |
| 48-63 | (S)-4-(3-(methylsulfonyl)phenyl)-2-phenyl-1-(((S)-1-(2,2,2-trifluoroethyl)pyrrolidin-3-yl)methyl)piperazine |
| 48-64 | (S)-1-(((1R,3r,5S)-6,6-difluorobicyclo[3.1.0]hexan-3-yl)methyl)-4-(3-(methylsulfonyl)phenyl)-2-phenylpiperazine |
| 48-65 | (R)-1-(((1R,3r,5S)-6,6-difluorobicyclo[3.1.0]hexan-3-yl)methyl)-4-(3-(methylsulfonyl)phenyl)-2-phenylpiperazine |
| 48-66 | (S)-1-(((1R,3s,5S)-6,6-difluorobicyclo[3.1.0]hexan-3-yl)methyl)-4-(3-(methylsulfonyl)phenyl)-2-phenylpiperazine |
| 48-67 | (R)-1-(((1R,3s,5S)-6,6-difluorobicyclo[3.1.0]hexan-3-yl)methyl)-4-(3-(methylsulfonyl)phenyl)-2-phenylpiperazine |
| 48-68 | (2S)-2-isopropyl-4-(3-(methylsulfonyl)phenyl)-1-((6-(trifluoromethyl)piperidin-3-yl)methyl)piperazine |
| 48-69 | (S)-1-(((3R,6s)-1,1-difluorospiro[2.5]octan-6-yl)methyl)-4-(3-(methylsulfonyl)phenyl)-2-phenylpiperazine |
| 48-70 | (R)-1-(((3S,6s)-1,1-difluorospiro[2.5]octan-6-yl)methyl)-4-(3-(methylsulfonyl)phenyl)-2-phenylpiperazine |
| 48-71 | (S)-1-(((3S,6r)-1,1-difluorospiro[2.5]octan-6-yl)methyl)-4-(3-(methylsulfonyl)phenyl)-2-phenylpiperazine |
| 48-72 | (R)-1-(((3R,6r)-1,1-difluorospiro[2.5]octan-6-yl)methyl)-4-(3-(methylsulfonyl)phenyl)-2-phenylpiperazine |

TABLE 1-continued

| Cpd No. | Compound Name[a] |
|---|---|
| 48-73 | (2S)-2-(4-fluorophenyl)-4-(3-(methylsulfonyl)phenyl)-1-((5-(trifluoromethyl)tetrahydrofuran-2-yl)methyl)piperazine |
| 48-74 | (2S)-2-(4-fluorophenyl)-4-(3-(methylsulfonyl)phenyl)-1-((5-(trifluoromethyl)tetrahydrofuran-2-yl)methyl)piperazine |
| 48-75 | (1R,3s,5S)-3-(((R)-4-(3-(methylsulfonyl)phenyl)-2-phenylpiperazin-1-yl)methyl)-8-(2,2,2-trifluoroethyl)-8-azabicyclo[3.2.1]octane |
| 48-76 | (1R,3s,5S)-3-(((S)-4-(3-(methylsulfonyl)phenyl)-2-phenylpiperazin-1-yl)methyl)-8-(2,2,2-trifluoroethyl)-8-azabicyclo[3.2.1]octane |
| 48-77 | (4-((S)-4-(((1r,4S)-4-isopropylcyclohexyl)methyl)-3-phenylpiperazin-1-yl)-2-(methylsulfonyl)phenyl)methanol |
| 48-78 | (4-((R)-4-(((1r,4R)-4-isopropylcyclohexyl)methyl)-3-phenylpiperazin-1-yl)-2-(methylsulfonyl)phenyl)methanol |
| 48-79 | (4-((S)-3-isopropyl-4-(((1r,4S)-4-methoxy-4-(trifluoromethyl)cyclohexyl)methyl)piperazin-1-yl)-2-(methylsulfonyl)phenyl)methanol |
| 48-80 | (4-((S)-3-isopropyl-4-(((1s,4R)-4-methoxy-4-(trifluoromethyl)cyclohexyl)methyl)piperazin-1-yl)-2-(methylsulfonyl)phenyl)methanol |
| 48-81 | (S)-3-(3-phenyl-4-((1-(2,2,2-trifluoroethyl)piperidin-4-yl)methyl)piperazin-1-yl)benzenesulfonamide |
| 48-82 | (R)-3-(3-phenyl-4-((1-(2,2,2-trifluoroethyl)piperidin-4-yl)methyl)piperazin-1-yl)benzenesulfonamide |
| 49-1 | (4-((S)-3-isopropyl-4-(((3R,6S)-6-(trifluoromethyl)tetrahydro-2H-pyran-3-yl)methyl)piperazin-1-yl)-2-(methylsulfonyl)phenyl)methanol |
| 49-2 | (4-((S)-3-isopropyl-4-(((3R,6R)-6-(trifluoromethyl)tetrahydro-2H-pyran-3-yl)methyl)piperazin-1-yl)-2-(methylsulfonyl)phenyl)methanol |
| 49-3 | (4-((S)-3-isopropyl-4-(((3S,6S)-6-(trifluoromethyl)tetrahydro-2H-pyran-3-yl)methyl)piperazin-1-yl)-2-(methylsulfonyl)phenyl)methanol |
| 49-4 | (4-((S)-3-isopropyl-4-(((3S,6R)-6-(trifluoromethyl)tetrahydro-2H-pyran-3-yl)methyl)piperazin-1-yl)-2-(methylsulfonyl)phenyl)methanol |
| 49-5 | (S)-2-isopropyl-4-(3-(methylsulfonyl)phenyl)-1-(((3R,6S)-6-(trifluoromethyl)tetrahydro-2H-pyran-3-yl)methyl)piperazine |
| 49-6 | (S)-2-isopropyl-4-(3-(methylsulfonyl)phenyl)-1-(((3R,6R)-6-(trifluoromethyl)tetrahydro-2H-pyran-3-yl)methyl)piperazine |
| 49-7 | (S)-2-isopropyl-4-(3-(methylsulfonyl)phenyl)-1-(((3S,6S)-6-(trifluoromethyl)tetrahydro-2H-pyran-3-yl)methyl)piperazine |
| 49-8 | (S)-2-isopropyl-4-(3-(methylsulfonyl)phenyl)-1-(((3S,6R)-6-(trifluoromethyl)tetrahydro-2H-pyran-3-yl)methyl)piperazine |
| 49-9 | (S)-2-(4-fluorophenyl)-4-(3-(methylsulfonyl)phenyl)-1-(((3R,6S)-6-(trifluoromethyl)tetrahydro-2H-pyran-3-yl)methyl)piperazine |
| 49-10 | (2S)-2-(4-fluorophenyl)-4-(3-(methylsulfonyl)phenyl)-1-(((3R)-6-(trifluoromethyl)tetrahydro-2H-pyran-3-yl)methyl)piperazine |
| 49-11 | (S)-2-(4-fluorophenyl)-4-(3-(methylsulfonyl)phenyl)-1-(((3S,6S)-6-(trifluoromethyl)tetrahydro-2H-pyran-3-yl)methyl)piperazine |
| 49-12 | (2S)-2-(4-fluorophenyl)-4-(3-(methylsulfonyl)phenyl)-1-(((3S)-6-(trifluoromethyl)tetrahydro-2H-pyran-3-yl)methyl)piperazine |
| 50-1 | 4-((S)-3-isopropyl-4-(((1s,4R)-4-(trifluoromethyl)cyclohexyl)methyl)piperazin-1-yl)-2-(methylsulfonyl)benzonitrile |
| 50-2 | 4-((S)-3-isopropyl-4-(((1r,4S)-4-(trifluoromethyl)cyclohexyl)methyl)piperazin-1-yl)-2-(methylsulfonyl)benzonitrile |
| 50-3 | 2-(methylsulfonyl)-4-((R)-3-phenyl-4-(((1r,4R)-4-(trifluoromethyl)cyclohexyl)methyl)piperazin-1-yl)benzonitrile |
| 50-4 | 2-(methylsulfonyl)-4-((S)-3-phenyl-4-(((1r,4S)-4-(trifluoromethyl)cyclohexyl)methyl)piperazin-1-yl)benzonitrile |
| 50-5 | 2-(methylsulfonyl)-4-((R)-3-phenyl-4-(((1s,4S)-4-(trifluoromethyl)cyclohexyl)methyl)piperazin-1-yl)benzonitrile |
| 50-6 | 2-(methylsulfonyl)-4-((S)-3-phenyl-4-(((1s,4R)-4-(trifluoromethyl)cyclohexyl)methyl)piperazin-1-yl)benzonitrile |
| 51-1 | (2S)-2-isopropyl-4-(3-(methylsulfonyl)phenyl)-1-((tetrahydro-2H-pyran-3-yl)methyl)piperazine |
| 51-2 | (S)-2-isopropyl-4-(3-(methylsulfonyl)phenyl)-1-((tetrahydro-2H-pyran-4-yl)methyl)piperazine |
| 51-3 | (2S)-1-((6,6-dimethyltetrahydro-2H-pyran-3-yl)methyl)-2-isopropyl-4-(3-(methylsulfonyl)phenyl)piperazine |
| 51-4 | (2S)-4-(3-(methylsulfonyl)phenyl)-2-phenyl-1-((tetrahydro-2H-pyran-3-yl)methyl)piperazine |
| 51-5 | (S)-4-(3-(methylsulfonyl)phenyl)-2-phenyl-1-((tetrahydro-2H-pyran-4-yl)methyl)piperazine |
| 51-6 | (4-((S)-3-isopropyl-4-(((1r,4S)-4-methoxycyclohexyl)methyl)piperazin-1-yl)-2-(methylsulfonyl)phenyl)methanol |
| 51-7 | (4-((S)-3-isopropyl-4-(((1s,4R)-4-methoxycyclohexyl)methyl)piperazin-1-yl)-2-(methylsulfonyl)phenyl)methanol |
| 52-1 | (2S)-2-isopropyl-1-(((1-methyl-6-(trifluoromethyl)piperidin-3-yl)methyl)-4-(3-(methylsulfonyl)phenyl)piperazine |
| 53-1 | (S)-4,4-dimethyl-1-((4-(3-(methylsulfonyl)phenyl)-2-phenylpiperazin-1-yl)methyl)cyclohexan-1-ol |

TABLE 1-continued

| Cpd No. | Compound Name[a] |
|---|---|
| 53-2 | (R)-4,4-dimethyl-1-((4-(3-(methylsulfonyl)phenyl)-2-phenylpiperazin-1-yl)methyl)cyclohexan-1-ol |
| 54-1 | (R)-N-(4-(3-isopropyl-4-(4-(trifluoromethyl)pyrimidin-2-yl)piperazin-1-yl)-2-(methylsulfonyl)benzyl)acetamide |
| 54-2 | (R)-N-((2-(4-(4-fluoro-3-(methylsulfonyl)phenyl)-2-isopropylpiperazin-1-yl)-4-(trifluoromethyl)pyrimidin-5-yl)methyl)acetamide |

[a]Compound names were generated using ChemBioDraw Ultra 13.0

In another embodiment, a compound of the invention is a compound depicted in Table 2, or a pharmaceutically acceptable salt thereof.

TABLE 2

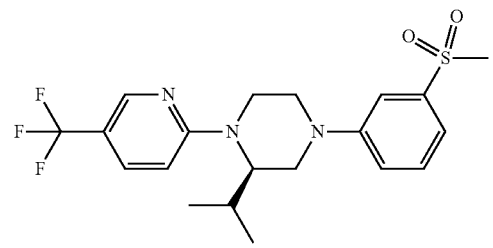 [SMILES: CC(C)[C@@H]1CN(c2cccc(S(C)(=O)=O)c2)CCN1c1ccc(C(F)(F)F)cn1]

Cpd No 7-35

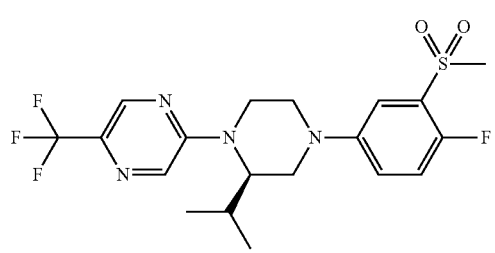 [SMILES: CC(C)[C@@H]1CN(c2ccc(F)c(S(C)(=O)=O)c2)CCN1c1cnc(C(F)(F)F)cn1]

Cpd No 7-44

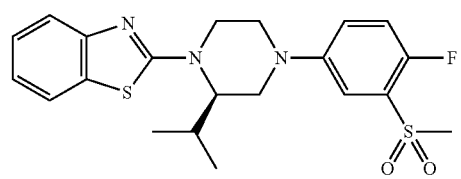 [SMILES: CC(C)[C@@H]1CN(c2ccc(F)c(S(C)(=O)=O)c2)CCN1c1nc2ccccc2s1]

Cpd No 7-57

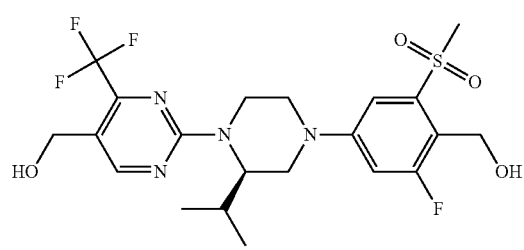 [SMILES: CC(C)[C@@H]1CN(c2cc(F)c(CO)c(S(C)(=O)=O)c2)CCN1c1ncc(CO)c(C(F)(F)F)n1]

Cpd No 11-6

TABLE 2-continued

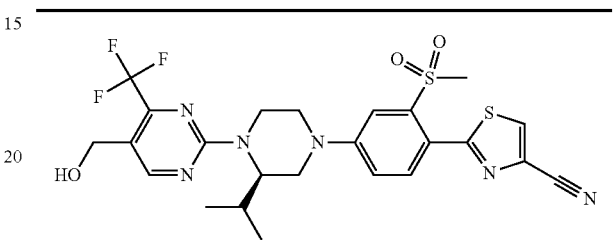

Cpd No 11-12

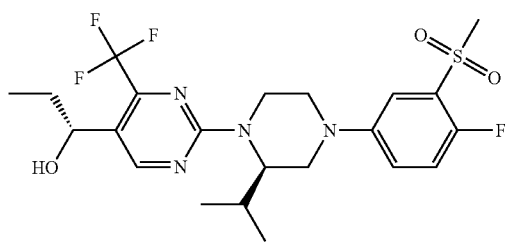 [SMILES: CC[C@@H](O)c1cnc(N2CCN(c3ccc(F)c(S(C)(=O)=O)c3)C[C@H]2C(C)C)nc1C(F)(F)F]

Cpd No 12-7

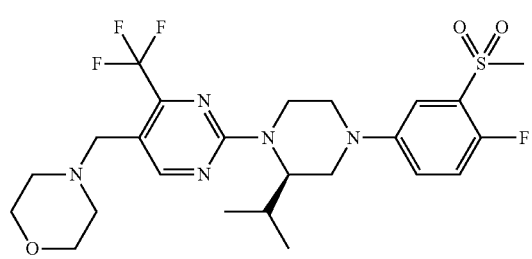 [SMILES: CC(C)[C@@H]1CN(c2ccc(F)c(S(C)(=O)=O)c2)CCN1c1ncc(CN2CCOCC2)c(C(F)(F)F)n1]

Cpd No 15-5

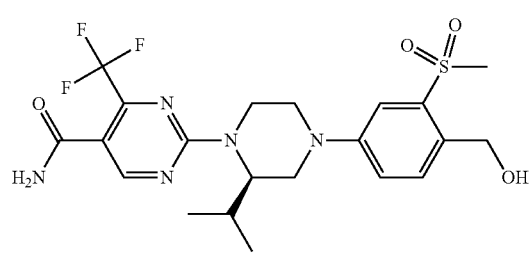 [SMILES: CC(C)[C@@H]1CN(c2ccc(CO)c(S(C)(=O)=O)c2)CCN1c1ncc(C(N)=O)c(C(F)(F)F)n1]

Cpd No 17-25

TABLE 2-continued
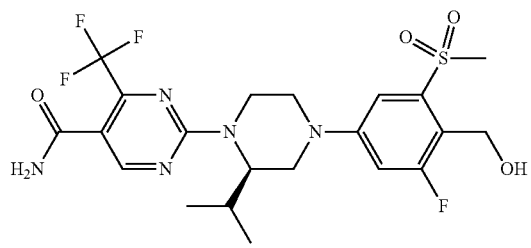
Cpd No 17-28
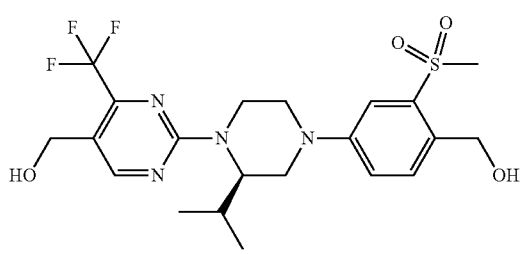 [SMILES: CC(C)[C@@H]1CN(c2ccc(CO)c(S(C)(=O)=O)c2)CCN1c1ncc(CO)c(C(F)(F)F)n1]
Cpd No 19-1
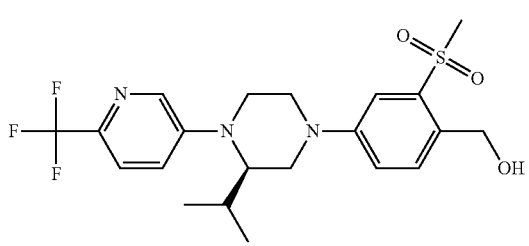 [SMILES: CC(C)[C@@H]1CN(c2ccc(CO)c(S(C)(=O)=O)c2)CCN1c1ccc(C(F)(F)F)nc1]
Cpd No 20-4
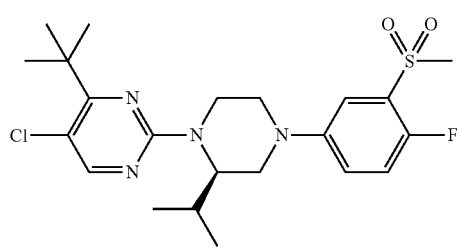 [SMILES: CC(C)[C@@H]1CN(c2ccc(F)c(S(C)(=O)=O)c2)CCN1c1ncc(Cl)c(C(C)(C)C)n1]
Cpd No 22-3
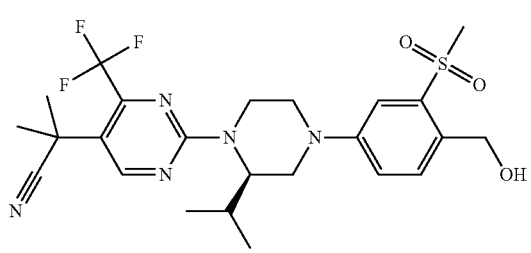 [SMILES: CC(C)[C@@H]1CN(c2ccc(CO)c(S(C)(=O)=O)c2)CCN1c1ncc(C(C)(C)C#N)c(C(F)(F)F)n1]
Cpd No 25-1
TABLE 2-continued
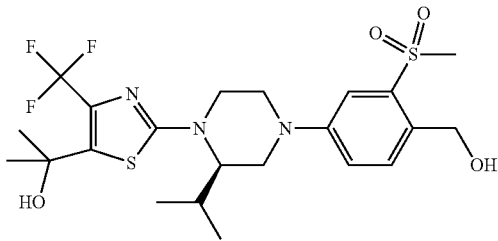 [SMILES: CC(C)[C@@H]1CN(c2ccc(CO)c(S(C)(=O)=O)c2)CCN1c1nc(C(F)(F)F)c(C(C)(C)O)s1]
Cpd No 27-1
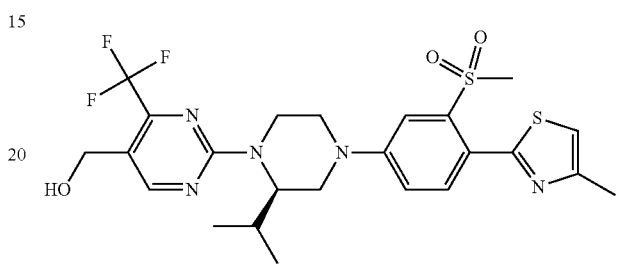
Cpd No 28-1
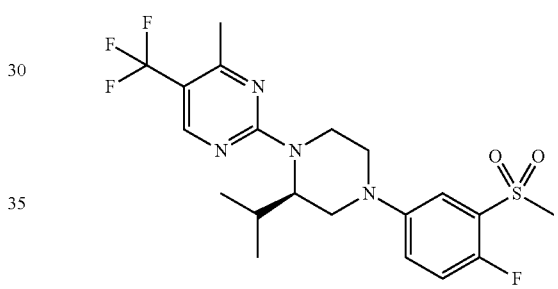
Cpd No 37-1
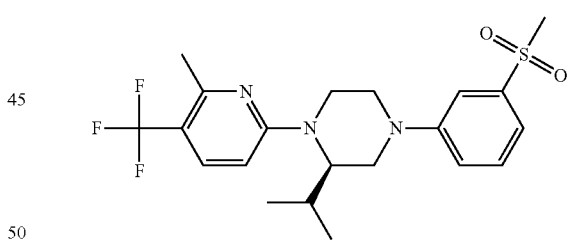
Cpd No 37-2
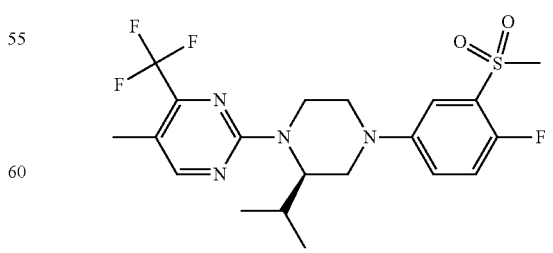
Cpd No 37-3

TABLE 2-continued
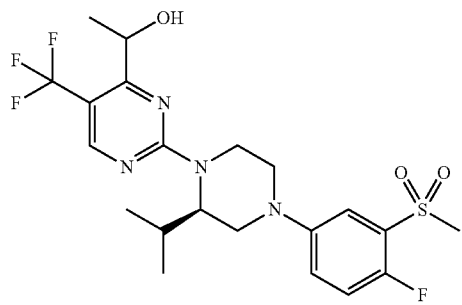 [SMILES: CC(O)c1nc(N2CCN(c3ccc(F)c(S(C)(=O)=O)c3)C[C@H]2C(C)C)ncc1C(F)(F)F]
Cpd No 38-1
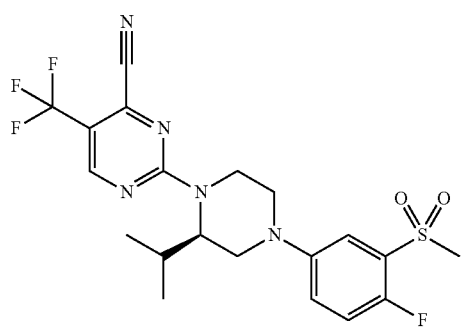 [SMILES: CC(C)[C@@H]1CN(c2ccc(F)c(S(C)(=O)=O)c2)CCN1c1ncc(C(F)(F)F)c(C#N)n1]
Cpd No 43-1
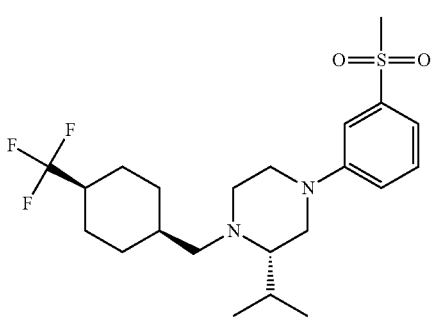
Cpd No 48-11
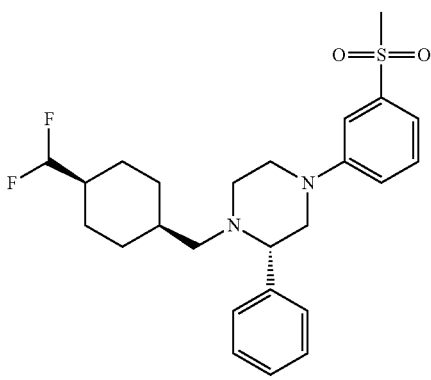 [SMILES: CS(=O)(=O)c1cccc(N2CCN(C[C@H]3CC[C@@H](C(F)F)CC3)[C@@H](c3ccccc3)C2)c1]
Cpd No 48-17
TABLE 2-continued
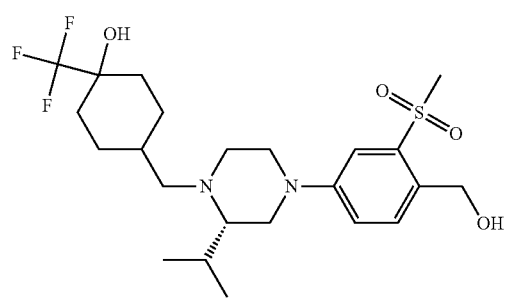 [SMILES: CC(C)[C@H]1CN(c2ccc(CO)c(S(C)(=O)=O)c2)CCN1CC1CCC(O)(C(F)(F)F)CC1]
Cpd No 48-38
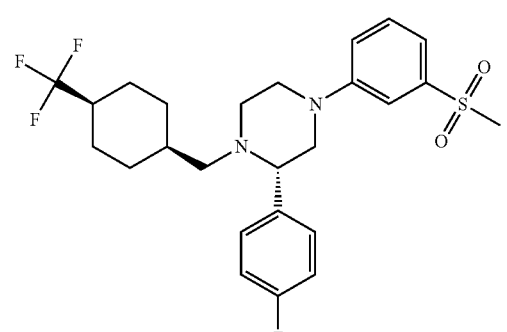
Cpd No 48-43
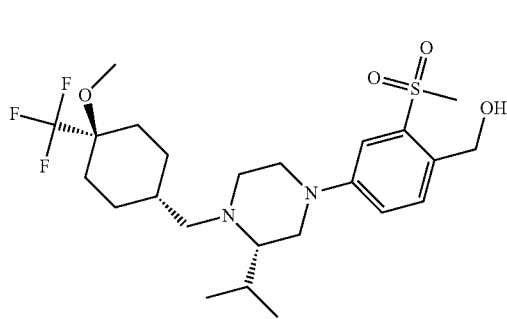 [SMILES: CO[C@]1(C(F)(F)F)CC[C@@H](CN2CCN(c3ccc(CO)c(S(C)(=O)=O)c3)C[C@@H]2C(C)C)CC1]
Cpd No 48-79
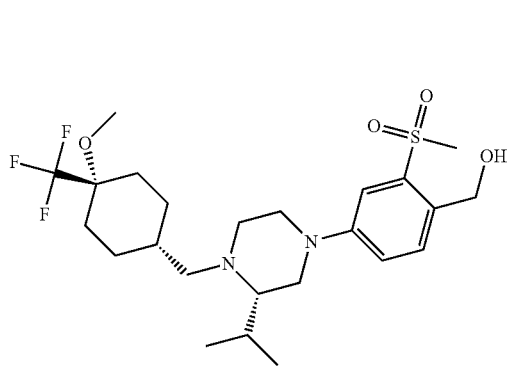 [SMILES: CO[C@]1(C(F)(F)F)CC[C@H](CN2CCN(c3ccc(CO)c(S(C)(=O)=O)c3)C[C@@H]2C(C)C)CC1]
Cpd No 48-80

TABLE 2-continued
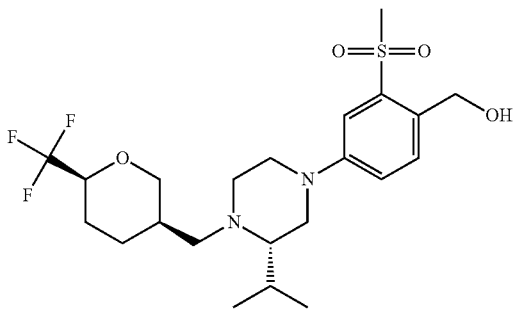 [SMILES: CC(C)[C@H]1CN(c2ccc(CO)c(S(C)(=O)=O)c2)CCN1C[C@H]1CC[C@@H](C(F)(F)F)OC1]
Cpd No 49-1
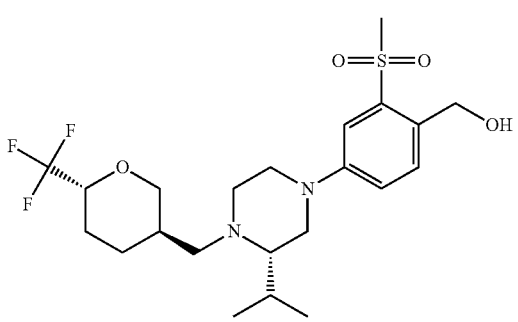 [SMILES: CC(C)[C@H]1CN(c2ccc(CO)c(S(C)(=O)=O)c2)CCN1C[C@H]1CC[C@H](C(F)(F)F)OC1]
Cpd No 49-2
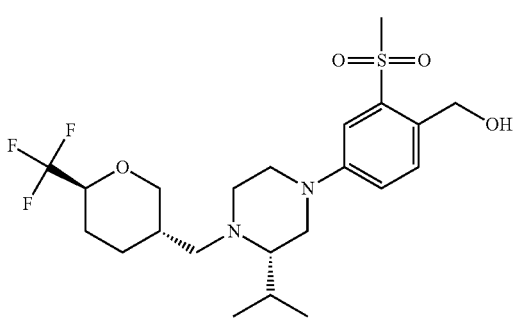 [SMILES: CC(C)[C@H]1CN(c2ccc(CO)c(S(C)(=O)=O)c2)CCN1C[C@@H]1CC[C@@H](C(F)(F)F)OC1]
Cpd No 49-3
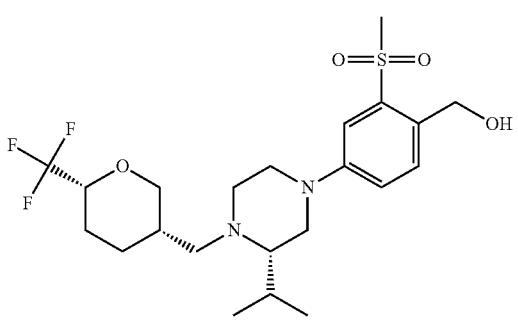 [SMILES: CC(C)[C@H]1CN(c2ccc(CO)c(S(C)(=O)=O)c2)CCN1C[C@@H]1CC[C@H](C(F)(F)F)OC1]
Cpd No 49-4
TABLE 2-continued
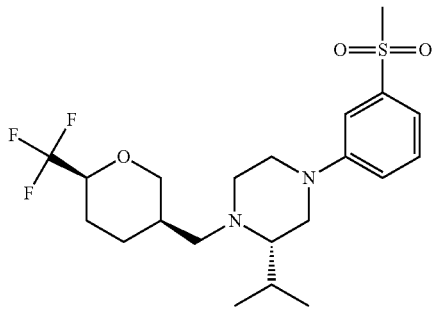 [SMILES: CC(C)[C@H]1CN(c2cccc(S(C)(=O)=O)c2)CCN1C[C@H]1CC[C@@H](C(F)(F)F)OC1]
Cpd No 49-5
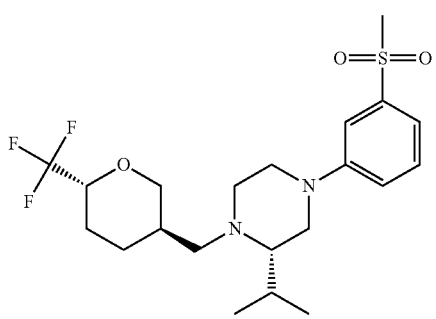 [SMILES: CC(C)[C@H]1CN(c2cccc(S(C)(=O)=O)c2)CCN1C[C@H]1CC[C@H](C(F)(F)F)OC1]
Cpd No 49-6
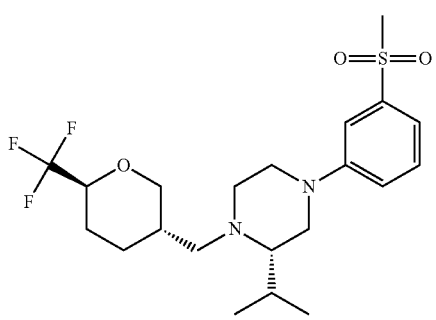 [SMILES: CC(C)[C@H]1CN(c2cccc(S(C)(=O)=O)c2)CCN1C[C@@H]1CC[C@@H](C(F)(F)F)OC1]
Cpd No 49-7
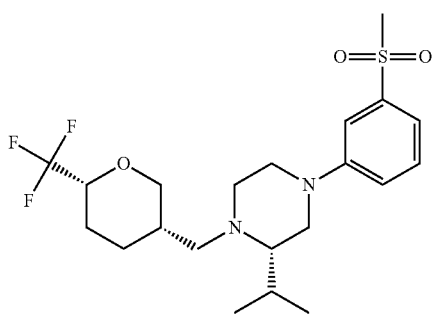 [SMILES: CC(C)[C@H]1CN(c2cccc(S(C)(=O)=O)c2)CCN1C[C@@H]1CC[C@H](C(F)(F)F)OC1]
Cpd No 49-8

TABLE 2-continued

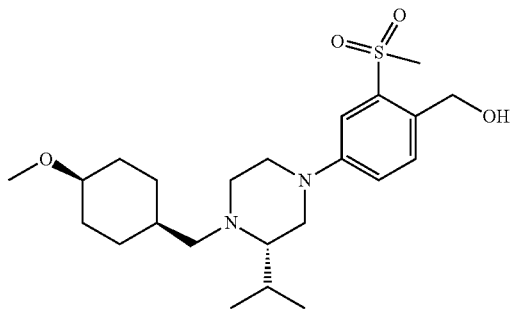 [SMILES: CO[C@H]1CC[C@@H](CN2CCN(c3ccc(CO)c(S(C)(=O)=O)c3)C[C@@H]2C(C)C)CC1]

Cpd No 51-7

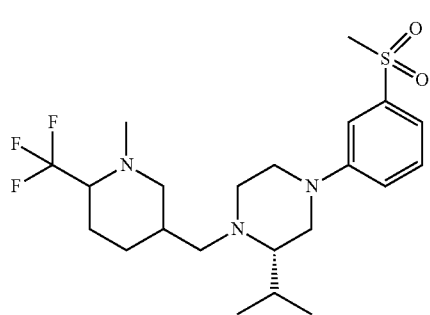 [SMILES: CC(C)[C@H]1CN(c2cccc(S(C)(=O)=O)c2)CCN1CC1CCC(C(F)(F)F)N(C)C1]

Cpd No 52-1

4. Uses, Formulation and Administration

Pharmaceutically Acceptable Compositions

In one embodiment, provided herein is a pharmaceutical composition comprising a compound of the invention and a pharmaceutically acceptable carrier or diluent.

In the pharmaceutical compositions of the invention, the compound of the invention is present in an effective amount. The interrelationship of dosages for animals and humans (based on milligrams per meter squared of body surface) is described in Freireich et al., Cancer Chemother. Rep, 1966, 50: 219. Body surface area may be determined approximately from height and weight of the patient. See, e.g., Scientific Tables, Geigy Pharmaceuticals, Ardsley, N.Y., 1970, 537.

The LXR modulators herein (e.g., compound(s) of the invention) can be formulated as pharmaceutical compositions and administered to a subject, such as a human, in a variety of forms adapted to the chosen route of administration. Typical routes of administering such pharmaceutical compositions include, without limitation, oral, topical, buccal, transdermal, inhalation, parenteral, sublingual, rectal, vaginal, and intranasal. The term parenteral as used herein includes subcutaneous injections, intravenous, intramuscular, intrathecal, intrasternal injection or infusion techniques. Methods of formulating pharmaceutical compositions are well known in the art, for example, as disclosed in "Remington: The Science and Practice of Pharmacy," University of the Sciences in Philadelphia, ed., 21st edition, 2005, Lippincott, Williams & Wilkins, Philadelphia, Pa. Each of the LXR modulators may be used alone or in combination as a part of a pharmaceutical composition of the invention.

The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Thus, the present compounds may be systemically administered, e.g., orally, in combination with a pharmaceutically acceptable excipient such as an inert diluent or an assimilable edible carrier. They may be enclosed in hard or soft shell gelatin capsules, may be compressed into tablets or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like.

Suitable tablets may be obtained, for example, by mixing one or more compounds of the invention with known excipients, for example inert diluents, carriers, disintegrants, adjuvants, surfactants, binders and/or lubricants. The tablets may also consist of several layers.

The compounds of the invention can be suitably formulated into pharmaceutical compositions for administration to a subject. The pharmaceutical compositions of the invention optionally include one or more pharmaceutically acceptable carriers and/or diluents therefor, such as lactose, starch, cellulose and dextrose. Other excipients, such as flavoring agents; sweeteners; and preservatives, such as methyl, ethyl, propyl and butyl parabens, can also be included. More complete listings of suitable excipients can be found in the Handbook of Pharmaceutical Excipients (5th Ed., Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

Typically, for oral therapeutic administration, a compound of the invention may be incorporated with excipient and used in the form of ingestible tablets, buccal tablets, troches, capsules, elixirs, suspensions, syrups, wafers, and the like.

Typically for parenteral administration, solutions of a compound of the invention can generally be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms.

Typically, for injectable use, sterile aqueous solutions or dispersion of, and sterile powders of, a compound of the invention for the extemporaneous preparation of sterile injectable solutions or dispersions.

For nasal administration, the compounds of the invention can be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

For buccal or sublingual administration, the compounds of the invention can be formulated with a carrier such as sugar, acacia, tragacanth, or gelatin and glycerine, as tablets, lozenges or pastilles.

For rectal administration, the compounds of the invention can be formulated in the form of suppositories containing a conventional suppository base such as cocoa butter.

Topical and/or local administration of the compounds of the invention can be achieved in a variety of ways including but not limited to ointments, lotions, pastes, creams, gels, powders, drops, sprays, solutions, inhalants, patches, suppositories, retention enemas, chewable or suckable tablets or pellets and aerosols. Topical and/or local administration may also involve the use of transdermal administration such as transdermal patches or iontophoresis devices. For topical and/or local administration, the compounds of the invention can be formulated as ointments, creams, milks, salves, powders, impregnated pads, syndets, solutions, gels, sprays, foams, suspensions, lotions, sticks, shampoos or washing bases. Compounds of the invention may also be administered in the form of suspensions of lipid or polymer vesicles or nanospheres or microspheres or polymer patches and hydrogels for controlled release.

Uses of Compounds and Pharmaceutically Acceptable Compositions

Provided herein is a method of treating a subject with a disease or disorder that is treatable by modulation of LXR. In one embodiment, LXR is modulated by upregulating LXR activity. The method comprises administering an effective amount of the compound of the invention. Moreover, provided herein is the use of a compound of the invention for the manufacture of a medicament for treating a subject with a disease or disorder that is treatable by upregulating LXR activity in a subject in need thereof.

The methods provided herein may be useful for disorders treatable with LXR modulation, in particular LXR agonism.

Compounds of the invention are useful for the treatment or prevention of diseases or disorders associated with altered cholesterol transport, reverse cholesterol transport, fatty acid metabolism, cholesterol absorption, cholesterol re-absorption, cholesterol secretion, cholesterol excretion, or cholesterol metabolism. Representative diseases or disorders include, but are not limited to, a lipid disorder; cancer, particularly hormone-dependent cancers, including ovarian cancer, breast cancer, and prostate cancer, and skin cancers including melanoma, basal cell carcinoma, and squamous cell carcinoma; acneiform skin condition; skin inflammatory disease; immunological disorder; condition characterized by a perturbed epidermal barrier function; condition of disturbed differentiation or excess proliferation of the epidermis or mucous membrane; cardiovascular disease; reproductive tract disorders; optic nerve and retinal pathology; degenerative neuropathy occurring in a disease; autoimmune disease; traumatic damage to the central or peripheral nervous system; neurodegenerative disease; a degenerative process due to aging; diseases or disorders of the kidney; and osteoporosis and related diseases.

In another embodiment, the disease or disorder is hyperlipidemia, hypercholesterolemia, hyperlipoproteinemia, hypertriglyceridemia, lipodystrophy, hepatic steatosis, non-alcoholic steatohepatitis (NASH), nonalcoholic fatty liver disease (NAFLD), hyperglycemia, insulin resistance, diabetes mellitus, dyslipidemia, atherosclerosis, gallstone disease, acne vulgaris, dermatitis (including but not limited to, psoriasis, contact dermatitis, atopic dermatitis, and eczema), skin wounds, skin aging, photoaging, wrinkling, diabetes, Niemann-Pick disease type C, Parkinson's disease, Alzheimer's disease, inflammation, xanthoma, obesity, metabolic syndrome, syndrome X, stroke, peripheral occlusive disease, memory loss, diabetic neuropathies, proteinuria, glomerulopathies (including but not limited to, diabetic nephropathy, hypertensive nephropathy, IGA nephropathy, focal segmental glomerulosclerosis), hyperphosphatemia, cardiovascular complications of hyperphosphatemia, acute coronary syndrome, cancer, multiple sclerosis, or osteoporosis.

In another embodiment, the disease or disorder is cancer, including, but not limited to, bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer and testicular cancer. Cancers may be solid tumors that may or may not be metastatic. Cancers may also occur, as in leukemia, as a diffuse tissue.

In some embodiments, cancers that may be treated by the compounds, compositions and methods described herein include, but are not limited to, the following: cardiac cancers, including, for example, sarcoma, e.g., angiosarcoma, fibrosarcoma, rhabdomyosarcoma, and liposarcoma; myxoma; rhabdomyoma; fibroma; lipoma and teratoma; lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma; gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel or colon, e.g., adenocarcinoma, tubular adenoma, villous adenoma, hamartoma, and leiomyoma; genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma; liver cancers, including, for example, hepatoma, e.g., hepatocellular carcinoma; cholangiocarcinoma; hepatoblastoma; angio sarcoma; hepatocellular adenoma; and hemangioma; bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors; nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma; gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa thecal cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma; hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non Hodgkin's lymphoma (malignant lymphoma) and Waldenstrom's macroglobulinemia; skin cancers, including, for example, malignant melanoma, basal cell carcinoma, squamous cell carcinoma, Kaposi's sarcoma, moles dysplastic nevi, lipoma, angioma, dermatofibroma, keloids, psoriasis; and adrenal gland cancers, including, for example, neuroblastoma.

In another embodiment, the disease or disorder is Rett syndrome.

In another embodiment, the disease or disorder is acute coronary syndrome and related conditions. Such related conditions include e.g., heart attack, myocardial infarction, acute myocardial infarction, non-ST-segment elevation myocardial infarction, ST-segment elevation myocardial infarction, unstable angina, stable angina, angina pectoris, exercise induced angina, coronary artery disease, coronary heart disease, acute myocardial ischemia, ischaemic heart disease, ischemia, recurrent ischemia, congestive heart disease, congestive heart failure, cardiomyopathy, hypertensive heart disease, heart failure, diastolic heart failure, systolic heart failure, cor pulmonale, cardiac dysrhythmias, abnormalities of heart rhythm, inflammatory heart disease, endocarditis, inflammatory cardiomegaly, myocarditis, cerebrovascular disease, peripheral arterial disease, reperfusion injury, restenosis, atherosclerotic lesions, or chronic atherosclerotic inflammation.

In another embodiment, the disease or disorder is common acne; comedones; polymorphs; rosacea; nodulocystic acne; acne conglobate; senile acne; secondary acne, including but not limited to solar, medicinal and occupational acne; ichthyosis; ichthyosiform conditions; Darier's disease; palmoplantar keratoderma; leukoplakia; leukoplakiform conditions; cutaneous or mucous (oral) lichen; dermatological conditions or afflictions with an inflammatory immunoallergic component, with or without a cellular proliferation disorder, including but not limited to cutaneous psoriasis, mucous psoriasis, ungual psoriasis, psoriatic rheumatism, cutaneous atopy, including eczema, respiratory atopy and gingival hypertrophy; benign or malignant dermal or epidermal proliferations, of viral or non-viral origin, including but not limited to common warts, flat warts, epidermodysplasia verruciformis, oral or florid papillomatoses, and T lymphoma or cutaneous T-cell lymphoma; proliferations that may be induced by ultraviolet light, including but not limited to basocellular epithelioma and spinocellular epithelioma; precancerous skin lesions, including but not limited to keratoacanthomas; immune dermatitides, including but not limited to lupus erythematosus; bullous immune diseases; collagen diseases, including but not limited to scleroderma; dermatological or systemic conditions or afflictions with an immunological component; skin disorders due to exposure to UV radiation; photo-induced or chronological aging of the skin; actinic pigmentations; keratosis; pathology associated with chronological or actinic aging, including but not limited to xerosis; sebaceous function disorders, including but not limited to hyperseborrhea of acne, simple seborrhea, seborrheic dermatitis, sebopsoriasis, seborrheic eczema, dandruff, and pityriasis capitis; cicatrization disorders, including but not limited to stretch marks; pigmentation disorders, including but not limited to hyperpigmentation, melasma, hypopigmentation, and vitiligo; and alopecia, including but not limited to chemotherapy-associated alopecia and radiation-associated alopecia.

In one embodiment, the disease or disorder is hypercholesterolemia, atherosclerosis or dyslipidemia. In another embodiment, the disease or disorder is atherosclerosis, Alzheimer's disease, dermatitis or cancer. In yet another embodiment, the disease or disorder is atherosclerosis, Alzheimer's disease, acute coronary syndrome, melanoma or atopic dermatitis.

The present invention also provides a method for increasing reverse cholesterol transport and/or for inhibiting the progression of or promoting the regression of atherosclerosis.

The present invention also provides a method of treating diseases or disorders associated with a need for increasing high density lipoprotein (HDL)-cholesterol levels comprising the administration of an effective amount of a compound of the invention to a mammal (particularly a human) in need thereof.

The present invention also provides a method of treating a disease or disorder associated with a need for decreasing low density lipoprotein (LDL)-cholesterol levels comprising the administration of an effective amount of a compound of the invention to a mammal (particularly a human) in need thereof.

Additionally, provided herein is a method of increasing the expression of an ATP-Binding Cassette protein in a subject's cells, thereby increasing reverse cholesterol transport in a subject using the compounds of the invention and compositions provided herein.

Standard physiological, pharmacological and biochemical procedures are known to the art and are available for evaluating compounds of the present invention for the ability to modulate LXR activity. Such assays include, for example, binding assays, fluorescence polarization assays, FRET based co-activator recruitment assays, and cell-based co-transfection assays. Compounds of the present invention can be evaluated for their ability to modulate the expression of genes known to be modulated by LXR. Established animal models can be used to study the profiles of compounds of the present invention in relation to parameters directly relevant to diseases or disorders, including atherosclerosis, Alzheimer's disease, and skin conditions. Thus, compounds of the present invention can be tested in vivo in animal models by a variety of routes of administration, for example, oral gavage. Typically, in vivo compound exposure can be examined in plasma and in tissues of interest. LXR activity (as detected by gene expression of LXR-responsive genes) can be examined in whole blood and tissues of interest. Lipids can be quantified in the plasma and the liver.

In particular, compounds of the present invention can be tested for their activity on ATP-Binding Cassette (ABC) cholesterol transporters, such as ABCA1 and ABCG1, and on lipogenic markers, such as SREBP1c at the gene and protein expression level. The functional consequences of ABC transporter induction can be examined in cellular models for cholesterol efflux and in animal models for the reverse cholesterol pathway and atherosclerosis. Lipogenic markers can be examined in animal models by measuring plasma and liver triglyceride levels.

The compounds of the present invention can be used alone (i.e., as a monotherapy) or in combination with one or more other therapeutic agent effective for treating any of the above indications. The pharmaceutical compositions can comprise the disclosed compounds alone as the only pharmaceutically active agent or can comprise one or more additional pharmaceutically active agents.

The present invention also provides combination therapy for treating or ameliorating a disease or a disorder described herein. In some embodiments, the combination therapy comprises administering at least one compound represented by Formula I in combination with one or more agents for treating or ameliorating a disease or a disorder described herein.

In some embodiments, the compounds of the invention are used in combination with one or more additional agents for the treatment of diabetes, dyslipidemia, cardiovascular disease, hypertension, or obesity. Agents for the treatment of diabetes include insulins, such as Humulin® (Eli Lilly), Lantus® (Sanofi Aventis), Novolin® (Novo Nordisk), and Exubera® (Pfizer); PPAR gamma agonists, such as Avandia® (rosiglitizone maleate, GSK) and Actos® (pioglitazone hydrochloride, Takeda/Eli Lilly); sulfonylureas, such as Amaryl® (glimepiride, Sanofi Aventis), Diabeta® (glyburide, Sanofi Aventis), Micronase®/Glynase® (glyburide, Pfizer), and Glucotrol®/Glucotrol XL® and (glipizide, Pfizer); meglitinides, such as Prandin®/NovoNorm® (repaglinide, Novo Nordisk), Starlix® (nateglinide, Novartis), and Glufast® (mitiglinide, Takeda); biguanides, such as Glucophage®/Glucophage XR® (metformin HCl, Bristol Myers Squibb) and Glumetza® (metformin HCl extended release tablets, Depomed); thiazolidinediones; amylin analogs, GLP-1 analogs or agonists (including Byetta® (exenatide, Amylin/Eli Lilly) and Victoza® (recombinant liraglutide, Novo Nordisk)); DPP-IV inhibitors including Tradjenta™ (Eli Lilly/Boehringer Ingelheim), Januvia® (Merck), Galvus® (Novartis), and Onglyza® (Bristol-Myers Squibb/AstraZeneca); PTB-1 B inhibitors; protein kinase inhibitors (including AMP-activated protein kinase inhibitors); glucagon antagonists, glycogen synthase kinase-3 beta inhibitors; glucose-6-phoshatase inhibitors; glycogen phosphorylase inhibitors; sodium glucose co-transporter inhibitors, and alpha-glucosidase inhibitors, such as Precose®/Glucobay®/Prandase®/Glucor® (acarbose, Bayer) and Glyset® (miglitol, Pfizer). Agents for the treatment of dyslipidemia and cardiovascular disease include statins, fibrates, and ezetimbe. Agents for the treatment of hypertension include alpha-blockers, beta-blockers, calcium channel blockers, diuretics, angiotensin converting enzyme (ACE) inhibitors, dual ACE and neutral endopeptidase (NEP) inhibitors, angiotensin-receptor blockers (ARBs), aldosterone synthase inhibitors, aldosterone-receptor antagonists, or endothelin receptor antagonists. Agents for the treatment of obesity include orlistat, phentermine, sibutramine and rimonabant.

An embodiment of the invention includes administering at least one LXR modulator compound of the invention or composition thereof in a combination therapy with combination products, such as Avandamet® (metformin HCl and rosiglitazone maleate, GSK); Avandaryl® (glimepiride and rosiglitazone maleate, GSK); Metaglip® (glipizide and metformin HCl, Bristol Myers Squibb); and Glucovance® (glyburide and metformin HCl, Bristol Myers Squibb).

In some embodiments, the combination therapy comprises administering at least one compound of the invention in combination with one or more compound selected from the group of, for example, beta secretase (BACE1) inhibitors; gamma-secretase inhibitors; amyloid aggregation inhibitors (e.g., ELND-005); directly or indirectly acting neuroprotective and/or disease-modifying substances; antioxidants (e.g., vitamin E or ginkolide); anti-inflammatory substances (e.g., Cox inhibitors, NSAIDs); HMG-CoA reductase inhibitors (statins); acetylcholinesterase inhibitors (e.g., donepezil, rivastigmine, tacrine, galantamine, memantine; tacrine); NMDA receptor antagonists (e.g., memantine); AMPA receptor agonists; AMPA receptor positive modulators, AMPAkines, monoamine receptor reuptake inhibitors, substances modulating the concentration or release of neurotransmitters; substances inducing the secretion of growth hormone (e.g., ibutamoren mesylate and capromorelin); CB-1 receptor antagonists or inverse agonists; antibiotics (e.g., minocyclin or rifampicin); PDE2, PDE4, PDE5, PDE9, PDE10 inhibitors, GABAA receptor inverse agonists, GABAA receptor antagonists, nicotinic receptor agonists or partial agonists or positive modulators, alpha4beta2 nicotinic receptor agonists or partial agonists or positive modulators, alpha7 nicotinic receptor agonists or partial agonists or positive modulators; histamine H3 antagonists, 5 HT-4 agonists or partial agonists, 5HT-6 antagonists, alpha2-adrenoreceptor antagonists, calcium antagonists, muscarinic receptor M1 agonists or partial agonists or positive modulators, muscarinic receptor M2 antagonists, muscarinic receptor M4 antagonists, metabotropic glutamate-receptor 5 positive modulators, antidepressants, such as citalopram, fluoxetine, paroxetine, sertraline and trazodone; anxiolytics, such as lorazepam and oxazepam; antiphychotics, such as aripiprazole, clozapine, haloperidol, olanzapine, quetiapine, risperidone and ziprasidone, and other substances that modulate receptors or enzymes in a manner such that the efficacy and/or safety of the compounds according to the invention is increased and/or unwanted side effects are reduced.

In some embodiments, the compounds described herein are used in combination with one or more additional therapies, including therapies to alleviate pain and anxiety, prevent recurrences of ischaemia and prevent or limit progression to acute myocardial infarction. Such additional therapies include antithrombotic treatment, as well as coronary angiography followed by revascularization. Further additional therapies include smoking cessation, exercise, and management of hypertension and blood glucose.

In some embodiments, the compounds described herein are used in combination with one or more agents for antiplatelet or anticoagulant therapy, including aspirin, clopidogrel, prasugrel, ticagrelor, and glycoprotein IIb/IIIa inhibitors including eptifibatide, tirofiban and abciximab.

In some embodiments, the compounds described herein are used in combination with one or more agents for antithrombin therapy, including fondaparinux, heparin, and bivalirudin.

In some embodiments, the compounds described herein are used in combination with one or more lipid lowering agents, including a statin, nicotinic acid, bile acid binding resin, and ezetimibe.

In some embodiments, the compounds described herein are used in combination with one or more treatments for revascularization, including coronary angiography and bypass surgery.

In some embodiments, the compounds described herein are used in combination with one or more agents, including nitrates (sublingual, oral or intravenous), beta-blockers, calcium antagonists (e.g., diltiazem, verapamil), and angiotensin-converting enzyme (ACE) inhibitors.

In some embodiments, the compounds described herein are used in combination with one or more agents selected from anti-platelets, nitrates, beta blockers, glycoprotein IIB/IIIA inhibitors, anticoagulants, low molecular weight heparins, direct thrombin inhibitors, and adenosine diphosphate receptor antagonists.

In some embodiments, the compounds described herein are used in combination with one or more agents for the treatment of cancer, including but not limited to breast cancer, ovarian cancer, prostate cancer, skin cancers including melanoma, basal cell carcinoma, and squamous cell carcinoma, renal cell carcinoma, colorectal carcinoma, pancreatic cancer, gastric cancer, leukemia and lymphoma.

In some embodiments, the compounds described herein are used in combination with immunotherapies, including but not limited to cell-based therapies, antibody therapies and cytokine therapies for the treatment of a disease or disorder disclosed herein.

In certain embodiments, compounds according to the invention are used in combination with one or more passive immunotherapies, including but not limited to naked monoclonal antibody drugs and conjugated monoclonal antibody drugs. Examples of naked monoclonal antibody drugs that can be used include, but are not limited to rituximab (Rituxan®), an antibody against the CD20 antigen; trastuzumab (Herceptin®), an antibody against the HER2 protein; alemtuzumab (Campath), an antibody against the CD52 antigen; cetuximab (Erbitux®), an antibody against the EGFR protein; and bevacizumab (Avastin®) which is an anti-angiogenesis inhibitor of VEGF protein.

Examples of conjugated monoclonal antibodies that can be used include, but not limited to, radiolabeled antibody ibritumomab tiuxetan (Zevalin®); radiolabeled antibody tositumomab (Bexxar®); and immunotoxin gemtuzumab ozogamicin (Mylotarg®) which contains calicheamicin; BL22, an anti-CD22 monoclonal antibody-immunotoxin conjugate; radiolabeled antibodies such as OncoScint® and ProstaScint®; brentuximab vedotin (Adcetris®); ado-trastuzumab emtansine (Kadcyla®, also called TDM-1)

Further examples of therapeutic antibodies that can be used include, but are not limited to, REOPRO® (abciximab), an antibody against the glycoprotein IIb/IIIa receptor on platelets; ZENAPAX® (daclizumab) an immunosuppressive, humanized anti-CD25 monoclonal antibody; PANOREX™, a murine anti-17-IA cell surface antigen IgG2a antibody; BEC2, a murine anti-idiotype (GD3 epitope) IgG antibody; IMC-C225, a chimeric anti-EGFR IgG antibody; VITAXIN™ a humanized anti-aVI33 integrin antibody; Campath 1H/LDP-03, a humanized anti CD52 IgG1 antibody; Smart M195, a humanized anti-CD33 IgG antibody; LYMPHOCIDE™, a humanized anti-CD22 IgG antibody; LYMPHOCIDE™ Y-90; Lymphoscan; Nuvion® (against CD3; CM3, a humanized anti-ICAM3 antibody; IDEC-114 a primatized anti-CD80 antibody; IDEC-131 a humanized anti-CD40L antibody; IDEC-151 a primatized anti-CD4 antibody; IDEC-152 a primatized anti-CD23 antibody; SMART anti-CD3, a humanized anti-CD3 IgG; 5G1.1, a humanized anti-complement factor 5 (C5) antibody; D2E7, a humanized anti-TNF-α antibody; CDP870, a humanized anti-TNF-α Fab fragment; IDEC-151, a primatized anti-CD4 IgG1 antibody; MDX-CD4, a human anti-CD4 IgG antibody; CD20-streptdavidin (+biotin-yttrium 90); CDP571, a humanized anti-TNF-α IgG4 antibody; LDP-02, a humanized anti-α4β7 antibody; OrthoClone OKT4A, a humanized anti-CD4 IgG antibody; ANTOVA™, a humanized anti-CD40L IgG antibody; ANTEGREN™, a humanized anti-VLA-4 IgG antibody; and CAT-152, a human anti-TGF-β2 antibody.

In certain embodiments, compounds according to the invention are used in combination with one or more targeted immunotherapies containing toxins but not an antibody, including but not limited to denileukin diftitox (Ontak®), IL-2 linked to diphtheria toxin.

The compounds according to the invention may also be used in combination with adjuvant immunotherapies for the treatment of a disease or disorder disclosed herein. Such adjuvant immunotherapies include, but are not limited to, cytokines, such as granulocyte-macrophage colony-stimulating factor (GM-CSF), granulocyte-colony stimulating factor (G-CSF), macrophage inflammatory protein (MIP)-1-alpha, interleukins (including IL-1, IL-2, IL-4, IL-6, IL-7, IL-12, IL-15, IL-18, IL-21, and IL-27), tumor necrosis factors (including TNF-alpha), and interferons (including IFN-alpha, IFN-beta, and IFN-gamma); aluminum hydroxide (alum); Bacille Calmette-Guérin (BCG); Keyhole limpet hemocyanin (KLH); Incomplete Freund's adjuvant (IFA); QS-21; DETOX; Levamisole; and Dinitrophenyl (DNP), and combinations thereof, such as, for example, combinations of interleukins, for example IL-2, with other cytokines, such as IFN-alpha.

In certain embodiments, compounds according to the invention are used in combination with vaccine therapy, including but not limited to autologous and allogeneic tumor cell vaccines, antigen vaccines (including polyvalent antigen vaccines), dendritic cell vaccines; and viral vaccines.

In another embodiment, the present disclosure comprises administering to a subject with cancer an effective amount of a compound described herein and one or more additional anti-cancer therapies selected from: surgery, anti-cancer agents/drugs, biological therapy, radiation therapy, anti-angiogenesis therapy, immunotherapy, adoptive transfer of effector cells, gene therapy or hormonal therapy. Examples of anti-cancer agents/drugs are described below.

In one embodiment, the anti-cancer agent/drug is, for example, adriamycin, aactinomycin, bleomycin, vinblastine, cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride; Yervoy® (ipilimumab); Mekinist™ (trametinib); peginterferon alfa-2b, recombinant interferon alfa-2b; Sylatron™ (peginterferon alfa-2b); Tafinlar® (dabrafenib); Zelboraf® (vemurafenib); and nivolumab.

The compounds according to the present invention can be administered in combination with existing methods of treating cancers, for example by chemotherapy, irradiation, or surgery. Thus, there is further provided a method of treating cancer comprising administering an effective amount of a compound according to Formula I, or a pharmaceutically acceptable salt form thereof, to a subject in need of such treatment, wherein an effective amount of at least one additional cancer chemotherapeutic agent is administered to the subject. Examples of suitable chemotherapeutic agents include any of: abarelix, ado-trastuzumab emtansine, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, emtansine, epirubicin, eribulin, erlotinib, estramustine, etoposide phosphate, etoposide, everolimus, exemestane, fentanyl citrate, filgrastim, floxuridine, fludarabine, fluorouracil, fruquintinib, fulvestrant, gefitinib, gemcitabine, gemtuzumab ozogamicin, goserelin acetate, histrelin acetate, ibritumomab tiuxetan, idarubicin, Ifosfamide, imatinib mesylate, interferon alfa 2a, irinotecan, ixabepilone, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, paclitaxel albumin-stabilized nanoparticle formulation, pamidronate, panitumumab, pegaspargase, pegfilgrastim, pemetrexed disodium, pentostatin, pertuzuma, pipobroman, plicamycin, procarbazine, quinacrine, rasburicase, rituximab, sorafenib, streptozocin, sulfatinib, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, volitinib, vorinostat, and zoledronate.

In particular embodiments, compounds according to the invention are used in combination with one or more anti-cancer agent selected from methotrexate, paclitaxel albumin-stabilized nanoparticle formulation, ado-trastuzumab emtansine, eribulin, doxorubicin, fluorouracil, everolimus, anastrozole, pamidronate disodium, exemestane, capecitabine, cyclophosphamide, docetaxel, epirubicin, toremifene, fulvestrant, letrozole, gemcitabine, gemcitabine hydrochloride, goserelin acetate, trastuzumab, ixabepilone, lapatinib ditosylate, megestrol acetate, tamoxifen citrate, pamidronate disodium, and pertuzumab for the treatment of breast cancer.

Other anti-cancer agents/drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; beta-clamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane;

fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anti-cancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer; 5-fluorouracil; and leucovorin.

In one embodiment, the anti-cancer agent/drug is an agent that stabilizes mictotubules. As used herein, a "microtubulin stabilizer" means an anti-cancer agent/drug which acts by arresting cells in the G2-M phases due to stabilization of microtubules. Examples of microtubulin stabilizers include ACLITAXEL® and Taxol® analogues. Additional examples of microtubulin stabilizers included without limitation the following marketed drugs and drugs in development: Discodermolide (also known as NVP-XX-A-296); Epothilones (such as Epothilone A, Epothilone B, Epothilone C (also known as desoxyepothilone A or dEpoA); Epothilone D (also referred to as KOS-862, dEpoB, and desoxyepothilone B); Epothilone E; Epothilone F; Epothilone B N-oxide; Epothilone A N-oxide; 16-aza-epothilone B; 21-aminoepothilone B (also known as BMS-310705); 21-hydroxyepothilone D (also known as Desoxyepothilone F and dEpoF), 26-fluoroepothilone); FR-182877 (Fujisawa, also known as WS-9885B), BSF-223651 (BASF, also known as ILX-651 and LU-223651); AC-7739 (Ajinomoto, also known as AVE-8063A and CS-39.HCl); AC-7700 (Ajinomoto, also known as AVE-8062, AVE-8062A, CS-39-L-Ser.HCl, and RPR-258062A); Fijianolide B; Laulimalide; Caribaeoside; Caribaeolin; Taccalonolide; Eleutherobin; Sarcodictyin; Laulimalide; Dictyostatin-1; Jatrophane esters; and analogs and derivatives thereof.

In another embodiment, the anti-cancer agent/drug is an agent that inhibits mictotubules. As used herein, a "microtubulin inhibitor" means an anti-cancer agent which acts by inhibiting tubulin polymerization or microtubule assembly. Examples of microtubulin inhibitors include without limitation the following marketed drugs and drugs in development: Erbulozole (also known as R-55104); Dolastatin 10 (also known as DLS-10 and NSC-376128); Mivobulin isethionate (also known as CI-980); Vincristine; NSC-639829; ABT-751 (Abbot, also known as E-7010); Altorhyrtins (such as Altorhyrtin A and Altorhyrtin C); Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9); Cemadotin hydrochloride (also known as LU-103793 and NSC-D-669356); Auristatin PE (also known as NSC-654663); Soblidotin (also known as TZT-1027), LS-4559-P (Pharmacia, also known as LS-4577); LS-4578 (Pharmacia, also known as LS-477-P); LS-4477 (Pharmacia), LS-4559 (Pharmacia); RPR-112378 (Aventis); Vincristine sulfate; DZ-3358 (Daiichi); GS-164 (Takeda); GS-198 (Takeda); KAR-2 (Hungarian Academy of Sciences); SAH-49960 (Lilly/Novartis); SDZ-268970 (Lilly/Novartis); AM-97 (Armad/Kyowa Hakko); AM-132

(Armad); AM-138 (Armad/Kyowa Hakko); IDN-5005 (Indena); Cryptophycin 52 (also known as LY-355703); Vitilevuamide; Tubulysin A; Canadensol; Centaureidin (also known as NSC-106969); T-138067 (Tularik, also known as T-67, TL-138067 and TI-138067); COBRA-1 (Parker Hughes Institute, also known as DDE-261 and WHI-261); H10 (Kansas State University); H16 (Kansas State University); Oncocidin A1 (also known as BTO-956 and DIME); DDE-313 (Parker Hughes Institute); SPA-2 (Parker Hughes Institute); SPA-1 (Parker Hughes Institute, also known as SPIKET-P); 3-IAABU (Cytoskeleton/Mt. Sinai School of Medicine, also known as MF-569); Narcosine (also known as NSC-5366); Nascapine, D-24851 (Asta Medica), A-105972 (Abbott); Hemiasterlin; 3-BAABU (Cytoskeleton/Mt. Sinai School of Medicine, also known as MF-191); TMPN (Arizona State University); Vanadocene acetylacetonate; T-138026 (Tularik); Monsatrol; Inanocine (also known as NSC-698666); 3-IAABE (Cytoskeleton/Mt. Sinai School of Medicine); A-204197 (Abbott); T-607 (Tularik, also known as T-900607); RPR-115781 (Aventis); Eleutherobins (such as Desmethyleleutherobin, Desaetyleleutherobin, Isoeleutherobin A, and Z-Eleutherobin); Halichondrin B; D-64131 (Asta Medica); D-68144 (Asta Medica); Diazonamide A; A-293620 (Abbott); NPI-2350 (Nereus); TUB-245 (Aventis); A-259754 (Abbott); Diozostatin; (−)-Phenylahistin (also known as NSCL-96F037); D-68838 (Asta Medica); D-68836 (Asta Medica); Myoseverin B; D-43411 (Zentaris, also known as D-81862); A-289099 (Abbott); A-318315 (Abbott); HTI-286 (also known as SPA-110, trifluoroacetate salt) (Wyeth); D-82317 (Zentaris); D-82318 (Zentaris); SC-12983 (NCI); Resverastatin phosphate sodium; BPR-0Y-007 (National Health Research Institutes); SSR-250411 (Sanofi); Combretastatin A4; eribulin (Halaven®); and analogs and derivatives thereof.

In another embodiment, compounds according to the invention are used in combination with alkylating agents, antimetabolites, natural products, or hormones. Examples of alkylating agents useful in the methods of the invention include but are not limited to, nitrogen mustards (e.g., mechloroethamine, cyclophosphamide, chlorambucil, melphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites useful in the methods of the invention include but are not limited to folic acid analog (e.g., methotrexate), or pyrimidine analogs (e.g., fluorouracil, floxouridine, Cytarabine), and purine analogs (e.g., mercaptopurine, thioguanine, pentostatin). Examples of natural products useful in the methods of the invention include but are not limited to vinca alkaloids (e.g., vinblastin, vincristine), epipodophyllotoxins (e.g., etoposide, teniposide), antibiotics (e.g., actinomycin D, daunorubicin, doxorubicin, bleomycin, plicamycin, mitomycin) or enzymes (e.g., L-asparaginase). Examples of hormones and antagonists useful for the treatment of cancer include but are not limited to adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), and gonadotropin releasing hormone analog (e.g., leuprolide). Other agents that can be used in the methods of the invention for the treatment of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), and adrenocortical suppressant (e.g., mitotane, aminoglutethimide). Other anticancer agents/drugs include, but are not limited to inhibitors of the enzyme poly ADP ribose polymerase (PARP), including olaparib, iniparib, rucaparib, veliparib; inhibitors of vascular endothelial growth factor (VEGF) receptor tyrosine kinases, including cediranib; programmed cell death protein 1 (PD-1) inhibitors, including nivolumab (Bristol-Myers Squibb Co.) and pembrolizumab (Merck & Co., Inc.; MK-3475); MEK inhibitors, including cobimetinib; B-Raf enzyme inhibitors, including vemurafenib; cytotoxic T lymphocyte antigen (CTLA-4) inhibitors, including tremelimumab; programmed death-ligand 1 (PD-L1) inhibitors, including MEDI4736 (AstraZeneca); inhibitors of the Wnt pathway; inhibitors of epidermal growth factor receptor (EGFR) including AZD9291 (AstraZeneca), erlotinib, gefitinib, panitumumab, and cetuximab; adenosine A2A receptor inhibitors; adenosine A2B receptor inhibitors; and Wnt pathway inhibitors.

The compounds of the invention can be used in combination with one or more therapeutic strategies including immune checkpoint inhibitors, including inhibitors of PD-1 and CTLA-4 for the treatment of cancer.

In particular embodiments, a compound described in the methods herein is used in combination with one or more anti-cancer agent selected from Yervoy® (ipilimumab), Mekinist™ (trametinib), peginterferon alfa-2b, recombinant interferon alfa-2b, Sylatron™ (peginterferon alfa-2b), Tafinlar® (dabrafenib), Zelboraf® (vemurafenib), and nivolumab for the treatment of melanoma.

In some embodiments, compounds of the invention are used in combination with one or more other therapeutic agent effective for treating Rett syndrome. In some embodiments, the compounds of the invention are used in combination with one or more additional therapies, including therapies for the treatment of seizures, muscle stiffness therapy, physical therapy, occupational therapy, speech therapy, nutritional support therapy, nasogastric tube feeding and gastrostomy.

Combination therapy includes co-administration of a compound of the invention and one or more other agent, sequential administration of a compound of the invention and one or more other agent, administration of a composition containing a compound of the invention and one or more other agent, or simultaneous administration of separate compositions containing a compound of the invention and one or more other agent.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

General Description of Synthetic Methods

The compounds of the present invention can be readily prepared according to the following reaction schemes and examples, or modifications thereof, using readily available starting materials, reagents and conventional synthesis procedures. Many of the reactions can also be carried out under microwave conditions or using conventional heating or utilizing other technologies such as solid phase reagents/scavengers or flow chemistry. In these reactions, it is also possible to make use of variants which are themselves known to those of ordinary skill in this art, but are not mentioned in greater detail. Furthermore, other methods for preparing compounds of the invention will be readily apparent to a person of ordinary skill in the art in light of the following reaction schemes and examples. In cases where synthetic intermediates and final products contain potentially reactive functional groups, for example amino, hydroxy, thiol and carboxylic acid groups, that may interfere with the desired reaction, it may be advantageous to employ protected forms of the intermediate. Methods for the selection, introduction and subsequent removal of protecting groups are well known to those skilled in the art. In the discussion below $R^1$, $R^2$, $R^3$, $R^4$, $R^{10}$, $R^{21}$, $R^{22}$, $R^{23}$, $R^{24}$, $R^{25}$, $R^{30}$, $R^{31}$, $R^{40}$, $R^{41}$, A, L, Y, m and n have the meanings indicated above unless otherwise indicated. The abbreviations used in these experimental details are listed below and additional ones should be known to a person skilled in the art of synthesis. In addition one can refer to the following references for suitable methods of synthesis as described in March, Advanced Organic Chemistry, 3rd edition, John Wiley & Sons, 1985, Greene and Wuts, Protective Groups in Organic Synthesis, 2nd edition, John Wiley & Sons, 1991, and Richard Larock, Comprehensive Organic Transformations, 4th edition, VCH publishers Inc., 1989.

Generally, reagents in the reaction schemes are used in equimolar amounts; however, in certain cases it may be desirable to use an excess of one reagent to drive a reaction to completion. This is especially the case when the excess reagent can be readily removed by evaporation or extraction. Bases employed to neutralize HCl in reaction mixtures are generally used in slight to substantial excess (1.05-5 equivalents).

The the following abbreviations may be employed:

| Abbreviation | Meaning |
| --- | --- |
| Boc | tert-butoxy carbonyl or t-butoxy carbonyl |
| (Boc)$_2$O | di-tert-butyl dicarbonate |
| Cbz | Benzyloxycarbonyl |
| CbzCl | Benzyl chloroformate |
| DAST | diethylaminosulfur trifluoride |
| DIEA | N,N-diisopropylethylamine |
| DMF | N,N-dimethylformamide |
| EDC•HCl, EDCI | 1-[3-(dimethylamino)propyl]-3-ethylcarbodiimide hydrochloride |
| Equiv | equivalents |
| h, hr | hour(s) |
| HOBt | 1-hydroxybenzotriazole |
| HATU | 2-(7-Aza-1H-benzotriazole-1-yl)-1,1,3,3-tetramethyluronium hexafluorophosphate |
| HBTU | 2-(1H-Benzotriazol-1-yl)-1,1,3,3-tetramethyluronium hexafluorophosphate |
| KHMDS | potassium hexamethyldisilazane |
| LAH or LiAlH$_4$ | lithium aluminum hydride |
| LC-MS | liquid chromatography-mass spectroscopy |
| LHMDS | lithium hexamethyldisilazane |
| Me | methyl |
| MsCl | methanesulfonyl chloride |
| min | minute |
| MS | mass spectrum |
| NBS | N-bromosuccinimide |
| NCS | N-chlorosuccinimide |
| NMP | N-methylpyrrolidinone |
| Pd$_2$(dba)$_3$ | tris(dibenzylideneacetone)dipalladium(0) |
| PE | petroleum ether |
| PMB | 4-methoxybenzyl |
| Quant | quantitative yield |

-continued

| Abbreviation | Meaning |
| --- | --- |
| rt | room temperature |
| Satd | saturated |
| SFC | supercritical fluid chromatography |
| SPA | scintillation proximity assay |
| SPE | solid phase extraction |
| TBAF | tetrabutylammonium fluoride |
| TBS | t-butyldimethylsilyl |
| TBDPS | t-butyldiphenylsilyl |
| TBSCl | t-butyldimethylsilyl chloride |
| TBDPSCl | t-butyldiphenylsilyl chloride |
| TEA | triethylamine or Et$_3$N |
| TFA | trifluoroacetic acid |
| Tlc, TLC | thin layer chromatography |
| TMS | trimethylsilyl |
| TMSCl | chlorotrimethylsilane or trimethylsilyl chloride |
| t$_R$ | retention time |
| TsOH | p-toluenesulfonic acid |
| XPhos | 2-Dicyclohexylphosphino-2',4',6'-triisopropylbiphenyl |

In a first process a compound of Formula I, is prepared from a piperazine of Formula II and a substituted benzene of Formula III (Equation 1). In a first variation of this process, G1 is I, Br, Cl or OSO$_2$CF$_3$ and a palladium source and suitable ligand are employed under an inert atmosphere. Suitable palladium sources include Pd$_2$(dba)$_3$ and suitable ligands include XPhos. In a second variation of this process, $G^1$ is B(OH)$_2$ and the reaction is catalyzed by Cu(OAc)$_2$ under an air or oxygen atmosphere. In a third variation of this process, $G^1$ is F or Cl, $R^2$ is an electron withdrawing group such as cyano or CO$_2$Me and the reaction is accomplished by heating in the presence of a base such as i-Pr$_2$NEt.

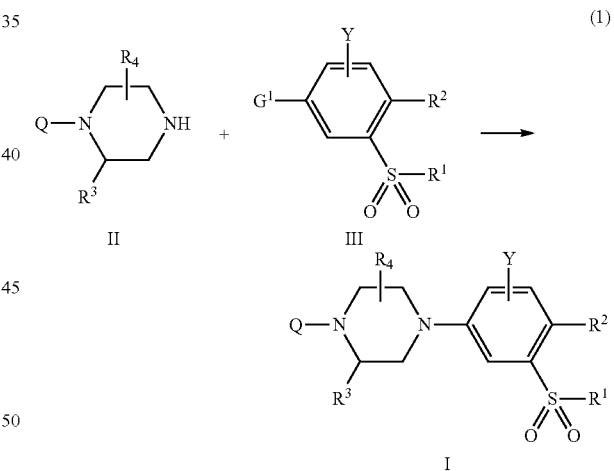

(1)

Certain piperazines II e.g., $R^3$=i-Pr, i-Bu, Bn, wherein Q is a t-butoxycarbonyl or benzyloxcarbonyl group, are commercially available.

In a second process, a compound of Formula I, is prepared from a piperazine of Formula V and a compound of Formula IV (Equation 2). When Q is $R^{10}$OC(O)—, $G^2$ is chlorine. Alternatively, when Q is t-BuOC(O)—, $G^2$ is OC(O)Ot-Bu. When Q is a heteroaryl group, in a first variation, $G^2$ is Br, Cl, F or SO$_2$G$^3$, wherein $G^3$ is Me or optionally substituted benzyl, the reaction is accomplished by heating in the presence of a suitable base such as i-Pr$_2$NEt. Alternatively, in a second variation, when Q is a heteroaryl group and $G^2$ is Br, I or SO$_2$CF$_3$ and the reaction is accomplished in the presence of and a suitable palladium source and ligand.

Suitable palladium sources include $Pd_2(dba)_3$ and suitable ligands include XPhos. Alternatively, $Pd(t-Bu_3P)_2$ is employed. When Q is $R^{30}$-L and L is $CH_2$ or CHMe, $G^2$ is Cl, Br, I or $SO_2Me$ and the reaction is accomplished by heating in the presence of a weak base such as $NaHCO_3$ or $i-Pr_2NEt$, preferably in a dipolar aprotic solvent such as DMF or MeCN.

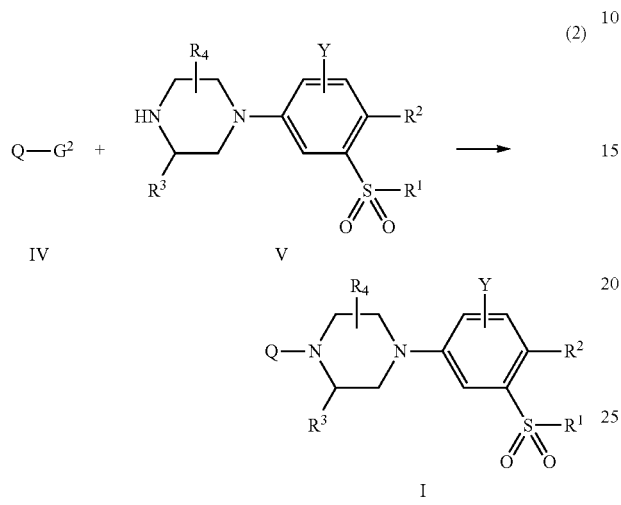

(2)

In a third process, a compound of Formula I, wherein Q is $R^{30}$-L or $R^{40}$-L, is prepared by reductive amination of an aldehyde of Formula VI or VII with a piperazine of Formula V (Equation 3), using a reducing agent such as $NaCNBH_3$ or $NaBH(OAc)_3$.

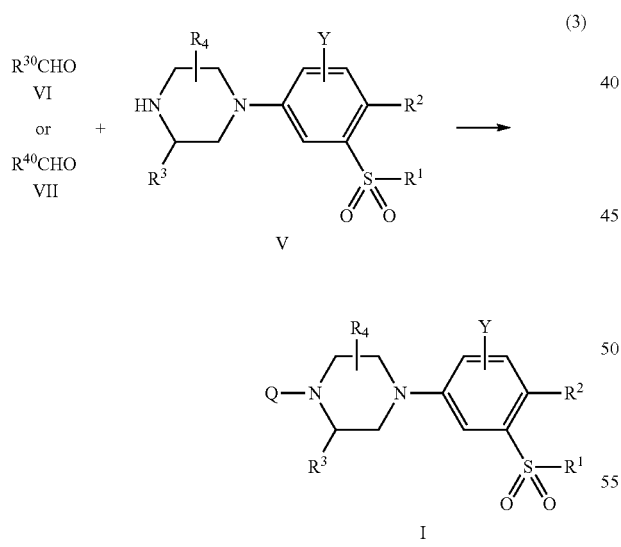

(3)

In a fourth process, a compound of Formula I, wherein Q is $R^{30}$-L or $R^{40}$-L, is prepared by acylation of a piperazine of Formula V with a carboxylic acid of Formulae VIII or IX, followed by reduction (Equation 4). Amide formation is accomplished using a peptide coupling reagent such as HATU or EDC, in the presence of a base such as $i-Pr_2NEt$ in a solvent such as $CH_2Cl_2$ or DMF. Reduction of the amide is carried using a reducing agent such as $LiAlH_4$ or $BH_3$.

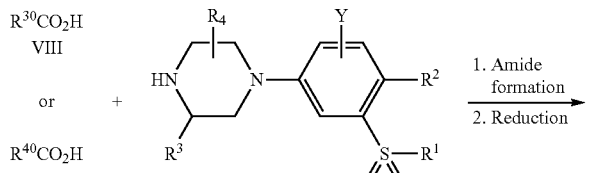

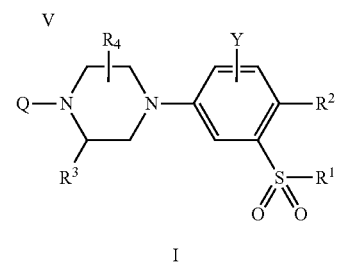

In a fifth process, a compound of Formula II is prepared by removal of protecting group PG from an intermediate of Formula XI. Intermediates of Formula XI are prepared from piperazines of Formula X by the methods of second, third and fourth processes.

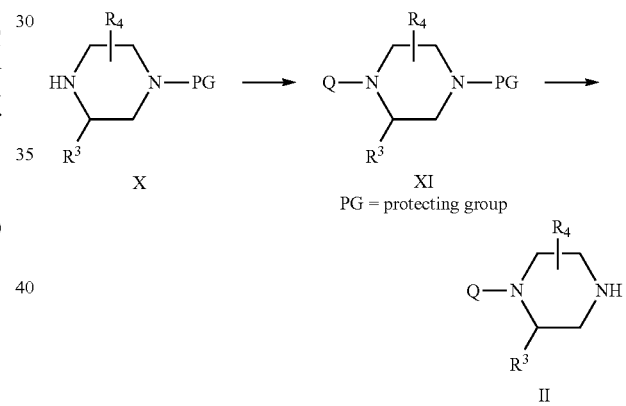

(5)

Compounds of Formula I are also prepared from other compounds of Formula I by a transformation of groups on the molecule by variety of processes including, but not limited to, those listed below:

(a) a cyano group is converted to $CONH_2$ using $H_2O_2$ and $K_2CO_3$ in DMSO
(b) an ester group group is reduced to a primary alcohol using DiBAl or $LiBH_4$
(c) a primary alcohol group is oxidized to an aldehyde using Dess-Martin periodinane or Swern oxidation and the to a secondary alcohol by reaction with Grignard reagent or alkyllithium
(d) an ester group is converted to a tertiary alcohol by reaction with an excess of a Grignard reagent or alkyllithium
(e) an aryl bromide, aryl iodide, or heteroaryl halide is converted to the corresponding methyl compound by reaction with trimethyl borate in the presence of a palladium catalyst
(f) an aryl bromide, aryl iodide, or heteroaryl halide is converted to the corresponding cyclopropyl compound by reaction with cyclopropylboronic acid or cyclopropyl trifluoroborate in the presence of a palladium catalyst (g) an aryl bromide is converted to an aryl methyl sulfone by reaction with MeSO$_2$Na in the presence of CuI and sodium prolinate (h) alkyl ester is hydrolyzed to the corresponding carboxylic acid (i) a carboxylic acid is reacted with acetic hydrazide, followed by treatment with POCl$_3$ to give a 1,3,4-oxadiazole (j) a tertiary alcohol is treated with a strong acid such as HCl in a solvent such as CDCl$_3$ or toluene to give an alkene (k) a primary alcohol is reacted with MsCl, followed by a secondary amine to give a tertiary amine (l) a carboxylic acid is reacted with an amine in the presence of a peptide coupling reagent such HATU or EDC, in the presence of a base such as i-Pr2NEt to give an amide (m) a 2-aminopyrimidine is halogenated at the 5-position using NCS or NBS (n) a tertiary alcohol is treated with DAST to give the corresponding fluoro compound Analytical Methods Where NMR data are presented, spectra were obtained on a Varian 400 (400 MHz) or 300 (300 MHz) and are reported as ppm downfield from tetramethylsilane with number of proton, multiplicities and coupling constants indicated parenthetically along with reference to deuterated solvent.

LC-MS data were obtained by utilizing the following chromatographic conditions:

| Method 1 (10-80, 2 min) | | |
|---|---|---|
| Column | Xtimate ™ C18 2.1 * 30 mm, 3 μm | |
| Mobile Phase | A: water (4 L) + TFA (1.5 mL) | |
| | B: acetonitrile (4 L) + TFA (0.75 mL) | |
| TIME (min) | A % | B % |
| 0 | 90 | 10 |
| 0.9 | 20 | 80 |
| 1.5 | 20 | 80 |
| 1.51 | 90 | 10 |
| 2 | 90 | 10 |
| Flow Rate | 1.2 mL/min | |
| wavelength | UV 220 nm | |
| Oven Temp | 50° C. | |
| MS ionization | ESI | |

| Method 2 (30-90, 2 min) | | |
|---|---|---|
| Column | Xtimate ™ C18 2.1 * 30 mm, 3 μm | |
| Mobile Phase | A: water (4 L) + TFA (1.5 mL) | |
| | B: acetonitrile (4 L) + TFA (0.75 mL) | |
| TIME (min) | A % | B % |
| 0 | 70 | 30 |
| 0.9 | 10 | 90 |
| 1.5 | 10 | 90 |
| 1.51 | 70 | 30 |
| 2 | 70 | 30 |
| Flow Rate | 1.2 mL/min | |
| wavelength | UV 220 nm | |
| Oven Temp | 50° C. | |
| MS ionization | ESI | |

| Method 3 (0-60, 2 min) | | |
|---|---|---|
| Column | Xtimate ™ C18 2.1 * 30 mm, 3 μm | |
| Mobile Phase | A: water (4 L) + TFA (1.5 mL) | |
| | B: acetonitrile (4 L) + TFA (0.75 mL) | |
| TIME (min) | A % | B % |
| 0 | 100 | 0 |
| 0.9 | 40 | 60 |
| 1.5 | 40 | 60 |
| 1.51 | 100 | 0 |
| 2 | 100 | 0 |
| Flow Rate | 1.2 mL/min | |
| wavelength | UV 220 nm | |
| Oven Temp | 50° C. | |
| MS ionization | ESI | |

Method 4:

HPLC System: Waters ACQUITY; Column: Waters ACQUITY CSH™ C18 1.7 μM Guard column: Waters Assy. Frit, 0.2 μM, 2.1 mm; Column tem: 40° C. Mobile Phase: A: TFA: Water (1:1000, v:v) Mobile phase B: TFA: ACN (1:1000, v:v); Flow Rate: 0.65 mL/min; Injection Volume: 2 μL; Acquisition time: approximately 1.5 minute.

| Gradient Program: | |
|---|---|
| Time (min) | B % |
| 0 | 10 |
| 0.8 | 90 |
| 1.20 | 90 |
| 1.21 | 10 |

Mass Spectrometer Parameters

Mass Spectrometer: Waters SQD; Ionization: Positive Electrospray Ionization (ESI); Mode Scan (100-1400 m/z in every 0.2 second); ES Capillary Voltage: 3.5 kv; ES Cone Voltage: 25 v Source Temperature: 120° C.; Disolvation Temperature: 500° C.; Desolvation Gas Flow: Nitrogen Setting 650 (L/hr); Cone Gas Flow: Nitrogen Setting 50 (L/hr)

Example 1

(R)-tert-butyl 2-isopropyl-4-(3-(methylsulfonyl)phenyl)piperazine-1-carboxylate (Cpd. No. 1-1)

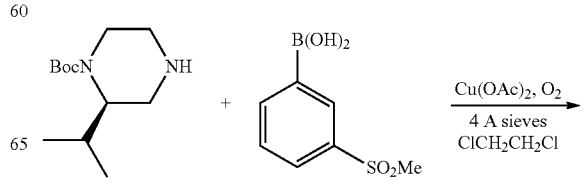

-continued

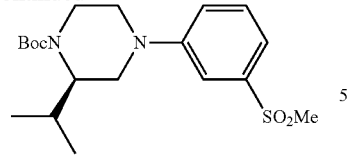

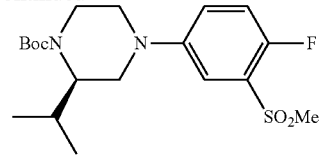

A mixture of (R)-tert-butyl 2-isopropylpiperazine-1-carboxylate (377 mg, 1.65 mmol), (3-(methylsulfonyl)phenyl) boronic acid (660 mg, 3.30 mmol), Cu(OAc)$_2$.H$_2$O (33 mg, 0.17 mmol), powdered 4 A sieves (930 mg) and dry 1,2-dichloroethane (8 mL) was heated at 70° C. under O$_2$ (1 atm, balloon) for 18 h. The mixture was diluted with EtOAc (75 mL) and filtered through Celite. The filtrate was concentrated to leave a brown oil (1.34 g). Chromatography on a 40-g silica cartridge, eluted with a 0-100% EtOAc in hexanes gradient afforded an oil (604 mg). Prep HPLC afforded the title compound (329 mg, 52%) as an oil. LC-MS Method 4 $t_R$=0.97 min, m/z=383, 368, 327, 283. 1H NMR (CDCl$_3$) δ 0.86 (d, 3H), 1.02 (d, 3H), 1.44 (s, 9H), 2.17-2.30 (m, 1H), 2.75-2.90 (m, 2H), 3.01 (s, 3H), 3.02-3.15 (m, 1H), 3.48-3.57 (m, 1H), 3.68-3.74 (m, 1H), 3.95-4.10 (m, 1H), 7.05-7.12 (m, 1H), 7.29-7.45 (m, 3H).

The following compounds are prepared using a similar procedure:

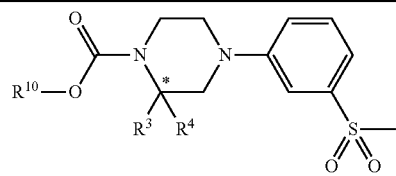

| Cpd No. | R³ | R⁴ | *Stereochem | R¹⁰ | Mass Observed |
|---|---|---|---|---|---|
| 1-2 | i-Bu | H | S | t-Bu | 383, 368, 327, 283 |
| 1-3 | i-Bu | H | R | t-Bu | 397, 341, 297 |
| 1-4 | CO$_2$Me | H | S | t-Bu | 397, 382, 341, 297 |
| 1-5 | Ph | H | RS | t-Bu | 399, 343, 299 |
| 1-6 | Ph | H | S | t-Bu | 417, 361, 317 |
| 1-7 | Bn | H | S | t-Bu | 439, 417, 361, 317 |
| 1-8 | Bn | H | R | t-Bu | 431, 375, 331 |
| 1-9 | 2-Br—Ph | H | RS | t-Bu | 431, 375, 331 |
| 1-10 | Ph | Me | RS | t-Bu | 516.8 |
| 1-11 | c-hex | H | RS | t-Bu | 431.3 |
| 1-12 | 4-Br—Ph | H | RS | t-Bu | 423.2 |
| 1-13 | i-Bu | H | R | Bn | 516.8 |
| 1-14 | Ph | H | RS | Bn | 431 |

Example 2

(R)-tert-butyl 4-(4-fluoro-3-(methylsulfonyl)phenyl)-2-isopropylpiperazine-1-carboxylate (Cpd 2-1)

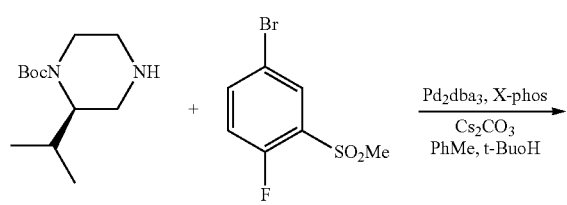

A 50-mL RBF, equipped with a stir bar, was charged with (R)-tert-butyl 2-isopropylpiperazine-1-carboxylate (250 mg, 1.1 mmol), 4-bromo-1-fluoro-2-(methylsulfonyl)benzene (277 mg, 1.1 mmol), Pd2(dba)3 (66 mg, 0.066 mmol), X-phos (157 mg, 0.33 mmol) and Cs$_2$CO$_3$ (892 mg, 2.74 mmol). The flask was sealed with a rubber septum and flushed with N$_2$ for 10 min. Dry toluene (5 mL) and dry t-BuOH (1 mL) were introduced by syringe and the mixture was heated at 110° C. for 20 h. The mixture was diluted with EtOAc (90 mL), washed with water (10 mL) and brine (10 mL), and dried over Na2SO4. Removal of the solid left a yellow solid (730 mg) which was purified by chromatography on a 40-g silica cartridge, eluted with a 0-100% EtOAc in hexanes gradient, to afford (R)-tert-butyl 4-(4-fluoro-3-(methylsulfonyl)phenyl)-2-isopropylpiperazine-1-carboxylate (420 mg, 95%). $^1$H NMR (CDCl$_3$) δ 0.88 (d, 3H), 1.00 (d, 3H), 1.44 (s, 9H), 2.22-2.34 (m, 1H), 2.68-2.71 (m, 2H), 3.02-3.14 (m, 1H), 3.18 (s, 3H), 3.36-3.44 (m, 1H), 3.54-3.62 (m, 1H), 3.70-3.90 (m, 1H), 4.00-4.15 (m, 1H), 7.05-7.18 (m, 2H), 7.36-7.39 (m, 1H). $^{19}$F NMR (CDCl$_3$) δ −122.5. LC-MS Method 4 $t_R$=1.01 min, m/z=423, 401, 345.

The following compounds are prepared using a similar procedure:

| Cpd No | R¹ | R² | R³ | Stereochem | Mass Observed |
|---|---|---|---|---|---|
| 2-2 | Me | H | i-Pr | R | 383, 327, 283 |
| 2-3 | Me | CO$_2$Me | Ph | S | 497.1 |
| 2-4 | Me | 4-ethoxycarbonyl-2-thiazolyl | i-Pr | RS | 538.2 |
| 2-5 | NMePMB | F | i-Pr | R | 558, 536 |

Example 3

(R)-tert-butyl 4-(4-cyano-3-(methylsulfonyl)phenyl)-2-isopropylpiperazine-1-carboxylate (Cpd No 3-1)

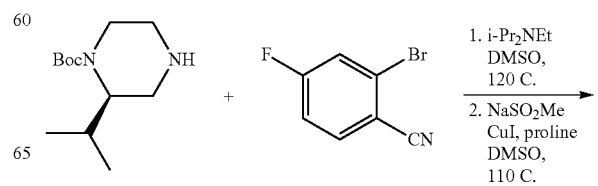

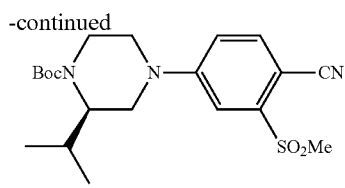

Step 1

A stirred solution of (R)-tert-butyl 2-isopropylpiperazine-1-carboxylate (360 mg, 1.58 mmol), 2-bromo-4-fluorobenzonitrile (316 mg, 1.58 mmol), i-Pr$_2$NEt (0.6 mL, 3.3 mmol) and DMSO (4 mL) was heated at 120° C. for 2 h. The mixture was cooled to rt and used directly in the next step.

Step 2

NaSO$_2$Me (1.61 g, 15.8 mmol) and proline (55 mg, 0.47 mmol) were added to the mixture. The mixture was sparged with N$_2$ for 10 min and CuI (54 mg, 0.28 mmol) was added. The mixture was heated at 110° C. under N$_2$ for 16 h. The mixture was cooled, diluted with EtOAc (100 mL), washed with water (2×10 mL) and brine (10 mL), and dried over Na$_2$SO$_4$. Removal of the solvent left an orange oil (677 mg). Chromatography on a 40-g silica cartridge eluted with a 0-100% EtOAc in hexanes gradient afforded (R)-tert-butyl 4-(3-bromo-4-cyanophenyl)-2-isopropylpiperazine-1-carboxylate (403 mg, 62%) and the title compound (75 mg, 11%). LC-MS Method 4 t$_R$=0.96 min, m/z=408, 352, 308.

Cpd No 3-2, tert-butyl (R)-2-isopropyl-4-(3-(methylsulfonyl)-4-(trifluoromethyl)phenyl)piperazine-1-carboxylate, is prepared following similar procedures using 2-bromo-4-fluoro-1-(trifluoromethyl)benzene in Step 1. LC-MS m/z=473, 395, 351.

Cpd No 3-3, (R)-2-(4-(4-fluoro-3-(methylsulfonyl)phenyl)-2-isopropylpiperazin-1-yl)-4-methyl-5-(methylsulfonyl)pyrimidine, is prepared from was prepared from (R)-5-bromo-2-(4-(4-fluoro-3-(methylsulfonyl)phenyl)-2-isopropylpiperazin-1-yl)-4-methylpyrimidine using the conditions in Step 2. LC-MS m/z=471.

Example 4

(R)-tert-butyl 4-(4-carbamoyl-3-(methylsulfonyl)phenyl)-2-isopropylpiperazine-1-carboxylate (Cpd 4-1)

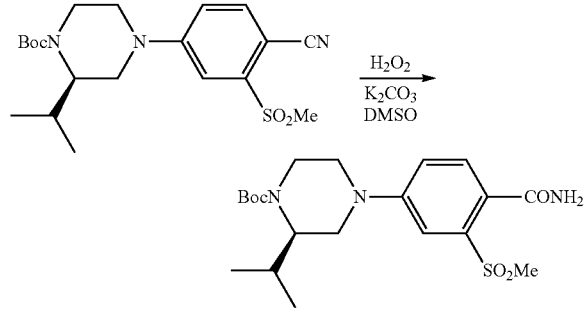

To a stirred solution of (R)-tert-butyl 4-(4-cyano-3-(methylsulfonyl)phenyl)-2-isopropylpiperazine-1-carboxylate (21 mg, 0.052 mmol) in DMSO (1 mL), were added solid K$_2$CO$_3$ (4 mg, 0.029 mmol) and 30% H$_2$O$_2$ (0.1 mL). The mixture was stirred at rt for 7 h, diluted with MeOH and purified by prep HPLC to afford the title compound (9.6 mg, 44%). LC-MS Method 4 t$_R$=0.85 min, m/z=370, 326.

The following compounds are prepared from the corresponding nitriles using similar procedures.

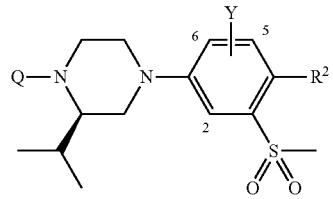

| Cpd No. | R$^2$ | Y | Q | Mass Observed |
|---|---|---|---|---|
| 4-2 | CONH$_2$ | H | 4-CF$_3$-2-pyrimidinyl | 472 |
| 4-3 | CONH$_2$ | 2-Cl | 4-CF$_3$-2-pyrimidinyl | 506 |
| 4-4 | CONH$_2$ | 6-Cl | 4-CF$_3$-2-pyrimidinyl | 506 |
| 4-5 | F | H | 4-carbamoyl-2-pyrimidinyl | 422 |
| 4-6 | CH$_2$OH | H | 2-carbamoyl-2-pyridinyl | 433.1 |
| 4-7 | F | H | 5-CF$_3$-4-carbamoyl-2-pyridinyl | 490 |

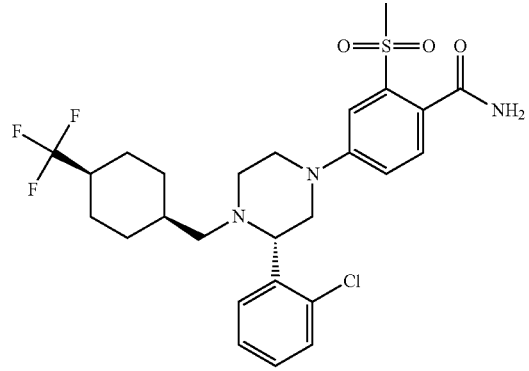 [SMILES: CS(=O)(=O)c1cc(N2CCN(C[C@H]3CC[C@@H](C(F)(F)F)CC3)[C@@H](c3ccccc3Cl)C2)ccc1C(N)=O]

Cpd No 4-8[a], m/z = 558.1

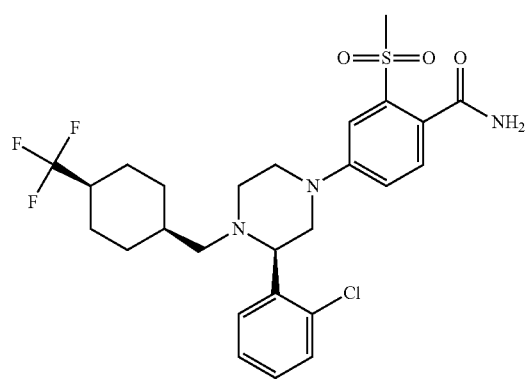 [SMILES: CS(=O)(=O)c1cc(N2CCN(C[C@H]3CC[C@@H](C(F)(F)F)CC3)[C@H](c3ccccc3Cl)C2)ccc1C(N)=O]

Cpd No 4-9[a], m/z = 558.1

[a]Isomers are separated on a chiral column, stereochemistry assigned arbitrarily.

Example 5

(2R)-2,2,3,3-tetrafluorocyclobutyl 4-(4-fluoro-3-(methylsulfonyl)phenyl)-2-isopropylpiperazine-1-carboxylate (Cpd No 5-1)

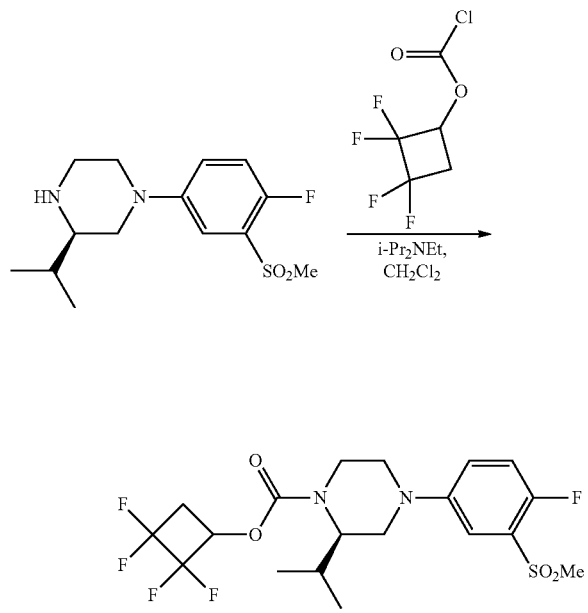

To a stirred solution of (R)-1-(4-fluoro-3-(methylsulfonyl)phenyl)-3-isopropylpiperazine (10 mg, 32 μmol) and i-Pr$_2$NEt (25 μL, 0.14 mmol) in CH$_2$Cl$_2$ (1 mL) was added 0.11 M 2,2,3,3-tetrafluorocyclobutyl chloroformate in ether (0.6 mL, 0.06 mmol). The mixture was stirred at rt for 1 h and concentrated. The residue was purified by prep HPLC to afford the title compound (7 mg, 44%) as an oil. LC-MS Method 4 t$_R$=1.03 min, m/z=471.

The following compounds are prepared by analogous procedures:

| Cpd No. | R$^2$ | R$^3$ | *Stereochem | R$^{10}$ | Mass Observed |
|---|---|---|---|---|---|
| 5-2 | F | i-Pr | R | CF$_3$CMe$_2$ | 455 |
| 5-3 | F | i-Pr | R | CF$_3$CHMe | 441 |
| 5-4 | F | i-Pr | R | CF$_3$CH$_2$ | 427 |
| 5-5 | H | Ph | RS | i-Bu | 417 |
| 5-6 | H | i-Pr | R | t-BuCH$_2$ | 397 |
| 5-7 | H | i-Pr | R | i-Bu | 383 |
| 5-8 | H | Ph | RS | i-Pr | 403 |

Example 6 tert-butyl (S)-2-(2-hydroxypropan-2-yl)-4-(3-(methylsulfonyl)phenyl)piperazine-1-carboxylate (Cpd 6-1)

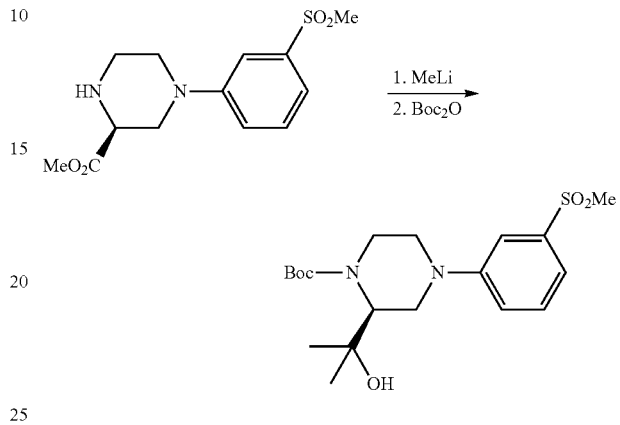

To a stirred, ice-cold suspension of methyl (S)-4-(3-(methylsulfonyl)phenyl)piperazine-2-carboxylate (28 mg, 0.084 mmol) in dry THF (2 mL) was added 2.2 M MeLi in Et$_2$O (0.1 mL, 0.22 mmol). The mixture was allowed to warm to rt and stirred overnight. Water (2 mL) was added, followed by Boc$_2$O (100 mg). The mixture was stirred for 1 d and concentrated to leave an aqueous residue which was partitioned between brine (10 mL) and EtOAc (100 mL). The organic layer was dried over Na$_2$SO$_4$ and concentrated to leave an oil (18 mg). Prep HPLC gave the title compound (1.3 mg, 4%) as an oil. $^1$H NMR (CD$_3$OD) δ 1.24 (s, 3H), 1.26 (s, 3H), 1.42 (s, 9H), 3.03-3.10 (m, 1H), 3.09 (s, 3H), 3.21-3.33 (m, 1H), 3.44-3.56 (m, 2H), 3.84-3.92 (m, 1H), 4.10-4.20 (m, 2H), 7.22-7.52 (m, 4H). LC-MS m/z=399, 343, 325

Example 7

(R)-2-(4-(4-fluoro-3-(methylsulfonyl)phenyl)-2-isopropylpiperazin-1-yl)-4-(trifluoromethyl)pyrimidine

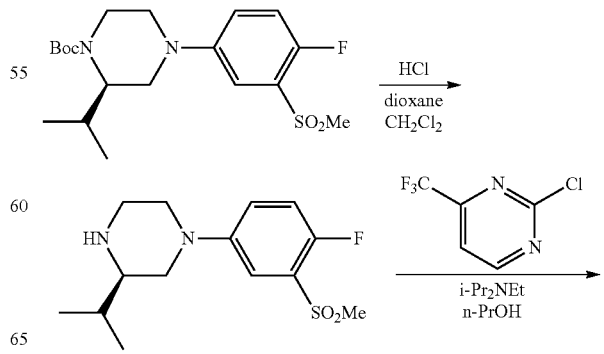

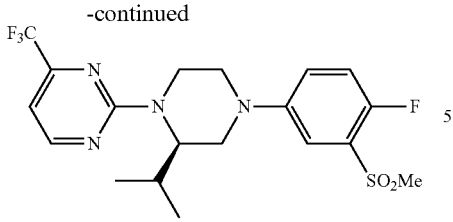

Step 1
To a stirred solution of (R)-tert-butyl 4-(4-fluoro-3-(methylsulfonyl)phenyl)-2-isopropylpiperazine-1-carboxylate (420 mg, 1.05 mmol) in $CH_2Cl_2$ (5 mL) was added 4 M HCl in dioxane (5 mL, 20 mmol). The mixture was stirred at rt for 2 h and concentrated to provide (R)-1-(4-fluoro-3-(methylsulfonyl)phenyl)-3-isopropylpiperazine as its HCl salt (415 mg, quant). LC-MS Method 4 $t_R$=0.57 min, m/z=301.

Step 2
A mixture of (R)-1-(4-fluoro-3-(methylsulfonyl)phenyl)-3-isopropylpiperazine HCl salt (34 mg, 0.1 mmol), 2-chloro-4-(trifluoromethyl)pyrimidine (28 mg, 0.15 mmol), i-$Pr_2NEt$ (0.11 mL, 0.6 mmol) and n-PrOH (0.5 mL) was heated in the microwave at 150 C for 2 h. The mixture was diluted with MeOH (1 mL) and purified by prep HPLC to afford (R)-2-(4-(4-fluoro-3-(methylsulfonyl)phenyl)-2-isopropylpiperazin-1-yl)-4-(trifluoromethyl)pyrimidine TFA salt (26 mg, 46%) as a solid. $^1$H NMR ($CD_3OD$) δ 0.90 (d, 3H), 1.11 (d, 3H), 2.42-2.55 (m, 1H), 2.74-2.86 (m, 2H), 3.23 (s, 3H), 3.28-3.38 (m, 1H), 3.60-3.66 (m, 1H), 3.80-3.86 (m, 1H), 4.66-4.74 (m, 1H), 4.80-4.85 (m, 1H), 6.83 (d, 1H), 7.22-7.35 (m, 2H), 7.39-7.42 (m, 1H), 8.56 (d, 1H). $^{19}$F NMR ($CD_3OD$)-72.5, −78.0, −125.0. LC-MS Method 4 $t_R$=1.08 min, m/z=448.

The following compounds are prepared using procedures analogous to those described above:

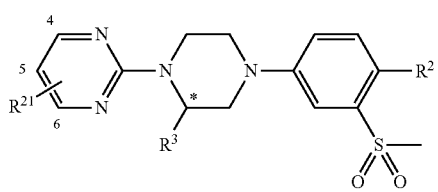

| Cpd No. | $R^2$ | $R^3$ | *Stereochem | $R^{10}$ | Mass Observed |
|---|---|---|---|---|---|
| 7-2 | H | i-Pr | R | H | 361 |
| 7-3 | H | i-Pr | R | 4,6-dimethyl | 389 |
| 7-4 | H | i-Pr | R | 5-Cl | 397, 395 |
| 7-5 | H | i-Pr | R | 5-cyclopropyl | 401.2 |
| 7-6 | H | i-Pr | R | 4-i-Pr | 403.2 |
| 7-7 | F | i-Pr | R | 4-cyano | 404 |
| 7-8 | F | i-Pr | R | 4-cyano-6-methyl | 418 |
| 7-9 | H | i-Pr | R | 5-$MeO_2C$ | 419 |
| 7-10 | F | i-Pr | R | 4-cyclopropyl | 419 |
| 7-11 | H | i-Pr | R | 5-difluoromethoxy | 427.0 |
| 7-12 | F | i-Pr | R | 4-methyl-5-chloro | 429, 428 |
| 7-13 | H | i-Pr | R | 4-$CF^3$ | 429 |
| 7-14 | F | i-Pr | R | 5-$MeO_2C$ | 437 |
| 7-15 | F | i-Pr | R | 4-$MeO_2C$ | 437 |
| 7-16 | H | i-Pr | R | 5-Br | 438.9 |
| 7-17 | CN | i-Pr | R | 4-$CF_3$ | 454 |
| 7-18 | F | i-Pr | R | 4-$CF_3$-6-Me | 461 |
| 7-19 | F | i-Pr | R | 4-Me-5-$EtO_2C$ | 465 |
| 7-20 | F | i-Pr | R | 4-Me-5-Br | 471 |
| 7-21 | F | i-Pr | R | 4-$CF_3$-5-cyano | 472.1 |
| 7-22 | F | $CH_2CF_3$ | RS | 4-Me-5-$EtO_2C$ | 505 |
| 7-23 | F | i-Pr | R | 4-Me-5-F | 411 |
| 7-24 | H | $CMe_2OH$ | R | 4-$CF_3$ | 445 |
| 7-25 | H | $CF_2Me$ | R | 4-$CF_3$ | 451.2 |
| 7-26 | H | $CF_2Me$ | S | 4-$CF_3$ | 451.2 |
| 7-27 | H | $CF_3$ | R | 4-$CF_3$ | 455.2 |
| 7-28 | H | $CF_3$ | S | 4-$CF_3$ | 455.2 |
| 7-29 | F | t-Bu | RS | 4-$CF_3$ | 461 |
| 7-30$^a$ | H | Ph | S | 4-$CF_3$ | 463 |
| 7-31$^a$ | H | Ph | R | 4-$CF_3$ | 463.1 |
| 7-32 | F | i-Pr | R | 4-$CF_3$ | 544 |

$^a$Isomers are separated on a chiral column, stereochemistry assigned arbitrarily.

The following compounds are prepared using procedures analogous to those described above:

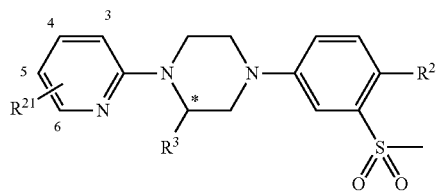

| Cpd No. | $R^2$ | $R^3$ | *Stereochem | $R^{10}$ | Mass Observed |
|---|---|---|---|---|---|
| 7-33 | F | i-Pr | R | 5-F-6-$CF_3$ | 464 |
| 7-34 | H | i-Pr | R | 5-$CHF_2$ | 410.1 |
| 7-35 | H | i-Pr | R | 5-$CF_3$ | 428 |
| 7-36 | F | i-Pr | R | 5-$CF_3$ | 446 |
| 7-37 | CN | i-Pr | R | 5-$CF_3$ | 453 |
| 7-38 | CN | i-Pr | R | 6-$CF_3$ | 453 |
| 7-39 | CN | i-Pr | R | 4-$CF_3$ | 453 |
| 7-40 | H | Ph | S | 5-$CF_3$ | 462 |
| 7-41 | F | i-Pr | R | 3-Cl-6-$CF_3$ | 480 |
| 7-42 | F | i-Pr | R | 3-nitro-5-$CF_3$ | 491 |
| 7-43 | F | i-Pr | R | 5-$EtO_2C$-6-$CF_3$ | 526, 504 |

The following compounds are prepared using procedures analogous to those described above:

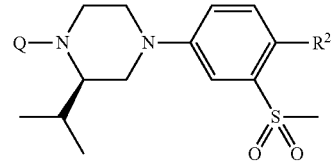

| Cpd No. | $R^2$ | Q | Mass Observed |
|---|---|---|---|
| 7-44 | F | 5-CF3-2-pyrazinyl | 447 |
| 7-45 | F | 6-CF3-2-pyrazinyl | 447 |
| 7-46 | H | 6-Me-3-pyridazinyl | 375.2 |
| 7-47 | H | 6-c-Pr-3-pyridazinyl | 401.0 |
| 7-48 | H | 6-$CF_3$-3-pyridazinyl | 429.1 |
| 7-49 | F | 6-$CF_3$-3-pyridazinyl | 447.1 |
| 7-50 | H | 2-$CF_3$-4-pyrimidinyl | 429 |

-continued

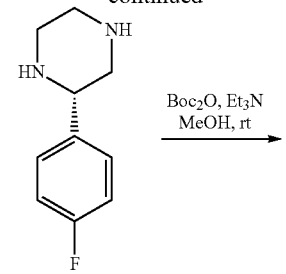

| Cpd No. | R² | Q | Mass Observed |
|---|---|---|---|
| 7-51 | H | 5-CF3-1,2,4-thiadiazol-3-yl | 435 |
| 7-52 | F | 2-benzoxazolyl | 418 |
| 7-53 | F | 6-cyano-2-benzothiazolyl | 459 |
| 7-54 | F | 4-fluoro-2-benzothiazolyl | 452 |
| 7-55 | F | 6-fluoro-2-benzothiazolyl | 452 |
| 7-56 | F | 2-benzothiazolyl | 434 |
| 7-57 | F | thiazolo[5,4-b]pyridin-2-yl | 435 |
| 7-58 | F | thiazolo[4,5-c]pyridin-2-yl | 435 |
| 7-59 | F | thiazolo[4,5-b]pyridin-2-yl | 435 |

The following compound is prepared using procedures analogous to those described above, combined with those in Example 18:

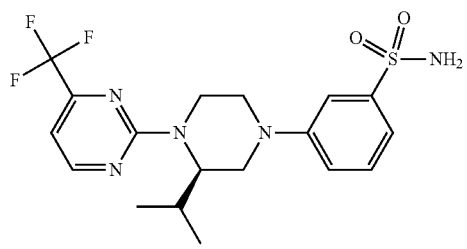

Cpd No 7-60
Mass observed: 430.1

Example 8

(R)-2-(2-(4-fluorophenyl)-4-(3-(methylsulfonyl)phenyl)piperazin-1-yl)-4-(trifluoromethyl)pyrimidine

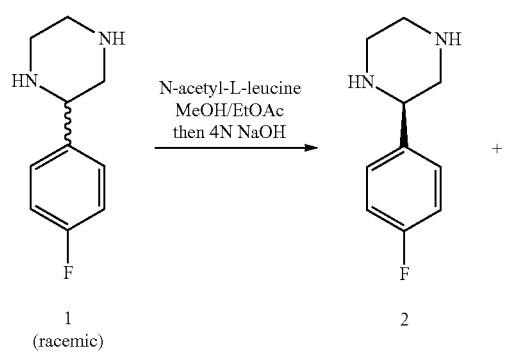

1 (racemic)

N-acetyl-L-leucine
MeOH/EtOAc
then 4N NaOH
→

2

+

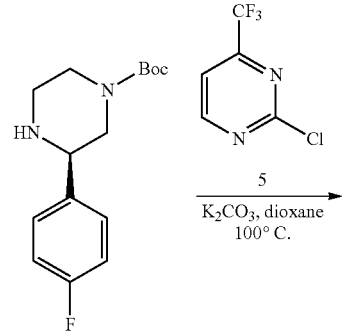

3

Boc₂O, Et₃N
MeOH, rt
→

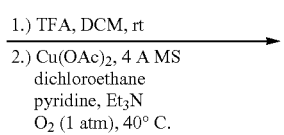

4
93% ee

K₂CO₃, dioxane
100° C.
→

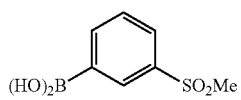

6

1.) TFA, DCM, rt
2.) Cu(OAc)₂, 4 A MS
    dichloroethane
    pyridine, Et₃N
    O₂ (1 atm), 40° C.
→

(HO)₂B—⟨⟩—SO₂Me

7

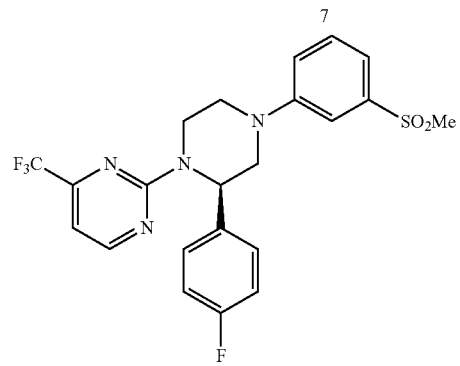

8

Step 1:
To a solution of compound racemic 1 (1180 mg, 6.56 mmol) in 12 mL of MeOH was added a solution of N-acetyl-L-leucine (1920 mg, 11.09 mmol) in 7 mL of MeOH. To this solution was added 64 mL of EtOAc slowly down the walls of the flask at rt. After 15 h the resulting precipitate was filtered off, washed with EtOAc, and dried under high vacuum. After drying, the white solid was taken up in 4 N NaOH (30 mL) and the product was extracted with CH₂Cl₂ (4×30 mL). The CH₂Cl₂ layers were combined, dried over Na₂SO₄ and evaporated to give a white solid material. Recrystallization of this material from EtOAc (~15 mL) gave white crystalline compound 3 upon standing after ~24 h at rt. Additional crystalline material was collected after three crystallizations from the EtOAc mother liquor. The mother liquor was evaporated to afford 300 mg of compound 2 as a white solid which was determined to be 93% enantiopure after chiral HPLC analysis of the subsequent Boc protected material (see compound 4 of next step). Based on literature precedence, this compound was assigned as the R isomer. (Fink, D. M. et al.; "Preparation of substituted bis aryl and heteroaryl compounds as selective 5HT2a antagonists" PCT Int. Appl. WO2006086705; Aug. 17, 2006) LC-MS tR=0.210 min in 2 min chromatography, MS (ESI) m/z 181.19 [M+H]+. 1H NMR (CD3OD) δ 7.34-7.30 (2H, m), 7.01-6.97 (2H, m), 3.67 (dd, J=2.8, 11.0 Hz, 1H), 2.98-2.94 (m, 1H), 2.90-2.81 (m, 3H), 2.73 (dd, J=3.6, 13.0 Hz, 1H), 2.57 (dd, J=10.4, 12.2 Hz, 1H).

Step 2

To a solution of compound 2 (300 mg, 1.67 mmol) in MeOH (10 mL) was added Et₃N (0.58 mL, 4.18 mmol) at rt. To this solution was added a solution of Boc₂O (363 mg, 1.67 mmol) in 2 mL of MeOH dropwise at rt over a 5 min period. After stirring at rt for 2 h, the MeOH was removed by rotovap. The crude product was dissolved in 15 mL of CH₂Cl₂ and washed twice with water (10 mL). The CH₂Cl₂ layer was dried over Na₂SO₄ and evaporated to give crude compound 4. Purification by ISCO flash chromatography gave 465 mg of compound 4 (99% yield). Chiral HPLC analysis of compound 4 revealed a 27:1 mixture of enantiomers (93% ee). Based on literature precedence, the major enantiomer was assigned as the R isomer. (Fink, D. M. et al.; "Preparation of substituted bis aryl and heteroaryl compounds as selective 5HT2a antagonists" PCT Int. Appl. WO2006086705; Aug. 17, 2006) LC-MS tR=1.022 min in 2 min chromatography, MS (ESI) m/z 281.31 [M+H]+. 1H NMR (CDCl3) 7.39-7.34 (m, 2H), 7.04-7.00 (m, 2H), 4.03 (bs, 2H), 3.68 (dd, J=2.8, 10.6 Hz, 1H), 3.06 (d, J=9.2 Hz, 1H), 2.89-2.83 (m, 2H), 2.68 (bs, 1H), 1.72 (bs, 1H), 1.47 (s, 9H).

Step 3

A suspension of 4 (50 mg, 0.18 mmol), 5 (0.04 mL, 0.36 mmol) and K2CO3 (75 mg, 0.54 mmol) in dioxane (3 mL) was heated to 100° C. in C a sealed vial for 24 h. The mixture was filtered through a pad of celite and the celite was washed with EtOAc. The solvent was removed by rotovap to afford crude compound 6. Purification using ISCO flash chromatography afforded 68 mg of compound 6 (89% yield). LC-MS tR=2.275 min in 3 min chromatography, MS (ESI) m/z 427.38 [M+H]+. 1H NMR (CDCl3) 8.52 (d, J=5.2 Hz, 1H), 7.33-7.29 (m, 2H), 7.01-6.96 (m, 2H), 6.82 (d, J=5.2 Hz, 1H), 5.97 (bs, 1H), 4.66 (d, J=12.4 Hz, 1H), 4.55 (bs, 1H), 4.09-3.89 (m, 1H), 3.40 (d, J=12.4 Hz, 1H), 3.22 (bs, 1H), 3.07 (bs, 1H), 1.44 (s, 9H).

Step 4

To a solution of 6 (23 mg, 0.054 mmol) in 2 mL of CH₂Cl₂ was added 1 mL of TFA at rt. After stirring for 1 h at rt, the solvents were removed under rotovap and the crude piperazine intermediate (as TFA salt) was placed under high vacuum for 1 h. This material was used directly for the next step without further purification.

Step 5

In a separate flask, a suspension of compound 7 (22 mg, 0.11 mmol), Cu(OAc)₂ (1 mg, 0.005 mmol) and 4 A MS (25 mg) in 3 mL of dichloroethane was stirred at rt for 5 min. A solution of the above crude piperazine (TFA salt), Et₃N (0.015 mL, 0.108 mmol) and pyridine (0.009 mL, 0.108 mmol) in 1 mL of dichloroethane was added at rt. The light blue reaction mixture was evacuated, purged with O₂, and stirred at 40° C. under 1 atm of 0₂ for 24 h. The mixture was then filtered through celite, evaporated, and purified on the Gilson-HPLC to afford 6 mg of compound 8 (23% yield). LC-MS tR=2.09 min in 3 min chromatography, MS (ESI) m/z 481.35 [M+H]+. 1H NMR (CD₃OD) 8.61 (d, J=4.8 Hz, 1H), 7.50-7.45 (m, 3H), 7.41 (t, J=2.0 Hz, 1H), 7.33 (dd, J=1.2, 7.4 Hz, 1H), 7.27 (dd, J=2.0, 8.4 Hz, 1H), 7.04-6.98 (m, 2H), 6.94 (d, J=5.2 Hz, 1H), 6.02 (t, J=4.0 Hz, 1H), 4.79-4.73 (m, 1H), 4.27-4.23 (m, 1H), 3.82-3.78 (m, 1H), 3.68-3.61 (m, 1H), 3.52 (dd, J=4.4, 13.2 Hz, 1H), 3.19-3.13 (m, 1H), 3.09 (s, 3H).

Example 9

(R)-ethyl 2-(4-(4-fluoro-3-(methylsulfonyl)phenyl)-2-isopropylpiperazin-1-yl)-4-(trifluoromethyl)pyrimidine-5-carboxylate

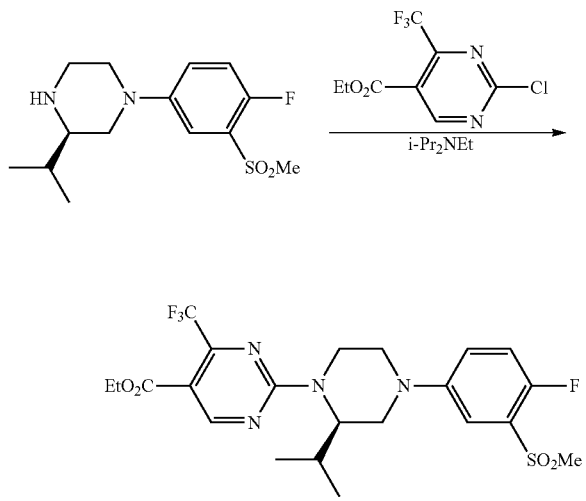

To a stirred solution of (R)-1-(4-fluoro-3-(methylsulfonyl)phenyl)-3-isopropylpiperazine (73 mg, 0.24 mmol) and i-Pr₂NEt (0.175 mL, 0.97 mmol) in dioxane (2 mL) was added ethyl 2-chloro-4-(trifluoromethyl)pyrimidine-5-carboxylate (62 mg, 0.24 mmol). The mixture was stirred at rt for 1 day and concentrated. The residue was taken up in EtOAc (90 mL), washed with 5% aq HCl (10 mL) and brine (10 mL), and dried over Na₂SO₄. Removal of the solvent left an oil (112 mg). Chromatography on a 40-g silica gel cartridge, eluted with an EtOAc/hexane gradient afforded the title compound (36 mg, 29%) as an oil. LC-MS Method 4 tR=1.12 min, m/z=541, 519.

The following compounds are prepared using procedures analogous to those described above:

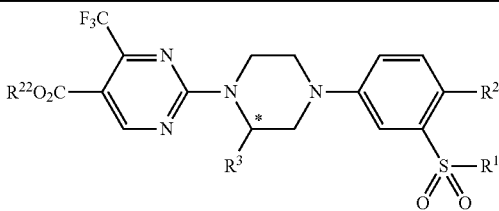

| Cpd No. | R¹ | R² | R³ | *Stereochem | R²² | Mass Observed |
|---|---|---|---|---|---|---|
| 9-2 | Me | F | i-Pr | R | Me | 505 |
| 9-3 | PMBNMe | F | i-Pr | R | Me | 663, 640 |
| 9-4 | Me | F | c-Pr | R | Et | 517.4 |
| 9-5 | Me | F | t-Bu | RS | Me | 519 |
| 9-6 | NHMe | F | i-Pr | R | Me | 543, 520 |
| 9-7 | Me | F | i-Bu | R | Et | 533 |
| 9-8 | Me | H | 4-Me-2-thiazolyl | S | Et | 556.5 |
| 9-9 | Me | F | 4-F—Ph | R | Me | 557.5 |
| 9-10 | Me | CH₂OAc | i-Pr | R | Et | 573.2 |
| 9-11 | Me | 5-Me-(1,3,4-oxadiazol-2yl) | i-Pr | R | Et | 583 |
| 9-12 | Me | 3-Me-(1,2,4-oxadiazol-5-yl) | i-Pr | R | Et | 583 |
| 9-13 | Me | 5-Me-(1,3,4-thiadiazol-2yl) | i-Pr | R | Et | 599 |
| 9-14 | Me | 4-carbamoyl-2-thiazolyl | i-Pr | R | Et | 627.2 |

Example 10

(R)-2-(2-(4-(4-fluoro-3-(methylsulfonyl)phenyl)-2-isopropylpiperazin-1-yl)-4-(trifluoromethyl)pyrimidin-5-yl)propan-2-ol

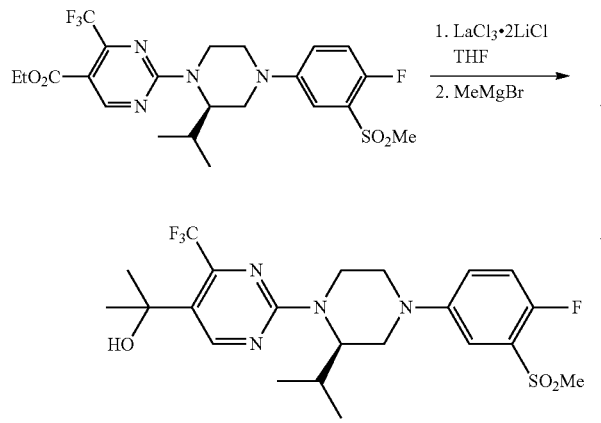

To a stirred solution of (R)-ethyl 2-(4-(4-fluoro-3-(methylsulfonyl)phenyl)-2-isopropylpiperazin-1-yl)-4-(trifluoromethyl)pyrimidine-5-carboxylate (292 mg, 0.56 mmol) in dry THF (4 mL) at rt, was added 0.6 M LaCl₃·2LiCl in THF (0.94 mL, 0.56 mmol). The mixture was stirred at rt for 1 h, cooled in an ice bath and treated with 3 M MeMgBr in THF (0.95 mL, 2.8 mmol). The ice bath was maintained for 2 h and then allowed to melt. After an additional 2 h (internal temperature=15° C.), satd aq NaHCO3 (10 mL) was added. The mixture was extracted with EtOAc (100 mL). The organic layer was washed with brine (10 mL), dried over Na₂SO₄ and concentrated to afford an orange oil (228 mg) which was purified by prep HPLC. Fractions containing the title compound were treated with solid K₂CO₃, pooled and concentrated without heating above rt. The aqueous residue was diluted with brine (15 mL) and extracted with CH₂Cl₂ (3×50 mL). The organic layer was dried over Na₂SO₄ and K₂CO₃ and concentrated to provide the title compound (96 mg, 33%). LC-MS Method 4 tR=1.01 min, m/z=505, 487. 1H NMR (CD₃OD) δ 0.80 (d, 3H), 1.11 (d, 3H), 1.58 (s, 6H), 2.42-2.55 (m, 1H), 2.73-2.86 (m, 2H), 3.22 (s, 3H), 3.25-3.38 (m, 1H), 3.58-3.64 (m, 1H), 3.80-3.86 (m, 1H), 4.63-4.68 (m, 1H), 4.78-4.86 (m, 1H), 7.21-7.34 (m, 2H), 7.38-7.42 (m, 1H), 8.76 (s, 1H).

The following compounds are prepared following a procedure analogous to that described above:

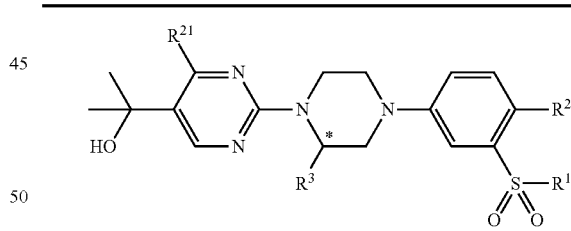

| Cpd No. | R¹ | R² | R³ | *Stereochem | R²¹ | Mass Observed |
|---|---|---|---|---|---|---|
| 10-2 | NH₂ | F | i-Pr | R | CF₃ | 506 |
| 10-3 | NHMe | F | i-Pr | R | CF₃ | 542, 520 |
| 10-4 | Me | F | t-Bu | RS | CF₃ | 519 |
| 10-5 | Me | CH₂OH | i-Pr | S | CF₃ | 517.2 |
| 10-6 | Me | F | CH₂CF₃ | RS | Me | 491 |
| 10-7 | Me | CH₂OH | i-Pr | R | CF₃ | 517 |

The following compounds are prepared from the corresponding methyl or ethyl esters following a procedure analogous to that described above

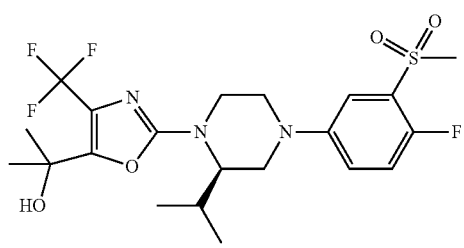

Cpd No 10-8, m/z = 494.2

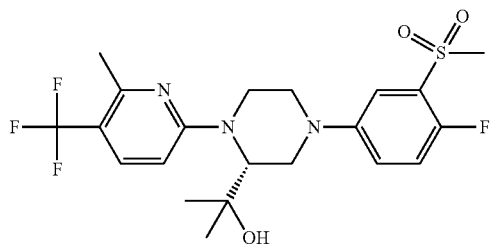

Cpd No 10-9, m/z = 476.2

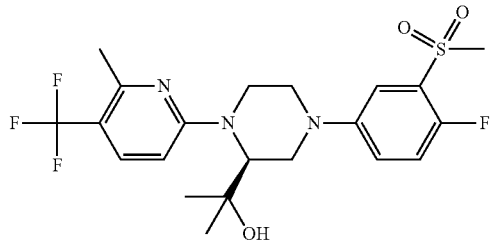

Cpd No 10-10, m/z = 476.1

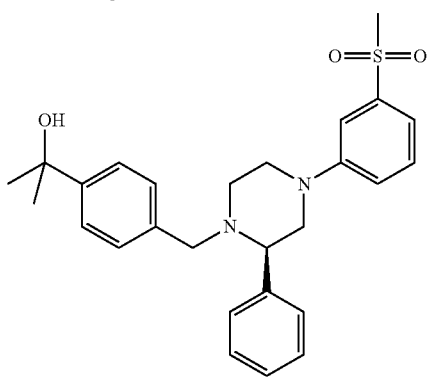

Cpd No 10-11[a], m/z = 487.0

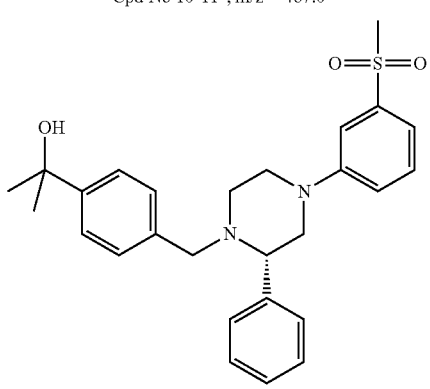

Cpd No 10-12[a], m/z = 487.1

-continued

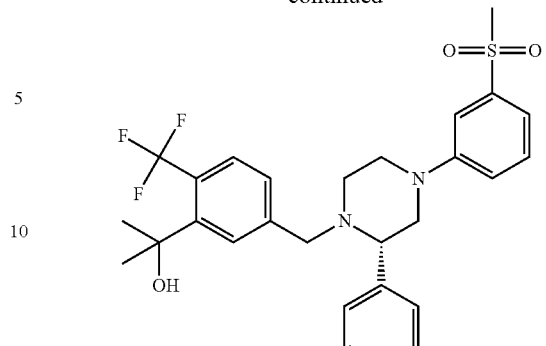

Cpd No 10-13[b], m/z = 533.5

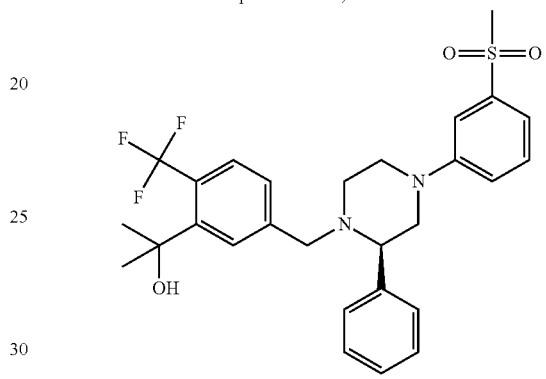

Cpd No 10-14[b], m/z = 533.5

[a,b]Isomers are separated on a chiral column, stereochemistry assigned arbitrarily.

Example 11

(R)-(2-(4-(4-fluoro-3-(methylsulfonyl)phenyl)-2-isopropylpiperazin-1-yl)-4-(trifluoromethyl)pyrimidin-5-yl)methanol

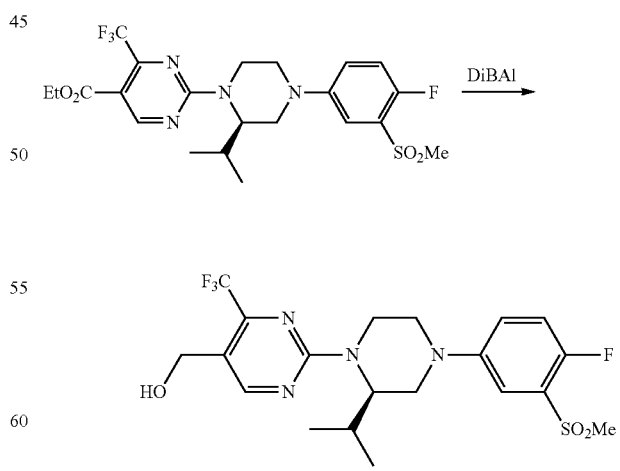

A stirred solution of (R)-ethyl 2-(4-(4-fluoro-3-(methylsulfonyl)phenyl)-2-isopropylpiperazin-1-yl)-4-(trifluoromethyl)pyrimidine-5-carboxylate (136 mg, 0.27 mmol) in dry toluene (4 mL) was cooled to −70° C. and 1 M DiBAl in toluene (1 mL, 1 mmol) was added dropwise over 2 min. The mixture was stirred at −70° C. for 1.5 h and aq Rochelle salt solution (1 mL) was added. The mixture was allowed to warm to rt, diluted with brine (10 mL) and extracted with EtOAc (2×60 mL). The combined organic layer was dried over Na$_2$SO$_4$ and concentrated to leave an oil (135 mg). A 14 mg aliquot was purified by prep HPLC to afford the title compound (6 mg) as an oil. LC-MS Method 4 tR=0.94 min, m/z=477. 1H NMR (CD$_3$OD) δ 0.80 (d, 3H), 1.13 (d, 3H), 2.42-2.56 (m, 1H), 2.74-2.90 (m, 2H), 3.22 (s, 3H), 3.30-3.40 (m, 1H), 3.60-3.66 (m, 1H), 3.82-3.86 (m, 1H), 4.59 (s, 2H), 4.66-4.72 (m, 1H), 4.82-4.86 (m, 1H), 7.23-7.36 (m, 2H), 7.38-7.43 (m, 1H), 8.60 (s, 1H).

The following compounds are prepared following a procedure analogous to that described above:

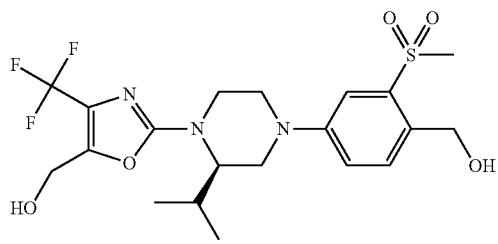

Cpd No 11-16, mass observed 478.1

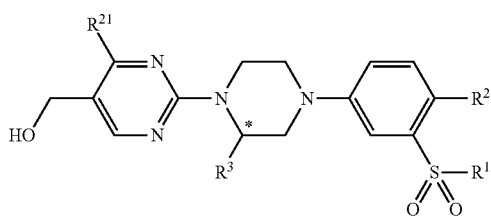

| Cpd No. | R$^1$ | R$^2$ | R$^3$ | *Stereochem | R$^{21}$ | Mass Observed |
|---|---|---|---|---|---|---|
| 11-2 | NH$_2$ | F | i-Pr | R | CF$_3$ | 478 |
| 11-3 | Me | Cl | i-Pr | R | CF$_3$ | 493.1 |
| 11-4$^a$ | Me | CH$_2$OH | CH(OMe)Me | S | CF$_3$ | 505.1 |
| 11-5$^a$ | Me | CH$_2$OH | CH(OMe)Me | S | CF$_3$ | 505.1 |
| 11-6 | Me | CH$_2$OH | i-Pr | R | CF$_3$ | 507.1 |
| 11-7 | Me | F | 4-F—Ph | R | CF$_3$ | 529.5 |
| 11-8 | Me | 4-Me-2-oxazolyl | i-Pr | R | CF$_3$ | 540.2 |
| 11-9 | Me | 5-Me-(1,3,4-oxadiazol-2yl) | i-Pr | R | CF$_3$ | 541 |
| 11-10 | Me | 3-Me-(1,2,4-oxadiazol-5-yl) | i-Pr | R | CF$_3$ | 523, 541, 563 |
| 11-11 | Me | 5-Me-(1,3,4-thiadiazol-2yl) | i-Pr | R | CF$_3$ | 557 |
| 11-12 | Me | 4-cyano-2-thiazolyl | i-Pr | R | CF$_3$ | 567.1 |
| 11-13 | Me | 4-H$_2$NCO-2-thiazolyl | i-Pr | R | CF$_3$ | 585.1 |
| 11-14 | Me | F | H | R | Me | 423 |

$^a$Isomers are separated on a chiral column, stereochemistry assigned arbitrarily.

The following compounds are prepared from the corresponding methyl or ethyl esters following a procedure analogous to that described above

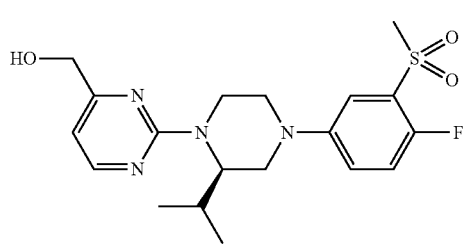

Cpd No 11-15, mass observed 409

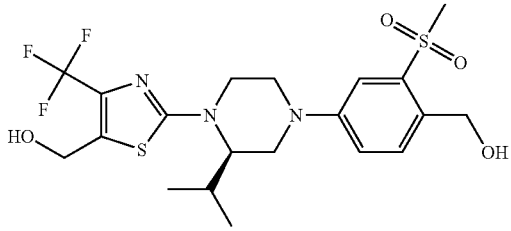

Cpd No 11-17, mass observed 494.1

Example 12

1-(2-((R)-4-(4-fluoro-3-(methylsulfonyl)phenyl)-2-isopropylpiperazin-1-yl)-4-(trifluoromethylpyrimidin-5-yl)ethanol (Cpd No 12-1)

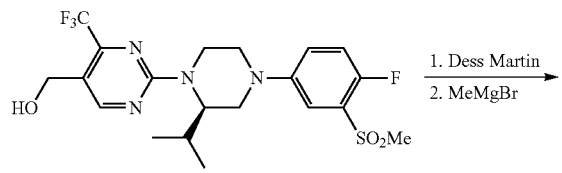

Step 1

To a stirred, ice-cold solution of (R)-(2-(4-(4-fluoro-3-(methylsulfonyl)phenyl)-2-isopropylpiperazin-1-yl)-4-(trifluoromethyl)pyrimidin-5-yl)methanol (120 mg, 0.25 mmol) in dry CH$_2$Cl$_2$ (10 mL) was added Dess-Martin periodinane (534 mg, 1.26 mmol). The ice bath was allowed to melt and the mixture was stirred for 3 h. Satd aq NaHCO3 (20 mL) and solid Na$_2$S$_2$O$_3$ (0.5 g) were added and the mixture was stirred for 0.5 h. The mixture was extracted with CH$_2$Cl$_2$ (2×40 mL). The combined organic layer was washed with brine (10 mL), dried over Na$_2$SO$_4$ and concentrated to leave crude (R)-2-(4-(4-fluoro-3-(methylsulfonyl)phenyl)-2-isopropylpiperazin-1-yl)-4-(trifluoromethyl)pyrimidine-5-carbaldehyde (120 mg as a brown oil.

Step 2

To a stirred, ice-cold solution of (R)-2-(4-(4-fluoro-3-(methylsulfonyl)phenyl)-2-isopropylpiperazin-1-yl)-4-(trifluoromethyl)pyrimidine-5-carbaldehyde (120 mg, 0.25 mmol) in dry THF (5 mL) was added 3 M MeMgBr in THF (0.25 mL, 0.75 mmol). The mixture was stirred in the ice bath for 2 h, quenched with satd aq NH$_4$Cl (20 mL) and extracted with EtOAc (80 mL). The organic layer was washed with brine (10 mL), dried over Na$_2$SO$_4$ and concentrated to leave an oil (117 mg). Chromatography on a 40-g silica gel cartridge afforded the title compound (59 mg, %) as an oil. LC-MS Method 4 t$_R$=0.99 min, m/z=491. $^1$H NMR (CDCl$_3$) δ 0.80 (d, 3H), 1.09 (d, 3H), 1.47 (d, 3H), 2.38-2.46 (m, 1H), 2.76-2.88 (m, 2H), 3.20 (s, 3H), 3.24-3.37 (m, 1H), 3.49-3.55 (m, 1H), 3.67-3.74 (m, 1H), 4.61-4.67 (m, 1H), 4.79-4.85 (m, 1H), 5.11-5.20 (q, 1H), 7.07-7.18 (m, 2H), 7.37-7.41 (m, 1H), 8.77 (s, 1H).

The epimeric alcohols were separated on a chiral column to give Cpd No 12-2, mass observed 491.2, and Cpd No 12-3, mass observed 491.2.

The following compounds are prepared following similar procedures:

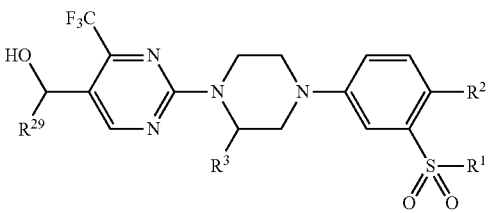

| Cpd No. | R$^1$ | R$^2$ | R$^3$ | *Stereochem | R$^{29}$ | Mass Observed |
|---|---|---|---|---|---|---|
| 12-4$^a$ | Me | CN | i-Pr | R | Me | |
| 12-5$^a$ | Me | CN | i-Pr | R | Me | |
| 12-6 | Me | F | i-Pr | R | Et$^a$ | |
| 12-7 | Me | F | i-Pr | R | Et$^a$ | |
| 12-8 | NHMe | F | i-Pr | R | Me | |
| 12-9 | Me | F | 4-F—Ph | R | Me | |

$^a$Isomers are separated on a chiral column, stereochemistry assigned arbitrarily..

Example 13

(R)-1-(2-(4-(4-fluoro-3-(methylsulfonyl)phenyl)-2-isopropylpiperazin-1-yl)-4-(trifluoromethyl)pyrimidin-5-yl)ethanone (Cpd No 13-1)

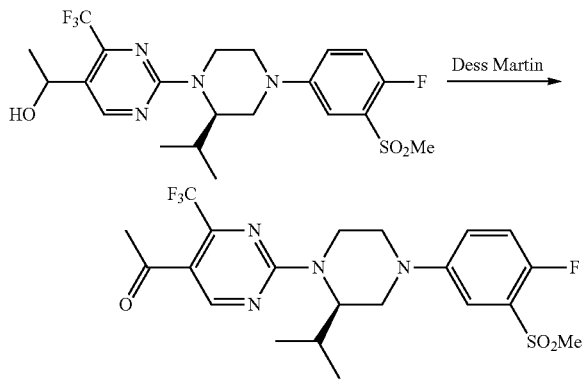

The title compound was prepared following the procedure in Step 1 immediately above. LC-MS Method 4 tR=1.01 min, m/z=489. 1H NMR (CD3OD) δ 0.82 (d, 3H), 1.16 (d, 3H), 2.48-2.58 (m, 4H), 2.78-2.92 (m, 2H), 3.22 (s, 3H), 3.36-3.44 (m, 1H), 3.66-3.72 (m, 1H), 3.84-3.90 (m, 1H), 4.68-4.84 (m, 1H), 4.86-5.00 (m, 1H), 7.22-7.38 (m, 2H), 7.40-7.45 (m, 1H), 8.93 (s, 1H).

The following compounds are prepared following a similar procedure:

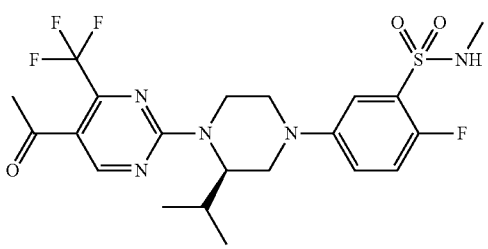

Cpd No 13-2, m/z = 504

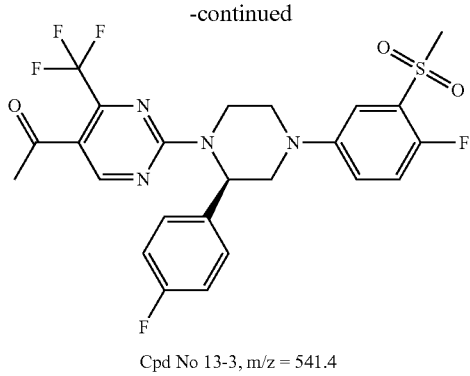

Cpd No 13-3, m/z = 541.4

Example 14

(R)-2-(4-(4-fluoro-3-(methylsulfonyl)phenyl)-2-isopropylpiperazin-1-yl)-5-(prop-1-en-2-yl)-4-(trifluoromethyl)pyrimidine (Cpd No 14-1)

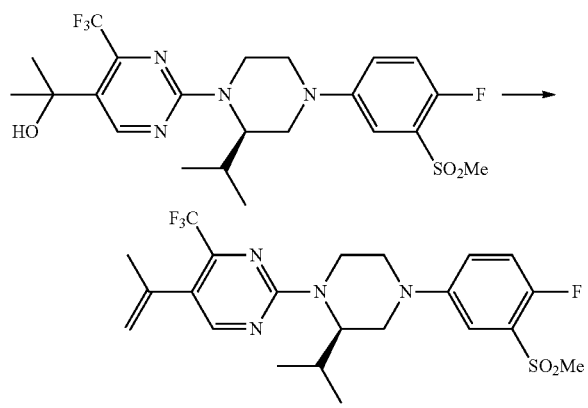

A solution of (R)-2-(2-(4-(4-fluoro-3-(methylsulfonyl)phenyl)-2-isopropylpiperazin-1-yl)-4-(trifluoromethyl)pyrimidin-5-yl)propan-2-ol (5 mg) in CDCl3 (1 mL) was allowed to stand at rt for 1 h. The mixture was applied to a 2 g silica SPE catridge which was eluted with hexanes (15 mL), followed by 10% EtOAc in hexanes (15 mL) to give two fractions. The more polar eluate was concentrated to leave the title compound (1 mg) as an oil. LC-MS Method 4 tR=1.16 min, m/z=487.

The following compound is prepared following a similar procedure:

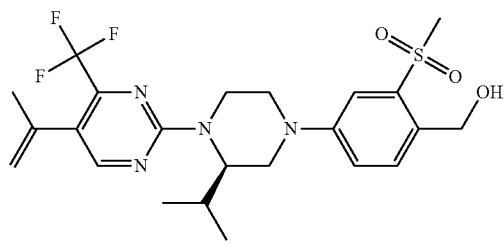

Cpd No 14-2, m/z = 499

Example 15

(R)-2-(4-(4-fluoro-3-(methylsulfonyl)phenyl)-2-isopropylpiperazin-1-yl)-5-((3-fluoroazetidin-1-yl)methyl)-4-(trifluoromethyl)pyrimidine (Cpd No 15-1)

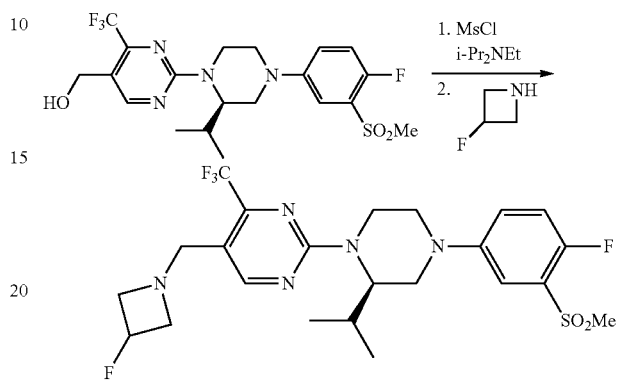

To a stirred, ice-cold solution of (R)-(2-(4-(4-fluoro-3-(methylsulfonyl)phenyl)-2-isopropylpiperazin-1-yl)-4-(trifluoromethyl)pyrimidin-5-yl)methanol (51 mg, 0.11 mmol) and i-Pr$_2$NEt (0.055 mL, 0.31 mmol) in CH$_2$Cl$_2$ (5 mL) was added methanesulfonyl chloride (0.001 mL, 0.13 mmol). The ice bath was allowed to melt and the mixture was stirred for 2 d at rt. The mixture was diluted with EtOAc (80 mL), washed with 5% aq HCl (10 mL) and 3:1 brine/satd aq NaHCO$_3$ (10 mL), and dried over Na$_2$SO$_4$. Removal of the solvent left an oil (52 mg) which was taken up in MeCN (2 mL). To this solution were added i-Pr$_2$NEt (0.075 mL, 0.42 mmol) and 3-fluoroazetidine HCl salt (24 mg, 0.21 mmol). The mixture was stirred at rt for 2 d and purified by prep HPLC to afford the title compound as its TFA salt (38 mg, 53%). LC-MS Method 4 t$_R$=0.69 min, m/z=534. $^1$H NMR (CD$_3$OD) δ 0.82 (d, 3H), 1.14 (d, 3H), 2.47-2.58 (m, 1H), 2.77-2.90 (m, 2H), 3.23 (s, 3H), 3.35-3.45 (m, 1H), 3.65-3.72 (m, 1H), 3.83-3.90 (m, 1H), 4.38-4.50 (m, 2H), 4.54 (s, 2H), 4.58-4.80 (m, 3H), 4.82-4.86 (m, 1H), 5.31-5.38 (m, 0.5H), 5.45-5.52 (m, 0.5H), 7.23-7.36 (m, 2H), 7.39-7.43 (m, 1H), 8.64 (s, 1H).

The following compounds are prepared following a similar procedure:

| Cpd No. | R$^{28}$ | Mass Observed |
|---|---|---|
| 15-2 | NH$_2$ | 498.0 |
| 15-3 | Me$_2$N | 504 |
| 15-4 | 3-hydroxy-1-azetidinyl | 532 |
| 15-5 | 4-morpholinyl | 546 |
| 15-6 | t-BuNMe | 546 |
| 15-7 | MeSO$_2$N | 576, 554 |
| 15-8 | MeS | 507 |

| | | |
|---|---|---|
| 15-9 | HO(CH₂)₃NMe | 548 |
| 15-10 | MeOCH₂CH₂NMe | 548 |

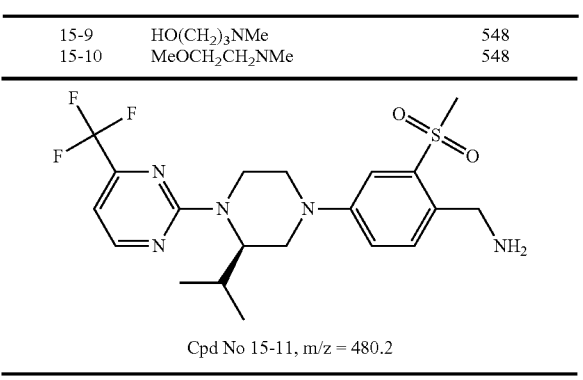

Cpd No 15-11, m/z = 480.2

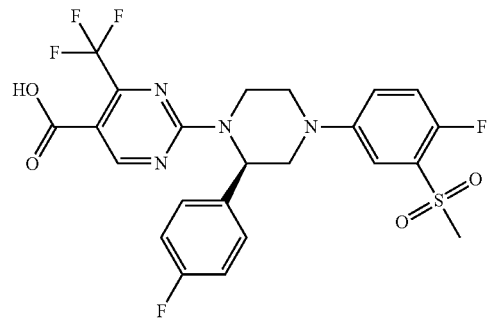

Cpd No 16-2, m/z = 543.4

Example 16

(R)-2-(4-(4-fluoro-3-(methylsulfonyl)phenyl)-2-isopropylpiperazin-1-yl)-4-(trifluoromethyl)pyrimidine-5-carboxylic acid (Cpd No 16-1)

Example 17

(R)-2-(4-(4-fluoro-3-(methylsulfonyl)phenyl)-2-isopropylpiperazin-1-yl)-N,N-dimethyl-4-(trifluoromethyl)pyrimidine-5-carboxamide (Cpd No 17-1)

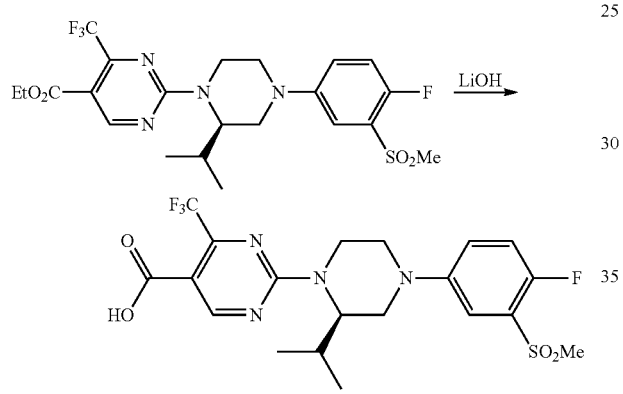

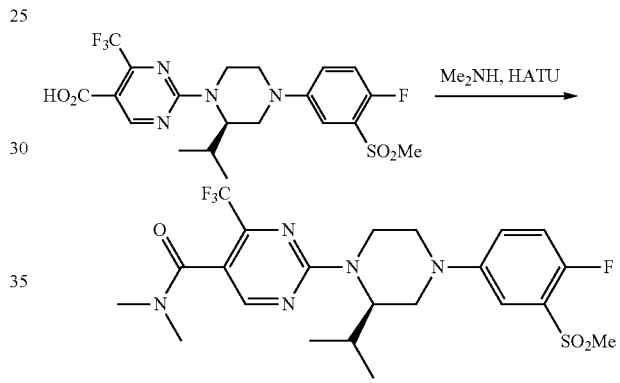

To a stirred solution of (R)-ethyl 2-(4-(4-fluoro-3-(methylsulfonyl)phenyl)-2-isopropylpiperazin-1-yl)-4-(trifluoromethyl)pyrimidine-5-carboxylate (223 mg, 0.43 mmol) in MeOH (10 mL), THF (5 mL) and water (5 mL) was added LiOH.H₂O (150 mg, 3.6 mmol). The mixture was stirred at rt for 26 h and concentrated. The aqueous residue was diluted with 5% aq HCl (20 mL) and EtOAc (90 mL). The organic layer was separated, washed with brine (10 mL), dried over Na₂SO₄ and concentrated to afford (R)-2-(4-(4-fluoro-3-(methylsulfonyl)phenyl)-2-isopropylpiperazin-1-yl)-4-(trifluoromethyl)pyrimidine-5-carboxylic acid (241 mg, quant) which was used without further purification. LC-MS Method 4 $t_R$=0.98 min, m/z=491.

The following compound is prepared following a similar procedure:

To a stirred mixture of (R)-2-(4-(4-fluoro-3-(methylsulfonyl)phenyl)-2-isopropylpiperazin-1-yl)-4-(trifluoromethyl)pyrimidine-5-carboxylic acid (10 mg, 20 μmol), 2 M Me₂NH in THF (0.1 mL, 0.2 mmol), i-Pr₂NEt (15 μL, 82 μmol) and CH₂Cl₂ (1 mL) was added HATU (12 mg, 32 μmol). The mixture was stirred overnight and concentrated. The residue was purified by prep HPLC to afford the title compound (3.4 mg, 32%). LC-MS Method 4 tR=0.93 min, m/z=518. 1H NMR (CD₃OD) δ 0.83 (d, 3H), 1.12 (d, 3H), 2.45-2.55 (m, 1H), 2.81-2.93 (m, 2H), 2.94 (s, 3H), 3.08 (s, 3H), 3.22 (s, 3H), 3.35-3.45 (m, 1H), 3.62-3.68 (m, 1H), 4.82-4.87 (d, 1H), 4.68-4.72 (m, 1H), 5.83-5.89 (m, 1H), 7.22-7.37 (m, 2H), 7.39-7.43 (m, 1H), 8.46 (s, 1H).

The amides below are prepared following a similar procedure:

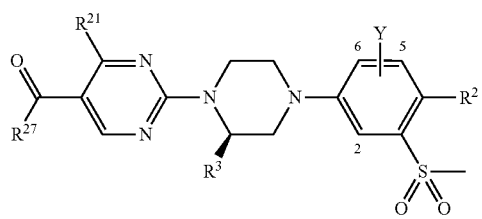

-continued

| Cpd No. | R² | Y | R³ | R²¹ | R²⁷ | Mass Observed |
|---|---|---|---|---|---|---|
| 17-2 | F | H | i-Pr | CF₃ | NH₂ | 490.1 |
| 17-3 | F | H | i-Pr | CF₃ | MeNH | 504 |
| 17-4 | F | H | i-Pr | CF₃ | 3-amino-1-azetidinyl | 545 |
| 17-5 | F | H | i-Pr | CF₃ | 3-hydroxy-1-azetidinyl | 546 |
| 17-6 | F | H | i-Pr | CF₃ | MeO(CH₂)₂NH | 548 |
| 17-7 | F | H | i-Pr | CF₃ | HO(CH₂)₂NHMe | 548 |
| 17-8 | F | H | i-Pr | CF₃ | 4-morpholinyl | 560 |
| 17-9 | F | H | i-Pr | CF₃ | 3-methoxy-1-azetidinyl | 560 |
| 17-10 | F | H | i-Pr | CF₃ | n-BuNMe | 560 |
| 17-11 | F | H | i-Pr | CF₃ | HO(CH₂)₃NMe | 584, 562 |
| 17-12 | F | H | i-Pr | CF₃ | MeO(CH₂)₂NMe | 562 |
| 17-13 | F | H | i-Pr | CF₃ | MeO(CH₂)₃NMe | 576 |
| 17-14 | F | H | i-Pr | CF₃ | MeO(CH₂)₂NEt | 576 |
| 17-15 | F | H | i-Pr | CF₃ | HO(CH₂)₃NHEt | 576 |
| 17-16 | F | H | i-Pr | CF₃ | EtO₂CCH₂NMe | 590 |
| 17-17 | F | H | i-Pr | CF₃ | HOCMe₂(CH₂)₂NMe | 590 |
| 17-18 | F | H | i-Pr | CF₃ | EtO₂C(CH₂)₂NMe | 604 |
| 17-19 | F | H | i-Pr | CF₃ | MeOC(=O)NH(CH₂)₃NMe | 619 |
| 17-20 | F | H | i-Pr | CF₃ | 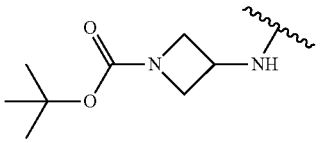 | 645, 589 |
| 17-21 | F | H | i-Pr | CF₃ | 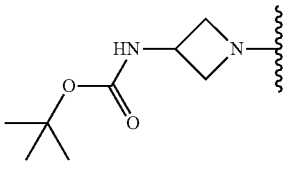 [SMILES: *N1CC(NC(=O)OC(C)(C)C)C1] | 645 |
| 17-22 | F | H | i-Pr | CF₃ | 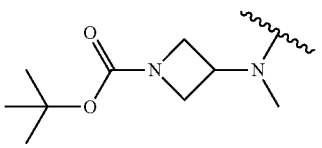 [SMILES: *N(C)C1CN(C(=O)OC(C)(C)C)C1] | 659, 603, 559 |
| 17-23 | F | H | i-Pr | CF₃ | BocNH(CH₂)₃NMe | 661, 605, 561 |
| 17-24 | F | H | i-Pr | Me | NH₂ | 436 |
| 17-25 | CH₂OH | H | i-Pr | CF₃ | NH₂ | 524.1 |
| 17-26 | F | H | i-Pr | Me | MeO(CH₂)₂NMe | 508 |
| 17-27 | F | H | i-Pr | Me | HO(CH₂)₃NMe | 508 |
| 17-28 | CH₂OH | 5-F | i-Pr | CF₃ | NH₂ | 542.1 |
| 17-29 | CH₂OH | 6-F | i-Pr | CF₃ | NH₂ | 520.1 |
| 17-30 | F | H | i-Pr | Me | MeO(CH₂)₂NEt | 522 |
| 17-31 | F | H | i-Pr | Me3 | MeO(CH₂)₃NMe | 522 |
| 17-32 | F | H | 4-F—Ph | CF₃ | MeONMe | 586.5 |
| 17-33 | F | H | 4-F—Ph | CF₃ | Me₂N | 570.3 |

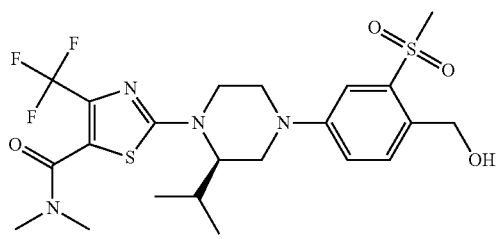

Cpd No 17-34, m/z = 557.1

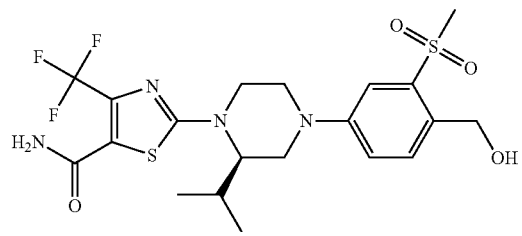
Cpd No 17-35, m/z = 529.2
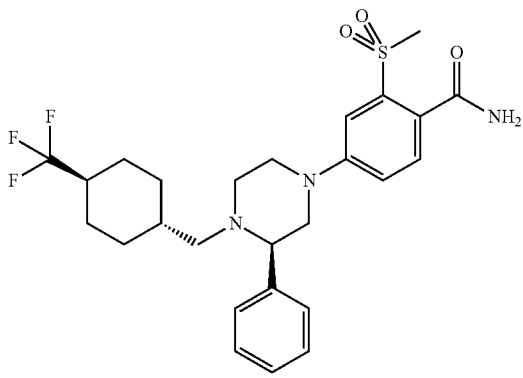
Cpd No 17-36[a], m/z = 524.1
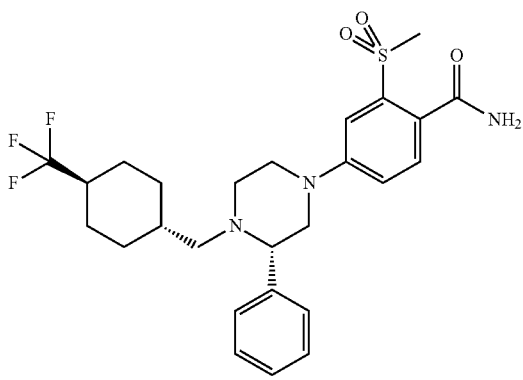
Cpd No 17-37[a], m/z = 524.1
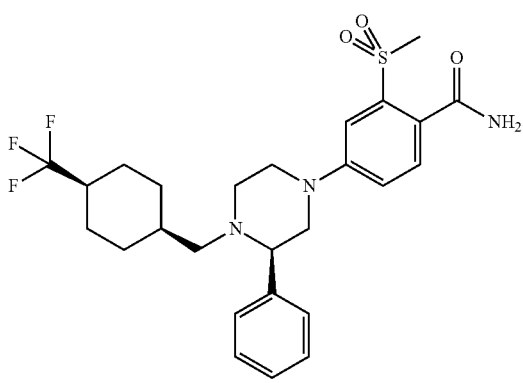
Cpd No 17-38[b], m/z = 524.1

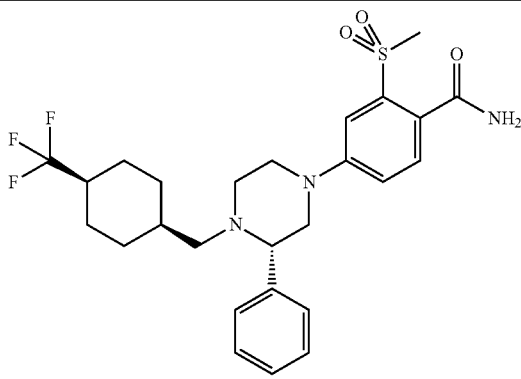

Cpd No 17-39[b], m/z = 524.1

[a,b]Isomers are separated on a chiral column, stereochemistry assigned arbitrarily.

Example 18

(R)-2-fluoro-5-(3-isopropyl-4-(5-(trifluoromethyl)pyridin-2-yl)piperazin-1-yl)benzenesulfonamide (Cpd No 18-1)

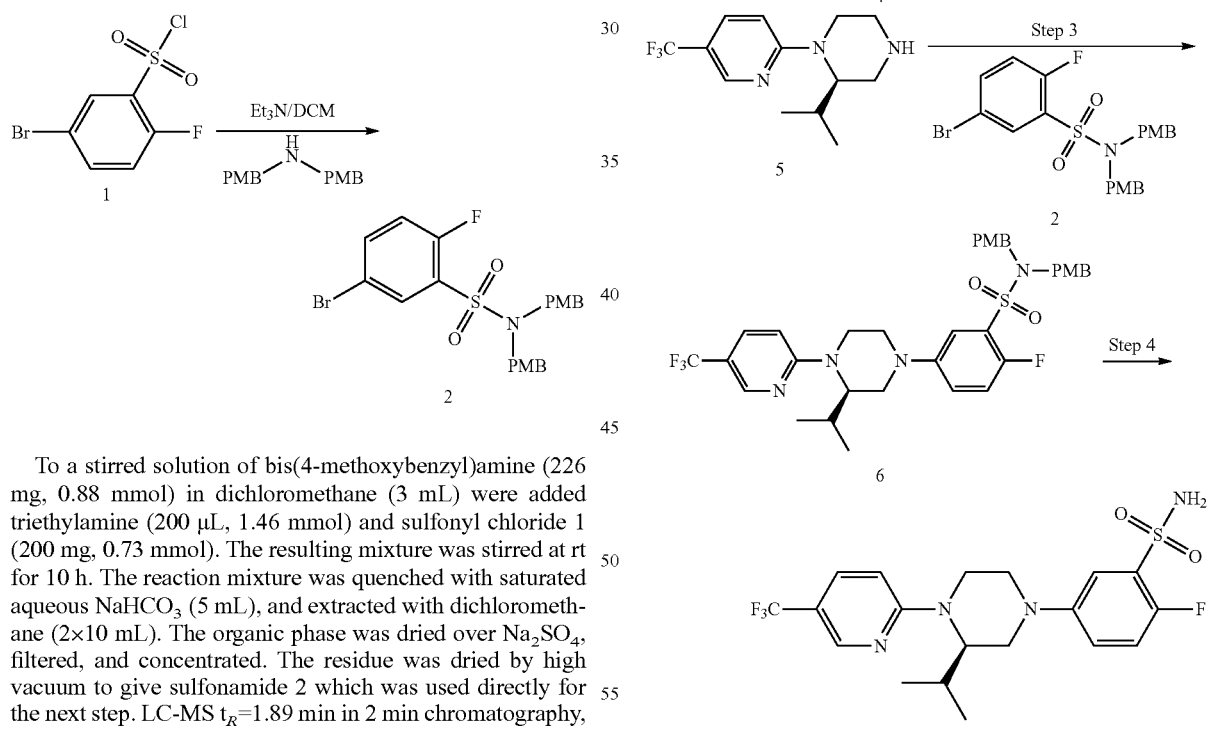

To a stirred solution of bis(4-methoxybenzyl)amine (226 mg, 0.88 mmol) in dichloromethane (3 mL) were added triethylamine (200 μL, 1.46 mmol) and sulfonyl chloride 1 (200 mg, 0.73 mmol). The resulting mixture was stirred at rt for 10 h. The reaction mixture was quenched with saturated aqueous NaHCO$_3$ (5 mL), and extracted with dichloromethane (2×10 mL). The organic phase was dried over Na$_2$SO$_4$, filtered, and concentrated. The residue was dried by high vacuum to give sulfonamide 2 which was used directly for the next step. LC-MS $t_R$=1.89 min in 2 min chromatography, MS (ESI) m/z 516 [M+23]$^+$.

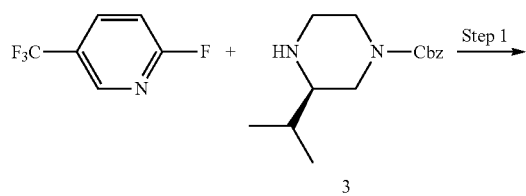

Step 1:
To a solution of 2-fluoro-5-(trifluoromethyl)pyridine (125 mg, 0.75 mmol), CsF (137 mg, 0.9 mmol) in anhydrous DMSO (0.35 mL) was added 3 (80 mg, 0.3 mmol). With use of microwave power of 200 W, the reaction mixture was ramped from rt to 180° C. over 2 min, and then held at this temp. For 2 h. After cooling to rt, the resulting reaction mixture was diluted with H$_2$O (10 mL) and extracted with EtOAc (2×10 mL). The organic layers were washed with brine, dried over anhydrous Na$_2$SO$_4$, filtered and concentrated in vacuo. The residue was purified by silica gel chromatography (hexanes/EtOAc) to give the product 4 (62 mg, 50% yield). LC-MS $t_R$=1.96 min in 2 min chromatography, MS (ESI) m/z 408.06 [M+H]$^+$.

Step 2:

To a solution of 4 (62 mg, 0.15 mmol) in MeOH (3 mL) was added Pd/C (w/w 10%, 20 mg). The mixture was stirred at rt under H$_2$ (1 atm) overnight. When TLC and LCMS showed that the starting material was consumed, the mixture was purged with N$_2$, filtered and concentrated under vacuum to afford the crude product 5. It was used directly for the next step without further purifications. LC-MS $t_R$=1.12 min in 2 min chromatography, MS (ESI) m/z 274.32 [M+H]$^+$.

Step 3:

To a mixture of bromide 2 (170 mg, 0.37 mmol), amine 5 (50 mg, 0.18 mmol), Xphos (24 mg, 0.05 mmol) and cesium carbonate (150 mg, 0.46 mmol) in toluene (1.5 mL) was added Pd$_2$(dba)$_3$ (21 mg, 0.023 mmol). The mixture was purged with nitrogen and the tube was sealed. It was heated in an oil bath at 100° C. for 5 h. After cooling to rt, the reaction mixture was filtered and concentrated. The residue was purified by silica gel chromatography (hexanes/EtOAc) to afford the product 6 (54 mg, 43% yield). LC-MS tR=2.17 min in 2 min chromatography, MS (ESI) m/z 687.49 [M+H]+.

Step 4:

At 0° C., to a solution of 6 (34 mg, 0.05 mmol) in dichloromethane (1 mL) was added TfOH (9 μL, 0.1 mmol). The reaction mixture was stirred for 15 min at 0° C. and then neutralized by saturated NaHCO$_3$ solution. The mixture was extracted with DCM (3×10 mL) and the combined organic layers were dried over anhydrous Na$_2$SO$_4$, filtered and concentrated under vacuum. The residue was purified by silica gel chromatography (hexanes/EtOAc=1/1) to afford the title compound (15 mg, 70% yield). LC-MS tR=1.70 min in 2 min chromatography, MS (ESI) m/z 447.03 [M+H]+. 1H NMR (CD3OD 400 MHz): δ 8.31 (s, 1H), 7.78 (d, J=8.8 Hz, 1H), 7.42-7.41 (m, 1H), 7.22-7.05 (m, 2H), 7.03 (d, J=9.6 Hz, 1H), 4.45 (d, J=13.2 Hz, 1H), 4.32 (d, J=8.4 Hz, 1H), 3.83 (d, J=12.4 Hz, 1H), 3.62 (d, J=8.4 Hz, 1H), 3.48-3.41 (m, 1H), 2.90-2.81 (m, 2H), 2.80-2.53 (m, 1H), 1.13 (d, J=6.8 Hz, 3H), 0.84 (d, J=6.8 Hz, 3H).

Example 19

(R)-(2-(4-(4-(hydroxymethyl)-3-(methylsulfonyl)phenyl)-2-isopropylpiperazin-1-yl)-4-(trifluoromethyl)pyrimidin-5-yl)methanol (Cpd No 19-1)

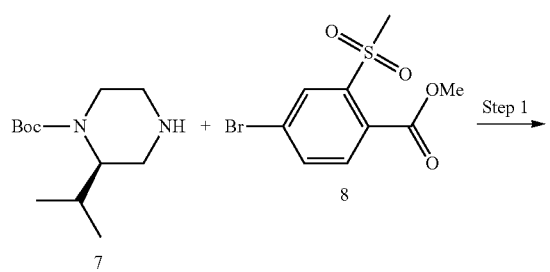

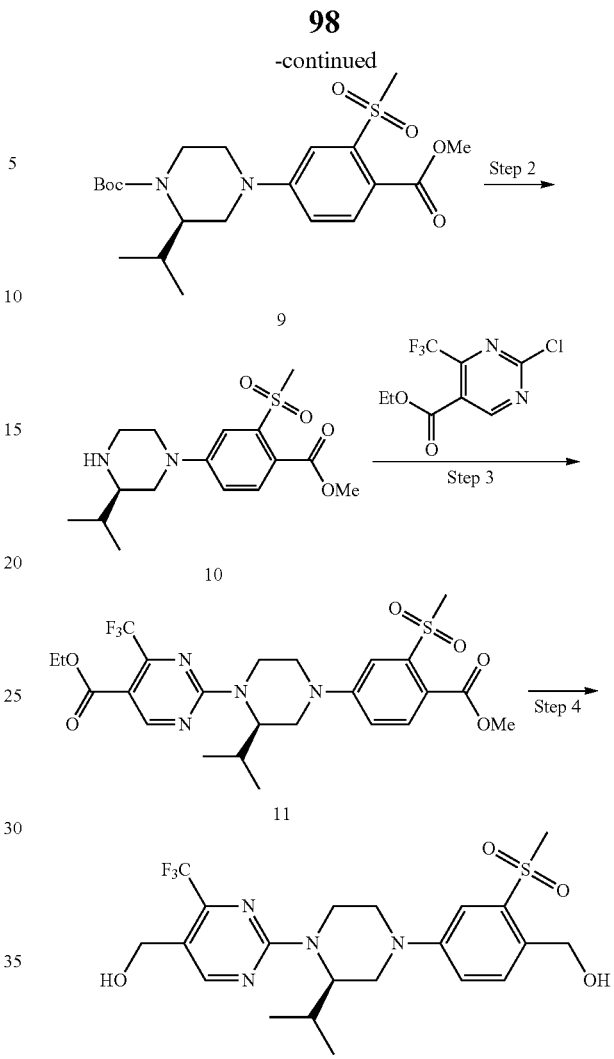

Step 1:

To a mixture of amine 7 (740 mg, 3.0 mmol), bromide 8 (1.05 g, 3.6 mmol), Xphos (160, 0.33 mmol) and Cesium carbonate (2.93 g, 9.0 mmol) in toluene (7 mL) was added Pd$_2$(dba)$_3$ (140 mg, 0.15 mmol). The mixture was purged with nitrogen and the tube was sealed. It was heated in an oil bath at 100° C. for 10 h. After cooling to rt, the reaction mixture was filtered and concentrated. The residue was purified by silica gel chromatography (EtOAc/hexanes=40/60) to afford the coupling product 9 (1.17 g, 86% yield). LC-MS tR=1.66 min in 2 min chromatography, MS (ESI) m/z 463 [M+23]+.

Step 2:

To a solution of 9 (1.17 g, 2.65 mmol) in dichloromethane (10 mL) at 0° C. was added TFA (2 mL). The reaction mixture was stirred at rt for 1 h. After completed the reaction, the reaction mixture was neutralized with sat. NaHCO$_3$ and extracted with EtOAc (3×25 mL). The organic layers were dried over brine, anhydrous Na$_2$SO$_4$, filtered, concentrated to afford the crude free amine 10, which was used directly for the next step without further purifications. LC-MS tR=0.65 min in 2 min chromatography, MS (ESI) m/z 341.2 [M+H]+.

Step 3:

To a solution of 10 (2.65 mmol from step 2) in DMSO (5.5 mL) was added Ethyl 2-chloro-4-(trifluoromethyl)pyrimidine-5-carboxylate (1.35 g, 5.3 mmol) and DIEA (1.4 mL, 7.95 mmol). The mixture was allowed to stir at 60° C. for 2 h. After the reaction completed, the mixture was diluted with H2O (30 mL) and extracted with EtOAc (2×30 mL). The organic layers were washed with brine, dried over anhydrous Na2SO4, filtered and concentrated in vacuo. The residue was purified by silica gel chromatography (EtOAc/hexanes=30/70) to give the product 11 (1.39 g, 94% yield). LC-MS tR=1.88 min in 2 min chromatography, MS (ESI) m/z 559.3 [M+H]+.

Step 4:

To a solution of 11 (1.39 g, 2.5 mmol) in dry toluene (45 mL) at 0° C. was added diisobutylaluminum hydride (1.0 M in toluene, 15 mL, 15 mmol) slowly. After addition, the mixture was stirred at 0° C. for 2 h and quenched with NH4Cl solution (5 mL). The reaction mixture was poured into a vigorously stirred solution of potassium sodium tartrate (1.0 M, 40 mL) and stirred vigorously until two phases clearly separated. The organic layer was separated, and the aqueous layer was extracted with EtOAc (3×30 mL). The organic layers were washed with brine, dried over anhydrous $Na_2SO_4$, filtered and concentrated in vacuo. The crude product was purified by silica gel chromatography (EtOAc/hexanes=60/40) afford the title compound (960 mg, 79% yield). LC-MS tR=1.48 min in 2 min chromatography, MS (ESI) m/z 489.3 [M+H]+. 1H NMR (CD3OD 400 MHz): δ 8.61 (s, 1H), 7.56 (d, J=2.4 Hz, 1H), 7.54 (d, J=8.4 Hz, 1H), 7.27 (dd, J1=2.4 Hz J2=8.4 Hz, 1H), 4.91 (s, 2H), 4.86-4.84 (m, 1H), 4.70 (d, J=10.4 Hz, 1H), 4.61 (s, 2H), 3.97 (d, J=12.4 Hz, 1H), 3.75 (d, J=10.4 Hz, 1H), 3.40-3.33 (m, 1H), 3.22 (s, 3H), 2.94-2.83 (m, 2H), 2.50-2.41 (m, 1H), 1.13 (d, J=6.8 Hz, 3H), 0.82 (d, J=6.8 Hz, 3H).

The following compound is prepared using similar procedures:

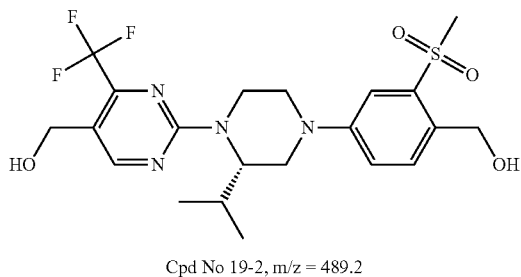 [SMILES: CC(C)[C@H]1CN(c2ccc(CO)c(S(C)(=O)=O)c2)CCN1c1ncc(CO)c(C(F)(F)F)n1]

Cpd No 19-2, m/z = 489.2

Example 20

(R)-4-(4-fluoro-3-(methylsulfonyl)phenyl)-2-isopropyl-1-(5-(trifluoromethyl)pyridin-3-yl)piperazine (Cpd No 20-1)

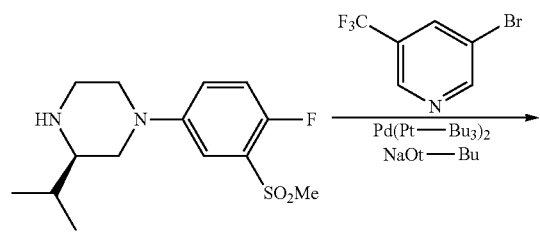

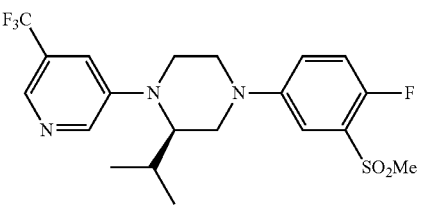

A stirred mixture of (R)-1-(4-fluoro-3-(methylsulfonyl)phenyl)-3-isopropylpiperazine (20 mg, 0.067 mmol), 3-bromo-5-(trifluoromethyl)pyridine (19 mg, 0.085 mmol), sodium t-butoxide (10 mg, 0.1 mmol), Pd(t-Bu$_3$)$_2$ (4 mg, 0.009 mmol) and dry toluene (1 mL) was placed under an N2 atmosphere and heated in a 100° C. oil bath for 1 day. After concentration, the residue was taken up in MeCN (2 mL), H$_2$O (0.5 mL) and HOAc (3 drops), filtered and purified by prep HPLC to afford the title compound (0.6 mg, 2.5%) as an oil. LC-MS Method 4 tR=0.95 min, m/z=446. 1H NMR (CD$_3$OD) δ 0.86 (d, 3H), 1.10 (d, 3H), 2.42-2.55 (m, 1H), 2.95-3.10 (m, 2H), 3.23 (s, 3H), 3.50-3.65 (m, 2H), 3.78-3.91 (m, 3H), 7.22-7.32 (m, 2H), 7.39-7.44 (m, 1H), 7.61 (m, 1H), 8.12 (m, 1H), 8.48 (m, 1H).

The following compounds are prepared using a similar procedure:

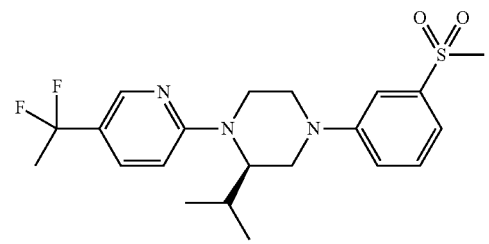

Cpd No 20-2, m/z = 424.1

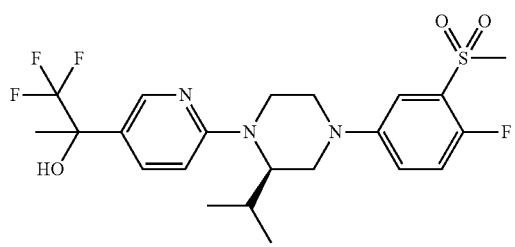

Cpd No 20-3, m/z = 490

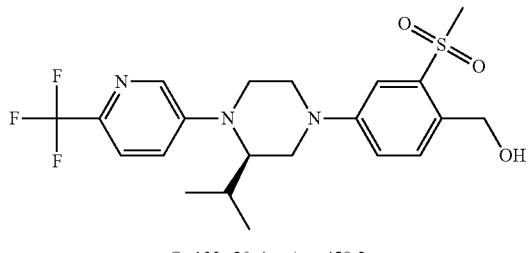

Cpd No 20-4, m/z = 458.2

Example 21

(R)-2-(4-(4-fluoro-3-(methylsulfonyl)phenyl)-2-isopropylpiperazin-1-yl)-5-(trifluoromethyl)pyridin-3-amine (Cpd No 21-1)

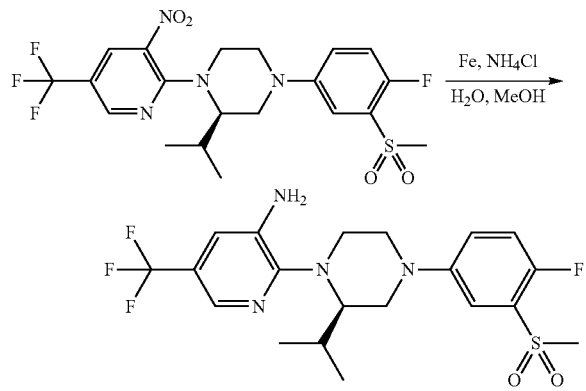

To a stirred solution of (R)-4-(4-fluoro-3-(methylsulfonyl)phenyl)-2-isopropyl-1-(3-nitro-5-(trifluoromethyl)pyridin-2-yl)piperazine (10 mg, 0.02 mmol) in MeOH (1 mL) and water (1 mL) were added iron powder (36 mg, 0.75 mmol) and NH$_4$Cl (22 mg, 0.4 mmol). The mixture was heated in a 70° C. oil bath for 1.5 h, cooled to rt, diluted with MeOH (1 mL), filtered and purified by prep HPLC to afford the title compound (1.4 mg, 10%) as its TFA salt. LC-MS Method 4 t$_R$=1.03 min, 461.

Example 22

(R)-5-chloro-4-cyclopropyl-2-(4-(4-fluoro-3-(methylsulfonyl)phenyl)-2-isopropylpiperazin-1-yl)pyrimidine (Cpd No 22-1) and (R)-5-chloro-2-(4-(2-chloro-4-fluoro-3-(methylsulfonyl)phenyl)-2-isopropylpiperazin-1-yl)-4-cyclopropylpyrimidine (Cpd No 22-2)

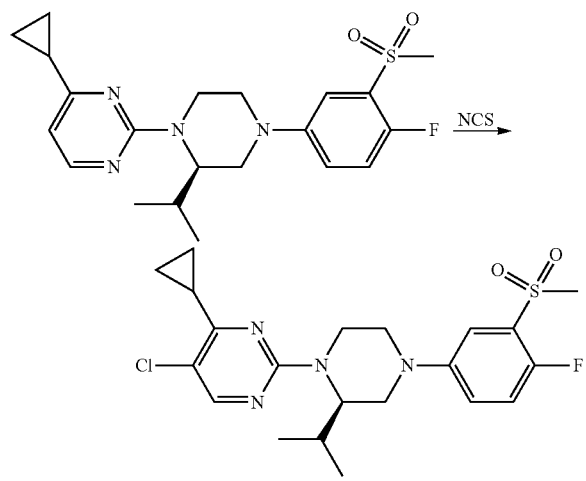

To a stirred solution of (R)-4-cyclopropyl-2-(4-(4-fluoro-3-(methylsulfonyl)phenyl)-2-isopropylpiperazin-1-yl)pyrimidine TFA salt (14 mg, 0.026 mmol) and N-chlorosuccinimide (5.3 mg, 0.04 mmol) in DMF (0.5 mL) was heated in the microwave at 100° C. for 2 h. The mixture was diluted with MeOH and purified by prep HPLC to afford two products.

(R)-5-chloro-4-cyclopropyl-2-(4-(4-fluoro-3-(methylsulfonyl)phenyl)-2-isopropylpiperazin-1-yl)pyrimidine (0.7 mg) as an oil. LC-MS Method 4 tR=1.17 min, m/z=455, 453. 1H NMR (CD$_3$OD) δ 0.89 (d, 3H), 1.05-1.17 (m, 7H), 2.32-2.47 (m, 1H), 2.72-2.87 (m, 2H), 3.22 (s, 3H), 3.25-3.35 (m, 2H), 3.53 (m, 1H), 3.76-3.83 (m, 1H), 4.50-4.57 (m, 1H), 4.66-4.76 (m, 1H), 7.22-7.32 (m, 2H), 7.36-7.39 (m, 1H), 8.09 (s, 1H).

(R)-5-chloro-2-(4-(2-chloro-4-fluoro-3-(methylsulfonyl)phenyl)-2-isopropylpiperazin-1-yl)-4-cyclopropylpyrimidine (3.9 mg, %) as an oil. LC-MS Method 4 tR=1.19 min, m/z=491, 490, 489, 488, 487. 1H NMR (CD3OD) δ 0.88 (d, 3H), 1.04 (d, 3H), 1.05-1.18 (m, 4H), 2.32-2.39 (m, 1H), 2.65-2.80 (m, 2H), 2.81-2.87 (m, 1H), 3.17-3.33 (m, 3H), 3.37 (s, 3H), 4.49-4.55 (m, 1H), 4.66-4.71 (m, 1H), 7.24-7.32 (m, 1H), 7.48-7.54 (m, 1H), 8.09 (s, 1H).

The following compounds are prepared using a similar procedure:

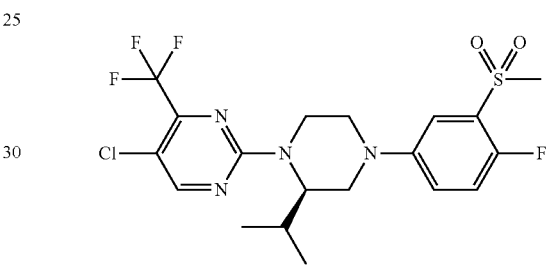

Cpd No 22-3, m/z = 483, 481

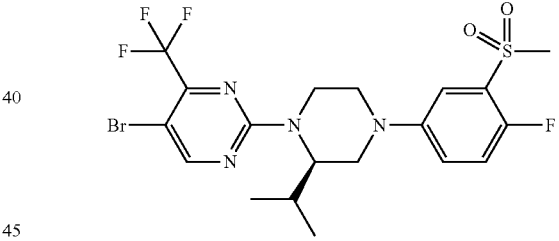

Cpd No 22-4, m/z = 527, 525

N-bromosuccinmide is used in place of N-chlorosuccinimide

Example 23

(R)-2-(4-(4-fluoro-3-(methylsulfonyl)phenyl)-2-isopropylpiperazin-1-yl)-4-isopropoxy-6-(trifluoromethyl)pyrimidine (Cpd No 23-1)

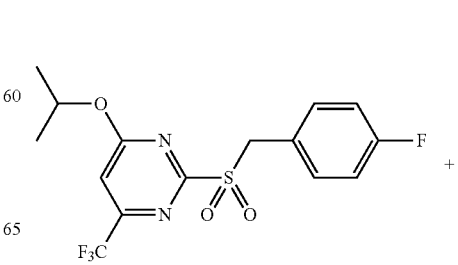

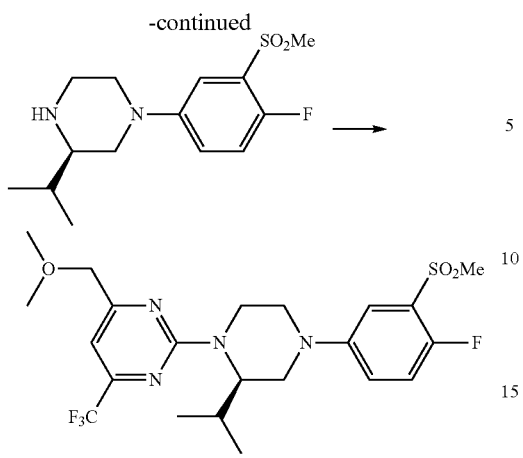

A solution of 2-((4-fluorobenzyl)sulfonyl)-4-isopropoxy-6-(trifluoromethyl)pyrimidine (37 mg, 0.098 mmol) and (R)-1-(4-fluoro-3-(methylsulfonyl)phenyl)-3-isopropylpiperazine (29 mg, 0.097 mmol) in dioxane was heated in the microwave at 120° C. for 12 h. Prep HPLC afforded the title compound (4.4 mg, 9%) as an oil. LC-MS Method 4 $t_R$=1.25 min, m/z=505. 1H NMR (CD$_3$OD) δ 0.93 (d, 3H), 1.11 (d, 3H), 1.38 (d, 6H), 2.40-2.55 (m, 1H), 2.75-2.90 (m, 3H), 3.22 (s, 3H), 3.59-3.66 (m, 1H), 3.81-3.85 (m, 1H), 4.60-4.67 (m, 1H), 4.77-4.84 (m, 1H), 5.32-5.40 (m, 1H), 6.19 (s, 1H), 7.23-7.43 (m, 3H)

Example 24

(R)-2-(4-(4-fluoro-3-(methylsulfonyl)phenyl)-2-isopropylpiperazin-1-yl)-6-(trifluoromethyl)pyrimidin-4-ol (Cpd No 24-1)

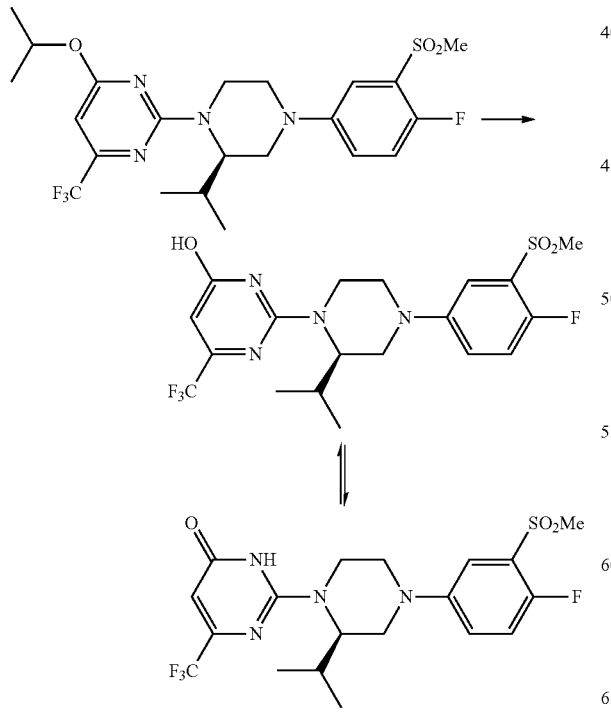

To a stirred solution of (R)-2-(4-(4-fluoro-3-(methylsulfonyl)phenyl)-2-isopropylpiperazin-1-yl)-4-isopropoxy-6-(trifluoromethyl)pyrimidine (3.8 mg) in glacial HOAc (0.1 mL) was added conc H$_2$SO$_4$ (0.1 mL). The mixture was heated at 90° C. for 15 min. Prep HPLC afforded the title compound (0.9 mg) as an oil. LC-MS Method 4 $t_R$=0.94 min, m/z=463.

Example 25

(R)-2-(2-(4-(4-(hydroxymethyl)-3-(methylsulfonyl)phenyl)-2-isopropylpiperazin-1-yl)-4-(trifluoromethyl)pyrimidin-5-yl)-2-methylpropanenitrile (Cpd No 25-1)

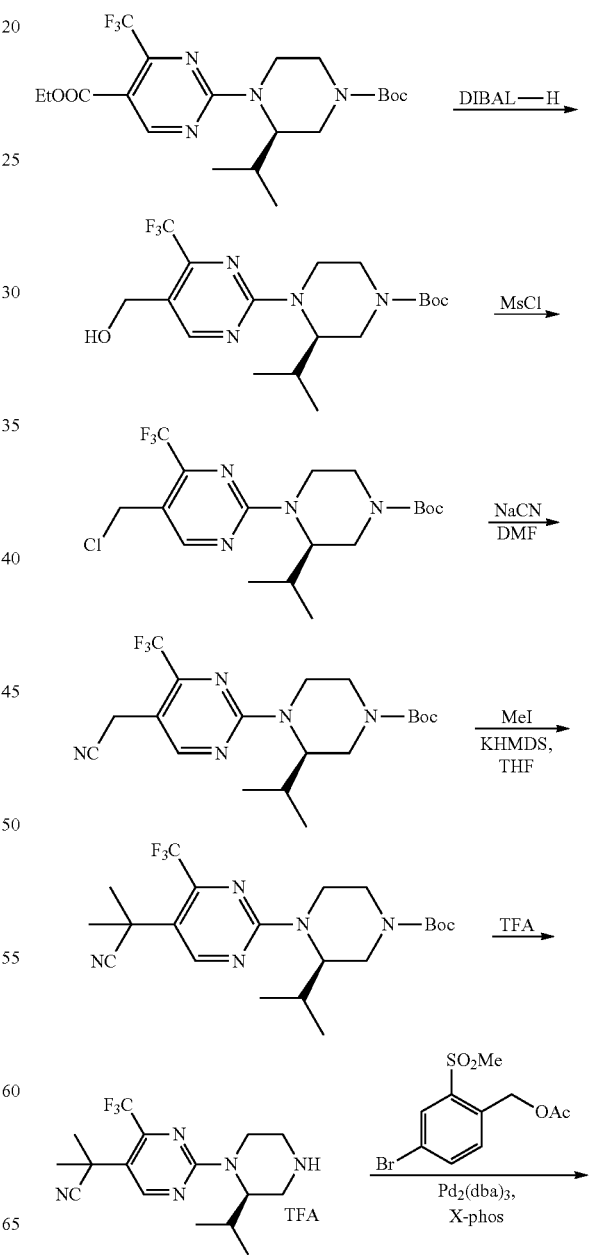

-continued

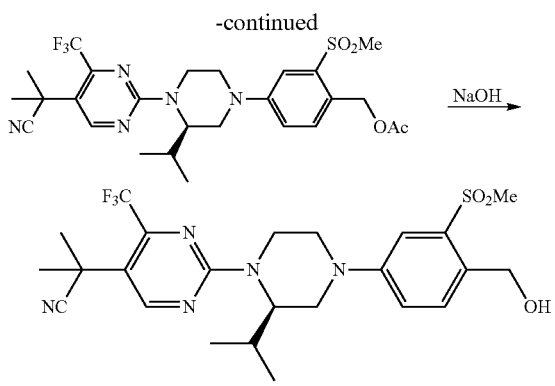

'Step 1

To a solution of (R)-ethyl 2-(4-(tert-butoxycarbonyl)-2-isopropylpiperazin-1-yl)-4-(trifluoromethyl)pyrimidine-5-carboxylate (600 mg, 1.34 mmol) in anhydrous toluene (10 mL) was added DIBAL-H (2.01 mL, 2.01 mmol, 1 M in toluene) under $N_2$. The reaction mixture was stirred at −78° C. for 30 min. The reaction mixture was quenched with sat. NH4Cl solution (10 mL) at −78° C. The mixture was filtered, then the filtrate was diluted with water (50 mL) and extracted with EtOAc (3×50 mL). The combined organic layers were washed with brine (100 mL), dried over anhydrous $Na_2SO_4$, filtered and concentrated under reduced pressure. The residue was purified by column chromatography on silica gel to afford (R)-tert-butyl 4-(5-(hydroxymethyl)-4-(trifluoromethyl)pyrimidin-2-yl)-3-isopropylpiperazine-1-carboxylate (457 mg, 84%) as a yellow oil.

Step 2

To a solution of (R)-tert-butyl 4-(5-(hydroxymethyl)-4-(trifluoromethyl)pyrimidin-2-yl)-3-isopropylpiperazine-1-carboxylate (450 mg, 1.11 mmol) and $Et_3N$ (561.7 mg, 5.55 mmol) in anhydrous $CH_2Cl_2$ (6 mL) was added MsCl (254.2 mg, 2.22 mmol) under $N_2$. The reaction mixture was stirred at rt for 8 h. The mixture was added with water (30 mL) and extracted with EtOAc (3×30 mL). The combined organic layers were washed with brine (50 mL), dried over anhydrous $Na_2SO_4$, filtered and concentrated under reduced pressure. The residue was purified by column chromatography on silica gel to afford (R)-tert-butyl 4-(5-(chloromethyl)-4-(trifluoromethyl)pyrimidin-2-yl)-3-isopropylpiperazine-1-carboxylate (289.4 mg, 61%) as a yellow oil.

Step 3

To a solution of (R)-tert-butyl 4-(5-(chloromethyl)-4-(trifluoromethyl)pyrimidin-2-yl)-3-isopropylpiperazine-1-carboxylate (289 mg, 0.68 mmol) in DMF (3 mL) was added NaCN (50 mg, 1.02 mmol). The reaction mixture was stirred at rt for 3 h. The mixture was added with water (20 mL) and extracted with EtOAc (3×20 mL). The combined organic layers were washed with brine (50 mL), dried over anhydrous $Na_2SO_4$, filtered and concentrated under reduced pressure. The residue was purified by preparative TLC with petroleum ether/EtOAc 4/1 to afford (R)-tert-butyl 4-(5-(cyanomethyl)-4-(trifluoromethyl)pyrimidin-2-yl)-3-isopropylpiperazine-1-carboxylate (177 mg, 63%) as a yellow oil.

Step 4

To a solution of (R)-tert-butyl 4-(5-(cyanomethyl)-4-(trifluoromethyl)pyrimidin-2-yl)-3-isopropylpiperazine-1-carboxylate (60 mg, 0.15 mmol) in anhydrous THF (3 mL) was added KHMDS (0.75 mL, 0.75 mmol, 1 M in THF) at −78° C. under $N_2$. The reaction mixture was stirred at −78° C. for 30 min, then MeI (85.2 mg, 0.6 mmol) was added to the reaction mixture. The reaction mixture was stirred for 1 h. The mixture was added with water (10 mL) and extracted with EtOAc (3×10 mL). The combined organic layers were washed with brine (25 mL), dried over anhydrous $Na_2SO_4$, filtered and concentrated under reduced pressure. The residue was purified by preparative TLC with petroleum ether/EtOAc 5/1 to afford (R)-tert-butyl 4-(5-(2-cyanopropan-2-yl)-4-(trifluoromethyl)pyrimidin-2-yl)-3-isopropylpiperazine-1-carboxylate (60 mg, 94%) as a white solid.

Step 5

To a solution of (R)-tert-butyl 4-(5-(2-cyanopropan-2-yl)-4-(trifluoromethyl)pyrimidin-2-yl)-3-isopropylpiperazine-1-carboxylate (20 mg, 0.0453 mmol) in $CH_2Cl_2$ (2.5 mL) was added TFA (0.5 mL). The reaction mixture was stirred at rt for 1 h. The mixture was concentrated under reduced pressure to afford crude (R)-2-(2-(2-isopropylpiperazin-1-yl)-4-(trifluoromethyl)pyrimidin-5-yl)-2-methylpropanenitrile TFA salt (15 mg, 71%) as a yellow solid, which was used for the next step directly without further purification.

Step 6

To a solution of (R)-2-(2-(2-isopropylpiperazin-1-yl)-4-(trifluoromethyl)pyrimidin-5-yl)-2-methylpropanenitrile TFA salt (15 mg, 0.044 mmol), 4-bromo-2-(methylsulfonyl)benzyl acetate (16.3 mg, 0.053 mmol), X-phos (4.2 mg, 8.8 μmol) and $Cs_2CO_3$ (115 mg, 0.352 mmol) in anhydrous toluene (1 mL) was added $Pd_2$(dba)$_3$ (9.8 mg, 8.8 μmol). The reaction mixture was stirred at 100° C. for 3 h under $N_2$. The reaction mixture was concentrated under reduced pressure to afford crude (R)-4-(4-(5-(2-cyanopropan-2-yl)-4-(trifluoromethyl)pyrimidin-2-yl)-3-isopropylpiperazin-1-yl)-2-(methylsulfonyl)benzyl acetate, which was used for the next step directly without further purification.

Step 7

To a solution of (R)-4-(4-(5-(2-cyanopropan-2-yl)-4-(trifluoromethyl)pyrimidin-2-yl)-3-isopropylpiperazin-1-yl)-2-(methylsulfonyl)benzyl acetate (0.044 mmol) in H2O (0.5 mL) and $CH_3OH$ (0.5 mL) was added NaOH (18 mg, 0.44 mmol). The reaction mixture was stirred at rt for 1 h. The mixture was added with water (10 mL) and extracted with EtOAc (3×10 mL). The combined organic layers were washed with brine (25 mL), dried over anhydrous $Na_2SO_4$, filtered and concentrated under reduced pressure. The residue was purified by basic preparative HPLC to afford (R)-2-(2-(4-(4-(hydroxymethyl)-3-(methylsulfonyl)phenyl)-2-isopropylpiperazin-1-yl)-4-(trifluoromethyl)pyrimidin-5-yl)-2-methylpropanenitrile (5.3 mg, 23%) as a white solid. LC-MS tR=1.214 min in 2 min chromatography, MS (ESI) m/z 526.2 [M+H]+. 1H NMR ($CD_3OD$): δ 8.73 (s, 1H), 7.56-7.54 (m, 2H), 7.27 (dd, $J_1$=2.4, 8.4 Hz, 1H), 4.91 (s, 2H), 4.86-4.80 (m, 1H), 4.67 (d, J=9.6 Hz, 1H), 3.97 (d, J=12.4 Hz, 1H), 3.76 (d, J=12.0 Hz, 1H), 3.42-3.38 (m, 1H), 3.28 (s, 3H), 2.94-2.83 (m, 2H), 2.51-2.41 (m, 1H), 1.84 (s, 6H), 1.14 (d, J=6.4 Hz, 3H), 0.83 (d, J=6.4 Hz, 3H).

Example 26

(R)-2-(2-(4-(4-fluoro-3-(methylsulfonyl)phenyl)-2-isopropylpiperazin-1-yl)-4-(trifluoromethyl)thiazol-5-yl)propan-2-ol (Cpd No 26-1)

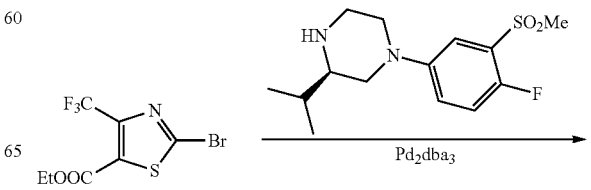

-continued

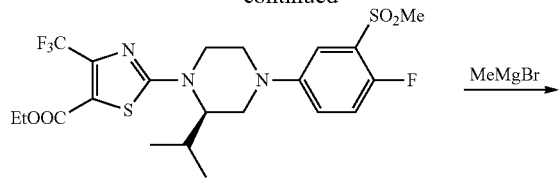

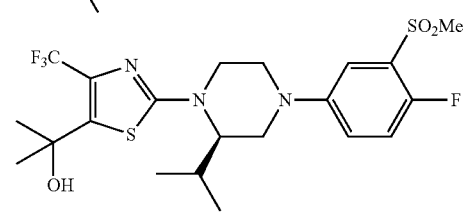

Step 1

To a solution of ethyl 2-bromo-4-(trifluoromethyl)thiazole-5-carboxylate (100 mg, 0.33 mol) and (R)-1-(4-fluoro-3-(methylsulfonyl)phenyl)-3-isopropylpiperazine (99 mg, 0.33 mmol) in toluene (5 mL) was added X-phos (7.6 mg, 0.016 mmol), Pd$_2$dba$_3$ (15 mg, 0.016 mmol) and cesium carbonate (326 mg, 1 mmol). The mixture was stirred at 100° C. for 3 h under N$_2$. The mixture was added with water (20 mL) and extracted with EtOAc (3×30 mL). The combined organic layers were dried over anhydrous Na$_2$SO$_4$, filtered, concentrated under reduced pressure. The residue was purified by preparative TLC with petroleum ether/EtOAc 2/1 to afford (R)-ethyl 2-(4-(4-fluoro-3-(methylsulfonyl)phenyl)-2-isopropylpiperazin-1-yl)-4-(trifluoromethyl)thiazole-5-carboxylate (60 mg, 35%).

Step 2

To a solution of (R)-ethyl 2-(4-(4-fluoro-3-(methylsulfonyl)phenyl)-2-isopropylpiperazin-1-yl)-4-(trifluoromethyl)thiazole-5-carboxylate (30 mg, 57 μmmol) in THF (2 mL) at 0° C. was added MeMgBr (0.19 mL, 0.57 mmol, 3 M in Et2O) under N2. Then the reaction mixture was stirred at rt for 2 h. The mixture was quenched with sat. NH4Cl solution (10 mL) and extracted with EtOAc (3×20 mL). The combined organic layers were dried over anhydrous Na$_2$SO$_4$, filtered, concentrated under reduced pressure. The residue was purified by preparative TLC with petroleum ether/EtOAc 3/1 to afford the title compound (9.00 mg, 31%). LC-MS tR=1.271 min in 2 min chromatography, m/z 510.1 [M+H]+. 1H NMR (CD3OD): δ 7.20 (dd, J=3.2, 5.6 Hz, 1H), 7.38-7.26 (m, 2H), 4.06 (d, J=13.6 Hz, 1H), 3.81 (d, J=12.4 Hz, 1H), 3.72 (d, J=10.8 Hz, 1H), 3.60 (d, J=11.6 Hz, 1H), 3.53-3.47 (m, 1H), 3.26 (s, 3H), 2.98-2.88 (m, 2H), 2.52-2.48 (m, 1H), 1.61 (s, 6H), 1.11 (d, J=6.8 Hz, 3H), 0.97 (d, J=6.8 Hz, 3H).

The following compound was prepared using similar procedures:

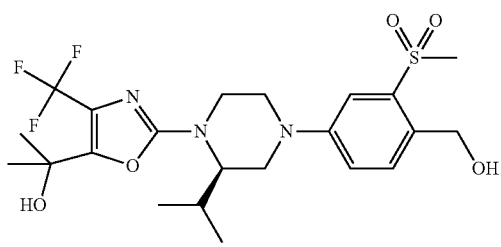

Cpd No 26-2, m/z = 506.2

Example 27

(R)-2-(2-(4-(4-(hydroxymethyl)-3-(methylsulfonyl)phenyl)-2-isopropylpiperazin-1-yl)-4-(trifluoromethyl)thiazol-5-yl)propan-2-ol (Cpd No 27-1)

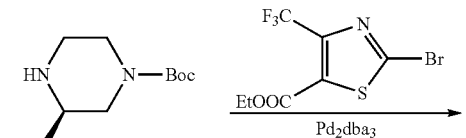

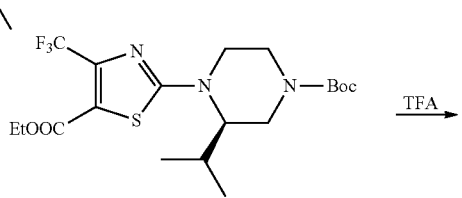

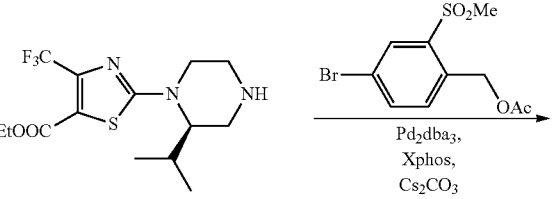

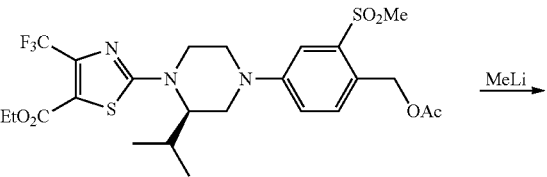

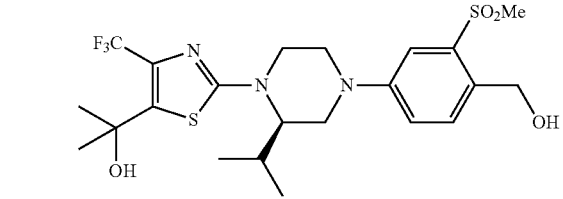

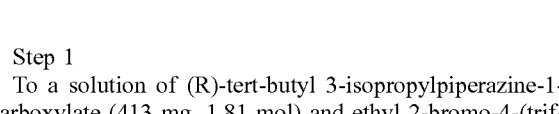

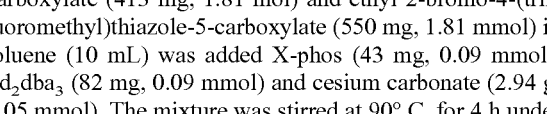

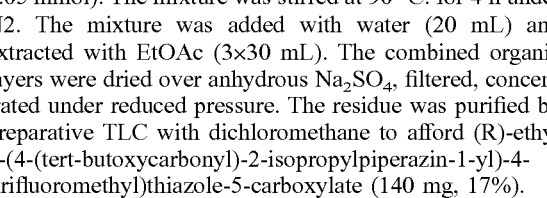

Step 1

To a solution of (R)-tert-butyl 3-isopropylpiperazine-1-carboxylate (413 mg, 1.81 mol) and ethyl 2-bromo-4-(trifluoromethyl)thiazole-5-carboxylate (550 mg, 1.81 mmol) in toluene (10 mL) was added X-phos (43 mg, 0.09 mmol), Pd$_2$dba$_3$ (82 mg, 0.09 mmol) and cesium carbonate (2.94 g, 9.05 mmol). The mixture was stirred at 90° C. for 4 h under N2. The mixture was added with water (20 mL) and extracted with EtOAc (3×30 mL). The combined organic layers were dried over anhydrous Na$_2$SO$_4$, filtered, concentrated under reduced pressure. The residue was purified by preparative TLC with dichloromethane to afford (R)-ethyl 2-(4-(tert-butoxycarbonyl)-2-isopropylpiperazin-1-yl)-4-(trifluoromethyl)thiazole-5-carboxylate (140 mg, 17%).

Step 2

To a solution of (R)-ethyl 2-(4-(tert-butoxycarbonyl)-2-isopropylpiperazin-1-yl)-4-(trifluoromethyl)thiazole-5-carboxylate (140 mg, 0.31 mmol) in dichloromethane (8 mL) was added TFA (2 mL) at 0° C. The mixture was stirred at rt for 2 h. The reaction mixture was concentrated under reduced pressure, the residue was added with sat. NaHCO3 solution (10 mL) and extracted with EtOAc (3×20 mL). The combined organic layers were dried over anhydrous Na$_2$SO$_4$, filtered and concentrated under reduced pressure to afford crude (R)-ethyl 2-(2-isopropylpiperazin-1-yl)-4-(trifluoromethyl)thiazole-5-carboxylate (120 mg, 100%).

Step 3

To a solution of (R)-ethyl 2-(2-isopropylpiperazin-1-yl)-4-(trifluoromethyl)thiazole-5-carboxylate (120 mg, 0.34 mol) and 4-bromo-2-(methylsulfonyl)benzyl acetate (104.6 mg, 0.34 mmol) in toluene (5 mL) was added X-phos (8.1 mg, 0.017 mmol), Pd$_2$dba$_3$ (15.7 mg, 0.017 mmol) and cesium carbonate (331.5 mg, 1.02 mmol). The mixture was stirred at 90° C. for 4 h under N$_2$. The mixture was added with water (20 mL) and extracted with EtOAc (3×30 mL). The combined organic layers were dried over anhydrous Na2SO4, filtered and concentrated under reduced pressure. The residue was purified by preparative TLC with petroleum ether/EtOAc 2/1 to afford (R)-ethyl 2-(4-(4-(acetoxymethyl)-3-(methylsulfonyl)phenyl)-2-isopropylpiperazin-1-yl)-4-(trifluoromethyl)thiazole-5-carboxylate (80 mg, 41%).

Step 4

To a solution of (R)-ethyl 2-(4-(4-(acetoxymethyl)-3-(methylsulfonyl)phenyl)-2-isopropylpiperazin-1-yl)-4-(trifluoromethyl)thiazole-5-carboxylate (25 mg, 43 µmol) in THF (1 mL) was added MeLi (0.268 mL, 0.43 mmol, 1.3 M) at −78° C. under N$_2$. The reaction was stirred at −78° C. for 2 h under N$_2$. The mixture was quenched with sat. NH$_4$Cl solution (10 mL) and extracted with EtOAc (3×20 mL). The combined organic layers were dried over anhydrous Na$_2$SO$_4$, filtered and concentrated under reduced pressure. The residue was purified by basic preparative HPLC to afford (R)-2-(2-(4-(4-(hydroxymethyl)-3-(methylsulfonyl)phenyl)-2-isopropylpiperazin-1-yl)-4-(trifluoromethyl)thiazol-5-yl)propan-2-ol (0.4 mg, 1.8%). LC-MS tR=1.197 min in 2 min chromatography, m/z 522.2 [M+H]+. 1H NMR (CD3OD): δ 7.57-7.55 (m, 2H), 7.29-7.26 (m, 1H), 4.88 (s, 2H), 4.07-4.03 (m, 1H), 3.94-3.91 (m, 1H), 3.74-3.65 (m, 2H), 3.53-3.50 (m, 1H), 3.22 (s, 3H), 3.03-2.97 (m, 2H), 2.39-2.47 (m, 1H), 1.62-1.60 (m, 6H), 1.13-1.09 (m, 3H), 0.97-0.92 (m, 3H).

Example 28

(R)-(2-(2-isopropyl-4-(3-(methylsulfonyl)-4-(4-methylthiazol-2-yl)phenyl)piperazin-1-yl)-4-(trifluoromethyl)pyrimidin-5-yl)methanol (Cpd No 28-1)

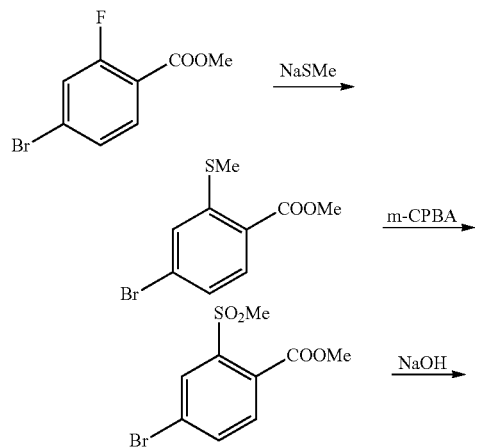

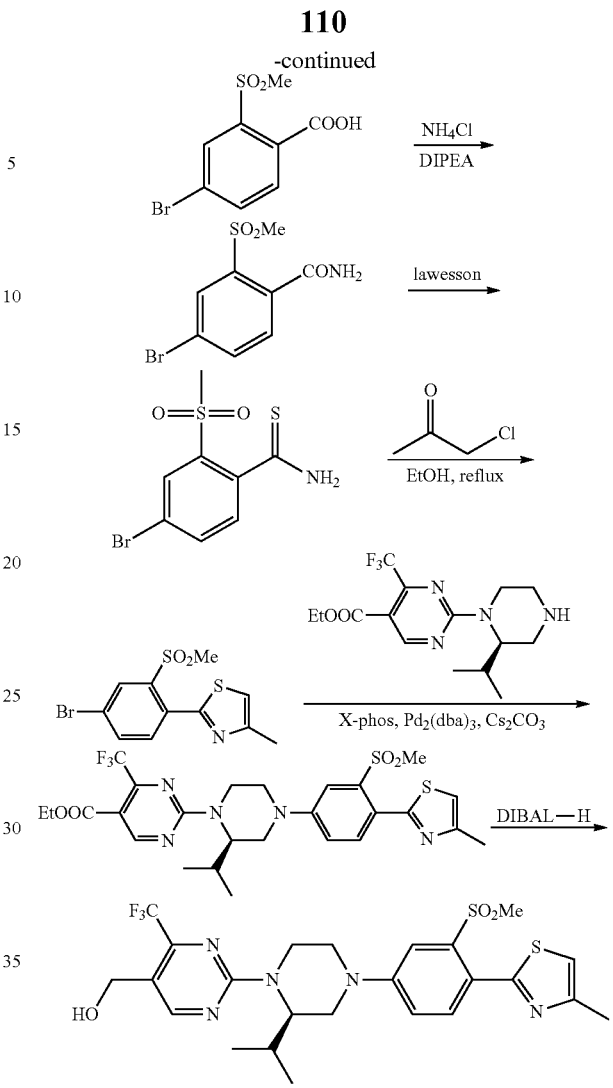

Step 1

To a solution of methyl 4-bromo-2-fluorobenzoate (25 g, 0.11 mol) in THF (1 L) was added NaSMe (11.3 g, 0.16 mol). The mixture was stirred at reflux overnight. Water (1 L) was added to the mixture and the mixture was concentrated under reduced pressure. The aqueous layer was extracted with EtOAc (3×500 mL). The combined organic layers were washed with brine (500 mL), dried over anhydrous Na2SO4, filtered and concentrated to afford crude methyl 4-bromo-2-(methylthio)benzoate (crude 25.6 g, 90%) as a white solid, which was used for the next step directly without further purification. 1H NMR (DMSO-d6): δ 7.82 (dd, J=2.8, 8.4 Hz, 1H), 7.48 (s, 1H), 7.45 (dd, J=1.6, 6.4 Hz, 1H), 3.83 (s, 3H), 2.46 (s, 3H).

Step 2

To a solution of methyl 4-bromo-2-(methylthio)benzoate (crude 10.8 g, 0.041 mol) in CH$_2$Cl$_2$ (500 mL) was added m-CPBA (21.4 g, 0.124 mol). The mixture was stirred at rt overnight. The mixture was washed successively with sat. Na$_2$S$_2$O$_3$ solution (300 mL), sat. NaHCO$_3$ solution (300 mL) and brine (300 mL), dried over anhydrous Na$_2$SO$_4$, filtered and concentrated under reduced pressure. The residue was purified by chromatography column on silica gel eluting with petroleum ether: EtOAc 3:1 to afford methyl4-bromo-2-(methylsulfonyl) benzoate (7.9 g, 65%) as a white solid.

1H NMR (CDCl$_3$): δ 8.28 (d, J=2.0 Hz, 1H), 7.82 (dd, J=2.0, 8.4 Hz, 1H), 7.60 (d, J=8.0 Hz, 1H), 3.97 (s, 3H), 3.37 (s, 3H).

Step 3

To a solution of methyl 4-bromo-2-(methylsulfonyl)benzoate (1.0 g, 3.4 mmol) in methanol (3 mL) and H2O (1 mL) was added NaOH (410 mg, 10.2 mmol). The mixture was stirred at 60° C. for 4 h. The mixture was concentrated under reduced pressure and the mixture was adjusted to pH=4 with 1N HCl solution. The aqueous layer was extracted with EtOAc (3×20 mL). The combined organic layers were washed with brine, dried over anhydrous Na$_2$SO$_4$, filtered and concentrated under reduced pressure to afford crude 4-bromo-2-(methylsulfonyl)benzoic acid (crude 800 mg, 84%) as a white solid, which was used for the next step directly without further purification. LC-MS tR=0.850 min in 2 min chromatography. MS (ESI) m/z 262.9 [M+H—H$_2$O]+, 300.9 [M+Na]+. 1H NMR (DMSO-d6): δ 8.08 (d, J=2.0 Hz, 1H), 8.02 (dd, J=2.0, 8.0 Hz, 1H), 7.68 (d, J=8.4 Hz, 1H), 3.42 (s, 3H).

Step 4

To a solution of 4-bromo-2-(methylsulfonyl)benzoic acid (crude 1.4 g, 5.0 mmol) in DMF (20 mL) was added HATU (2.85 g, 7.5 mmol), NH$_4$Cl (800 mg, 15 mmol) and DIPEA (1.94 g, 15 mmol). The mixture was stirred at rt overnight. The mixture was added with water (40 mL) and extracted with EtOAc (3×50 mL). The combined organic layers were washed with water (3×50 mL) and brine, dried over anhydrous Na$_2$SO$_4$, filtered and concentrated under reduced pressure. The residue was purified by chromatography column on silica gel eluting with petroleum ether: EtOAc 1:5 to give 4-bromo-2-(methylsulfonyl)benzamide (1.1 g, 79%) as a white solid. LC-MS tR=0.663 min in 2 min chromatography. MS (ESI) m/z 277.9 [M+H]+.

Step 5

To a solution of 4-bromo-2-(methylsulfonyl)benzamide (20 mg, 0.072 mmol) in toluene (1 mL) was added Lawesson's Reagent (87 mg, 0.22 mmol). The mixture was stirred at 100° C. for 2 h. The mixture was filtered and the filtrate was concentrated under reduced pressure. The residue was purified by preparative TLC to afford 4-bromo-2-(methylsulfonyl)benzothioamide (15.0 mg, 71%) as a yellow solid. LC-MS tR=0.874 min in 2 min chromatography. MS (ESI) m/z 293.9 [M+H]+.

Step 6

To a solution of 4-bromo-2-(methylsulfonyl)benzothioamide (20 mg, 0.068 mmol) in ethanol (1 mL) was added 1-chloropropan-2-one (13 mg, 0.136 mmol). The mixture was stirred at reflux overnight. The mixture was concentrated under reduced pressure to afford crude 2-(4-bromo-2-(methylsulfonyl)phenyl)-4-methylthiazole (crude 17 mg, 75%) as a yellow oil, which was used for the next step directly without further purification. LC-MS tR=1.117 min in 2 min chromatography. MS (ESI) m/z 331.9 [M+H]+.

Step 7

To a solution of 2-(4-bromo-2-(methylsulfonyl)phenyl)-4-methylthiazole (17.0 mg, 0.051 mmol) in toluene (1 mL) was added (R)-ethyl 2-(2-isopropylpiperazin-1-yl)-4-(trifluoromethyl)pyrimidine-5-carboxylate (18 mg, 0.051 mmol), X-phos (5.0 mg, 0.010 mmol), Pd2dba3 (5 mg, 0.005 mmol) and Cs$_2$CO$_3$ (50 mg, 0.154 mmol). The mixture was stirred at reflux overnight. The mixture was added with water (10 mL) and extracted with EtOAc (3×10 mL). The combined organic layers were washed with brine, dried over anhydrous Na2SO4, filtered and concentrated under reduced pressure. The residue was purified by preparative TLC to give (R)-ethyl 2-(2-isopropyl-4-(3-(methylsulfonyl)-4-(4-methylthiazol-2-yl)phenyl)piperazin-1-yl)-4-(trifluoromethyl)pyrimidine-5-carboxylate (15.0 mg, 49%) as a yellow solid. LC-MS tR=1.442 min in 2 min chromatography. MS (ESI) m/z 598.1 [M+H]+.

Step 8

To a solution of (R)-ethyl 2-(2-isopropyl-4-(3-(methylsulfonyl)-4-(4-methylthiazol-2-yl)phenyl) piperazin-1-yl)-4-(trifluoromethyl)pyrimidine-5-carboxylate (15 mg, 0.025 mmol) in toluene (1 mL) was added DIBAL-H (0.075 mL, 0.075 mmol, 1M in toluene) at −78° C. under N$_2$. The mixture was stirred at −78° C. for 2 h. Saturated NH4Cl solution (5 mL) was added and the mixture was filtered. The filtrate was extracted with EtOAc (3×10 mL). The combined organic layers were washed with brine, dried over anhydrous Na2SO4, filtered and concentrated under reduced pressure. The residue was purified by preparative TLC to afford (R)-(2-(2-isopropyl-4-(3-(methylsulfonyl)-4-(4-methylthiazol-2-yl)phenyl)piperazin-1-yl)-4-(trifluoromethyl)pyrimidin-5-yl)methanol (14.50 mg, 63%) as a white solid. LC-MS tR=1.268 min in 2 min chromatography. MS (ESI) m/z 556.2 [M+H]+. 1H NMR (CDCl3): δ 8.55 (s, 1H), 7.69 (d, J=2.8 Hz, 1H), 7.47 (d, J=8.4 Hz, 1H), 7.06 (dd, J=2.8, 8.4 Hz, 1H), 6.98 (s, 1H), 4.84 (d, J=13.6 Hz, 1H), 4.70-4.68 (m, 3H), 3.94 (d, J=12.4 Hz, 1H), 3.76 (d, J=12.0 Hz, 1H), 3.50 (s, 3H), 3.39-3.32 (m, 1H), 3.07-2.97 (m, 2H), 2.48 (s, 3H), 2.39-2.33 (m, 1H), 1.89 (brs, 1H), 1.11 (d, J=6.4 Hz, 3H), 0.83 (d, J=6.4 Hz, 3H).

Example 29

(R)-2-(4-(4-fluoro-3-(methylsulfonyl)phenyl)-2-isopropylpiperazin-1-yl)-5-methoxy-4-(trifluoromethyl)pyrimidine (Cpd No 29-1)

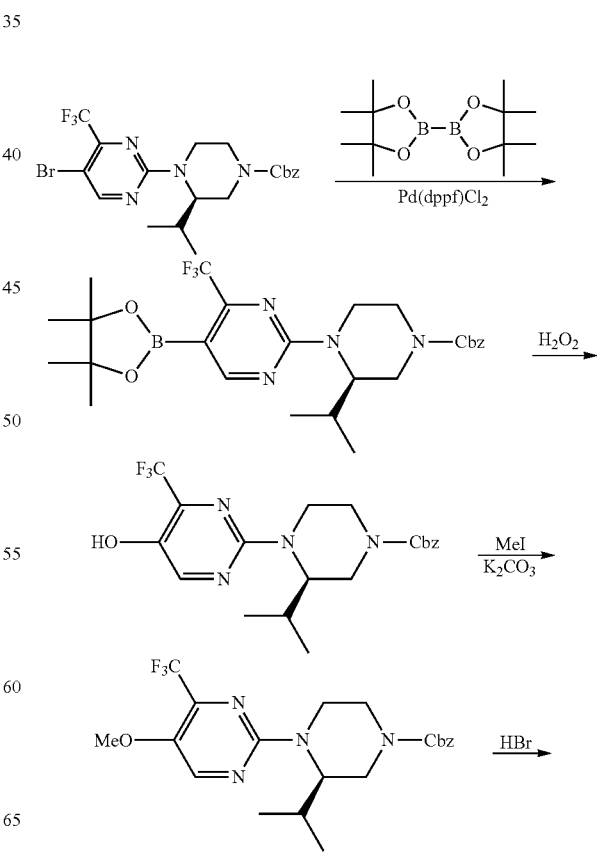

-continued

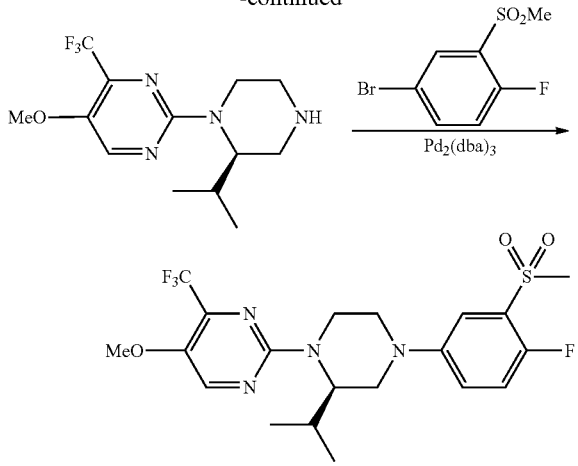

Step 1

To a solution of (R)-benzyl 4-(5-bromo-4-(trifluoromethyl)pyrimidin-2-yl)-3-isopropylpiperazine-1-carboxylate (250 mg, 0.514 mmol), 4,4,4',4',5,5,5',5'-octamethyl-2,2'-bi(1,3,2-dioxaborolane) (196 mg, 0.77 mmol) and KOAc (151 mg, 1.54 mmol) in dioxane (3 mL) was added Pd(dppf)Cl$_2$ (19 mg, 0.026 mmol) under N$_2$. The reaction mixture was stirred at 100° C. for 2 h. The mixture was filtered, the filtrate was added with water (10 mL) and extracted with EtOAc (3×10 mL). The combined organic layers were washed with brine, dried over anhydrous Na$_2$SO$_4$, filtered and concentrated to afford crude product. The crude product was purified by preparative TLC with petroleum ether:EtOAc=8:1 to afford (R)-benzyl 3-isopropyl-4-(5-(4,4,5,5-tetramethyl-1,3,2-dioxaborolan-2-yl)-4-(trifluoromethyl)pyrimidin-2-yl)piperazine-1-carboxylate (240 mg, 88%) as a yellow oil.

Step 2

To a solution of (R)-benzyl 3-isopropyl-4-(5-(4,4,5,5-tetramethyl-1,3,2-dioxaborolan-2-yl)-4-(trifluoromethyl)pyrimidin-2-yl)piperazine-1-carboxylate (250 mg, 0.47 mmol) and AcOH (1 mL) in THF (2 mL) was added H$_2$O$_2$ (5 mL). The reaction mixture was stirred at rt for 3 h. After quenching the reaction with saturated Na$_2$S$_2$O$_3$ solution, the mixture was extracted with EtOAc (3×20 mL). The combined organic layers were washed with saturated Na$_2$S$_2$O$_3$ solution, dried over anhydrous Na2SO4, filtered and concentrated to afford (R)-benzyl 4-(5-hydroxy-4-(trifluoromethyl)pyrimidin-2-yl)-3-isopropylpiperazine-1-carboxylate (180 mg, 90%), which was used for the next step directly without further purification.

Step 3

To a mixture of (R)-benzyl 4-(5-hydroxy-4-(trifluoromethyl)pyrimidin-2-yl)-3-isopropylpiperazine-1-carboxylate (180 mg, 0.42 mmol) and K$_2$CO$_3$ (290 mg, 2.1 mmol) in DMF (5 mL) was added MeI (89.5 mg, 0.63 mmol) under N$_2$. The reaction mixture was stirred at rt for 2 h. The reaction mixture was treated with water (20 mL) and extracted with EtOAc (3×20 mL). The combined organic layers were washed with brine, dried over anhydrous Na$_2$SO$_4$, filtered and concentrated to afford crude product. The crude product was purified by preparative TLC with petroleum ether:EtOAc=3:1 to afford (R)-benzyl 3-isopropyl-4-(5-methoxy-4-(trifluoromethyl)pyrimidin-2-yl)piperazine-1-carboxylate (80 mg, 43%) as a yellow oil.

Step 4

A solution of (R)-benzyl 3-isopropyl-4-(5-methoxy-4-(trifluoromethyl)pyrimidin-2-yl)piperazine-1-carboxylate (75 mg, 0.17 mmol) in HBr/AcOH (6 mL) was stirred at rt for 1 h. The reaction mixture was treated with water (10 mL) and extracted with EtOAc (3×10 mL). The aqueous layer was adjusted to pH=8-9 with saturated NaHCO$_3$ solution and extracted with EtOAc (3×10 mL). The combined organic layers were washed with brine, dried over anhydrous Na$_2$SO$_4$, filtered and concentrated to afford (R)-2-(2-isopropylpiperazin-1-yl)-5-methoxy-4-(trifluoromethyl)pyrimidine which was used for the next step directly without further purification.

Step 5

To a mixture of (R)-2-(2-isopropylpiperazin-1-yl)-5-methoxy-4-(trifluoromethyl)pyrimidine (15 mg, 49 μmol), 4-bromo-1-fluoro-2-(methylsulfonyl)benzene (15 mg, 59 μmol), Cs$_2$CO$_3$ (128 mg, 392 μmol) and X-phos (1.2 mg, 2.5 μmol) in anhydrous toluene (1 mL) was added Pd$_2$(dba)$_3$ (3 mg, 2.5 μmol) under N$_2$. The reaction mixture was stirred at 100° C. for 5 h. The mixture was filtered, the filtrate was added with water (10 mL) and extracted with EtOAc (3×10 mL). The combined organic layers were washed with brine, dried over anhydrous Na2SO4, filtered and concentrated to afford crude product. The crude product was purified by preparative TLC with petroleum ether:EtOAc=3:1 to afford (R)-2-(4-(4-fluoro-3-(methylsulfonyl)phenyl)-2-isopropylpiperazin-1-yl)-5-methoxy-4-(trifluoromethyl)pyrimidine (17.00 mg, 72%) as a white solid. LC-MS tR=1.328 min in 2 min chromatography, MS (ESI) m/z 477.1 [M+H]+. 1H NMR (CD3OD): δ 8.49 (s, 1H), 7.48-7.41 (m, 1H), 7.38-7.26 (m, 2H), 4.89-4.74 (m, 1H), 4.63-4.59 (m, 1H), 3.92 (s, 3H), 3.84 (d, J=12.4 Hz, 1H), 3.73-3.61 (m, 1H), 3.39-3.33 (m, 1H), 3.25 (s, 3H), 2.89-2.78 (m, 2H), 2.54-2.45 (m, 1H), 1.13 (d, J=6.8 Hz, 3H), 0.83 (d, J=6.8 Hz, 3H).

Example 30

(R)-2-(4-(4-fluoro-3-(methylsulfonyl)phenyl)-2-isopropylpiperazin-1-yl)-4-(trifluoromethyl)pyrimidin-5-ol (Cpd No 30-1)

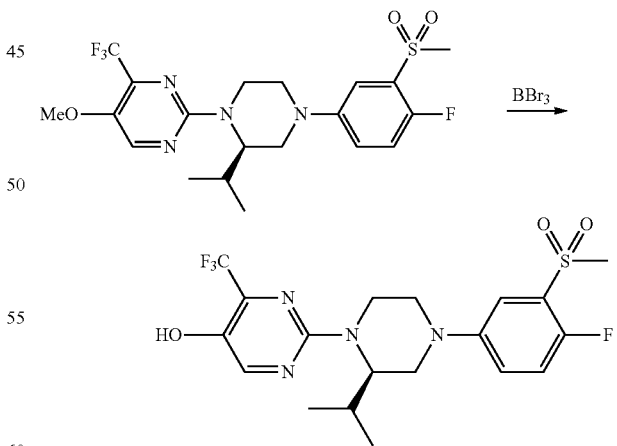

Step 1

To a solution of (R)-2-(4-(4-fluoro-3-(methylsulfonyl)phenyl)-2-isopropylpiperazin-1-yl)-5-methoxy-4-(trifluoromethyl)pyrimidine (10 mg, 21 μmol) in anhydrous CH$_2$Cl$_2$ (0.5 mL) was added BBr$_3$ (0.5 mL) under N2 at −78° C. The reaction mixture was stirred at −78° C. for 3 h and then at rt for 17 h. After quenching the reaction with methanol (1 mL) at −78° C., water (10 mL) was added to the mixture and the aqueous layer was extracted with EtOAc (3×10 mL). The combined organic layers were washed with brine, dried over anhydrous Na2SO4, filtered and concentrated to afford crude product. The crude product was purified by preparative TLC with petroleum ether: EtOAc=1:1 to afford (R)-2-(4-(4-fluoro-3-(methylsulfonyl) phenyl)-2-isopropylpiperazin-1-yl)-4-(trifluoromethyl)pyrimidin-5-ol (1.60 mg, 17%) as a white solid. LC-MS tR=1.215 min in 2 min chromatography, MS (ESI) m/z 463.1 [M+H]+. 1H NMR (CD$_3$OD): δ 8.24 (s, 1H), 7.42-7.38 (m, 1H), 7.36-7.25 (m, 2H), 4.70 (d, J=13.2 Hz, 1H), 4.56 (d, J=10.0 Hz, 1H), 3.83 (d, J=12.0 Hz, 1H), 3.61 (d, J=12.0 Hz, 1H), 3.25 (s, 3H), 2.88-2.77 (m, 3H), 2.56-2.43 (m, 1H), 1.12 (d, J=6.8 Hz, 3H), 0.83 (d, J=6.8 Hz, 3H).

Example 31

(R)-2-(4-((2-(4-(4-fluoro-3-(methylsulfonyl)phenyl)-2-isopropylpiperazin-1-yl)-4-(trifluoromethyl)pyrimidin-5-yl)methyl)phenyl)propan-2-ol (Cpd No 31-1)

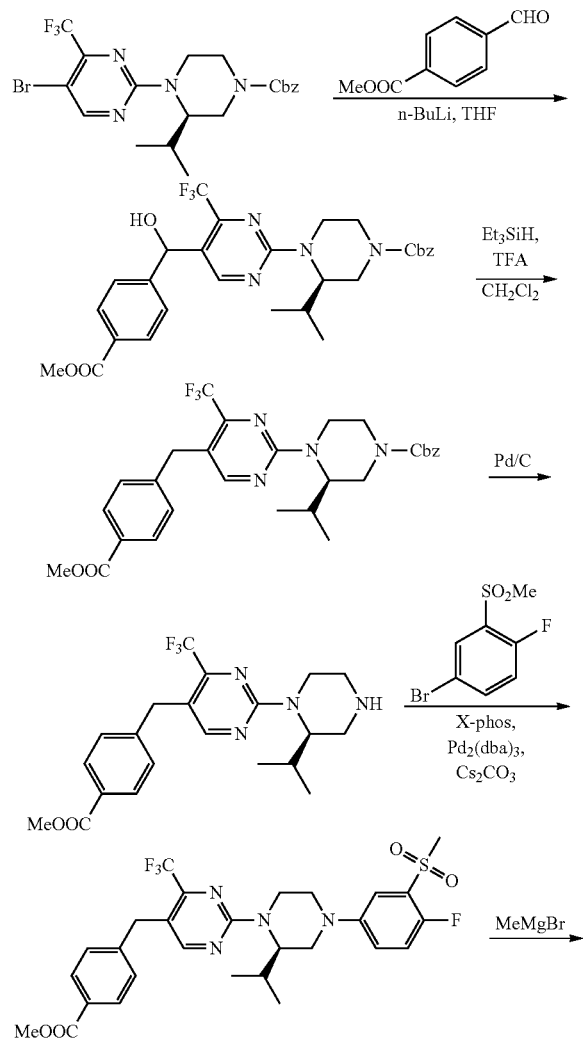

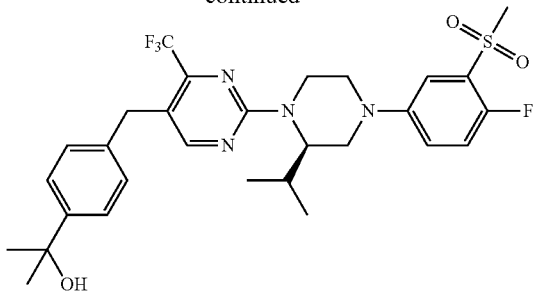

Step 1

To a solution of (R)-benzyl 4-(5-bromo-4-(trifluoromethyl)pyrimidin-2-yl)-3-isopropylpiperazine-1-carboxylate (250 mg, 0.51 mmol) in THF (5 mL) was added n-BuLi (0.72 mL, 0.67 mmol, 2.5 M in hexane) dropwise at −78° C. under N$_2$. The mixture was stirred at −78° C. for 5 min and methyl 4-formylbenzoate (93 mg, 0.57 mmol) was added at −78° C. under N$_2$. The mixture was stirred at −78° C. for 30 min. The reaction was quenched with sat. NH$_4$Cl solution (5 mL) at −78° C. The aqueous layer was extracted with EtOAc (3×10 mL). The combined organic layers were washed with brine (20 mL), dried over anhydrous Na$_2$SO$_4$, filtered and concentrated under reduced pressure. The residue was purified by preparative TLC (petroleum ether/EtOAc 3/1) to afford (3R)-benzyl 4-(5-(hydroxy(4-(methoxycarbonyl)phenyl)methyl)-4-(trifluoromethyl)pyrimidin-2-yl)-3-isopropylpiperazine-1-carboxylate (100 mg, 34%) as a white solid. LC-MS tR=1.395 min in 10-80AB_2MIN.M chromatography (Welch Xtimate C18, 2.1*30 mm, 3 um), MS (ESI) m/z 573.2 [M+H]+.

Step 2

To a solution of (3R)-benzyl 4-(5-(hydroxy(4-(methoxycarbonyl)phenyl)methyl)-4-(trifluoromethyl)pyrimidin-2-yl)-3-isopropylpiperazine-1-carboxylate (100 mg, 0.17 mmol) in CH$_2$Cl$_2$ (0.5 mL) was added Et$_3$SiH (0.5 mL) and TFA (0.5 mL) under N$_2$. The mixture was stirred at rt for 4 h. The formed mixture was filtered and the filtrate was concentrated under reduce pressure to afford crude (R)-benzyl 3-isopropyl-4-(5-(4-(methoxycarbonyl)benzyl)-4-(trifluoromethyl)pyrimidin-2-yl)piperazine-1-carboxylate (90 mg, 95%) as a yellow solid, which was used for the next step directly without further purification. LC-MS tR=1.605 min in 10-80AB_2MIN.M chromatography (Welch Xtimate C18, 2.1*30 mm, 3 um), MS (ESI) m/z 557.2 [M+H]+.

Step 3

To a solution of (R)-benzyl 3-isopropyl-4-(5-(4-(methoxycarbonyl)benzyl)-4-(trifluoromethyl) pyrimidin-2-yl)piperazine-1-carboxylate (20 mg, 0.036 mmol) in EtOAc (2 mL) was added Pd/C (15 mg, 10%, w/w). The mixture was stirred at rt under H$_2$ (30 psi) overnight. The mixture was filtered and the filtrate was concentrated under reduced pressure to afford crude (R)-methyl 4-((2-(2-isopropylpiperazin-1-yl)-4-(trifluoromethyl)pyrimidin-5-yl)methyl) benzoate (15 mg, 100%) as a yellow solid, which was used for the next step directly without further purification. LC-MS tR=1.031 min in 10-80AB_2MIN.M chromatography (Xtimate C18, 2.1*30 mm, 3 um), MS (ESI) m/z 423.2 [M+H]+.

Step 4

To a solution of (R)-methyl 4-((2-(2-isopropylpiperazin-1-yl)-4-(trifluoromethyl)pyrimidin-5-yl) methyl)benzoate (60 mg, 0.14 mmol) in toluene (3 mL) was added 4-bromo-1-fluoro-2-(methylsulfonyl)benzene (72 mg, 0.28 mmol), X-phos (14 mg, 0.03 mmol), Cs$_2$CO$_3$ (139 mg, 0.43 mmol)

and Pd$_2$(dba)$_3$ (26 mg, 0.03 mmol). The mixture was stirred at 100° C. overnight. The mixture was added with water (5 mL) and extracted with EtOAc (3×5 mL). The combined organic layers were washed with brine (15 mL), dried over anhydrous Na$_2$SO$_4$, filtered and concentrated under reduced pressure. The residue was purified by preparative TLC with petroleum ether/EtOAc 3/1 to afford (R)-methyl 4-((2-(4-(4-fluoro-3-(methylsulfonyl)phenyl)-2-isopropylpiperazin-1-yl)-4-(trifluoromethyl)pyrimidin-5-yl)methyl)benzoate (47 mg, 56%) as a white solid. LC-MS tR=1.444 min in 10-80AB_2MIN.M chromatography (Welch Xtimate C18, 2.1*30 mm, 3 um), MS (ESI) m/z 595.2 [M+H]+.

Step 5

To a solution of (R)-methyl 4-((2-(4-(4-fluoro-3-(methylsulfonyl)phenyl)-2-isopropylpiperazin-1-yl)-4-(trifluoromethyl)pyrimidin-5-yl)methyl)benzoate (10 mg, 0.017 mmol) in THF (25 mL) was added MeMgBr (0.06 mL, 0.17 mmol, 3 M in THF) dropwise at 0° C. under N2. The mixture was stirred at rt for 2 h. The mixture was quenched with sat. NH4Cl solution (5 mL) and extracted with EtOAc (3×10 mL). The combined organic layers were washed with brine (20 mL), dried over anhydrous Na2SO4, filtered and concentrated under reduced pressure. The residue was purified by preparative TLC with petroleum ether/EtOAc 3/1 and neutral preparative HPLC separation to afford (R)-2-(4-((2-(4-(4-fluoro-3-(methylsulfonyl)phenyl)-2-isopropylpiperazin-1-yl)-4-(trifluoromethyl)pyrimidin-5-yl)methyl)phenyl)propan-2-ol (3.30 mg, 33%) as a white solid. LC-MS tR=1.270 min in 10-80AB_2 min chromatography (Welch Shim-pack XR-ODS, 3.0*30 mm, 3 um), MS (ESI) m/z 595.4 [M+H]+. 1H NMR (CDCl3): δ 8.21 (s, 1H), 7.44-7.41 (m, 3H), 7.18-7.12 (m, 4H), 4.81 (d, J=12.8 Hz, 1H), 4.63 (d, J=10.0 Hz, 1H), 3.96 (s, 2H), 3.72 (d, J=12.4 Hz, 1H), 3.53 (d, J=11.6 Hz, 1H), 3.35-3.28 (m, 1H), 3.22 (s, 3H), 2.91-2.79 (m, 2H), 2.51-2.40 (m, 1H), 1.58 (s, 6H), 1.10 (d, J=6.4 Hz, 3H), 0.83 (d, J=6.4 Hz, 3H).

Example 32

(R)-4-((2-(4-(4-fluoro-3-(methylsulfonyl)phenyl)-2-isopropylpiperazin-1-yl)-4-(trifluoromethyl)pyrimidin-5-yl)methyl)benzoic acid (Cpd No 32-1)

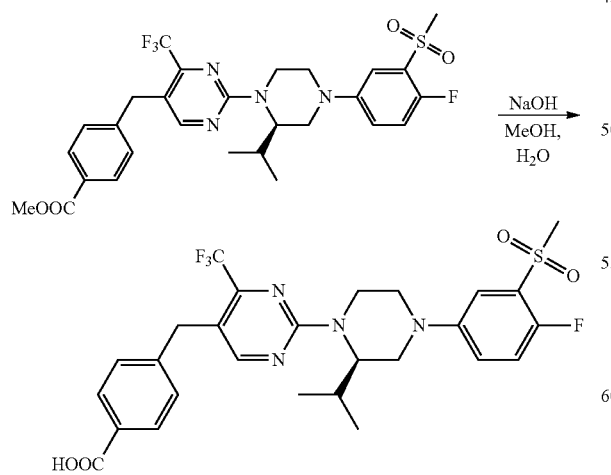

To a solution of (R)-methyl 4-((2-(4-(4-fluoro-3-(methylsulfonyl)phenyl)-2-isopropylpiperazin-1-yl)-4-(trifluoromethyl)pyrimidin-5-yl)methyl)benzoate (10 mg, 0.017 mmol) in MeOH (1 mL) and H$_2$O (0.3 mL) was added NaOH (6.7 mg, 0.17 mmol). The mixture was stirred at rt overnight. The mixture was added with water (5 mL) and adjusted to pH=5 with 1N HCl solution. The aqueous layer was extracted with EtOAc (3×5 mL). The combined organic layers were washed with brine (15 mL), dried over anhydrous Na$_2$SO$_4$, filtered and concentrated under reduced pressure. The residue was purified by preparative TLC (petroleum ether/EtOAc 3/1) and TFA preparative HPLC separation to afford (R)-4-((2-(4-(4-fluoro-3-(methylsulfonyl)phenyl)-2-isopropylpiperazin-1-yl)-4-(trifluoromethyl)pyrimidin-5-yl)methyl)benzoic acid (2.30 mg, 23%) as a white solid. LC-MS tR=1.211 min in 10-80AB_2 min chromatography (Welch Shim-pack XR-ODS, 3.0*30 mm, 3 um), MS (ESI) m/z 581.3 [M+H]+. 1H NMR (CDCl3): δ 8.22 (s, 1H), 8.03 (d, J=8.4 Hz, 2H), 7.42 (dd, J=2.8, 5.6 Hz, 1H), 7.27 (s, 1H), 7.25 (s, 1H), 7.18-7.12 (m, 2H), 4.82 (d, J=14.0 Hz, 1H), 4.63 (d, J=9.6 Hz, 1H), 4.05 (s, 2H), 3.72 (d, J=12.0 Hz, 1H), 3.54 (d, J=11.2 Hz, 1H), 3.36-3.30 (m, 1H), 3.22 (s, 3H), 2.89-2.80 (m, 2H), 2.47-2.43 (m, 1H), 1.10 (d, J=6.8 Hz, 3H), 0.83 (d, J=6.8 Hz, 3H).

Example 33

(R)-4-(4-fluoro-3-(methylsulfonyl)phenyl)-2-isopropyl-1-(2-methoxypyridin-4-yl)piperazine (Cpd No 33-1)

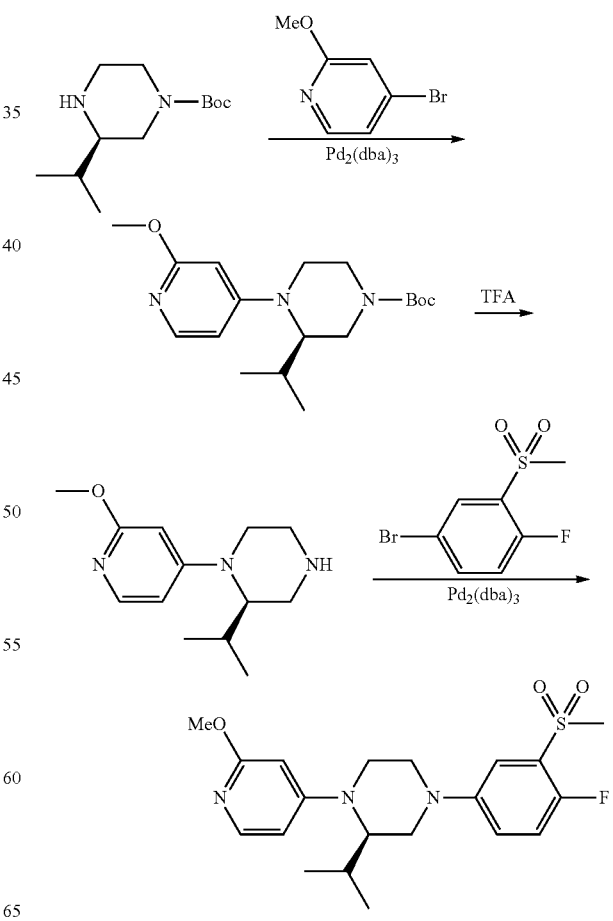

Step 1

To a mixture of (R)-tert-butyl 3-isopropylpiperazine-1-carboxylate (300 mg, 1.32 mmol), 4-bromo-2-methoxypyridine (264 mg, 1.58 mmol), X-phos (33 mg, 0.07 mmol) and $Cs_2CO_3$ (3.46 g, 10.6 mmol) in anhydrous toluene (4 mL) was added $Pd_2$ (dba)$_3$ (78 mg, 0.07 mmol) under N2. The reaction mixture was stirred at 100° C. for 5 h. The mixture was filtered, the filtrate was added with water (20 mL) and extracted with EtOAc (3×20 mL). The combined organic layers were washed with brine, dried over anhydrous $Na_2SO_4$, filtered and concentrated to afford crude product. The crude product was purified by preparative TLC with petroleum ether:EtOAc=3:1 to afford (R)-tert-butyl 3-isopropyl-4-(2-methoxypyridin-4-yl)piperazine-1-carboxylate (80 mg, 18%) as a yellow oil.

Step 2

To a solution of (R)-tert-butyl 3-isopropyl-4-(2-methoxypyridin-4-yl)piperazine-1-carboxylate (80 mg, 0.24 mmol) in $CH_2Cl_2$ (5 mL) was added TFA (1 mL). The reaction mixture was stirred at rt for 2 h. The reaction mixture was concentrated under reduced pressure, the residue was added with sat. $NaHCO_3$ solution (10 mL) and extracted with EtOAc (3×20 mL). The combined organic layers were dried over anhydrous $Na_2SO_4$, filtered and concentrated to afford crude (R)-2-isopropyl-1-(2-methoxypyridin-4-yl)piperazine (56 mg, 100%), which was used for the next step directly without further purification.

Step 3

To a solution of (R)-2-isopropyl-1-(2-methoxypyridin-4-yl)piperazine (56 mg, 0.24 mmol), 4-bromo-1-fluoro-2-(methylsulfonyl)benzene (73.4 mg, 0.29 mmol), X-phos (5.7 mg, 0.012 mmol) and $Cs_2CO_3$ (625.9 mg, 1.92 mmol) in anhydrous toluene (2 mL) was added $Pd_2$ (dba)$_3$ (13.4 mg, 0.012 mmol) under $N_2$. The reaction mixture was stirred at 100° C. for 2 h. The mixture was filtered, the filtrate was added with water (10 mL) and extracted with EtOAc (3×10 mL). The combined organic layers were washed with brine, dried over anhydrous $Na_2SO_4$, filtered and concentrated to afford crude product. The crude product was purified by preparative TLC with petroleum ether:EtOAc=1:1 to afford (R)-4-(4-fluoro-3-(methylsulfonyl)phenyl)-2-isopropyl-1-(2-methoxypyridin-4-yl)piperazine (73.00 mg, 75%) as a yellow solid. LC-MS tR=0.885 min in 2 min chromatography (Xtimate C18, 2.1*30 mm) MS (ESI) m/z 408.1 [M+H]+. 1H NMR (CD$_3$OD): δ 7.74 (d, J=6.4 Hz, 1H), 7.40-7.38 (m, 1H), 7.33-7.25 (m, 2H), 6.55 (dd, J=2.8, 6.4 Hz, 1H), 6.15 (d, J=2.4 Hz, 1H), 3.90-3.87 (m, 1H), 3.86 (s, 3H), 3.85-3.79 (m, 2H), 3.60 (d, J=11.6 Hz, 1H), 3.46-3.37 (m, 1H), 3.25 (s, 3H), 2.93-2.84 (m, 2H), 2.54-2.45 (m, 1H), 1.10 (d, J=6.4 Hz, 3H), 0.86 (d, J=6.8 Hz, 3H).

Example 34

1-(4-(4-fluoro-3-(methylsulfonyl)phenyl)-1-(5-(trifluoromethyl)pyridin-2-yl)piperazin-2-yl)-2-methylpropan-2-ol (Cpd. No. 34-1)

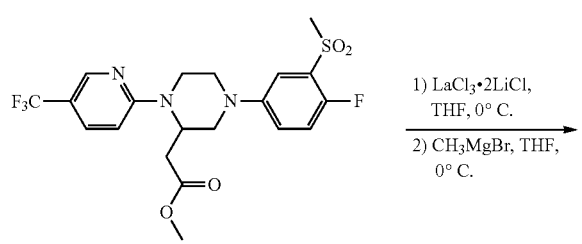

1) LaCl$_3$·2LiCl, THF, 0° C.

2) CH$_3$MgBr, THF, 0° C.

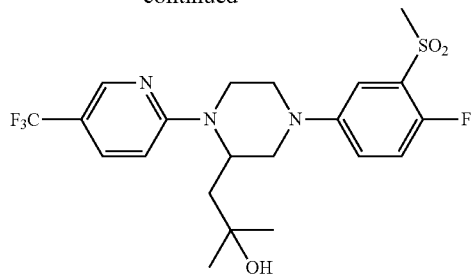

A solution of methyl 2-(4-(4-fluoro-3-(methylsulfonyl)phenyl)-1-(5-(trifluoromethyl)pyridin-2-yl)piperazin-2-yl)acetate (8.9 mg, 0.019 mmol) in dry THF (3 mL) was cooled to 0° C. LaCl$_3$.2LiCl (0.6M in THF, 2 eq.) was added. The mixture was stirred 1 h at 0° C. CH$_3$MgBr (3M in THF, 40 µL, 6 eq.) was added. The mixture was stirred 30 min. at 0° C. before being warmed to r.t. and stirred 2 h. The mixture was quenched by 5% HCl solution and purified by Gilson to afford 6.8 mg (76% yield) product. LC-MS (1 min. method): tR=0.96 min., m/z 476 (M+1). 1H NMR (CD3OD) δ 8.37 (s, 1H), 7.81 (dd, J=9.6 Hz, 1H), 7.42 (dd, J=5.6 Hz, 1H), 7.34 (m, 1H), 7.26 (t, J=9.2 Hz, 1H), 7.05 (d, J=9.6 Hz, 1H), 4.29 (d, 1H), 3.87 (d, 1H), 3.68 (d, 1H), 3.53 (td, 1H), 3.22 (s, 3H), 3.08 (dd, 1H), 2.96 (td, 1H), 2.19 (dd, 1H), 1.75 (dd, 1H), 1.29 (d, 6H). 19F NMR (CD$_3$OD) δ −125.5–63.3.

Example 35

2-(2-fluoro-2-methylpropyl)-4-(4-fluoro-3-(methylsulfonyl)phenyl)-1-(5-(trifluoromethyl)pyridin-2-yl)piperazine (Cpd. No. 35-1)

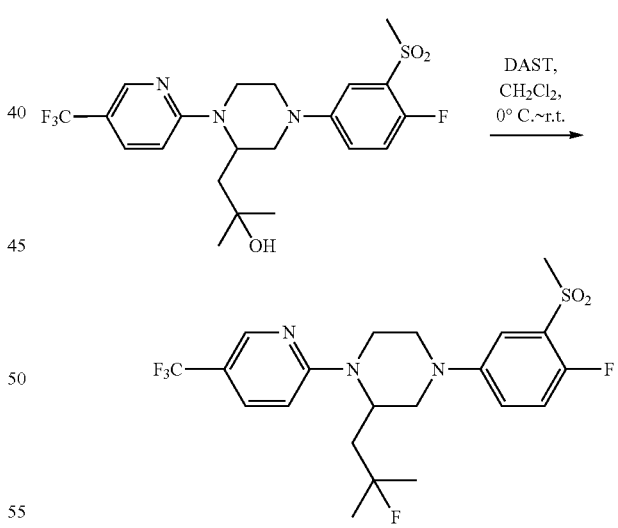

A solution of 1-(4-(4-fluoro-3-(methylsulfonyl)phenyl)-1-(5-(trifluoromethyl)pyridin-2-yl)piperazin-2-yl)-2-methylpropan-2-ol (5.5 mg, 0.016 mmol) in $CH_2Cl_2$ (2 mL) was cooled to 0° C. DAST (2 drops, excess) was added. After 15 min., the mixture was warmed to r.t. and stirred 2.5 h. It was quenched by 5% HCl solution and purified by Gilson to afford 1.27 mg (23% yield) product. LC-MS (1 min. method): t$_R$=1.05 min., m/z 478 (M+1). $^1$H NMR (CD$_3$OD) δ 8.38 (s, 1H), 7.75 (dd, J=9.2 Hz, 1H), 7.43 (dd, J=5.6 Hz, 1H), 7.33 (m, 1H), 7.26 (t, J=9.6 Hz, 1H), 6.91 (d, J=9.2 Hz, 1H), 5.04 (M, 1H), 4.38 (d, 1H), 3.84 (d, 1H), 3.66 (d, 1H), 3.41 (m, 1H), 3.13 (s, 3H), 3.00 (dd, 1H), 2.89 (td, 1H), 2.46

(td, 1H), 1.93 (s, 2H), 1.74 (m, 1H), 1.43 (dd, 6H). $^{19}$F NMR (CD$_3$OD) δ −125.2, −63.1, −49.0.

Example 36

(R)-4-chloro-2-(4-(4-fluoro-3-(methylsulfonyl)phenyl)-2-isopropylpiperazin-1-yl)-5-(trifluoromethyl)pyrimidine (Cpd No 36-1)

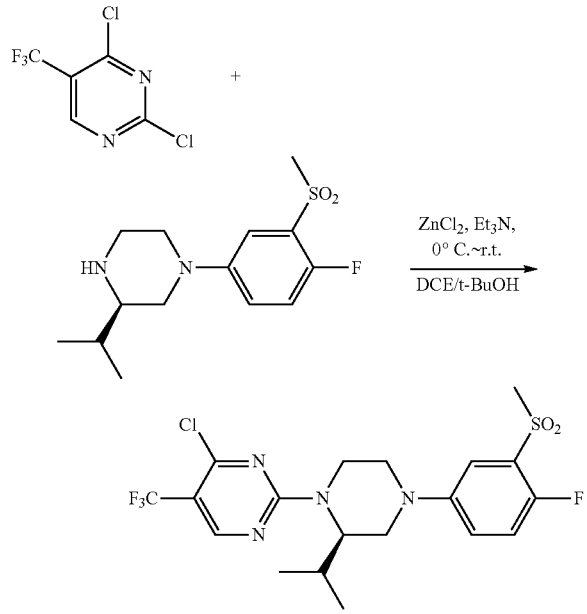

A solution of 2,4-dichloro-5-(trifluoromethyl)pyrimidine (22 mg, 1.02 eq.) in dichloroethane/t-Butanol (1:1, 5 mL) was cooled to 0° C. ZnCl$_2$ (1.0M in Ether, 220 μL, 2.2 eq.) was added. After 1 h, a solution of (R)-1-(4-fluoro-3-(methylsulfonyl)phenyl)-3-isopropylpiperazine (30 mg, 0.1 mmol) in dichloroethane/t-Butanol (1:1, 2 mL) was added at 0° C., followed by addition of triethylamine (20 μL, 1.5 eq.). The mixture was stirred overnight, with the ice/water bath melt by itself. The mixture was purified by Gilson to afford 14.5 mg (30% yield) product. LC-MS (1 min. method): t$_R$=1.11 min, m/z 481 (M+1). $^1$H NMR (CD$_3$OD) δ 8.53 (s, 1H), 7.41 (dd, J=5.6 Hz, 1H), 7.33 (m, 1H), 7.27 (t, J=9.2 Hz, 1H), 5.04 (m, 1H), 4.90-4.58 (m, 2H), 3.86 (d, 1H), 3.66 (d, 1H), 3.38 (dd, 1H), 3.23 (s, 3H), 2.84 (m, 2H), 2.50 (m, 1H), 1.12 (d, 3H), 0.83 (d, 3H). $^{19}$F NMR (CD$_3$OD) δ −124.8, −63.0.

Example 37

(R)-2-(4-(4-fluoro-3-(methylsulfonyl)phenyl)-2-isopropylpiperazin-1-yl)-4-methyl-5-(trifluoromethyl)pyrimidine Cpd No 37-1)

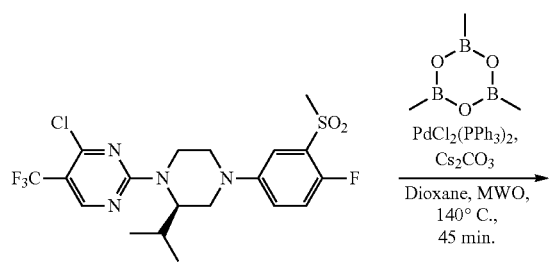

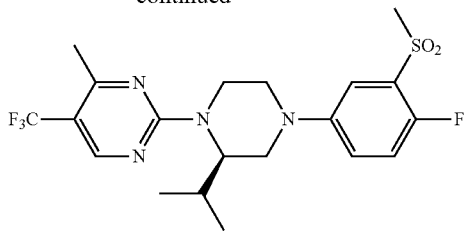

A mixture of (R)-4-chloro-2-(4-(4-fluoro-3-(methylsulfonyl)phenyl)-2-isopropylpiperazin-1-yl)-5-(trifluoromethyl)pyrimidine (13.5 mg, 0.028 mmol), 2,4,6-trimethyl-1,3,5,2,4,6-trioxatriborinane (7 mg, 2 eq.), Bis(triphenylphosphine)palladium(II) dichloride (2 mg, 10 mol %), Cesium carbonate (15 mg, excess), and dry 1,4-Dioxane (1 mL) was degassed, refilled with Nitrogen gas for 3 times. The mixture was heated at 140° C. in Microwave Oven for 45 min. After concentration and acidification, the residue was purified by Gilson to afford 10.5 mg (81% yield) product. LC-MS (1 min. method): t$_R$=1.12 min., m/z 461 (M+1). H$^1$ NMR (CD$_3$OD) δ 8.41 (s, 1H), 7.40 (dd, J=5.6 Hz, 1H), 7.32 (m, 1H), 7.27 (t, J=9.2 Hz, 1H), 4.96 (m, 1H), 4.77 (d, 1H), 3.83 (d, 1H), 3.63 (d, 1H), 3.33 (m, 1H), 3.23 (s, 3H), 2.79 (m, 2H), 2.49 (m, 1H), 2.46 (s, 3H), 1.12 (d, 3H), 0.82 (d, 3H). F$^{19}$ NMR (CD$_3$OD) δ −125.1, −62.0.

The following compounds are prepared by a similar procedure:

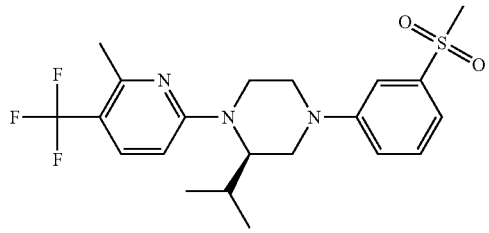

Cpd No 37-2, m/z = 417

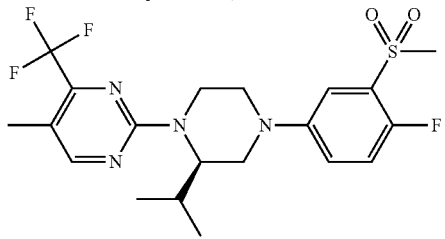

Cpd No 37-3, m/z = 461.3

Example 38

1-(2-((R)-4-(4-fluoro-3-(methylsulfonyl)phenyl)-2-isopropylpiperazin-1-yl)-5-(trifluoromethyl)pyrimidin-4-yl)ethan-1-ol (Cpd. No. 38-1)

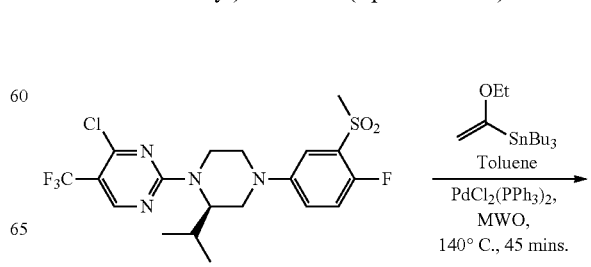

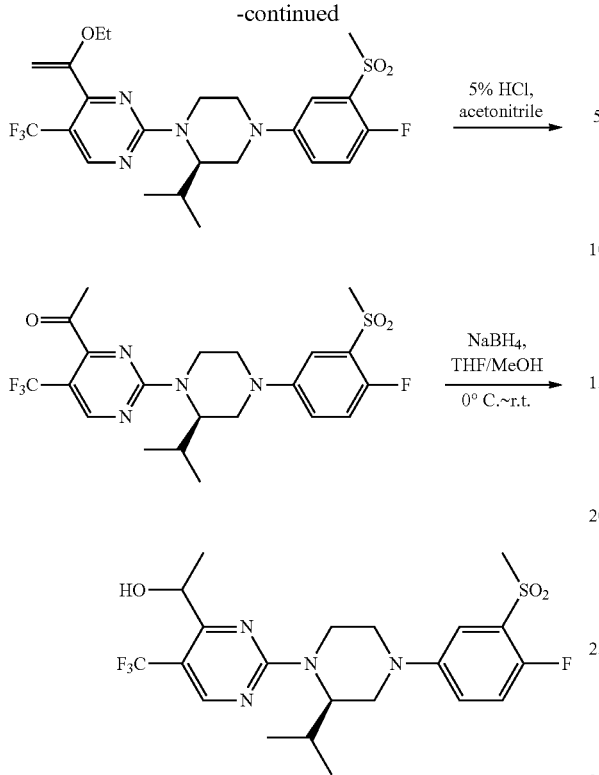

Step 1

A mixture of (R)-4-chloro-2-(4-(4-fluoro-3-(methylsulfonyl)phenyl)-2-isopropylpiperazin-1-yl)-5-(trifluoromethyl)pyrimidine (28 mg, 0.058 mmol), tributyl(1-ethoxyvinyl)stannane (42 mg, 2 eq.), Bis(triphenylphosphine)palladium(II) dichloride (4 mg, 10 mol %), and dry Toluene (2.5 mL) was degassed, refilled with Nitrogen gas for 3 times. The mixture was heated at 140° C. in Microwave Oven for 45 min. After concentration and acidification, the residue was purified by Gilson to afford 22.6 mg (75% yield) product. LC-MS (1 min. method): tR=1.14 min., m/z 517 (M+1).

Step 2

A mixture of (R)-4-(1-ethoxyvinyl)-2-(4-(4-fluoro-3-(methylsulfonyl)phenyl)-2-isopropylpiperazin-1-yl)-5-(trifluoromethyl)pyrimidine (22.6 mg, 0.044 mmol), 5% HCl/acetonitrile (1:1, 4 mL) was stirred 3 h at r.t. After concentration, the crude product was used for next steps without further purifications. LC-MS (1 min. method): tR=1.05 min., m/z 489 (M+1).

Step 3

A solution of (R)-1-(2-(4-(4-fluoro-3-(methylsulfonyl)phenyl)-2-isopropylpiperazin-1-yl)-5-(trifluoromethyl)pyrimidin-4-yl)ethan-1-one (0.015 mmol) in THF/Methanol (1:1, 2 mL) was cooled to 0° C. Sodium borohydride (3 mg, 5eq.) was added. 10 min. later, the mixture was warmed to r.t. and stirred 1 h. It was quenched by 1% HCl, concentrated and purified by Gilson to afford 2.9 mg (40% yield for 2 steps) product. LC-MS (1 min. method): tR=1.03 min., m/z 491 (M+1). 1H NMR (CD3OD) δ 8.50 (s, 1H), 7.42 (dd, J=6 Hz, 1H), 7.33 (m, 1H), 7.27 (t, J=9.6 Hz, 1H), 4.94 (q, 1H), 3.86 (d, 1H), 3.66 (d, 1H), 3.36 (m, 1H), 3.22 (s, 3H), 2.83 (m, 2H), 2.49 (m, 1H), 1.45 (s, 3H), 1.14 (d, 3H), 0.83 (d, 3H). $^{19}$F NMR (CD$_3$OD) δ −125.1, −59.6

Example 39

(R)-2-(2-(4-(4-fluoro-3-(methylsulfonyl)phenyl)-2-isopropylpiperazin-1-yl)-5-(trifluoromethyl)pyrimidin-4-yl)propan-2-ol (Cpd No 39-1)

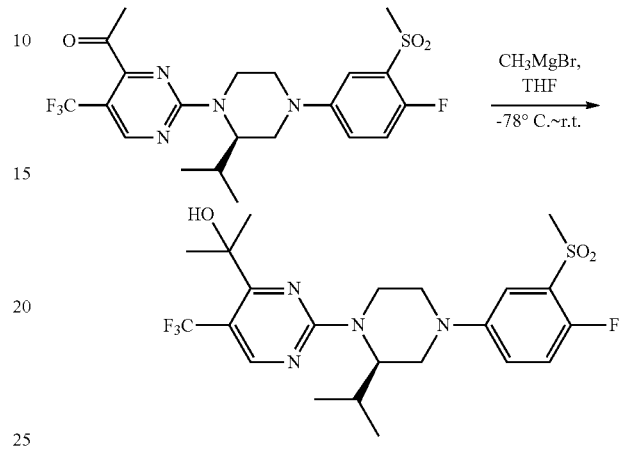

The title compound was prepared by the procedure of Example 34. The crude product was purified by prep HPLC to afford the desired product. LC-MS (1 min. method): $t_R$=1.78 min., m/z 505 (M+1). $^1$H NMR (CD$_3$OD) δ 8.56 (s, 1H), 7.41 (dd, J=5.6 Hz, 1H), 7.32 (m, 1H), 7.26 (t, J=9.2 Hz, 1H), 4.88 (d, 1H), 4.72 (d, 1H), 3.84 (d, 1H), 3.64 (d, 1H), 3.34 (m, 1H), 3.23 (s, 3H), 2.83 (m, 2H), 2.49 (m, 1H), 1.56 (s, 3H), 1.12 (d, 3H), 0.82 (d, 3H). $^{19}$F NMR (CD$_3$OD) δ −125.1, −56.1.

Example 40

(R)-5-cyclopropyl-2-(4-(4-fluoro-3-(methylsulfonyl)phenyl)-2-isopropylpiperazin-1-yl)-4-(trifluoromethyl)pyrimidine (Cpd No 40-1)

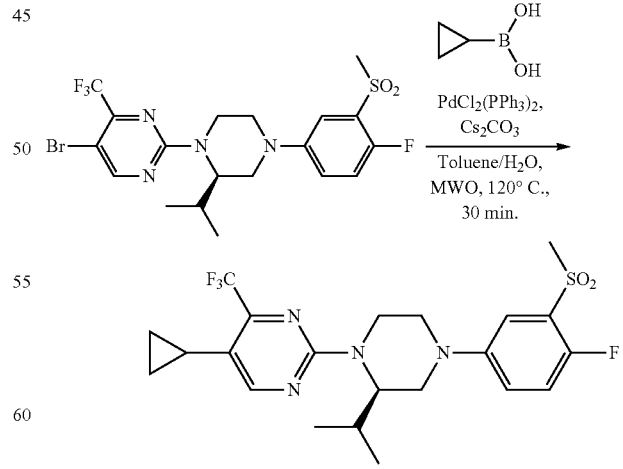

A mixture of (R)-5-bromo-2-(4-(4-fluoro-3-(methylsulfonyl)phenyl)-2-isopropylpiperazin-1-yl)-4-(trifluoromethyl)pyrimidine (12 mg, 0.023 mmol), cyclopropylboronic acid (8 mg, 4 eq.), bis(triphenylphosphine)palladium(II) dichloride (2 mg, 10 mol %), %), Cesium carbonate (8 mg, excess), and Toluene/water (2:1, 1.5 mL) was degassed, refilled with nitrogen gas 3 times. The mixture was heated at 120° C. in Microwave Oven for 30 min. After concentration and acidification, the residue was purified by prep HPLC to afford 10.3 mg (93% yield) product. LC-MS (1 min. method): $t_R$=1.15 min., m/z 487 (M+1). $^1$H NMR (CD$_3$OD) δ 8.28 (s, 1H), 7.39 (dd, J=5.6 Hz, 1H), 7.30 (m, 1H), 7.25 (t, J=9.2 Hz, 1H), 4.79 (d, 1H), 4.64 (d, 1H), 3.82 (d, 1H), 3.61 (d, 1H), 3.31 (m, 1H), 3.22 (s, 3H), 2.79 (m, 2H), 2.47 (m, 1H), 1.92 (m, 1H), 1.21 (s, 3H), 1.12 (d, 3H), 0.96 (q, 2H), 0.81 (d, 3H), 0.68 (q, 2H). $^{19}$F NMR (CD$_3$OD) δ −125.2, −68.7

The following compounds are prepared following a similar procedure:

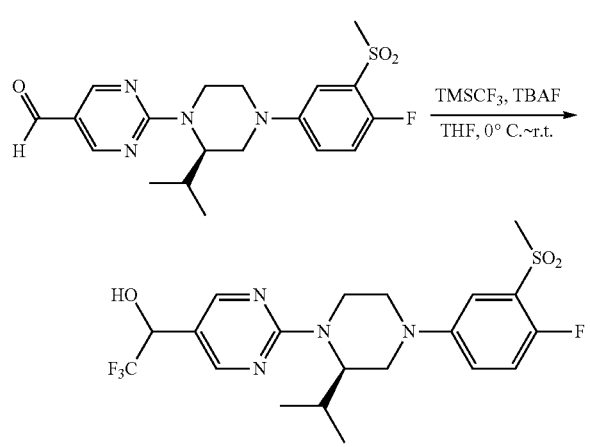

| Cpd No. | $R^{21a}$ | $R^{21b}$ | $R^{21c}$ | Mass Observed |
|---|---|---|---|---|
| 40-2 | c-Pr | Me | H | 414.4 |
| 40-3 | c-Pr | H | Me | 414.4 |
| 40-4 | c-Pr | CF$_3$ | H | 468.1 |

Example 41

2,2,2-trifluoro-1-(2-((R)-4-(4-fluoro-3-(methylsulfonyl)phenyl)-2-isopropylpiperazin-1-yl)pyrimidin-5-yl)ethan-1-ol (Cpd No 41-1)

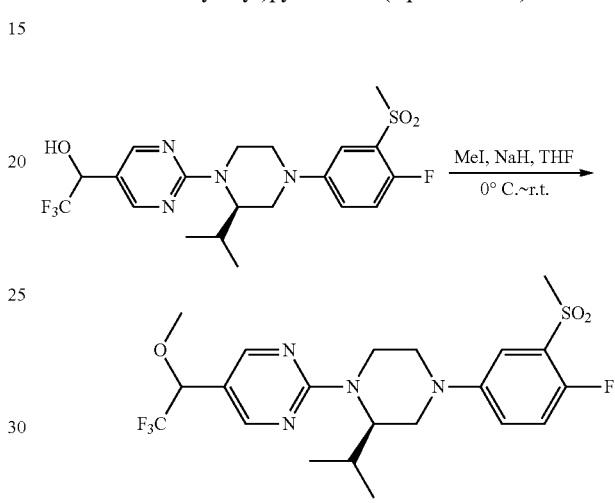

A solution of (R)-2-(4-(4-fluoro-3-(methylsulfonyl)phenyl)-2-isopropylpiperazin-1-yl)pyrimidine-5-carbaldehyde (23 mg, 0.057 mmol) in dry THF (5 mL) was cooled to 0° C. TMSCF$_3$ (60 μL, excess) was added. A solution of TBAF (1.0M in THF, 85 μL, 1.5 eq.) was added slowly. The mixture turned yellow. After 15 min, it was warmed to r.t. and stirred 1 h. LC-MS found reaction complete. The mixture was quenched by Sat. NH$_4$Cl solution (1.5 mL), concentrated and purified by Gilson to afford 21.4 mg (79% yield) product. LC-MS (1 min. method): $t_R$=0.99 min., m/z 477 (M+1). $^1$H NMR (CD$_3$OD) δ 8.40 (s, 1H), 7.39 (dd, J=5.6 Hz, 1H), 7.30 (m, 1H), 7.25 (t, J=9.2 Hz, 1H), 4.98 (q, 1H), 4.82 (d, 1H), 4.68 (d, 1H), 3.83 (d, 1H), 3.63 (d, 1H), 3.33 (m, 1H), 3.22 (s, 3H), 2.83 (m, 2H), 2.48 (m, 1H), 1.12 (d, 3H), 0.82 (d, 3H). $^{19}$F NMR (CD$_3$OD) δ −125.1, −80.8.

Example 42

2-((R)-4-(4-fluoro-3-(methylsulfonyl)phenyl)-2-isopropylpiperazin-1-yl)-5-(2,2,2-trifluoro-1-methoxyethyl)pyrimidine (Cpd No 42-1)

A solution 2,2,2-trifluoro-1-(2-((R)-4-(4-fluoro-3-(methylsulfonyl)phenyl)-2-isopropylpiperazin-1-yl)pyrimidin-5-yl)ethan-1-ol (20 mg, 0.042 mmol) in dry THF (4 mL) was cooled to 0° C. NaH (5 mg, excess) was added. After stirring 15 min, Methyl iodide (50 μL, excess) was added. After 10 min, the mixture was warmed to r.t., and stirred 3.5 h. The mixture was quenched by Sat. NH$_4$Cl solution, concentrated and purified by Gilson to afford 15.2 mg (74% yield) product. LC-MS (1 min. method): $t_R$=1.11 min., m/z 491 (M+1). $^1$H NMR (CD$_3$OD) δ 8.35 (s, 1H), 7.40 (dd, J=5.6 Hz, 1H), 7.31 (m, 1H), 7.25 (t, J=9.2 Hz, 1H), 4.86 (d, 1H), 4.68 (m, 1H), 3.84 (d, 1H), 3.62 (d, 1H), 3.42 (s, 3H), 3.34 (m, 1H), 3.22 (s, 3H), 2.81 (m, 2H), 2.48 (m, 1H), 1.12 (d, 3H), 0.83 (d, 3H). $^{19}$F NMR (CD$_3$OD) δ −125.2, −79.1.

Example 43

(R)-2-(4-(4-fluoro-3-(methylsulfonyl)phenyl)-2-isopropylpiperazin-1-yl)-5-(trifluoromethyl)pyrimidine-4-carbonitrile (Cpd No 43-1)

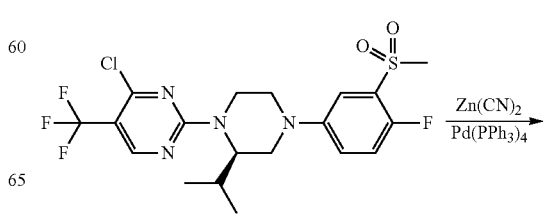

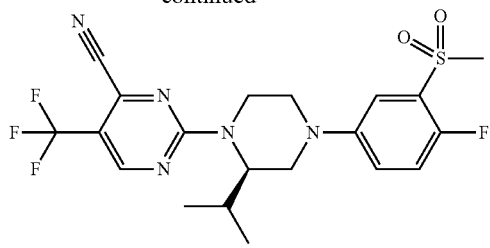

A mixture of (R)-4-chloro-2-(4-(4-fluoro-3-(methylsulfonyl)phenyl)-2-isopropylpiperazin-1-yl)-5-(trifluoromethyl)pyrimidine (8.4 mg, 0.017 mmol), Zn(CN)$_2$ (12 mg, 6 eq.), Pd(PPh$_3$)$_4$ (2 mg, 10 mol %), dry DMF (1 mL) was degassed and refilled with N$_2$ gas for three times. The mixture was put in Microwave Oven and heated for 45 min. at 12° C. The mixture was filtered and purified by prep HPLC to afford 5.8 mg (70% yield) product. LC-MS (1 min. method): t$_R$=1.09 min., m/z 472 (M+1). $^1$H NMR (CD$_3$OD) δ 8.76 (s, 1H), 7.42 (dd, J=5.6 Hz, 1H), 7.34 (m, 1H), 7.27 (t, J=9.5 Hz, 1H), 4.92 (m, 1H), 4.79-4.62 (m, 1H), 3.87 (d, 1H), 3.68 (d, 1H), 3.42 (td, 1H), 3.23 (s, 3H), 2.91-2.79 (m, 2H), 2.53 (m, 1H), 1.16 (s, 3H), 0.84 (s, 3H). $^{19}$F NMR (CD$_3$OD) δ −125.5, −62.2

Example 44

(R)-1-(2-(difluoromethoxy)pyridin-4-yl)-4-(4-fluoro-3-(methylsulfonyl)phenyl)-2-isopropylpiperazine
(Cpd No 44-1)

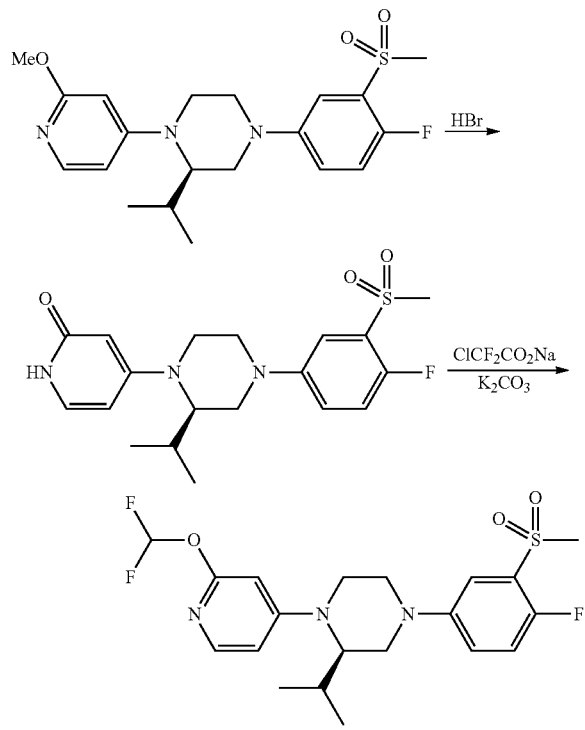

Step 1

A solution of (R)-4-(4-fluoro-3-(methylsulfonyl)phenyl)-2-isopropyl-1-(2-methoxypyridin-4-yl)piperazine (60.0 mg, 0.15 mmol) in 30% HBr in HOAc (5 mL) was stirred at 90° C. for 20 h. Water (10 mL) was added to the reaction mixture and the aqueous layer was extracted with EtOAc (3×10 mL). The combined organic layers were washed with brine (10 mL), dried over anhydrous Na$_2$SO$_4$, filtered and concentrated to afford crude product. The crude product was purified by preparative TLC eluting with CH$_2$Cl$_2$:CH$_3$OH=9:1 to afford (R)-4-(4-(4-fluoro-3-(methylsulfonyl)phenyl)-2-isopropylpiperazin-1-yl)pyridin-2 (1H)-one (35.0 mg, 60%) as a yellow solid. LC-MS t$_R$=0.919 min in 2 min chromatography, MS (ESI) m/z 394.1 [M+H]$^+$. $^1$H NMR (CD$_3$OD): δ 7.42-7.40 (m, 1H), 7.35-7.23 (m, 3H), 6.32 (dd, J=2.4, 7.6 Hz, 1H), 5.72 (d, J=2.4 Hz, 1H), 3.92-3.81 (m, 3H), 3.64 (d, J=12.0 Hz, 1H), 3.48-3.40 (m, 1H), 3.26 (s, 3H), 2.95-2.86 (m, 2H), 2.55-2.49 (m, 1H), 1.12 (d, J=6.4 Hz, 3H), 0.89 (d, J=6.8 Hz, 3H).

Step 2

To a solution of (R)-4-(4-(4-fluoro-3-(methylsulfonyl)phenyl)-2-isopropylpiperazin-1-yl)pyridin-2 (1H)-one (5 mg, 13 μmol) and K2CO3 (3 mg, 19.5 μmol) in DMF (0.5 mL) was added ClCF2CO2Na (2.5 mg, 19.5 μmol) under N2. The reaction mixture was stirred at 80° C. for 2 h. The reaction mixture was treated with water (10 mL) and extracted with EtOAc (3×10 mL). The combined organic layers were washed with brine (10 mL), dried over anhydrous Na2SO4, filtered and concentrated to afford crude product. The crude product was purified by preparative TLC eluting with petroleum ether:EtOAc 2:1 to afford (R)-1-(2-(difluoromethoxy)pyridin-4-yl)-4-(4-fluoro-3-(methylsulfonyl)phenyl)-2-isopropylpiperazine (1.70 mg, 30%) as a white solid. LC-MS tR=1.115 min in 2 min chromatography, MS (ESI) m/z 444.2 [M+H]+. 1H NMR (CD3OD): δ 7.81 (d, J=6.4 Hz, 1H), 7.42-7.41 (m, 1H), 7.40 (t, J=73.8 Hz, 1H), 7.33-7.26 (m, 2H), 6.72 (dd, J=2.4, 6.0 Hz, 1H), 6.34 (d, J=2.4 Hz, 1H), 3.93 (d, J=13.6 Hz, 1H), 3.85-3.82 (m, 2H), 3.63 (d, J=11.6 Hz, 1H), 3.50-3.42 (m, 1H), 3.26 (s, 3H), 2.96-2.87 (m, 2H), 2.56-2.48 (m, 1H), 1.13 (d, J=6.4 Hz, 3H), 0.86 (d, J=6.4 Hz, 3H).

The following compounds are prepared by similar procedures:

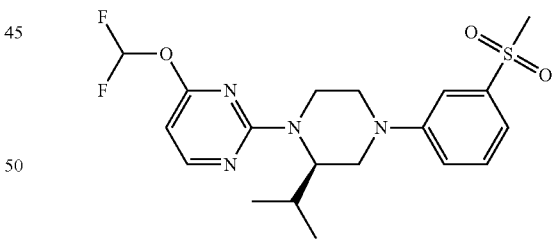

Cpd No 44-2, m/z = 427.0

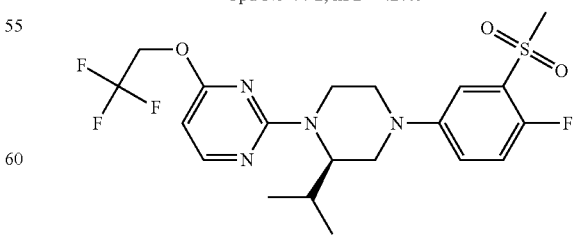

Cpd No 44-3, m/z = 477.2, using CF$_3$CH$_2$OTf in place of ClCF$_2$CO$_2$Na

Example 45

(S)-2-benzyl-1-(3-chloro-4-(trifluoromethyl)benzyl)-4-(3-(methylsulfonyl)phenyl)piperazine (Cpd No 45-1)

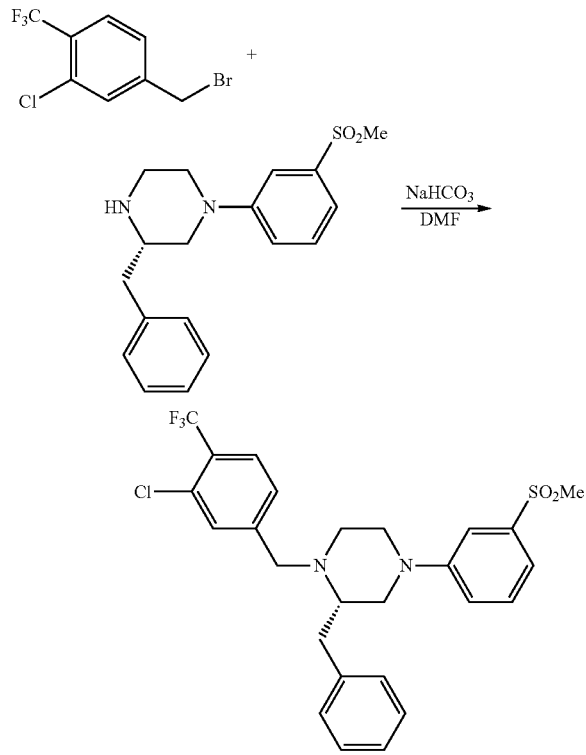

A stirred mixture of (S)-3-benzyl-1-(3-(methylsulfonyl)phenyl)piperazine HCl salt (20.5 mg, 0.056 mmol), 3-chloro-4-(trifluoromethyl)benzyl bromide (15.5 mg, 0.057 mmol), powdered NaHCO$_3$ (14 mg, 0.17 mmol) and dry DMF (1 mL) was heated at 50° C. for 16 h. Prep HPLC afforded the TFA salt of the title compound (15.5 mg, 43%). LC-MS Method 4 t$_R$=0.87 min, m/z=523, 525; $^1$H NMR (CD$_3$OD) δ 3.06 (s, 3H), 3.14-3.24 (m, 1H), 3.30-3.60 (m, 6H), 3.81-3.88 (m, 1H), 4.44-4.54 (m, 1H), 4.80-4.88 (m, 2H), 7.09-7.15 (m, 1H), 7.25-7.50 (m, 8H), 7.69-7.75 (m, 1H), 7.88-7.98 (m, 2H).

Example 46

1-(3-chloro-4-(trifluoromethyl)benzyl)-4-(3-(methylsulfonyl)phenyl)-2-phenylpiperazine (Cpd No 46-1)

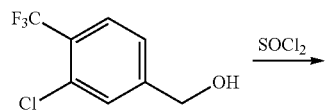

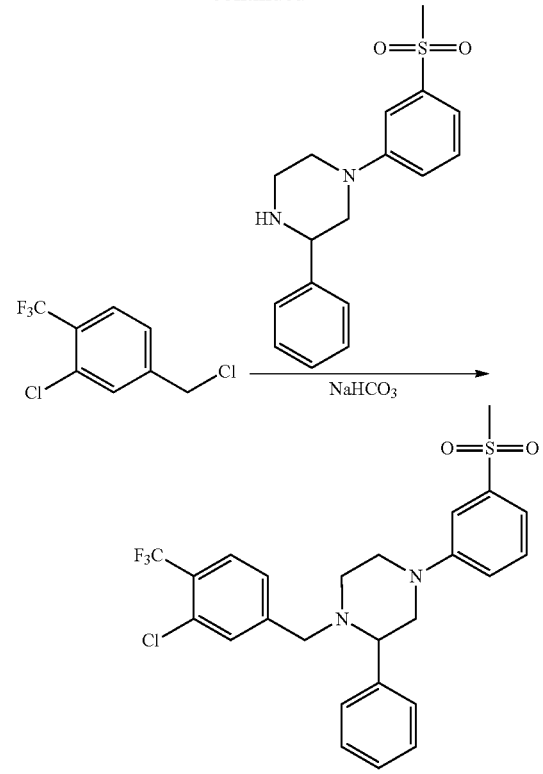

Step 1

To a solution of (3-chloro-4-(trifluoromethyl)phenyl)methanol (300 mg, 1.43 mmol) in anhydrous CH$_2$Cl$_2$ (10 mL) was added SOCl$_2$ (4.2 mL, 57.14 mmol) dropwise slowly at 0° C. under N2. The reaction mixture was stirred at 0° C. for 10 min and stirred at 40° C. for 23 h. The solvents were removed under reduced pressure to afford crude product. The crude product was purified by preparative TLC with petroleum ether:EtOAc=3:1 to afford 2-chloro-4-(chloromethyl)-1-(trifluoromethyl)benzene (234 mg, 72%) as an colorless oil.

Step 2

To a solution of 2-chloro-4-(chloromethyl)-1-(trifluoromethyl)benzene (200 mg, 0.88 mmol) and 1-(3-(methylsulfonyl)phenyl)-3-phenylpiperazine (182 mg, 0.58 mmol) in anhydrous DMF (6 mL) was added NaHCO3 (221 mg, 2.63 mmol) under N2. The reaction mixture was stirred at 100° C. for 2 h. The reaction mixture was added with water (50 mL) and extracted with EtOAc (3×30 mL). The combined organic layers were washed with brine (30 mL), dried over anhydrous Na2SO4, filtered and concentrated to afford crude product. The crude product was purified by preparative TLC with petroleum ether:EtOAc=3:1 to afford 1-(3-chloro-4-(trifluoromethyl)benzyl)-4-(3-(methylsulfonyl)phenyl)-2-phenylpiperazine (289 mg, 99%) as a yellow solid. LC-MS tR=1.433 min in 2.0 min chromatography, m/z 509.3 [M+H]+. 1H NMR (CD3OD): δ 7.68 (d, J=8.0 Hz, 1H), 7.57-7.52 (m, 3H), 7.46-7.38 (m, 5H), 7.35-7.30 (m, 2H), 7.25 (d, J=9.2 Hz, 1H), 3.81-3.70 (m, 3H), 3.54 (dd, J=3.6, 10.0 Hz, 1H), 3.08-2.92 (m, 4H), 3.00 (s, 3H), 2.42 (dt, J=3.6, 15.2 Hz, 1H).

The isomers were separated by HPLC on a chiral column to afford (R)-1-(3-chloro-4-(trifluoromethyl)benzyl)-4-(3-(methylsulfonyl)phenyl)-2-phenylpiperazine (Cpd No. 46-2) and (S)-1-(3-chloro-4-(trifluoromethyl)benzyl)-4-(3-(methylsulfonyl)phenyl)-2-phenylpiperazine (Cpd No 46-3).

The following compounds are prepared following a similar procedure:

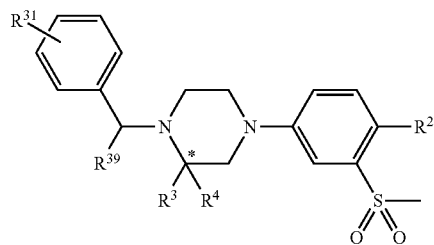

| Cpd No. | R² | R³ | R⁴ | *Stereochem | R³¹ | R³⁹ | Mass Observed |
|---|---|---|---|---|---|---|---|
| 46-4 | H | Ph | H | RS | H | H | 407.1 |
| 46-5ᵃ | H | Ph | H | R | 4-Me | H | 421.3 |
| 46-6ᵃ | H | Ph | H | S | 4-Me | H | 421.3 |
| 46-7 | H | Ph | H | R | 4-i-Pr | H | 449.1 |
| 46-8 | H | Ph | H | S | 4-i-Pr | H | 449.1 |
| 46-9 | CN | i-Pr | H | S | 4-CF₃ | H | 466.1 |
| 46-10ᵇ | H | Ph | H | R | 4-CHF₂O | H | 473.0 |
| 46-11ᵇ | H | Ph | H | S | 4-CHF₂O | H | 473.0 |
| 46-12 | H | Ph | H | RS | 2-CF₃ | H | 475.3 |
| 46-13 | H | Ph | H | SS | 3-CF₃ | H | 475.2 |
| 46-14ᶜ | H | Ph | H | R | 4-CF₃ | H | 475.3 |
| 46-15ᶜ | H | Ph | H | S | 4-CF₃ | H | 475.0 |
| 46-16ᵈ | H | Ph | H | S | 4-CF₃ | Me | 489.1 |
| 46-17ᵈ | H | Ph | H | R | 4-CF₃ | Me | 489.1 |
| 46-18ᵈ | H | Ph | H | S | 4-CF₃ | Me | 489.1 |
| 46-19ᵈ | H | Ph | H | R | 4-CF₃ | Me | 489.1 |
| 46-20ᵉ | H | Ph | Me | R | 4-CF₃ | H | 489.0 |
| 46-21ᵉ | H | Ph | Me | S | 4-CF₃ | H | 489.0 |
| 46-22ᶠ | H | Ph | H | R | 4-CF₃O | H | 491.0 |
| 46-23ᶠ | H | Ph | H | S | 4-CF₃O | H | 491.2 |
| 46-24 | H | 4-F—Ph | H | S | 4-CF₃ | H | 493.4 |
| 46-25ᵍ | H | Ph | H | R | 3-F-4-CF₃ | H | 493.3 |
| 46-26ᵍ | H | Ph | H | S | 3-F-4-CF₃ | H | 493.3 |
| 46-27 | H | c-hex | H | RS | 3-Cl-4-CF₃ | H | 515.2 |
| 46-28ʰ | H | Ph | H | S | 4-CF₃C(OH)Me | H | 519.5 |
| 46-29ʰ | H | Ph | H | R | 4-CF₃C(OH)Me | H | 519.4 |
| 46-30ʰ | H | Ph | H | S | 4-CF₃C(OH)Me | H | 519.5 |
| 46-31ʰ | H | Ph | H | R | 4-CF₃C(OH)Me | H | 519.5 |
| 46-33 | H | Bn | H | R | 3-Cl-4-CF₃ | H | 523 |
| 46-34ⁱ | H | Ph | Me | S | 3-Cl-4-CF₃ | H | 523.0 |
| 46-35ⁱ | H | Ph | Me | R | 3-Cl-4-CF₃ | H | 523.0 |
| 46-36 | H | Ph | H | RS | 3-MeO₂C-4-CF3 | H | 533.1 |
| 46-37 | H | Ph | H | RS | 3-Br-4-CF₃ | H | 553.0 |
| 46-38 | CO₂Me | Ph | H | RS | 3-Cl-4-CF₃ | H | 567.0 |

ᵃ,ᵇ,ᶜ,ᵈ,ᵉ,ᶠ,ᵍ,ʰ,ⁱIsomers are separated by HPLC on a chiral column, stereochemistry assigned arbitrarily.

The following compounds are prepared following a similar procedure:

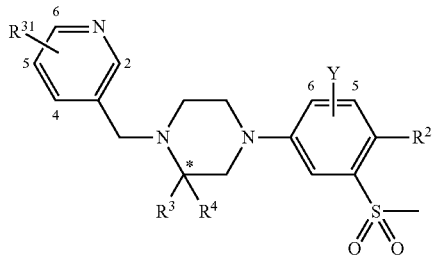

| Cpd No. | R² | Y | R³ | R⁴ | *Stereochem | R³¹ | Mass Observed |
|---|---|---|---|---|---|---|---|
| 46-39 | H | H | Ph | H | RS | H | 408.3 |
| 46-40 | H | H | Ph | H | RS | Me | 422.0 |
| 46-41 | H | H | i-Pr | H | S | 6-CF₃ | 442 |
| 46-42 | H | H | Ph | H | RS | 6-i-Pr | 450.0 |
| 46-43[a] | H | H | Ph | H | S | 6-CF₃ | 476 |
| 46-44[a] | H | H | Ph | H | R | 6-CF₃ | 476.2 |
| 46-45[b] | H | H | 2-Me—Ph | H | R | 6-CF₃ | 490.0 |
| 46-46[b] | H | H | 2-Me—Ph | H | S | 6-CF₃ | 490.0 |
| 46-47 | H | H | Ph | H | RS | 3-Me-6-CF₃ | 490.2 |
| 46-48 | H | H | Ph | H | RS | 5-Me-6-CF₃ | 490.2 |
| 46-49 | H | H | Ph | Me | RS | 6-CF₃ | 490.1 |
| 46-50 | H | 6-F | Ph | H | RS | 6-CF₃ | 494.1 |
| 46-51 | H | H | 4-F—Ph | H | RS | 6-CF₃ | 494.0 |
| 46-52 | F | H | Ph | H | RS | 6-CF₃ | 494.0 |
| 46-53 | H | 5-F | Ph | H | RS | 6-CF₃ | 494.0 |
| 46-54 | H | H | 4-Cl—Ph | H | RS | 6-CF₃ | 532.0 |
| 46-55 | H | H | 3-Cl—Ph | H | RS | 6-CF₃ | 510.0 |
| 46-56[c] | H | H | 2-Cl—Ph | H | R | 6-CF₃ | 531.9 |
| 46-57[c] | H | H | 2-Cl—Ph | H | S | 6-CF₃ | 531.9 |
| 46-58 | CONH₂ | H | Ph | H | RS | 6-CF₃ | 519.0 |
| 46-59 | CO₂Me | H | Ph | H | RS | 6-CF₃ | 534.2 |
| 46-60 | H | H | 2-Br—Ph | H | RS | 6-CF₃ | 575.9 |
| 46-61 | H | H | 4-Br—Ph | H | RS | 6-CF₃ | 575.9 |
| 46-62 | H | H | 3-Me—Ph | H | RS | 6-CF₃ | 490.1 |

[a,b,c]Isomers are separated by HPLC on a chiral column, stereochemistry assigned arbitrarily.

The following compounds are prepared following a similar procedure:

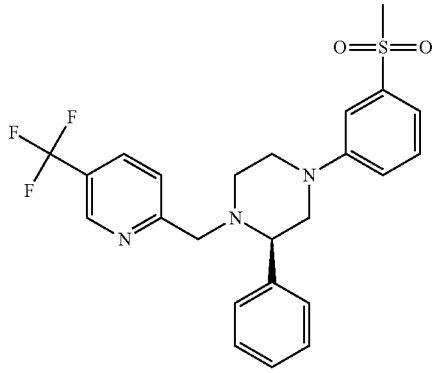

Cpd No 46-63[a], m/z = 476.0

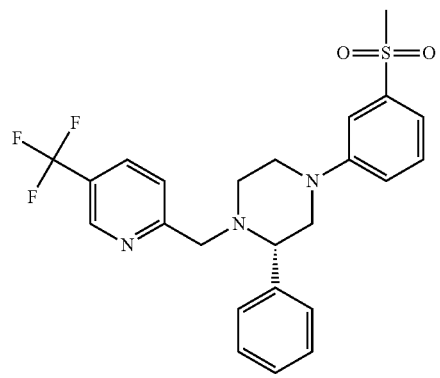

Cpd No 46-63[a], m/z = 476.0

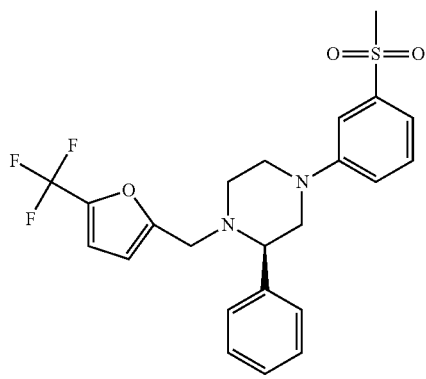

Cpd No 46-63[b], m/z = 465.0

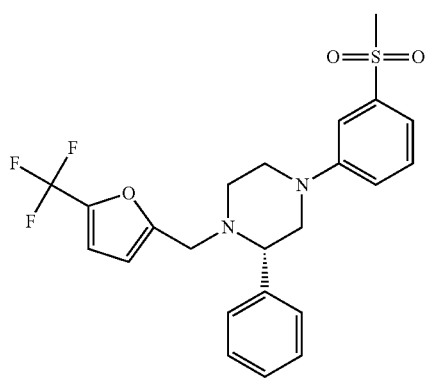

Cpd No 46-63[b], m/z = 465.0

[a,b]Isomers are separated by HPLC on a chiral column, stereochemistry assigned arbitrarily.

Example 47

(2-(methylsulfonyl)-4-(3-phenyl-4-((6-(trifluoromethyl)pyridin-3-yl)methyl)piperazin-1-yl)phenyl)methanol (Cpd No 47-1)

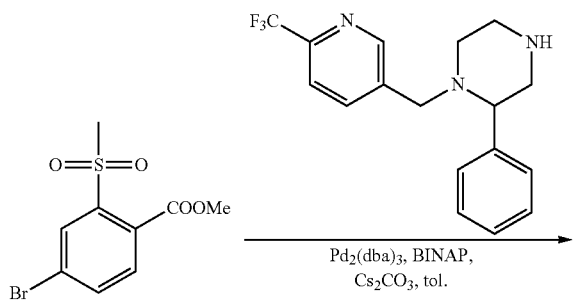

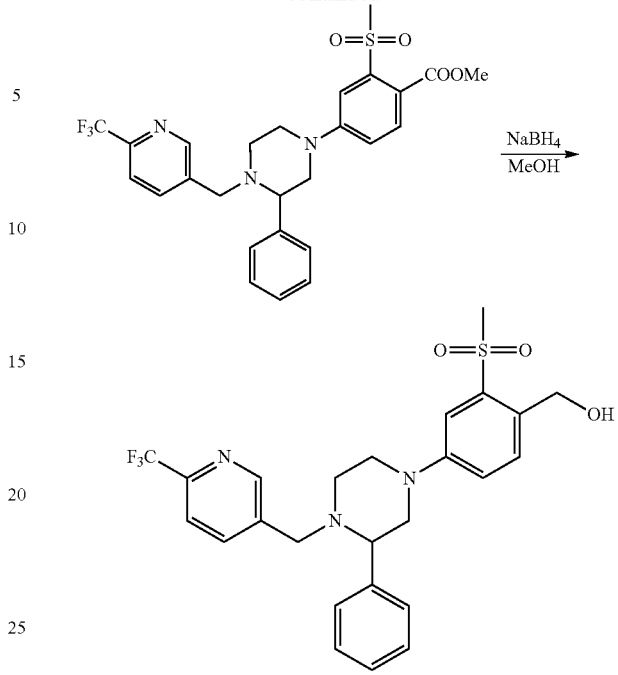

Step 1

To a solution of methyl 4-bromo-2-(methylsulfonyl)benzoate (200 mg, 0.68 mmol) in toluene (6 mL) was added 2-phenyl-1-((6-(trifluoromethyl)pyridin-3-yl)methyl)piperazine (219 mg, 0.68 mmol), BINAP (31 mg, 0.068 mmol), Pd2dba3 (60 mg, 0.068 mmol) and Cs2CO3 (665 mg, 2.04 mmol). The mixture was stirred at reflux for 8 h under $N_2$. The mixture was filtered, the filtrate was added with water (10 mL) and extracted with EtOAc (3×10 mL). The combined organic layers were washed with brine, dried over anhydrous $Na_2SO_4$, filtered and concentrated under reduced pressure. The residue was purified by preparative TLC to give methyl 2-(methylsulfonyl)-4-(3-phenyl-4-((6-(trifluoromethyl)pyridine-3-yl)methyl)piperazin-1-yl)benzoate (171 mg, 47%) as a yellow oil.

Step 2

To a solution of methyl 2-(methylsulfonyl)-4-(3-phenyl-4-((6-(trifluoromethyl)pyridin-3-yl)methyl)piperazin-1-yl)benzoate (30 mg, 0.056 mmol) in anhydrous MeOH (2 mL) was added $NaBH_4$ (6.4 mg, 0.169 mmol) at 0° C. under $N_2$. The mixture was stirred at rt for 4 h. The mixture was quenched with sat. $NH_4Cl$ solution (5 mL) and concentrated under reduced pressure, the residue was dissolved with EtOAc (10 mL). The organic layer was washed with water (3×10 mL) and brine (10 mL), dried over anhydrous $Na_2SO_4$, filtered and concentrated under reduced pressure. The residue was purified by preparative TLC to give (2-(methylsulfonyl)-4-(3-phenyl-4-((6-(trifluoromethyl)pyridin-3-yl)methyl)piperazin-1-yl)phenyl)methanol (15.90 mg, 56%) as a yellow solid. LC-MS tR=0.941 min in 2.0 min chromatography, m/z 528.2 [M+Na]+. 1H NMR (CDCl3): δ 8.57 (s, 1H), 7.73 (d, J=7.6 Hz, 1H), 7.56 (d, J=8.0 Hz, 1H), 7.44-7.43 (m, 3H), 7.35-7.27 (m, 4H), 6.99 (dd, J=2.8, 8.4 Hz, 1H), 4.74 (d, J=5.6 Hz, 2H), 3.81 (d, J=14.0 Hz, 1H), 3.61 (d, J=12.4 Hz, 2H), 3.46 (dd, J=2.4, 10.8 Hz, 1H), 3.07 (s, 3H), 3.03-2.95 (m, 1H), 2.94-2.85 (m, 3H), 2.36 (dt, J=2.8, 11.6 Hz, 1H).

The following compounds are prepared using procedures similar to those above:

| Cpd No. | R³ | *Stereochem | R³⁰ | Mass Observed |
|---|---|---|---|---|
| 47-2 | i-Pr | S | 4-CF₃-phenyl | 471.4 |
| 47-3 | i-Pr | S | 3-F-4-CF₃-phenyl | 489.3 |
| 47-4 | Ph | RS | 3-Cl-4-CF₃-phenyl | 538.9 |
| 47-5 | i-Pr | S | 5-CF₃-2-furanyl | 461.2 |

Example 48

(S)-4-((4-(3-(methylsulfonyl)phenyl)-2-phenylpiperazin-1-yl)methyl)-1-(trifluoromethyl)cyclohexanol (Cpd No 48-1)

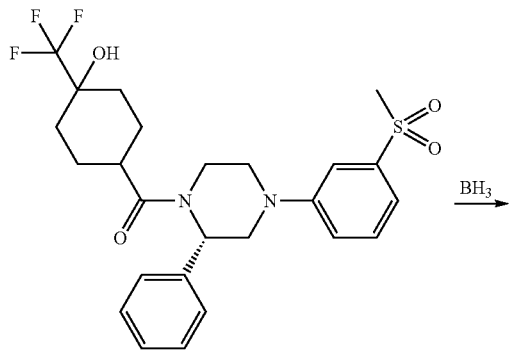

$\xrightarrow{BH_3}$

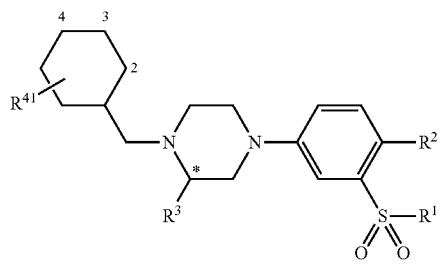

To (S)-(4-hydroxy-4-(trifluoromethyl)cyclohexyl)(4-(3-(methylsulfonyl)phenyl)-2-phenylpiperazin-1-yl)methanone (17 mg, 0.034 mmol) was added 1 M $BH_3$ in THF (2 mL, 2.0 mmol). The mixture was heated at reflux for 3 h, cooled to rt and treated with 1 M aq NaOH (5 mL). The mixture was concentrated. The aqueous residue was partitioned between $CH_2Cl_2$ (100 mL and brine (10 mL). The organic layer was dried over Na2SO4 and concentrated to leave an oil (16 mg). Prep HPLC afforded the title compound (6 mg, 35%) as an oil. LC-MS Method 4 tR=0.70 min, m/z=497. 1H NMR (CD₃OD) δ 0.89-1.03 (m, 1H), 1.30-1.60 (m, 5H), 1.77-1.84 (m, 1H), 1.85-1.99 (m, 1H), 2.10-2.18 (m, 1H), 2.92-3.01 (m, 1H), 3.09 (s, 3H), 3.13-3.23 (m, 1H), 3.40-3.50 (m, 3H), 3.98-4.18 (m, 3H), 4.50-4.61 (m, 1H), 7.34-7.67 (m, 9H).

The following compounds are prepared by a similar procedure:

| Cpd No. | R¹ | R² | R³ | *Stereochem | R⁴¹ | Mass Observed |
|---|---|---|---|---|---|---|
| 48-2 | Me | H | i-Pr | S | 4,4-diMe | 407.3 |
| 48-3 | Me | H | Ph | R | 4,4-diMe | 441.2 |
| 48-4 | Me | H | Ph | S | 4,4-diMe | 441.2 |
| 48-5ᵃ | Me | H | Ph | S | 4-HO-4-Me | 443.1 |
| 48-6ᵃ | Me | H | Ph | R | 4-HO-4-Me | 443.2 |
| 48-7ᵃ | Me | H | Ph | S | 4-HO-4-Me | 443.1 |
| 48-8ᵃ | Me | H | Ph | R | 4-HO-4-Me | 443.2 |
| 48-9ᵇ | Me | H | i-Pr | R | cis-4-CF₃ | 447.5 |
| 48-10ᵇ | Me | H | i-Pr | R | trans-4-CF₃ | 447.5 |

-continued

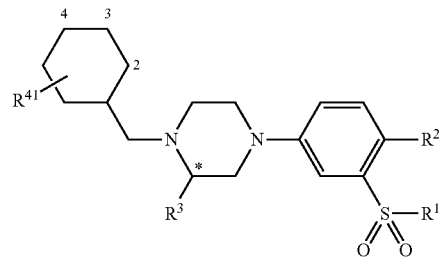

| Cpd No. | R¹ | R² | R³ | *Stereochem | R⁴¹ | Mass Observed |
|---|---|---|---|---|---|---|
| 48-11[b] | Me | H | i-Pr | S | cis-4-CF₃ | 447.3 |
| 48-12[b] | Me | H | i-Pr | S | trans-4-CF₃ | 447.3 |
| 48-13 | Me | H | Ph | S | 4,4-diF | 449 |
| 48-14[c] | Me | H | Ph | R | trans-4-i-Pr | 455.1 |
| 48-15[c] | Me | H | Ph | S | trans-4-i-Pr | 455.1 |
| 48-16[d] | Me | H | Ph | R | cis-4-CHF₂ | 463.1 |
| 48-17[d] | Me | H | Ph | S | cis-4-CHF₂ | 463.0 |
| 48-18[d] | Me | H | Ph | R | trans-4-CHF₂ | 463.1 |
| 48-19[d] | Me | H | Ph | S | trans-4-CHF₂ | 463.1 |
| 48-20[e] | NH₂ | H | Ph | R | trans-4-CHF₂ | 464.1 |
| 48-21[e] | NH₂ | H | Ph | S | trans-4-CHF₂ | 464.1 |
| 48-22[e] | NH₂ | H | Ph | R | cis-4-CHF₂ | 464.1 |
| 48-23[e] | NH₂ | H | Ph | S | cis-4-CHF₂ | 464.2 |
| 48-24 | Me | F | i-Pr | R | cis-4-CF₃ | 465 |
| 48-25 | Me | H | Ph | RS | trans-3-HOCMe₂ | 471 |
| 48-26[f] | Me | CH₂OH | Ph | S | 4,4-diMe | 471.3 |
| 48-27[f] | Me | CH₂OH | Ph | R | 4,4-diMe | 471.3 |
| 48-28[g] | Me | H | Ph | S | cis-4-MeCF₂ | 477.2 |
| 48-29[g] | Me | H | Ph | R | cis-4-MeCF₂ | 477.3 |
| 48-30[h] | Me | H | Ph | R | cis-4-CF₃ | 481.0 |
| 48-31[h] | Me | H | Ph | S | cis-4-CF₃ | 481.4 |
| 48-32[i] | Me | H | Ph | R | trans-4-CF₃ | 481.2 |
| 48-33[i] | Me | H | Ph | S | trans-4-CF₃ | 481.2 |
| 48-34[j] | NH₂ | H | Ph | R | trans-4-CF₃ | 482.0 |
| 48-35[j] | NH₂ | H | Ph | S | trans-4-CF₃ | 482.1 |
| 48-36[j] | NH₂ | H | Ph | R | cis-4-CF₃ | 482.0 |
| 48-37[j] | NH₂ | H | Ph | S | cis-4-CF₃ | 482.0 |
| 48-38 | Me | CH₂OH | i-Pr | S | 4-HO-4-CF₃ | 493.2 |
| 48-39[k] | Me | H | 4-F—Ph | S | 3-CF₃ | 499.3 |
| 48-40[k] | Me | H | 4-F—Ph | S | 3-CF₃ | 499.1 |
| 48-41[k] | Me | H | 4-F—Ph | S | 3-CF₃ | 499.3 |
| 48-42[k] | Me | H | 4-F—Ph | S | 3-CF₃ | 499.3 |
| 48-43 | Me | H | 4-F—Ph | S | cis-CF₃ | 499.4 |
| 48-44[l] | Me | CH₂OH | Ph | R | trans-4-CF₃ | 511.2 |
| 48-45[l] | Me | CH₂OH | Ph | S | trans-4-CF₃ | 511.2 |
| 48-46[m] | Me | H | 2-Cl—Ph | S | trans-4-CF₃ | 515.1 |
| 48-47[m] | Me | H | 2-Cl—Ph | R | trans-4-CF₃ | 515.1 |
| 48-48 | Me | F | 4-F—Ph | S | cis-CF₃ | 517.4 |
| 48-49 | Me | CH₂OMe | Ph | S | trans-4-CF₃ | 525 |
| 48-77[n] | Me | CH₂OH | Ph | S | trans-4-i-Pr | 485.2 |
| 48-78[n] | Me | CH₂OH | Ph | R | trans-4-i-Pr | 485.2 |
| 48-79[o] | Me | CH₂OH | i-Pr | S | 4-CF₃-4-MeO | 507.3 |
| 48-80[o] | Me | CH₂OH | i-Pr | S | 4-CF₃-4-MeO | 507.3 |

[a,b,c,d,e,f,g,h,i,j,k,l,m,n,o]Isomers are separated by HPLC on a chiral column, stereochemistry assigned arbitrarily.

The following compounds are prepared by a similar procedure:

| Cpd No. | R$^1$ | R$^2$ | R$^3$ | *Stereo-chem | R$^{47}$ | Mass Observed |
|---|---|---|---|---|---|---|
| 48-50 | Me | CH$_2$OH | i-Pr | S | H | 492.3 |
| 48-51$^a$ | Me | H | Ph | R | H | 496.0 |
| 48-52$^a$ | Me | H | Ph | S | H | 496.0 |
| 48-53$^a$ | Me | H | Ph | S | F | 536.4 |
| 48-54$^a$ | Me | H | Ph | R | F | 536.4 |
| 48-55$^b$ | Me | H | 2-Cl—Ph | S | H | 530.1 |
| 48-56$^b$ | Me | H | 2-Cl—Ph | R | H | 530.1 |
| 48-57 | Me | H | 4-F—Ph | S | F | 532.2 |
| 48-81$^c$ | NH$_2$ | H | Ph | S | H | 497.2 |
| 48-82$^c$ | NH$_2$ | H | Ph | R | H | 497.2 |

$^{a,b,c}$Isomers are separated by HPLC on a chiral column, stereochemistry assigned arbitrarily.

The following compounds are prepared by a similar procedure:

| Cpd No. | R$^2$ | R$^3$ | *Stereochem | **Stereochem | Mass Observed |
|---|---|---|---|---|---|
| 48-58$^a$ | CH$_2$OH | i-Pr | S | R | 478.0 |
| 48-59$^a$ | CH$_2$OH | i-Pr | S | S | 482.2 |
| 48-60$^b$ | H | Ph | R | R | 482.1 |
| 48-61$^b$ | H | Ph | S | R | 482.0 |
| 48-62$^b$ | H | Ph | R | S | 482.0 |
| 48-63$^b$ | H | Ph | S | S | 478.0 |

$^{a,b}$Isomers are separated by HPLC on a chiral column, stereochemistry assigned arbitrarily.

The following compounds are prepared by a similar procedure:

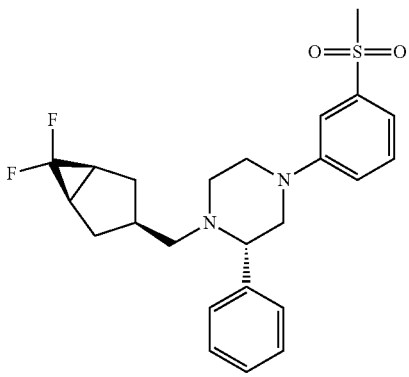

Cpd No 48-64$^a$, m/z = 447.1

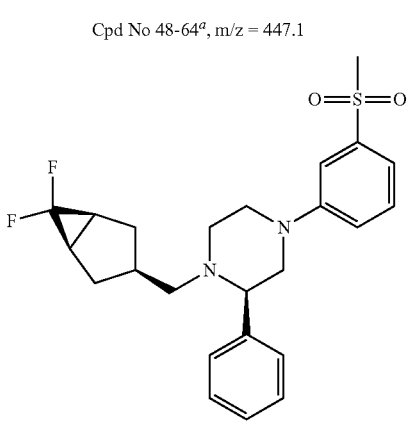

Cpd No 48-65$^a$, m/z = 447.1

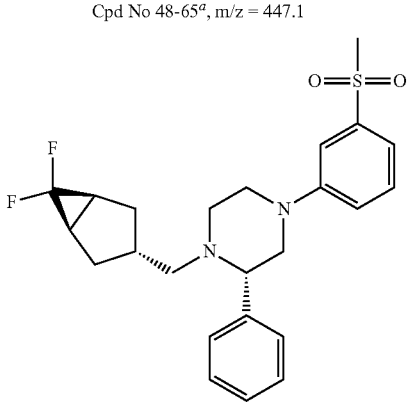

Cpd No 48-66$^a$, m/z = 447.1

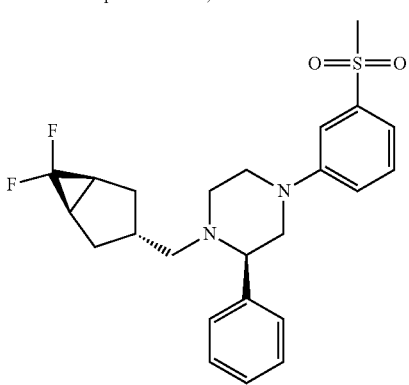

Cpd No 48-67$^a$, m/z = 447.1

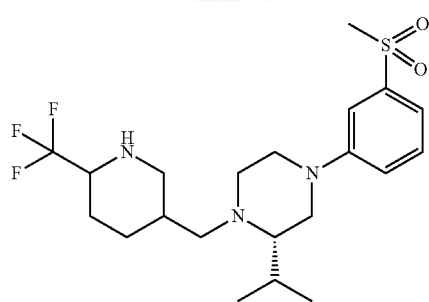
Cpd No 48-68, m/z = 448
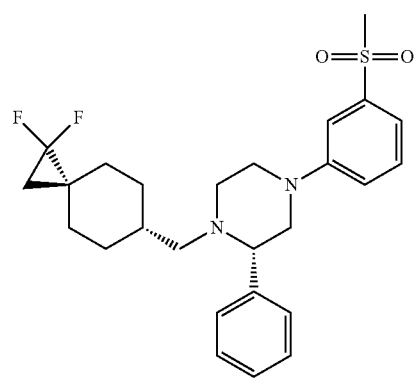
Cpd No 48-69[b], m/z = 475.1
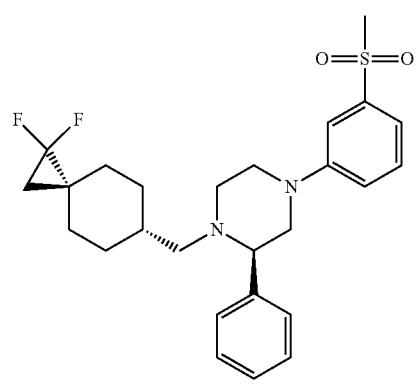
Cpd No 48-70[b], m/z = 475.1
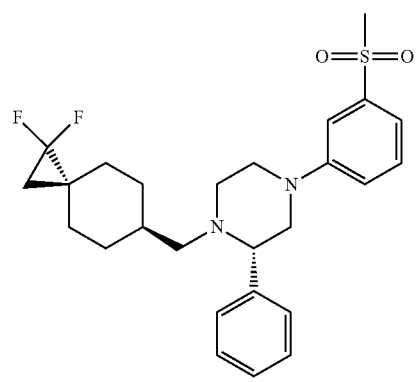
Cpd No 48-71[b], m/z = 475.1
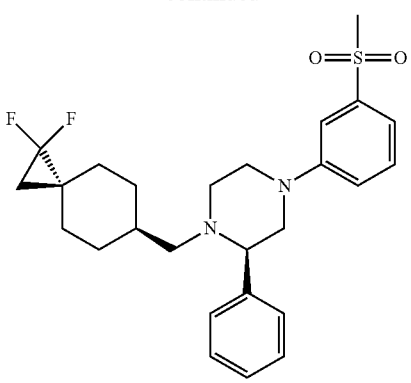
Cpd No 48-72[b], m/z = 475.1
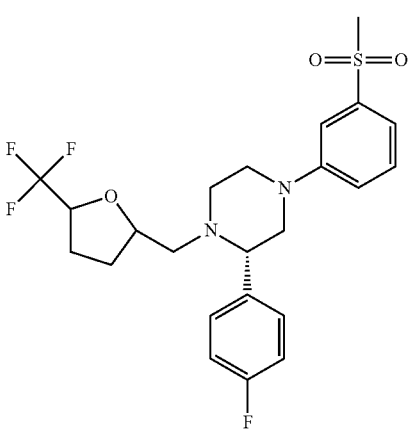
Cpd No 48-73[c], m/z = 487.1
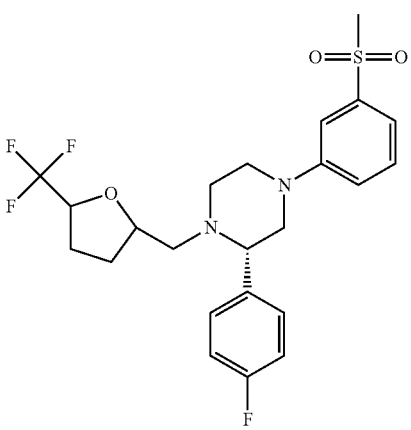
Cpd No 48-74[c], m/z = 487.1

145
-continued

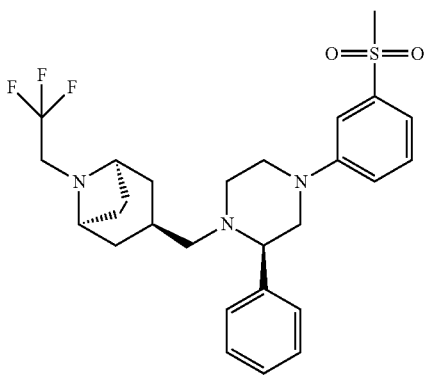

Cpd No 48-75[d], m/z = 522.1

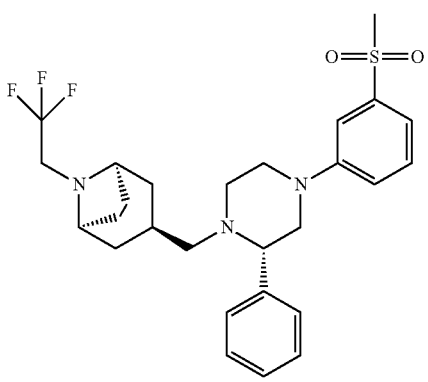

Cpd No 48-76[d], m/z = 522.2

[a,b,c,d]Isomers are separated by HPLC on a chiral column, stereochemistry assigned arbitrarily.

Example 49

(4-((3S)-3-isopropyl-4-((6-(trifluoromethyl)tetrahydro-2H-pyran-3-yl)methyl)piperazin-1-yl)-2-(methylsulfonyl)phenyl)methanol (Cpd Nos 49-1, 49-2)

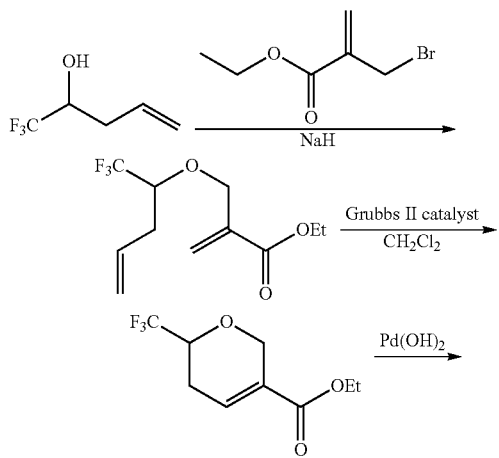

146
-continued

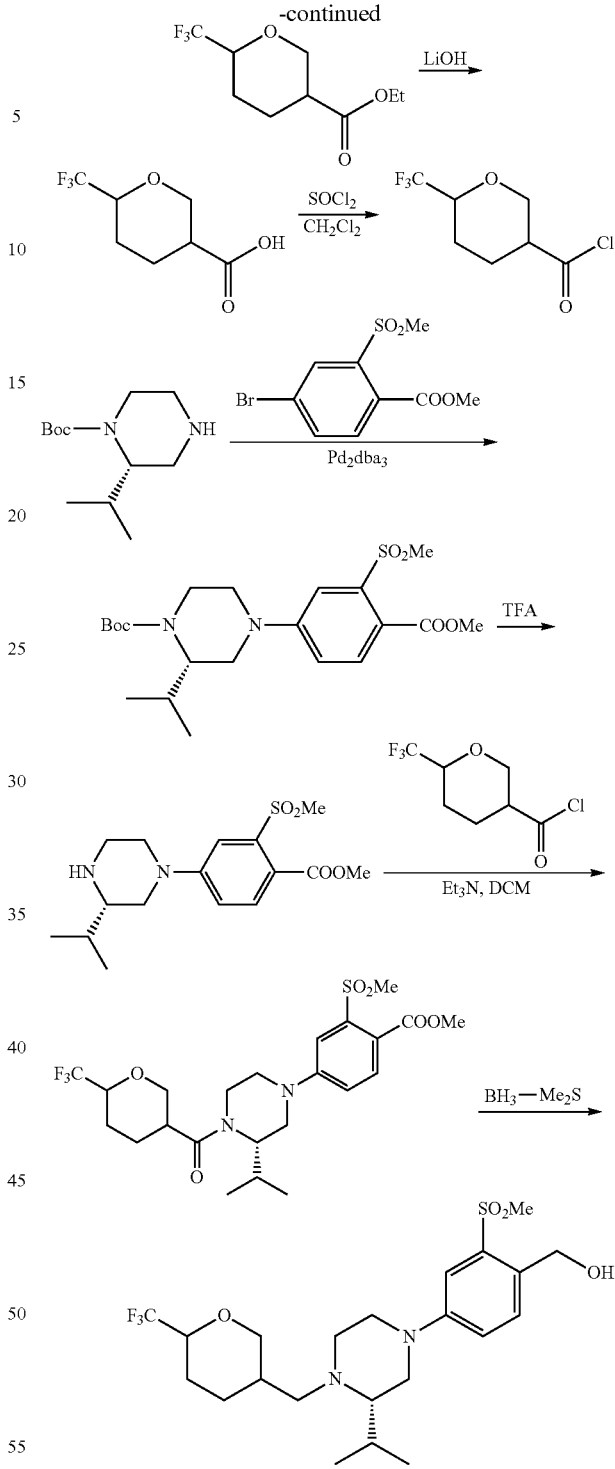

Step 1

To a solution of 1,1,1-trifluoropent-4-en-2-ol (500 mg, 3.57 mmol) in anhydrous DMF (10 mL) was added NaH (171 mg, 4.29 mmol, 60% in mineral) at 0° C. under $N_2$. The mixture was stirred at 0° C. for 10 min, then ethyl 2-(bromomethyl)acrylate (682 mg, 3.57 mmol) was added. The solution mixture was stirred at rt for 3 h under N2. The mixture was added with water (20 mL) and extracted with EtOAc (3×20 mL). The combined organic layers were washed with brine (20 mL), dried over anhydrous $Na_2SO_4$, filtered, concentrated under reduced pressure. The residue was purified by preparative TLC with petroleum ether/EtOAc 10/1 to afford ethyl 2-(((1,1,1-trifluoropent-4-en-2-yl)oxy)methyl)acrylate (322 mg, 36%) as a grey solid.

Step 2

To a solution of ethyl 2-(((1,1,1-trifluoropent-4-en-2-yl)oxy)methyl)acrylate (350 mg, 1.39 mmol) in $CH_2Cl_2$ (8 mL) was added Grubbs II catalyst (118 mg, 0.14 mmol) under $N_2$. The mixture was stirred at rt for 3 h. The mixture was concentrated under reduced pressure. The residue was purified by preparative TLC with petroleum ether/EtOAc 10/1 to afford ethyl 6-(trifluoromethyl)-5,6-dihydro-2H-pyran-3-carboxylate (246 mg, 79%) as a grey solid.

Step 3

To a solution of ethyl 6-(trifluoromethyl)-5,6-dihydro-2H-pyran-3-carboxylate (480 mg, 2.14 mmol) in anhydrous MeOH (10 mL) was added Pd(OH)$_2$/C (200 mg, 20% w/w). The mixture was stirred at rt overnight under $H_2$ (30 psi). The mixture was filtered and the filtrate was concentrated under reduced pressure to afford crude ethyl 6-(trifluoromethyl)tetrahydro-2H-pyran-3-carboxylate (365 mg, 75%) as a yellow solid, which was used for the next step directly without further purification.

Step 4

To a solution of ethyl 6-(trifluoromethyl)tetrahydro-2H-pyran-3-carboxylate (480 mg, 2.12 mmol) in MeOH (10 mL) and H2O (3 mL) was added LiOH (446 mg, 10.62 mmol). The mixture was stirred at rt for 3 h. The mixture was adjusted to pH=6 with 1N HCl solution. The mixture was diluted with H2O (15 mL) and extracted with EtOAc (3×20 mL). The combined organic layers were washed with water (40 mL), dried over anhydrous $Na_2SO_4$, filtered and concentrated under reduced pressure to afford crude 6-(trifluoromethyl)tetrahydro-2H-pyran-3-carboxylic acid (350 mg, 83%) as a yellow solid, which was used for the next step directly without further purification.

Step 5

To a solution of 6-(trifluoromethyl)tetrahydro-2H-pyran-3-carboxylic acid (20 mg, 0.10 mmol) in anhydrous $CH_2Cl_2$ (2 mL) was added $SOCl_2$ (120 mg, 1.01 mmol). The mixture was stirred at 0° C. for 3 h under $N_2$. The mixture was concentrated under reduced pressure to afford crude 6-(trifluoromethyl)tetrahydro-2H-pyran-3-carbonyl chloride (22 mg, 100%) as a yellow oil, which was used for the next step directly without further purification.

Step 6

To a solution of (S)-tert-butyl 2-isopropylpiperazine-1-carboxylate (400 mg, 1.76 mmol) in anhydrous toluene (10 mL) was added methyl 4-bromo-2-(methylsulfonyl)benzoate (1.03 g, 4.8 mmol), X-phos (80 mg, 0.17 mmol), $Cs_2CO_3$ (1.50 g, 4.62 mmol) and Pd$_2$(dba)$_3$ (200 mg, 0.22 mmol) under $N_2$. The reaction mixture was stirred at 100° C. overnight. The reaction was quenched with water (20 mL), and extracted with EtOAc (4×20 mL). The combined organic layers were dried over anhydrous $Na_2SO_4$, filtered, concentrated and then purified by preparative TLC with petroleum ether/EtOAc 5/1 to afford (S)-tert-butyl 2-isopropyl-4-(4-(methoxycarbonyl)-3-(methylsulfonyl)phenyl)piperazine-1-carboxylate (500 mg, 65% yield) as a grey solid.

Step 7

To a solution of (S)-tert-butyl 2-isopropyl-4-(4-(methoxycarbonyl)-3-(methylsulfonyl)phenyl)piperazine-1-carboxylate (300 mg, 0.79 mmol) in anhydrous $CH_2Cl_2$ (4 mL) was added TFA (1 mL). The mixture was stirred at rt for 2 h. The mixture was added with sat. NaHCO$_3$ solution (10 mL) and extracted with $CH_2Cl_2$ (3×10 mL). The combined organic layers were washed with brine (25 mL), dried over anhydrous Na2SO4, filtered and concentrated under reduce pressure to afford crude (S)-methyl 4-(3-isopropylpiperazin-1-yl)-2-(methylsulfonyl)benzoate (280 mg, 100%) as a yellow solid, which was used for the next step directly without further purification.

Step 8

To a solution of (S)-methyl 4-(3-isopropylpiperazin-1-yl)-2-(methylsulfonyl)benzoate (80 mg, 0.23 mmol) in anhydrous CH2Cl2 (5 mL) was added Et3N (71 mg, 0.70 mmol) and 6-(trifluoromethyl)tetrahydro-2H-pyran-3-carbonyl chloride (50 mg, 0.23 mmol). The mixture was stirred at rt for 2 h under $N_2$. The mixture was added with water (10 mL) and extracted with EtOAc (3×10 mL). The combined organic layers were washed with brine (20 mL), dried over anhydrous $Na_2SO_4$, filtered and concentrated under reduced pressure. The residue was purified by preparative TLC with petroleum ether/EtOAc 1/1 to afford methyl 4-((3S)-3-isopropyl-4-(6-(trifluoromethyl)tetrahydro-2H-pyran-3-carbonyl)piperazin-1-yl)-2-(methylsulfonyl)benzoate (40 mg, 33%) as a grey solid. This compound was separated into two pairs of isomers (A and B) by preparative tlc.

Step 9

To a solution of methyl 4-((3S)-3-isopropyl-4-(6-(trifluoromethyl)tetrahydro-2H-pyran-3-carbonyl)piperazin-1-yl)-2-(methylsulfonyl)benzoate isomer A (20 mg, 0.04 mmol) in anhydrous THF (2 mL) was added BH$_3$—Me$_2$S (0.13 mL, 1.35 mmol, 10 M) dropwise at 0° C. under $N_2$. The mixture was stirred at at 70° C. for 2 h under $N_2$. The mixture was added with water (5 mL) and extracted with EtOAc (3×5 mL). The combined organic layers were washed with brine (10 mL), dried over anhydrous $Na_2SO_4$, filtered, concentrated under reduced pressure. The residue was purified by preparative TLC with petroleum ether/EtOAc 1/1 and SFC separation to afford Cpd No 49-1 (4-((S)-3-isopropyl-4-(((3R,6S)-6-(trifluoromethyl)tetrahydro-2H-pyran-3-yl)methyl)piperazin-1-yl)-2-(methylsulfonyl)phenyl)methanol (1.50 mg, 22%) and Cpd No 49-2 (4-((S)-3-isopropyl-4-(((3R,6R)-6-(trifluoromethyl)tetrahydro-2H-pyran-3-yl)methyl)piperazin-1-yl)-2-(methylsulfonyl)phenyl)methanol (1.70 mg, 22%) as white solids.

Cpd No 49-1 (1.50 mg, 22%) as a white solid. LC-MS tR=0.852 min in 2 min chromatography (Welch Xtimate C18, 2.1*30 mm, 3 um), MS (ESI) m/z 479.1 [M+H]+. 1H NMR (CDCl3): δ 7.49 (d, J=2.8 Hz, 1H), 7.38 (d, J=8.4 Hz, 1H), 7.05 (dd, J=2.8 Hz, 8.4 Hz, 1H), 4.81 (s, 2H), 4.17-4.13 (m, 1H), 3.69-3.66 (m, 1H), 3.44-3.41 (m, 2H), 3.17 (s, 3H), 3.14-2.86 (m, 5H), 2.56 (dd, J=8.0 Hz, 12.4 Hz, 1H), 2.44-2.38 (m, 1H), 2.22-2.08 (m, 3H), 2.04-2.00 (m, 1H), 1.98-1.83 (m, 2H), 1.68-1.62 (m, 1H), 1.19-1.12 (m, 1H), 1.02 (d, J=6.8 Hz, 3H), 0.93 (d, J=6.8 Hz, 3H). Isomer SFC tR=7.63 min in 15 min chromatography (Column: OJ-H; Method Name: OJ-H_3_5_40_2.35 ml.met, ee=100%).

Cpd No 49-2 (1.70 mg, 22%) as a white solid. LC-MS tR=0.859 min in 2 min chromatography (Welch Xtimate C18, 2.1*30 mm, 3 um), MS (ESI) m/z 479.1 [M+H]+. 1H NMR (CDCl3): δ 7.49 (d, J=2.8 Hz, 1H), 7.37 (d, J=8.4 Hz, 1H), 7.04 (dd, J=2.8 Hz, 8.4 Hz, 1H), 4.81 (s, 2H), 4.38-4.29 (m, 1H), 3.71-3.62 (m, 1H), 3.51-3.42 (m, 2H), 3.17 (s, 3H), 3.14-3.08 (m, 2H), 3.00-2.90 (m, 2H), 2.86-2.78 (m, 1H), 2.61-2.52 (m, 1H), 2.36-2.28 (m, 1H), 2.18-2.02 (m, 3H), 2.01-1.87 (m, 3H), 1.71-1.65 (m, 1H), 1.21-1.13 (m, 1H), 1.02 (d, J=6.4 Hz, 3H), 0.90 (d, J=6.8 Hz, 3H). Isomer SFC tR=9.85 min in 15 min chromatography (Column: OJ-H; Method Name: OJ-H_3_5_40_2.35 ml.met, ee=100%).

(4-((3S)-3-isopropyl-4-((6-(trifluoromethyl)tetra-hydro-2H-pyran-3-yl)methyl)piperazin-1-yl)-2-(methylsulfonyl)phenyl)methanol (Cpd Nos 49-3, 49-4)

To a solution of methyl 4-((3S)-3-isopropyl-4-(6-(trifluoromethyl)tetrahydro-2H-pyran-3-carbonyl)piperazin-1-yl)-2-(methylsulfonyl)benzoate isomer B (20 mg, 0.04 mmol) in anhydrous THF (2 mL) was added $BH_3$-$Me_2S$ (0.13 mL, 1.35 mmol, 10 M) dropwise at 0° C. under $N_2$. The mixture was stirred at at 70° C. for 2 h under N2. The mixture was added with water (5 mL) and extracted with EtOAc (3×5 mL). The combined organic layers were washed with brine (10 mL), dried over anhydrous $Na_2SO_4$, filtered, concentrated under reduced pressure. The residue was purified by preparative TLC with petroleum ether/EtOAc 1/1 and SFC separation to afford Cpd No 49-3 (4-((S)-3-isopropyl-4-(((3S,6S)-6-(trifluoromethyl)tetrahydro-2H-pyran-3-yl)methyl)piperazin-1-yl)-2-(methylsulfonyl)phenyl)methanol (1.60 mg, 21%) and Cpd No 49-4 (4-((S)-3-isopropyl-4-(3S,6R)-6-(trifluoromethyl)tetrahydro-2H-pyran-3-yl)methyl)piperazin-1-yl)-2-(methylsulfonyl)phenyl)methanol (1.70 mg, 22%) as white solids.

Cpd No 49-3 (1.60 mg, 21%) as a white solid. LC-MS tR=0.743 min in 2 min chromatography (Welch Xtimate C18, 2.1*30 mm, 3 um), MS (ESI) m/z 479.1 [M+H]+. 1H NMR (CDCl$_3$): δ 7.45-7.42 (m, 1H), 7.33-7.31 (m, 1H), 7.02-6.98 (m, 1H), 4.75 (s, 2H), 3.97-3.90 (m, 1H), 3.72-3.62 (m, 2H), 3.45-3.35 (m, 2H), 3.10 (s, 3H), 3.06-2.85 (m, 5H), 2.39-2.15 (m, 4H), 1.99-1.86 (m, 1H), 1.75-1.61 (m, 4H), 1.03-0.98 (m, 3H), 0.95-0.85 (m, 3H). Isomer SFC tR=5.34 min in 15 min chromatography (Column: OJ-H; Method Name: OJ-H_3_5_40_2.35 ml.met, ee=94.7%).

Cpd No 49-4 (1.70 mg, 22%) as a white solid. LC-MS tR=0.747 min in 2 min chromatography (Welch Xtimate C18, 2.1*30 mm, 3 um), MS (ESI) m/z 479.1 [M+H]+. 1H NMR (CDCl3): δ 7.42 (d, J=2.8 Hz, 1H), 7.30 (d, J=8.4 Hz, 1H), 6.98 (dd, J=2.8 Hz, 8.4 Hz, 1H), 4.74 (d, J=6.8 Hz, 2H), 4.05 (d, J=11.6 Hz, 1H), 3.72-3.66 (m, 1H), 3.56-3.49 (m, 1H), 3.40-3.36 (m, 2H), 3.10 (s, 3H), 3.08-2.98 (m, 2H), 2.92-2.78 (m, 3H), 2.36-2.26 (m, 1H), 2.19-2.10 (m, 2H), 2.06-1.99 (m, 1H), 1.76-1.70 (m, 3H), 1.62-1.60 (m, 2H), 0.96 (d, J=6.8 Hz, 3H), 0.87 (d, J=6.8 Hz, 3H). Isomer SFC tR=5.71 min in 15 min chromatography (Column: OJ-H; Method Name: OJ-H_3_5_40_2.35 ml.met, ee=89.3%).

The following compounds are prepared by similar procedures:

| Cpd No. | R³ | *Stereo-chem | &Stereo-chem | #Stereo-chem | Mass Observed |
|---|---|---|---|---|---|
| 49-5ᵃ | i-Pr | S | R | S | 449.2 |
| 49-6ᵃ | i-Pr | S | R | R | 449.2 |
| 49-7ᵃ | i-Pr | S | S | S | 449.2 |
| 49-8ᵃ | i-Pr | S | S | R | 449.2 |
| 49-9ᵇ | 4-F—Ph | S | R | S | 523.1 |
| 49-10ᵇ | 4-F—Ph | S | R | R | 501.1 |
| 49-11ᵇ | 4-F—Ph | S | S | S | 523.1 |
| 49-12ᵇ | 4-F—Ph | S | S | R | 501.1 |

ᵃ,ᵇIsomers are separated by HPLC on a chiral column, stereochemistry at & and # centers assigned arbitrarily.

Example 50

4-((S)-3-isopropyl-4-(((1s,4R)-4-(trifluoromethyl)cyclohexyl)methyl)piperazin-1-yl)-2-(methylsulfonyl)benzonitrile (Cpd No 50-1)

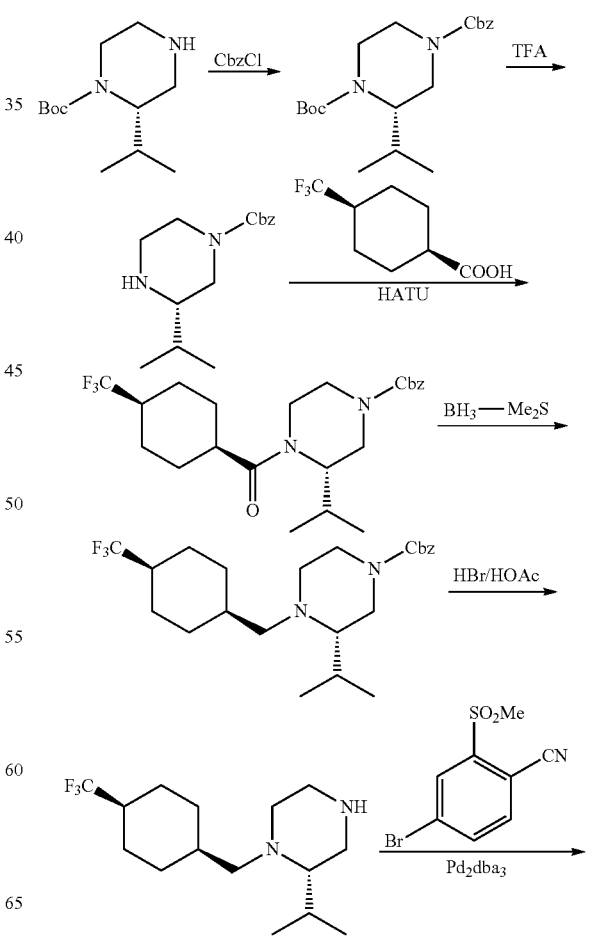

-continued

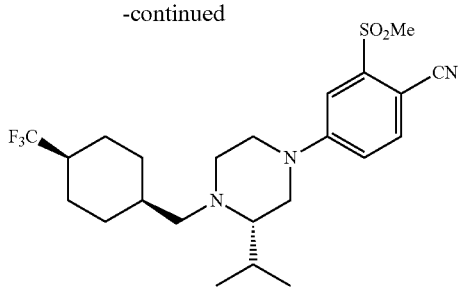

Step 1

A mixture of (5)-tert-butyl 2-isopropylpiperazine-1-carboxylate (1 g, 4.4 mmol), NaHCO₃ (1.1 g, 13.2 mmol), CbzCl (1.1 g, 6.6 mmol) in water (2 mL) and THF (6 mL) was stirred at rt overnight. The mixture was added with water (20 mL) and extracted with EtOAc (3×20 mL). The combined organic layers were dried over anhydrous Na₂SO₄, filtered, concentrated under reduced pressure. The residue was purified by chromatography column on silica gel with eluting with petroleum ether/EtOAc 50/1 to afford crude (S)-4-benzyl 1-tert-butyl 2-isopropylpiperazine-1,4-dicarboxylate (1.8 g, 90%) as a colorless oil, which was used for the next step directly without further purification. LC-MS tR=1.276 min in 2 min chromatography, m/z 263.2 [M+H-Boc]+

Step 2

To a solution of (S)-4-benzyl 1-tert-butyl 2-isopropylpiperazine-1,4-dicarboxylate (1.8 g, 4.9 mmol) in anhydrous CH₂Cl₂ (10 mL) was added TFA (1 mL). The mixture was stirred at rt for 3 h. After concentrated, the mixture was diluted with CH₂Cl₂ (10 mL), then the organic layer was washed with sat. NaHCO₃ solution (2×10 mL), water (10 mL) and brine (10 mL), dried over anhydrous Na₂SO₄, filtered and concentrated under reduced pressure to afford crude (S)-benzyl 3-isopropylpiperazine-1-carboxylate (1.5 g, >100%) as a colorless oil, which was used for the next step directly without further purification.

Step 3

A mixture of (S)-benzyl 3-isopropylpiperazine-1-carboxylate (200 mg, 0.76 mmol), cis-4-(trifluoromethyl)cyclohexanecarboxylic acid (299.2 mg, 1.53 mmol), HATU (288.8 mg, 0.76 mmol) and Et₃N (230.3 mg, 2.28 mmol) in anhydrous DMF (2 mL) was stirred at rt for 4 h. The mixture was added with water (5 mL) and extracted with EtOAc (3×5 mL). The combined organic layers were washed with water (10 mL), dried over anhydrous Na2SO4, filtered and concentrated under reduced pressure. The residue was purified by preparative TLC with petroleum ether/EtOAc 3/1 to afford (S)-benzyl 3-isopropyl-4-((cis)-4-(trifluoromethyl)cyclohexanecarbonyl)piperazine-1-carboxylate (150 mg, 51%) as a yellow oil.

Step 4

To a solution of (S)-benzyl 3-isopropyl-4-((cis)-4-(trifluoromethyl)cyclohexanecarbonyl)piperazine-1-carboxylate (50 mg, 0.11 mmol) in anhydrous THF (1 mL) was added BH₃-Me₂S (0.11 mL, 1.1 mmol, 10 M) under N₂. The mixture was stirred at 60° C. for 2 h. The mixture was added with MeOH (5 mL) slowly and concentrated under reduced pressure. The residue was purified by preparative TLC with petroleum ether/EtOAc 5/1 to afford (S)-benzyl 3-isopropyl-4-(((cis)-4-(trifluoromethyl)cyclohexyl)methyl)piperazine-1-carboxylate (35 mg, 74%) as a colorless oil. LC-MS tR=1.162 min in 2 min chromatography, m/z 427.2 [M+H]+

Step 5

A solution of (S)-benzyl 3-isopropyl-4-(((cis)-4-(trifluoromethyl)cyclohexyl)methyl)piperazine-1-carboxylate (35 mg, 0.08 mmol) in HBr/HOAc (0.5 mL, 37%) was stirred at rt for 2 h. The reaction mixture was treated with water (10 mL) and extracted with EtOAc (3×10 mL). The aqueous layer was adjusted to pH=8-9 with sat. NaHCO₃ solution and extracted with EtOAc (3×10 mL). The combined organic layers were washed with brine, dried over anhydrous Na₂SO₄, filtered and concentrated under reduced pressure to afford crude (S)-2-isopropyl-1-(((cis)-4-(trifluoromethyl)cyclohexyl)methyl)piperazine (24 mg, 100%) as a yellow oil, which was used for the next step directly without further purification. LC-MS tR=0.742 min in 2 min chromatography, m/z 293.2 [M+H]+

Step 6

A mixture of (S)-2-isopropyl-1-(((cis)-4-(trifluoromethyl)cyclohexyl)methyl)piperazine (20 mg, 0.07 mmol), 4-bromo-2-(methylsulfonyl)benzonitrile (21.4 mg, 0.08 mmol), Cs₂CO₃ (66.7 mg, 0.21 mmol), X-phos (8.4 mg, 0.01 mmol) and Pd₂(dba)₃ (12.5 mg, 0.01 mmol) in anhydrous toluene (0.5 mL) was stirred at 100° C. for 6 h under N₂. The mixture was added with water (5 mL) and extracted with EtOAc (3×5 mL). The combined organic layers were washed with water (2×10 mL) and brine (10 mL), dried over anhydrous Na₂SO₄, filtered and concentrated under reduced pressure. The residue was purified by basic preparative HPLC separation to afford 4-((S)-3-isopropyl-4-(((cis)-4-(trifluoromethyl)cyclohexyl)methyl)piperazin-1-yl)-2-(methylsulfonyl)benzonitrile (2.4 mg, 8%) as a colorless oil. LC-MS tR=0.954 min in 2 min chromatography, m/z 472.1 [M+H]+. 1H NMR (CD3OD): δ 7.76 (d, J=8.8 Hz, 1H), 7.50 (d, J=2.8 Hz, 1H), 7.17 (dd, J=2.8 Hz, 8.8 Hz, 1H), 3.71-3.66 (m, 2H), 3.28 (s, 3H), 3.25-3.23 (m, 1H), 3.18-3.14 (m, 1H), 2.88-2.82 (m, 1H), 2.50-2.44 (m, 1H), 2.28-2.27 (m, 1H), 2.26-2.20 (m, 1H), 2.19-2.15 (m, 1H), 2.13-2.10 (m, 1H), 1.93-1.91 (m, 1H), 1.83-1.52 (m, 8H), 1.06 (d, J=6.8 Hz, 3H), 0.97 (d, J=6.8 Hz, 3H).

The following compounds are prepared using similar procedures:

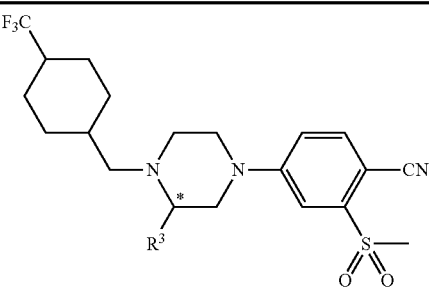

| Cpd No. | R³ | *Stereochem | Cyclohexane geometry | Mass Observed |
|---|---|---|---|---|
| 50-2 | i-Pr | S | trans | 472.1 |
| 50-3ᵃ | Ph | R | trans | 506.2 |
| 50-4ᵃ | Ph | S | trans | 506.2 |
| 50-5ᵇ | Ph | R | cis | 506.2 |
| 50-6ᵇ | Ph | S | cis | 506.2 |

ᵃ,ᵇIsomers are separated by HPLC on a chiral column, stereochemistry at * assigned arbitrarily.

Example 51

(2S)-2-isopropyl-4-(3-(methylsulfonyl)phenyl)-1-((tetrahydro-2H-pyran-3-yl)methyl)piperazine (Cpd No 51-1)

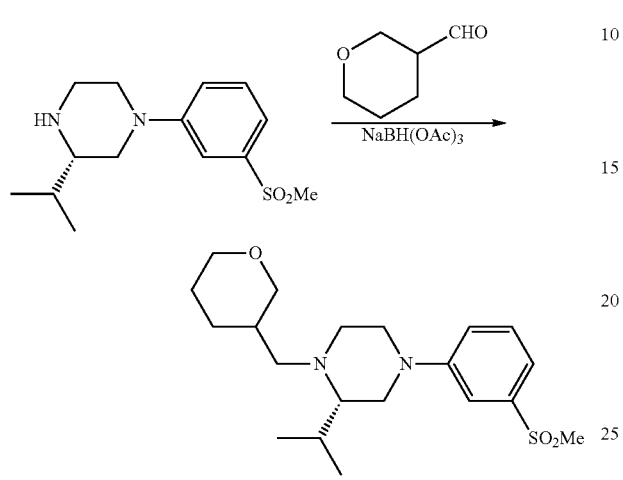

To a stirred solution of (S)-3-isopropyl-1-(3-(methylsulfonyl)phenyl)piperazine (10 mg, 0.035 mmol), tetrahydro-2H-pyran-3-carbaldehyde (8 mg, 0.070 mmol), acetic acid (4 µL, 0.070 mmol) and 1,2-dichloroethane (1 mL) was added NaBH(OAc)3 (37 mg.). 18 mmol). The mixture was stirred overnight. After concentration, the residue was taken up in MeOH and purified by prep HPLC to afford the title compound as its TFA salt (19 mg, quant). LC-MS Method 4 tR=0.56 min, m/z=381. 1H NMR (CD$_3$OD) δ 1.05-1.13 (m, 3H), 1.14-1.22 (m, 3H), 1.44-158 (m, 1H), 1.62-1.75 (m, 2H), 1.90-2.25 (m, 3H), 2.52-2.65 (m, 1H), 2.90-3.10 (m, 1H), 3.13 (s, 3H), 3.15-3.25 (m, 1H), 3.30-3.45 (m, 5H), 4.45-3.55 (m, 1H), 3.75-3.95 (m, 4H), 7.34-7.40 (m, 1H), 7.45-7.59 (m, 3H).

The following compounds are prepared using a similar procedure:

| Cpd No. | R$^2$ | R$^3$ | *Stereochem | R$^{40}$ | Mass Observed |
|---|---|---|---|---|---|
| 51-2 | H | i-Pr | S | 4-tetrahydropyranyl | 381 |
| 51-3 | H | i-Pr | S | 2,2-dimethyl-5-tetrahydropyranyl | 409 |
| 51-4 | H | Ph | S | 3-tetrahydropyranyl | 415 |
| 51-5 | H | Ph | S | 4-tetrahydropyranyl | 415 |
| 51-6[a] | CH$_2$OH | i-Pr | S | trans-4-methoxy-cyclohexyl | 439.4 |
| 51-7[a] | CH$_2$OH | i-Pr | S | cis-4-methoxy-cyclohexyl | 439.4 |

[a]Isomers are separated by HPLC on a chiral column, cis and trans geometry across the cyclohexane ring assigned arbitrarily.

Example 52

(2S)-2-isopropyl-1-((1-methyl-6-(trifluoromethyl)piperidin-3-yl)methyl)-4-(3-(methylsulfonyl)phenyl)piperazine (Cpd No 52-1)

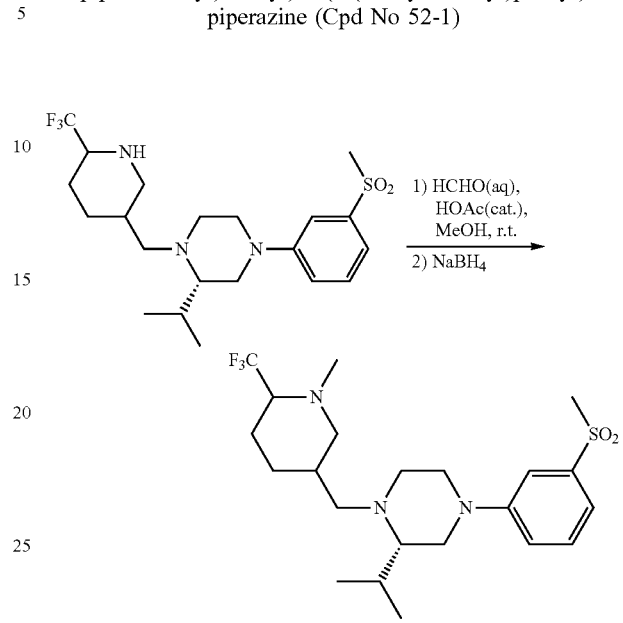

A mixture of (2S)-2-isopropyl-4-(3-(methylsulfonyl)phenyl)-1-((6-(trifluoromethyl)piperidin-3-yl)methyl)piperazine (12 mg, 0.027 mmol), formaldehyde (37% aqueous solution, 200 µL, excess), methanol (1.5 mL), acetic acid (3 drops) was stirred 1.5 h at r.t. Sodium borohydride (~12 mg, excess) was added and the mixture was stirred 30 min at r.t. LC-MS found reaction complete. The mixture was quenched by 1% HCl, concentrated, and purified by Gilson to afford 4.2 mg (34%) of the title compound. LC-MS (1 min. method): tR=0.58 min., m/z 462 (M+1). 1H NMR (CD3OD) δ 7.58-7.46 (m, 3H), 7.38 (d, J=8 Hz, 1H), 3.92 (d, 1H), 3.84 (m, 2H), 3.48-3.32 (m, 3H), 3.23 (m, 2H), 3.12 (s, 3H), 3.06 (m, 1H), 2.82 (m, 2H), 2.59 (d, 3H), 2.32 (m, 1H), 1.93 (m, 2H), 1.82 (m, 1H), 1.58 (m, 1H), 1.21 (d, 3H), 1.11 (d, 3H).

Example 53

(S)-4,4-dimethyl-1-((4-(3-(methylsulfonyl)phenyl)-2-phenylpiperazin-1-yl)methyl)cyclohexan-1-ol (Cpd No 53-1 and 53-2)

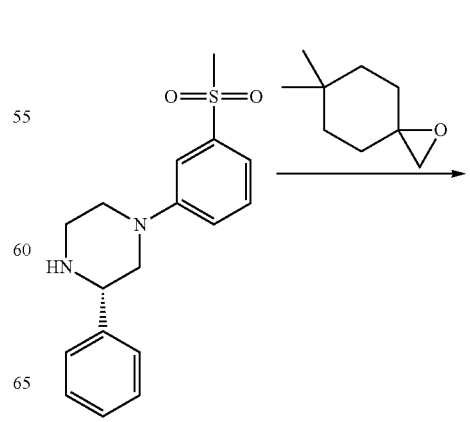

-continued

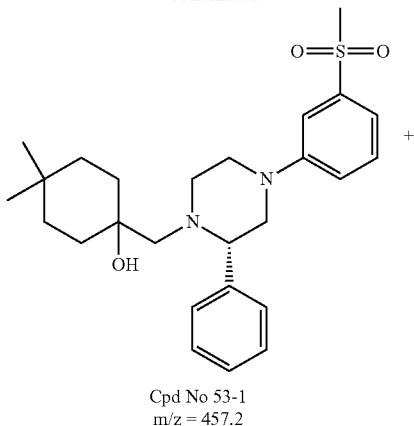

Cpd No 53-1
m/z = 457.2

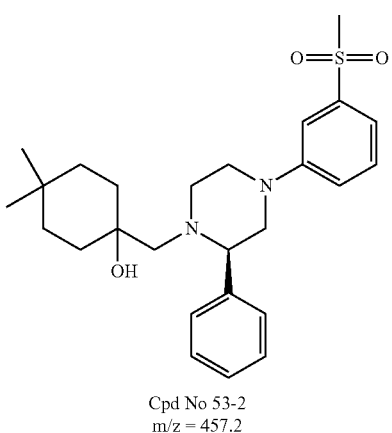

Cpd No 53-2
m/z = 457.2

Example 54

(R)—N-(4-(3-isopropyl-4-(4-(trifluoromethyl)pyrimidin-2-yl)piperazin-1-yl)-2-(methylsulfonyl)benzyl)acetamide (Cpd No 54-1)

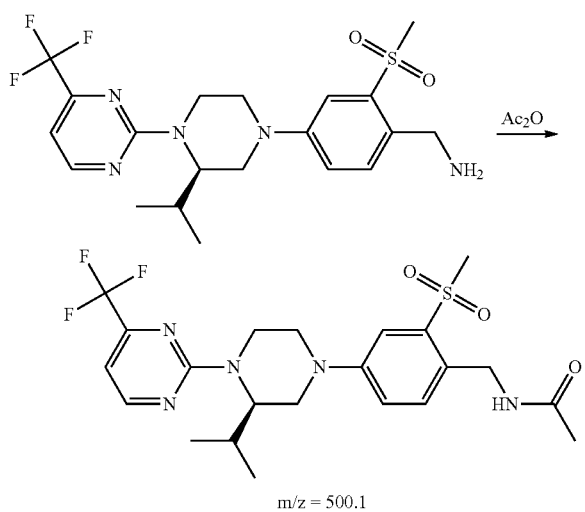

m/z = 500.1

The following compound is prepared using a similar procedure:

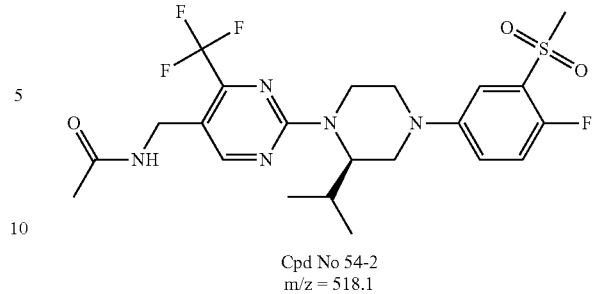

Cpd No 54-2
m/z = 518.1

Biological Test Example 1

LXR α/β Radioligand Binding Assay

Compounds of the invention were assessed in a competition binding assay where different concentrations of compounds were incubated with the LXR ligand binding domain (LBD) in the presence of radiolabeled LXR ligand [$^3$H]TO901317. The amount of the LXR-LBD that complexed with [$^3$H]TO901317 was measured by scintillation proximity assay (SPA) employing non-specific binding of LXR-LBD to poly-lysine coated Yttrium silicate beads. Partially purified LXR α or β LBD protein (15-45 nM) was incubated at rt for 30 min with 15 nM [$^3$H]TO901317 (25-40 Ci/mmol) and different concentrations of test compounds in 80 μL of phosphate buffered saline (PBS) buffer containing 2.5% DMSO, 1% glycerol, 2 mM EDTA, 2 mM CHAPS and 5 mM DTT in 96-well plates. Poly-lysine SPA beads (50 μg) were added to each well and the total volume was adjusted to 120 μL. The plates were shaken on an orbital shaker for 20 min and then allowed to settle for 10 more min at rt before a brief centrifugation at 2,000 rpm for 1 min. The SPA signal was measured on a MicroBeta® liquid scintillation counter (Perkin Elmer, Waltham, Mass.), and the results were used for calculating IC50 values based on the total binding (DMSO control) and non-specific binding (5 μM of unlabeled TO901317) controls. The $K_i$ values were calculated according to equation 1, where [RL] is the final concentration of [$^3$H]TO901317 in the assay, and the $K_d$ values of 20 nM and 10 nM of TO901317 for LBDs of LXRα and LXRβ, respectively, were determined by direct titration of the radioligand with these proteins.

$$Ki = \frac{IC50}{\left(1 + \frac{[RL]}{Kd}\right)} \quad (1)$$

Biological Test Example 2

LXR Luciferase Transcriptional Reporter Gene Assay

The LXR luciferase transcriptional reporter gene assay measures the ability of LXR ligands to promote transcriptional activation via the ligand binding domain (LBD) of LXR. The assay can be run in "agonist" mode to demonstrate agonist activity of compounds of the invention, and can also be run in "antagonist" mode with LXR antagonist compounds of the invention. HEK293 cells were plated in 100 mm dishes, grown to reach 80-90% confluency, and batch-transfected with an expression plasmid containing the Gal4 DNA binding domain fused to either the LBD of LXRα or LXRβ and a luciferase reporter plasmid pG5-Luc (Promega, Madison, Wis.), which has Gal4 response elements upstream of the firefly luciferase gene (luc+). Transfection was accomplished with Lipofectamine™ 2000 (Life Technologies, Grand Island, N.Y.) according to the manufacturer's suggested protocol. Five h following transfection, 15 mL of 10% charcoal-treated FBS (Hyclone, #SH30070.03) in DMEM were added to the transfected dishes without removing the transfection media, and the cells were incubated at 37° C. overnight. The next day, the transfected cells were trypsinized, washed with PBS, resuspended in 10% charcoal-treated DMEM media and plated into 96-well plates with 60,000-80,000 cells/100 μL per well. The cells were incubated at 37° C. for ~4 h before addition of 100 μL of test compound or control ligand at different concentrations (final DMSO concentration at 0.2%). Following incubation of the cells for 16 h with substances, the culture media were dumped and Bright-Glo™ luciferase reagent (Cat. #E2610, Promega, Madison, Wis.) was added to lyse the cells and initiate the luciferase reaction. Luminescence, as a measure of luciferase activity, was detected in an EnVision® multilabel reader (Perkin Elmer, Waltham, Mass.). Transcriptional activation in the presence of a test compound was expressed as fold-change in luminescence compared to that of cells incubated in the absence of the compound. $EC_{50}$ values were calculated using the XLfit™ program (IDBS, Guilford, UK).

To demonstrate the ability of compounds to antagonize transcription ("antagonist" mode), the assay was carried out identically, except that T0901317 (full LXR agonist), at a final concentration of 200 nM, was included with the test compound or control, to induce nearly maximal transcriptional activation.

Biological Test Example 3

Human LXRα and LXRβ Coactivator Recruitment FRET Assay

This assay is based on the ability of the LXR-LBDs (LXRα and LXRβ) to recruit and interact with a co-activator peptide. This assay was run in "agonist" mode, to characterize compounds of the invention that exhibit LXR agonist activity, and in "antagonist" mode to characterize compounds of the invention having LXR antagonist activity and which cause a concentration-dependent release of the co-activator peptide in the presence of the full LXR agonist T0901317. The interaction between glutathione S-transferase (GST)-tagged, recombinant human LXRα-LBD or LXRβ-LBD and fluorescein-conjugated co-activator peptide SRC2-3 (Cat# PV4588, Life Technologies, Grand Island, N.Y.) was measured via time resolved-fluorescence resonance energy transfer (TR-FRET). The assay was performed in 96-well half-area black Opti-plates (Cat# 3686, Corning, Lowell, Mass.) in 20 mM TRIS-HCl buffer, pH 8, containing 150 mM NaCl and 5 mM DDT in a total volume of 80 μL. Test compounds were dissolved in DMSO, and semi-log (3.162×) serial dilutions were also prepared in DMSO, as 40× solutions.

Two μL of the DMSO solutions were transferred to the plate and 38 μL of 10 nM LXRα-LBD or LXRβ-LBD (2×) were added immediately to the wells. The plate was shaken for 5 min at rt on an orbital micro shaker (DPC MicroMix® 5), after which 40 μL of 200 nM fluorescein-SRC2-3 peptide and 20 nM Terbium-anti-GST-antibody (Cat# PV3550, Life Technologies, Grand Island, N.Y.) solution (4×) were added to all. The plate was sealed and shaken for 2 min at rt, and incubated at rt for 2 h without agitation. The plate was read on an EnVision® multilabel reader (Perkin Elmer, Waltham, Mass.) via excitation at 340 nm (UV2-TRF filter) and detection of emitted energy at 520 nm (fluorescein filter) and 495 nm (Terbium) employing a LANCE/DELPHIA mirror. The delay and window times were set at 100 and 200 microseconds, respectively. The TR-FRET ratio values were obtained by normalization of the fluorescein signal (520) to the Terbium signal (495). Percent control/co-activator recruitment values were calculated based on the low TR-FRET ratio values obtained with DMSO control (minimal SRC2-3 recruitment) and the high signal observed with 5 μM T0901317 (full SRC2-3 recruitment). The percent control vs. compound concentration data were fit into a four-parameter model, and $EC_{50}$ values were calculated from the fit as the concentrations corresponding to the inflection points on the concentration-response curves.

When this assay was carried out in "antagonist" mode, 250 nM T0901317 (full LXR agonist) was added to induce nearly maximal SRC2-3 recruitment. Briefly, 5 μL of a 17× solution of T091317 (4.25 μM) was added to all wells containing the serial dilutions of tested compounds.

Percent inhibition/co-activator release values are calculated based on the high TR-FRET ratio values obtained with 250 nM T0901317 (~75% SRC2-3 recruitment) and the low signal observed with the antagonist compounds (SRC2-3 release).

TABLE 3

| | LXR Binding and Agonist Activities | | | | | |
|---|---|---|---|---|---|---|
| Cpd No | LXRα Binding[a] $K_i$; nM | LXRβ Binding[a] $K_i$; nM | Cell LXRα[b] $EC_{50}$; nM (efficacy; %) | Cell LXRβ[b] $EC_{50}$; nM (efficacy; %) | FRET LXRα[c] $EC_{50}$; nM (efficacy; %) | FRET LXRβ[c] $EC_{50}$; nM (efficacy; %) |
| 1-1 | 1690 | 157 | 2778 (44) | 467 (34) | 409 (60) | 15 (88) |
| 1-2 | | | 9219 (6) | 1425 (8) | 6810 (55) | 258 (65) |
| 1-3 | | | 955 (34) | 160 (25) | 1682 (43) | |
| 1-4 | | | 14195 (49) | 4216 (35) | 13535 (67) | 2057 (99) |
| 1-5 | | | 4297 (17) | 898 (21) | 4097 (63) | 227 (78) |
| 1-6 | | | >20000 | >20000 | 8387 (14) | 12472 (25) |
| 1-7 | | | 2550 (8) | >20000 | 11886 (33) | >50000 |
| 1-8 | | | 1146 (34) | 749 (18) | 105 (18) | 55 (20) |
| 1-9 | | | >20000 | >20000 | >50000 | 564 (32) |
| 1-10 | | | >20000 | >20000 | 3529 (28) | 500 (31) |
| 1-11 | | | 16278 (16) | 15706 (2) | 19055 (27) | 340 (25) |
| 1-12 | | | 2631 (26) | 948 (37) | 856 (46) | 81 (72) |
| 1-13 | | | 2139 (16) | 265 (7) | 586 (37) | 36 (52) |

TABLE 3-continued

| | LXR Binding and Agonist Activities | | | | | |
|---|---|---|---|---|---|---|
| Cpd No | LXRα Binding[a] K$_i$; nM | LXRβ Binding[a] K$_i$; nM | Cell LXRα[b] EC$_{50}$; nM (efficacy; %) | Cell LXRβ[b] EC$_{50}$; nM (efficacy; %) | FRET LXRα[c] EC$_{50}$; nM (efficacy; %) | FRET LXRβ[c] EC$_{50}$; nM (efficacy; %) |
| 1-14 | | | >20000 | >20000 | 1544 (27) | 192 (25) |
| 2-1 | | 209 | 5252 (61) | 684 (36) | 901 (48) | 56 (74) |
| 2-2 | >3333 | 1926 | >20000 | >20000 | 23192 (82) | |
| 2-3 | | | >20000 | 1686 (6) | 34889 (102) | 1143 (76) |
| 2-4 | 1075 | 197 | 4227 (62) | 588 (48) | | |
| 3-1 | | | 12810 (20) | 2307 (20) | 17952 (76) | 618 (75) |
| 3-2 | | | 14412 (19) | 2175 (14) | 11963 (54) | 931 (69) |
| 3-3 | >3333 | 288 | 9543 (37) | 762 (27) | | |
| 4-1 | | | 15676 (21) | 3010 (20) | 14491 (68) | 2410 (90) |
| 4-2 | | | 1172 (71) | 392 (54) | 293 (87) | |
| 4-3 | >3333 | >2500 | >20000 | 1679 (12) | | |
| 4-4 | >3333 | 1630 | 2852 (7) | 1354 (12) | | |
| 4-5 | 3250 | 495 | 15117 (37) | 1723 (24) | | |
| 4-6 | >3333 | 936 | 9385 (44) | 3617 (59) | | |
| 4-7 | 1682 | 173 | 2952 (73) | 477 (61) | | |
| 4-8 | 443 | 80 | 782 (91) | 545 (59) | | |
| 4-9 | 3654 | 926 | 15695 (21) | 5047 (31) | | |
| 5-1 | 483 | 54 | 1055 (79) | 272 (63) | | |
| 5-2 | 163 | 15 | 947 (73) | 111 (49) | | |
| 5-3 | 474 | 38 | 1595 (86) | 198 (58) | | |
| 5-4 | 2443 | 290 | 4910 (40) | 732 (32) | | |
| 5-5 | | | 3049 (6) | 593 (6) | 2503 (33) | 76 (35) |
| 5-6 | | | 1424 (48) | 392 (39) | 234 (52) | 14 (58) |
| 5-7 | | | 1919 (44) | 311 (32) | 340 (58) | 27 (85) |
| 5-8 | | | >20000 | >20000 | 19759 (41) | 732 (24) |
| 6-1 | | | >20000 | 4342 (40) | >50000 | 2648 (78) |
| 7-1 | 25 | 1 | 255 (92) | 53 (68) | 107 (84) | 6 (98) |
| 7-2 | | | >20000 | >20000 | 1027 (23) | 123 (31) |
| 7-3 | | | 7923 (24) | 1125 (20) | 510 (36) | 48 (51) |
| 7-4 | | | 1219 (70) | 185 (46) | 281 (76) | 17 (84) |
| 7-5 | 346 | 26 | 501 (64) | 93 (32) | 313 (60) | |
| 7-6 | 529 | 53 | 2059 (85) | 423 (38) | | |
| 7-7 | 421 | 47 | 1467 (69) | 404 (60) | | |
| 7-8 | >3333 | 1012 | 17317 (26) | 1521 (21) | | |
| 7-9 | | | 3532 (36) | 640 (24) | 480 (57) | 56 (81) |
| 7-10 | 236 | 13 | 586 (42) | 95 (23) | 292 (55) | |
| 7-11 | 898 | 78 | 3658 (71) | 1198 (48) | | |
| 7-12 | 105 | 9 | 997 (83) | 177 (58) | 677 (86) | |
| 7-13 | 43 | 4 | 257 (85) | 53 (68) | 89 (103) | 4 (125) |
| 7-14 | 2869 | 285 | 7124 (30) | 379 (17) | | |
| 7-15 | 213 | 20 | 1102 (85) | 213 (65) | | |
| 7-16 | | | 1282 (85) | 295 (62) | | 16 (92) |
| 7-17 | | | 1115 (69) | 316 (55) | | |
| 7-18 | 105 | 9 | 1110 (61) | 161 (44) | | |
| 7-19 | 162 | 17 | 909 (40) | 176 (32) | | |
| 7-20 | 101 | 8 | 787 (80) | 142 (57) | | |
| 7-21 | | 9 | 549 (86) | 152 (65) | | |
| 7-22 | | 17 | 1038 (43) | 191 (31) | | |
| 7-23 | | | 1531 (52) | 325 (36) | 1134 (73) | |
| 7-24 | 1033 | 43 | 1586 (50) | 275 (37) | 457 (83) | 14 (74) |
| 7-25 | 4820 | 504 | >20000 | >20000 | | |
| 7-26 | 193 | 29 | 1211 (37) | 240 (24) | | |
| 7-27 | 7188 | 522 | >20000 | >20000 | | |
| 7-28 | 422 | 40 | 2235 (40) | 446 (27) | | |
| 7-29 | | | 150 (92) | 52 (66) | 161 (101) | |
| 7-30 | | | >20000 | >20000 | >50000 | >50000 |
| 7-31 | 1097 | 94 | 3825 (35) | 1289 (48) | | |
| 7-32 | 91 | 9 | 1026 (79) | 201 (67) | | |
| 7-33 | | | 307 (115) | 80 (87) | | |
| 7-34 | 3277 | 284 | 13999 (55) | 1800 (29) | | |
| 7-35 | | | 138 (97) | 39 (96) | 13 (79) | 4 (171) |
| 7-36 | 30 | 4 | 333 (106) | 121 (93) | 415 (102) | |
| 7-37 | | | 1702 (96) | 517 (86) | 2635 (220) | 16 (89) |
| 7-38 | | | 2960 (86) | 573 (70) | 3148 (204) | 43 (109) |
| 7-39 | | | 1502 (80) | 544 (64) | 1433 (191) | 25 (115) |
| 7-40 | | | >20000 | >20000 | 45137 (70) | 4357 (48) |
| 7-41 | 72 | 8 | 949 (84) | 260 (81) | | |
| 7-42 | 623 | 67 | 3110 (46) | 667 (45) | | |
| 7-43 | 130 | 17 | 649 (77) | 158 (53) | | |
| 7-44 | 43 | 4 | 120 (97) | 19 (118) | | |
| 7-45 | 115 | 12 | 377 (85) | 136 (71) | | |
| 7-46 | 13567 | 2146 | 14681 (71) | 3788 (65) | | |
| 7-47 | 3101 | 478 | 4921 (84) | 1848 (48) | | |
| 7-48 | 877 | 116 | 2110 (98) | 780 (97) | | |

TABLE 3-continued

LXR Binding and Agonist Activities

| Cpd No | LXRα Binding[a] K$_i$; nM | LXRβ Binding[a] K$_i$; nM | Cell LXRα[b] EC$_{50}$; nM (efficacy; %) | Cell LXRβ[b] EC$_{50}$; nM (efficacy; %) | FRET LXRα[c] EC$_{50}$; nM (efficacy; %) | FRET LXRβ[c] EC$_{50}$; nM (efficacy; %) |
|---|---|---|---|---|---|---|
| 7-49 | 508 | 82 | 1335 (112) | 517 (100) | | |
| 7-50 | | | 2029 (50) | 257 (37) | 298 (59) | 19 (84) |
| 7-51 | | | 791 (99) | 324 (92) | 164 (112) | 22 (129) |
| 7-52 | 365 | 41 | 1018 (76) | 192 (48) | | |
| 7-53 | 553 | 27 | 795 (40) | 350 (26) | >50000 | |
| 7-54 | 68 | 9 | 371 (95) | 77 (80) | | |
| 7-55 | 120 | 14 | 439 (68) | 106 (55) | | |
| 7-56 | 146 | 15 | 770 (70) | 99 (51) | | |
| 7-57 | 87 | 12 | 245 (87) | 44 (90) | | |
| 7-58 | 2958 | 509 | 6486 (31) | 1154 (31) | | |
| 7-59 | 281 | 39 | 827 (84) | 289 (83) | | |
| 7-60 | 873 | 146 | 248 (95) | 59 (75) | 84 (97) | |
| 8-1 | 454 | 36 | 2160 (16) | 493 (31) | 665 (41) | 62 (75) |
| 9-1 | 85 | 13 | 743 (55) | 109 (31) | | |
| 9-2 | 95 | 10 | 543 (54) | 86 (34) | | 9 (91) |
| 9-3 | | 16 | 951 (50) | 280 (39) | | |
| 9-4 | | 13 | 1415 (37) | 318 (27) | | |
| 9-5 | 41 | 9 | 504 (46) | 82 (21) | | |
| 9-6 | 101 | 8 | 503 (59) | 74 (41) | | |
| 9-7 | 33 | 8 | 960 (34) | 194 (28) | | |
| 9-8 | 2345 | 659 | >20000 | 2469 (14) | | |
| 9-9 | | 298 | 3041 (6) | 780 (13) | | |
| 9-10 | 96 | 14 | 243 (59) | 48 (36) | | |
| 9-11 | 2141 | 839 | >20000 | 869 (9) | | |
| 9-12 | 2292 | 642 | 15144 (26) | 5002 (31) | | |
| 9-13 | 703 | 171 | 2862 (21) | 1204 (34) | | |
| 9-14 | 407 | 62 | 3003 (28) | 1099 (38) | | |
| 10-1 | 157 | 8 | 763 (37) | 80 (24) | 213 (44) | |
| 10-2 | 469 | 34 | 2692 (45) | 475 (39) | | |
| 10-3 | 135 | 5 | 646 (35) | 69 (24) | | |
| 10-4 | 59 | 6 | 1034 (28) | 128 (13) | | |
| 10-5 | 1280 | 230 | 3627 (67) | 980 (58) | | |
| 10-6 | | 862 | 9158 (22) | 1306 (17) | | |
| 10-7 | 261 | 18 | 1520 (51) | 235 (40) | | |
| 10-8 | 2188 | 132 | 4655 (96) | 901 (76) | | |
| 10-9 | | 2349 | >20000 | 7383 (29) | | |
| 10-10 | | 181 | 13605 (107) | 1962 (73) | | |
| 10-11 | | | >20000 | >20000 | >50000 | >50000 |
| 10-12 | >3333 | >2500 | >20000 | >20000 | 1367 (18) | 1141 (33) |
| 10-13 | | 226 | >20000 | >20000 | | |
| 10-14 | 4556 | 1479 | >20000 | >20000 | | |
| 11-1 | 146 | 9 | 590 (57) | 68 (40) | | |
| 11-2 | 357 | 35 | 1336 (57) | 243 (46) | | |
| 11-3 | 146 | 6 | 1014 (62) | 95 (44) | | |
| 11-4 | 1889 | 159 | 3106 (30) | 347 (24) | | |
| 11-5 | >3333 | 414 | 4667 (21) | 363 (16) | | |
| 11-6 | 71 | 2 | 216 (58) | 16 (46) | | |
| 11-7 | 1160 | 85 | 2240 (13) | 315 (14) | | |
| 11-8 | 1165 | 133 | 2934 (53) | 405 (53) | | |
| 11-9 | 1971 | 247 | 3283 (31) | 603 (39) | | |
| 11-10 | >3333 | 773 | 6291 (28) | 2253 (36) | | |
| 11-11 | 2047 | 246 | 3508 (31) | 1539 (48) | | |
| 11-12 | 194 | 8 | 488 (67) | 41 (73) | | |
| 11-13 | 706 | 65 | 2145 (52) | 374 (53) | | |
| 11-14 | >3333 | 515 | >20000 | >20000 | | |
| 11-15 | >3333 | 930 | 15615 (33) | 2479 (33) | | |
| 11-16 | 1278 | 95 | 2528 (91) | 467 (76) | | |
| 11-17 | 686 | 53 | 1514 (108) | 292 (89) | | |
| 12-1 | 230 | 23 | 969 (46) | 154 (37) | | |
| 12-2 | 233 | 11 | 746 (41) | 117 (36) | | |
| 12-3 | 168 | 6 | 769 (43) | 84 (29) | | |
| 12-4 | 1449 | 111 | 4457 (58) | 652 (50) | | |
| 12-5 | 1184 | 80 | 1481 (22) | 521 (40) | | |
| 12-6 | 266 | 22 | 2429 (43) | 289 (29) | | |
| 12-7 | 82 | 9 | 862 (25) | 49 (15) | | |
| 12-8 | 126 | 4 | 503 (56) | 59 (46) | | |
| 12-9 | 896 | 132 | 4884 (19) | 548 (15) | | |
| 13-1 | 62 | 3 | 253 (63) | 49 (51) | | |
| 13-2 | | 3 | 290 (73) | 33 (58) | | |
| 13-3 | | 88 | 2458 (21) | 360 (18) | | |
| 14-1 | 487 | 14 | 576 (58) | 90 (31) | | |
| 14-2 | | 1 | 186 (63) | 28 (42) | | |
| 15-1 | 255 | 16 | 1501 (18) | 116 (10) | | |
| 15-2 | >3333 | 1320 | >20000 | 3001 (13) | | |

TABLE 3-continued

LXR Binding and Agonist Activities

| Cpd No | LXRα Binding[a] $K_i$; nM | LXRβ Binding[a] $K_i$; nM | Cell LXRα[b] $EC_{50}$; nM (efficacy; %) | Cell LXRβ[b] $EC_{50}$; nM (efficacy; %) | FRET LXRα[c] $EC_{50}$; nM (efficacy; %) | FRET LXRβ[c] $EC_{50}$; nM (efficacy; %) |
|---|---|---|---|---|---|---|
| 15-3 | | 47 | 1144 (25) | 74 (17) | | |
| 15-4 | | 100 | 2838 (20) | 182 (13) | | |
| 15-5 | | 36 | 2592 (12) | 36 (3) | | |
| 15-6 | >3333 | 360 | >20000 | >20000 | | |
| 15-7 | 512 | 40 | 2315 (23) | 198 (18) | | |
| 15-8 | | 1 | 219 (44) | 34 (35) | | |
| 15-9 | 2064 | 146 | 4170 (10) | >20000 | | |
| 15-10 | 948 | 70 | 5353 (16) | >20000 | | |
| 15-11 | 2179 | 228 | 4307 (42) | 1025 (51) | | |
| 16-1 | 20173 | 1856 | >20000 | >20000 | | |
| 16-2 | | | >20000 | >20000 | | |
| 17-1 | 1115 | 123 | 6350 (18) | 244 (8) | | |
| 17-2 | 876 | 58 | 1789 (17) | 91 (10) | | |
| 17-3 | 2691 | 188 | 5514 (29) | 448 (18) | | |
| 17-4 | | 512 | >20000 | 833 (6) | | |
| 17-5 | | 396 | >20000 | >20000 | | |
| 17-6 | >3333 | 532 | >20000 | >20000 | | |
| 17-7 | >3333 | 507 | >20000 | >20000 | | |
| 17-8 | | 311 | >20000 | >20000 | | |
| 17-9 | >3333 | 410 | >20000 | >20000 | | |
| 17-10 | 558 | 65 | >20000 | >20000 | | |
| 17-11 | 4876 | 548 | >20000 | >20000 | | |
| 17-12 | | 210 | >20000 | >20000 | | |
| 17-13 | 2882 | 253 | >20000 | >20000 | | |
| 17-14 | 915 | 113 | >20000 | >20000 | | |
| 17-15 | >3333 | 360 | >20000 | >20000 | | |
| 17-16 | 2172 | 194 | >20000 | >20000 | | |
| 17-17 | >3333 | 618 | >20000 | >20000 | | |
| 17-18 | | 129 | >20000 | >20000 | | |
| 17-19 | >3333 | 584 | >20000 | >20000 | | |
| 17-20 | | 330 | >20000 | >20000 | | |
| 17-21 | | 111 | >20000 | >20000 | | |
| 17-22 | 670 | 116 | >20000 | >20000 | | |
| 17-23 | 1422 | 257 | >20000 | >20000 | | |
| 17-24 | >3333 | 611 | >20000 | >20000 | | |
| 17-25 | 1145 | 50 | 1127 (18) | 46 (13) | | |
| 17-26 | >3333 | 2334 | >20000 | >20000 | | |
| 17-27 | >3333 | >2500 | >20000 | >20000 | | |
| 17-28 | 886 | 34 | 913 (9) | 20 (9) | | |
| 17-29 | 1266 | 191 | 1950 (15) | 142 (17) | | |
| 17-30 | >3333 | 1804 | >20000 | >20000 | | |
| 17-31 | >3333 | 2448 | >20000 | >20000 | | |
| 17-32 | | 435 | >20000 | >20000 | | |
| 17-33 | 10568 | 1224 | >20000 | >20000 | | |
| 17-34 | 152 | 23 | 465 (98) | 105 (94) | | |
| 17-35 | 1663 | 111 | 1738 (19) | 161 (23) | | |
| 17-36 | | | >20000 | >20000 | 808 (46) | 1179 (79) |
| 17-37 | 3213 | 1007 | 16011 (50) | 3529 (24) | 605 (53) | 355 (85) |
| 17-38 | 3128 | 753 | 4828 (13) | 1790 (18) | 3368 (34) | 561 (71) |
| 17-39 | | 107 | 1648 (67) | 630 (26) | 267 (55) | 63 (61) |
| 18-1 | 73 | 12 | 591 (104) | 217 (93) | | |
| 19-1 | 81 | 3 | 244 (60) | 21 (56) | | |
| 19-2 | 1072 | 160 | 1735 (95) | 503 (73) | | |
| 20-1 | 166 | 24 | 678 (90) | 141 (75) | | |
| 20-2 | 631 | 73 | 3397 (64) | 706 (43) | | |
| 20-3 | 762 | 52 | 1905 (67) | 443 (48) | | |
| 20-4 | 41 | 20 | 139 (96) | 28 (105) | | |
| 21-1 | 608 | 31 | 3767 (74) | 562 (66) | | |
| 22-1 | | | 1482 (31) | 139 (14) | | |
| 22-2 | | 172 | 1227 (7) | 750 (10) | 271 (12) | |
| 22-3 | 3 | 1 | 92 (113) | 21 (114) | | |
| 22-4 | 4 | | 158 (115) | 33 (98) | | |
| 23-1 | 1181 | 212 | >20000 | >20000 | | |
| 24-1 | >3333 | 944 | >20000 | 5604 (21) | | |
| 25-1 | 32 | 4 | 174 (44) | 22 (31) | | |
| 26-1 | 111 | 5 | 584 (102) | 185 (98) | | |
| 26-2 | 1183 | 72 | 2233 (99) | 329 (74) | | |
| 27-1 | 27 | 10 | 225 (97) | 44 (98) | | |
| 28-1 | 29 | 3 | 66 (80) | 11 (79) | | |
| 29-1 | 9 | 3 | 266 (104) | 66 (71) | | |
| 30-1 | 169 | 24 | 3121 (100) | 729 (98) | | |
| 31-1 | 159 | 18 | 2718 (7) | >20000 | | |
| 32-1 | 197 | 22 | 4667 (6) | >20000 | | |
| 33-1 | 1316 | 114 | 3532 (17) | >20000 | | |

TABLE 3-continued

LXR Binding and Agonist Activities

| Cpd No | LXRα Binding[a] K$_i$; nM | LXRβ Binding[a] K$_i$; nM | Cell LXRα[b] EC$_{50}$; nM (efficacy; %) | Cell LXRβ[b] EC$_{50}$; nM (efficacy; %) | FRET LXRα[c] EC$_{50}$; nM (efficacy; %) | FRET LXRβ[c] EC$_{50}$; nM (efficacy; %) |
|---|---|---|---|---|---|---|
| 33-1 | 222 | 16 | 761 (54) | 53 (24) | | |
| 34-1 | 1242 | 151 | 2456 (78) | 670 (83) | | |
| 35-1 | 272 | 38 | 1522 (97) | 499 (88) | | |
| 36-1 | 30 | 4 | 305 (100) | 89 (86) | | |
| 37-1 | | 3 | 262 (91) | 41 (81) | | |
| 37-2 | 9 | 2 | 149 (114) | 49 (98) | | |
| 37-3 | | | 60 (102) | 11 (96) | | |
| 38-1 | 67 | 3 | 165 (89) | 44 (101) | | |
| 39-1 | 53 | 2 | 327 (96) | 86 (62) | | |
| 40-1 | | 1 | 269 (72) | 57 (48) | | |
| 40-2 | 173 | 14 | 3505 (14) | >20000 | | |
| 40-3 | 724 | 61 | >20000 | >20000 | | |
| 40-4 | 14 | 7 | 1057 (80) | 214 (58) | | |
| 41-1 | 1115 | 92 | 3334 (36) | 305 (19) | | |
| 42-1 | 366 | 33 | 763 (48) | 124 (20) | | |
| 43-1 | 26 | 4 | 136 (101) | 31 (95) | | |
| 44-1 | 45 | 7 | 258 (99) | 70 (83) | | |
| 44-2 | 520 | 35 | 2594 (24) | 205 (10) | | |
| 44-3 | 809 | 67 | 3520 (6) | >20000 | | |
| 45-1 | | | 3618 (61) | 1175 (42) | 627 (39) | 68 (61) |
| 46-1 | | | 1228 (47) | 692 (69) | 542 (75) | 156 (82) |
| 46-2 | | | >20000 | 1398 (10) | 3943 (35) | 1048 (57) |
| 46-3 | 91 | 15 | 1573 (64) | 603 (69) | 479 (70) | 86 (87) |
| 46-4 | | | >20000 | >20000 | 875 (41) | >50000 |
| 46-5 | | | >20000 | >20000 | >50000 | 7159 (57) |
| 46-6 | 519 | 63 | >20000 | >20000 | >50000 | >50000 |
| 46-7 | >3333 | >2500 | >20000 | >20000 | >50000 | >50000 |
| 46-8 | 1720 | 227 | 3200 (22) | 1358 (18) | 468 (15) | >50000 |
| 46-9 | >3333 | 231 | 2479 (57) | 1078 (49) | | |
| 46-10 | | | >20000 | >20000 | 40680 (55) | 24999 (94) |
| 46-11 | 3288 | 445 | 3753 (7) | >20000 | 17300 (33) | 600 (20) |
| 46-12 | | | >20000 | >20000 | >50000 | >50000 |
| 46-13 | | | >20000 | >20000 | 1903 (28) | 547 (21) |
| 46-14 | | | >20000 | >20000 | 14159 (37) | 2742 (49) |
| 46-15 | | 158 | 2993 (28) | 720 (26) | 1523 (28) | 418 (45) |
| 46-16 | | 503 | >20000 | >20000 | | |
| 46-17 | >3333 | >2500 | >20000 | >20000 | | |
| 46-18 | | 35 | 4598 (45) | 1434 (31) | | |
| 46-19 | >3333 | 1903 | >20000 | 4348 (6) | >50000 | >50000 |
| 46-20 | | | >20000 | >20000 | | |
| 46-21 | | 85 | 2026 (20) | 541 (12) | 3003 (24) | >50000 |
| 46-22 | | | >20000 | 2095 (9) | 4620 (42) | 1273 (73) |
| 46-23 | 1043 | 112 | 4367 (45) | 1432 (29) | 7039 (47) | 710 (57) |
| 46-24 | | 359 | 2711 (31) | 636 (27) | 2704 (39) | 347 (45) |
| 46-25 | | | >20000 | 2557 (13) | >50000 | 17972 (116) |
| 46-26 | | 58 | 1479 (62) | 676 (62) | 2855 (59) | 411 (73) |
| 46-27 | | | 1100 (77) | 645 (83) | 157 (79) | 28 (88) |
| 46-28 | 3653 | 501 | 4974 (24) | 1885 (16) | | |
| 46-29 | 6315 | 1858 | >20000 | >20000 | | |
| 46-30 | 1667 | 216 | 1787 (28) | 532 (12) | | |
| 46-31 | 6563 | 2166 | >20000 | >20000 | | |
| 46-33 | | | 2354 (44) | 1678 (36) | 2541 (37) | 649 (54) |
| 46-34 | | 32 | 2082 (24) | 587 (10) | 862 (40) | 257 (38) |
| 46-35 | | | >20000 | >20000 | >50000 | >50000 |
| 46-36 | | 244 | 11251 (20) | 4759 (14) | | |
| 46-37 | | 30 | 3451 (52) | 1194 (55) | | |
| 46-38 | | | 1088 (25) | 608 (26) | | |
| 46-39 | | | >20000 | >20000 | >50000 | >50000 |
| 46-40 | | | >20000 | >20000 | 4119 (38) | 17703 (23) |
| 46-41 | 1309 | 161 | 2425 (60) | 559 (68) | | |
| 46-42 | >3333 | >2500 | >20000 | 5895 (9) | 984 (53) | 1048 (53) |
| 46-43 | >3333 | 837 | 6210 (35) | 1701 (32) | 1324 (37) | 267 (54) |
| 46-44 | | | >20000 | 9199 (12) | 29585 (71) | 3963 (57) |
| 46-45 | | | >20000 | 7516 (44) | 6571 (43) | 1524 (74) |
| 46-46 | >3333 | 1983 | >20000 | 1989 (4) | 6694 (30) | 1214 (51) |
| 46-47 | | | 9863 (11) | 4077 (16) | 4523 (51) | 817 (54) |
| 46-48 | | | 3403 (25) | 957 (34) | 3011 (47) | 443 (55) |
| 46-49 | | | 3237 (12) | 1630 (8) | 264 (10) | 218 (15) |
| 46-50 | | | 10148 (7) | 7970 (17) | >50000 | 1907 (67) |
| 46-51 | | | 3658 (17) | 1312 (28) | 2299 (41) | 450 (51) |
| 46-52 | | | 11699 (17) | 2113 (20) | 5198 (20) | 1228 (42) |
| 46-53 | >3333 | 1520 | 11138 (23) | 3280 (28) | 2589 (46) | 924 (50) |
| 46-54 | | | >20000 | 2322 (7) | 1351 (49) | 1236 (52) |
| 46-55 | | | 2773 (7) | >20000 | 6541 (25) | 794 (27) |

TABLE 3-continued

LXR Binding and Agonist Activities

| Cpd No | LXRα Binding[a] $K_i$; nM | LXRβ Binding[a] $K_i$; nM | Cell LXRα[b] $EC_{50}$; nM (efficacy; %) | Cell LXRβ[b] $EC_{50}$; nM (efficacy; %) | FRET LXRα[c] $EC_{50}$; nM (efficacy; %) | FRET LXRβ[c] $EC_{50}$; nM (efficacy; %) |
|---|---|---|---|---|---|---|
| 46-56 | | | >20000 | >20000 | 26968 (47) | 2252 (40) |
| 46-57 | 188 | 61 | 1244 (42) | 383 (38) | 499 (41) | 55 (56) |
| 46-58 | | | 6986 (8) | 3444 (15) | >50000 | 2769 (36) |
| 46-59 | | | 4920 (6) | 3083 (8) | 19423 (109) | 3105 (70) |
| 46-60 | | | 4383 (33) | 1274 (25) | 6326 (39) | 949 (74) |
| 46-61 | | | >20000 | >20000 | | 1350 (44) |
| 46-62 | | | >20000 | 1716 (6) | 7774 (32) | 657 (27) |
| 46-63 | | | >20000 | >20000 | 12408 (30) | 7099 (50) |
| 46-64 | >3333 | >2500 | >20000 | 5804 (13) | 10360 (23) | 1864 (34) |
| 46-65 | | | >20000 | >20000 | >50000 | 5770 (25) |
| 46-66 | 1413 | 207 | 4577 (13) | >20000 | 1664 (20) | >50000 |
| 47-1 | | | 8405 (46) | 5144 (39) | 2019 (76) | 259 (63) |
| 47-2 | 119 | 27 | 455 (70) | 159 (65) | | |
| 47-3 | 422 | 39 | 1280 (60) | 363 (57) | | |
| 47-4 | | | 914 (96) | 515 (98) | 224 (109) | 22 (91) |
| 47-5 | 1091 | 109 | 1187 (62) | 248 (50) | | |
| 48-1 | | | 760 (31) | 158 (19) | 1517 (19) | |
| 48-2 | 81 | 9 | 175 (81) | 74 (91) | | |
| 48-3 | 2341 | 221 | 4273 (20) | 1748 (38) | 5191 (31) | 1321 (77) |
| 48-4 | 39 | 10 | 279 (61) | 68 (37) | 301 (39) | 18 (30) |
| 48-5 | 1270 | 123 | >20000 | >20000 | | |
| 48-6 | 30940 | >2500 | >20000 | >20000 | | |
| 48-7 | 4526 | 465 | 4661 (6) | >20000 | | |
| 48-8 | >3333 | >2500 | >20000 | >20000 | | |
| 48-9 | 490 | 128 | 3201 (94) | 1538 (79) | | |
| 48-10 | 1680 | 243 | 9657 (80) | 3031 (66) | | |
| 48-11 | | 2 | 53 (101) | 19 (111) | | |
| 48-12 | 245 | 25 | 363 (66) | 165 (77) | | |
| 48-13 | 867 | 126 | 2624 (20) | 6308 (13) | 632 (23) | 119 (21) |
| 48-14 | | | >20000 | >20000 | >50000 | 12255 (67) |
| 48-15 | | 44 | 1658 (31) | 564 (21) | 2311 (40) | 197 (32) |
| 48-16 | | | 2437 (10) | 941 (16) | 2449 (17) | 454 (47) |
| 48-17 | 60 | 5 | 127 (39) | 21 (23) | 287 (36) | |
| 48-18 | | | 18796 (7) | 5216 (15) | >50000 | 6083 (22) |
| 48-19 | 313 | 56 | 712 (25) | 232 (20) | 1877 (13) | 25048 (13) |
| 48-20 | 4673 | 1551 | >20000 | 2271 (6) | | |
| 48-21 | 517 | 175 | 2703 (20) | 933 (10) | | |
| 48-22 | 1501 | 918 | 9061 (8) | 1191 (8) | | |
| 48-23 | 94 | 11 | 319 (43) | 97 (14) | | |
| 48-24 | 765 | 55 | 1347 (88) | 563 (63) | | |
| 48-25 | 1243 | 178 | >20000 | >20000 | | |
| 48-26 | 39 | 8 | 364 (73) | 91 (45) | | |
| 48-27 | 2865 | 595 | 18123 (60) | 5288 (53) | | |
| 48-28 | | 1341 | >20000 | 6484 (12) | | |
| 48-29 | | 378 | 6290 (43) | 1505 (20) | | |
| 48-30 | 2544 | 632 | 4509 (17) | 1630 (28) | 12862 (55) | |
| 48-31 | 42 | 5 | 254 (61) | 95 (35) | 401 (56) | 22 (37) |
| 48-32 | | | 19000 (4) | 3338 (15) | 15299 (59) | 3798 (97) |
| 48-33 | | 41 | 1245 (49) | 466 (32) | 4869 (74) | 375 (82) |
| 48-34 | | | 9858 (48) | 3822 (32) | 2311 (25) | 704 (39) |
| 48-35 | | | 351 (62) | 120 (27) | 416 (52) | 46 (22) |
| 48-36 | | | >20000 | >20000 | >50000 | 16356 (25) |
| 48-37 | | | 2829 (39) | 1177 (19) | 2352 (33) | 1294 (30) |
| 48-38 | 244 | 27 | 106 (86) | 30 (81) | | |
| 48-39 | 32 | 7 | >20000 | >20000 | | |
| 48-40 | 2475 | 156 | >20000 | >20000 | | |
| 48-41 | 196 | 27 | 1459 (7) | >20000 | | |
| 48-42 | | 207 | >20000 | >20000 | | |
| 48-43 | | 15 | 240 (54) | 47 (32) | 207 (48) | 27 (43) |
| 48-44 | 10769 | 972 | 11556 (50) | 3096 (34) | | |
| 48-45 | 75 | 21 | 431 (65) | 140 (33) | | |
| 48-46 | | 27 | 1908 (35) | 910 (35) | | |
| 48-47 | | | >20000 | 1385 (26) | | |
| 48-48 | 156 | 23 | 460 (53) | 112 (31) | 1321 (42) | 142 (40) |
| 48-49 | 13790 | 1490 | 9842 (9) | 1348 (12) | | |
| 48-50 | 587 | 89 | 386 (77) | 104 (61) | | |
| 48-51 | | | >20000 | >20000 | 9405 (37) | 4851 (65) |
| 48-52 | | | 736 (30) | 129 (13) | 1063 (32) | 68 (30) |
| 48-53 | 2176 | 259 | 2169 (43) | 711 (20) | | |
| 48-54 | >3333 | 2386 | >20000 | >20000 | | |
| 48-55 | 277 | 67 | 2129 (42) | 547 (19) | | |
| 48-56 | | 1672 | >20000 | 4014 (16) | | |
| 48-57 | | 492 | 4500 (37) | 1272 (13) | | |
| 48-58 | >3333 | 680 | 3252 (56) | 1205 (47) | | |

TABLE 3-continued

LXR Binding and Agonist Activities

| Cpd No | LXRα Binding[a] $K_i$; nM | LXRβ Binding[a] $K_i$; nM | Cell LXRα[b] $EC_{50}$; nM (efficacy; %) | Cell LXRβ[b] $EC_{50}$; nM (efficacy; %) | FRET LXRα[c] $EC_{50}$; nM (efficacy; %) | FRET LXRβ[c] $EC_{50}$; nM (efficacy; %) |
|---|---|---|---|---|---|---|
| 48-59 | 3163 | 415 | 1189 (54) | 223 (37) | | |
| 48-60 | | | 18622 (13) | 6832 (7) | 16082 (27) | 1032 (33) |
| 48-61 | 1415 | 417 | 2312 (23) | 467 (5) | 347 (26) | 112 (23) |
| 48-62 | | | >20000 | 4682 (8) | 9984 (39) | 2100 (89) |
| 48-63 | >3333 | >2500 | >20000 | >20000 | 11662 (14) | 1553 (30) |
| 48-64 | 397 | 38 | 1817 (38) | 411 (11) | | |
| 48-65 | | | >20000 | 7046 (48) | | |
| 48-66 | 804 | 103 | 2518 (40) | 716 (20) | | |
| 48-67 | | | 7547 (30) | 2398 (47) | | |
| 48-68 | | 179 | 1224 (75) | 436 (64) | | |
| 48-69 | 111 | 14 | 425 (69) | 151 (43) | | |
| 48-70 | | 750 | 9091 (26) | 3726 (58) | | |
| 48-71 | 50 | 10 | 236 (57) | 75 (25) | | |
| 48-72 | | 825 | 7222 (11) | 2879 (31) | | |
| 48-73 | 2249 | 283 | >20000 | >20000 | | |
| 48-74 | 11432 | 2011 | >20000 | >20000 | | |
| 48-75 | | 940 | >20000 | 2400 (21) | | |
| 48-76 | | 67 | 1394 (54) | 374 (27) | | |
| 48-77 | 131 | 23 | 789 (53) | 360 (23) | | |
| 48-78 | 30736 | 2461 | 10997 (14) | 8336 (10) | | |
| 48-79 | 5 | 2 | 6 (58) | 1 (115) | | |
| 48-80 | 30 | 3 | 27 (73) | 18 (99) | | |
| 48-81 | 2299 | 479 | 1964 (37) | 822 (9) | | |
| 48-82 | 7398 | 2487 | >20000 | >20000 | | |
| 49-1 | 356 | 37 | 195 (64) | 110 (94) | | |
| 49-2 | 194 | 23 | 122 (63) | 78 (83) | | |
| 49-3 | 166 | 17 | 178 (75) | 58 (78) | | |
| 49-4 | 44 | 7 | 27 (80) | 20 (101) | | |
| 49-5 | 421 | 70 | 578 (64) | 266 (77) | | |
| 49-6 | 216 | 46 | 442 (56) | 114 (67) | | |
| 49-7 | 333 | 45 | 523 (82) | 132 (76) | | |
| 49-8 | 84 | 11 | 103 (79) | 36 (93) | | |
| 49-9 | 1215 | 150 | 1643 (32) | 575 (23) | | |
| 49-10 | 438 | 53 | 1575 (67) | 376 (37) | | |
| 49-11 | 1870 | 214 | 2460 (42) | 887 (21) | | |
| 49-12 | 1774 | 184 | 2637 (51) | 522 (25) | | |
| 50-1 | 107 | 6 | 181 (100) | 76 (88) | | |
| 50-2 | 358 | 51 | 721 (72) | 542 (85) | | |
| 50-3 | | | >20000 | >20000 | 12884 (71) | 1663 (52) |
| 50-4 | 2716 | 516 | 3065 (19) | 1278 (23) | 9561 (69) | 1630 (82) |
| 50-5 | 6547 | 688 | 10000 (7) | 997 (11) | | |
| 50-6 | 241 | 58 | 429 (81) | 226 (53) | | |
| 51-1 | >3333 | 1533 | 7863 (36) | 673 (32) | | |
| 51-2 | >3333 | >2500 | >20000 | 1362 (7) | | |
| 51-3 | 3173 | 482 | 3460 (51) | 590 (50) | | |
| 51-4 | >3333 | 546 | >20000 | >20000 | >50000 | >50000 |
| 51-5 | >3333 | 1017 | >20000 | >20000 | >50000 | >50000 |
| 51-6 | 2795 | 543 | 1772 (45) | 400 (45) | | |
| 51-7 | 303 | 51 | 154 (80) | 42 (84) | | |
| 52-1 | 144 | 19 | 137 (95) | 46 (74) | | |
| 53-1 | 971 | 121 | 3035 (70) | 1030 (53) | | |
| 53-2 | 1757 | 609 | 6741 (54) | 2082 (56) | | |
| 54-1 | 716 | 51 | 2197 (72) | 342 (61) | | |
| 54-2 | 863 | 81 | 3064 (29) | 812 (27) | | |

[a]Measured using the procedure of Biological Test Example 1;
[b]Measured using the procedure of Biological Test Example 2 in agonist mode;
[c]Measured using the procedure of Biological Test Example 3 in agonist mode; % efficacy indicated where determinable.

TABLE 4

LXR Antagonist Activities

| Cpd No | Cell LXRα[a] $IC_{50}$; nM (efficacy; %) | Cell LXRβ[a] $IC_{50}$; nM (efficacy; %) | FRET LXRα[b] $IC_{50}$; nM (efficacy; %) | FRET LXRβ[b] $IC_{50}$; nM (efficacy; %) |
|---|---|---|---|---|
| 1-1 | >10000 | 1996 (45) | | |
| 1-2 | | | | 199 (43) |
| 1-3 | 2871 (91) | 798 (106) | | |
| 1-5 | | | >50000 | >50000 |
| 1-6 | | | | |
| 1-7 | | | >50000 | 7325 (82) |
| 1-8 | 4712 (96) | 805 (105) | | |
| 1-12 | | | >50000 | >50000 |
| 1-13 | 4105 (131) | 756 (132) | | |
| 2-2 | | | | >50000 |

TABLE 4-continued

LXR Antagonist Activities

| Cpd No | Cell LXRα[a] IC$_{50}$; nM (efficacy; %) | Cell LXRβ[a] IC$_{50}$; nM (efficacy; %) | FRET LXRα[b] IC$_{50}$; nM (efficacy; %) | FRET LXRβ[b] IC$_{50}$; nM (efficacy; %) |
|---|---|---|---|---|
| 4-2 | >10000 | >10000 | | |
| 5-6 | 9461 (96) | 2963 (83) | | |
| 5-7 | 5116 (58) | 1674 (72) | | |
| 7-1 | >10000 | 6473 (118) | | |
| 7-2 | 5504 (58) | 1624 (88) | | |
| 7-4 | >10000 | 6576 (14) | | |
| 7-12 | >10000 | >10000 | | |
| 7-13 | 6827 (100) | 5287 (2) | | |
| 7-17 | 6031 (91) | 5205 (87) | | |
| 7-23 | >10000 | >10000 | | |
| 7-24 | | 9 (64) | | |
| 7-35 | >10000 | >10000 | | |
| 7-36 | >10000 | >10000 | | |
| 7-50 | 4587 (78) | 3741 (92) | | |
| 7-51 | 5324 (−12) | >10000 | | |
| 10-1 | 1102 (81) | 377 (78) | | |
| 10-3 | 2003 (83) | 242 (81) | | |
| 11-1 | >10000 | | | |
| 11-6 | 3864 (93) | 1355 (65) | | |
| 12-1 | 8047 (105) | 252 (65) | | |
| 12-7 | 686 (101) | 104 (87) | | |
| 15-1 | 902 (101) | 121 (95) | | |
| 15-3 | | 900 (93) | | |
| 15-4 | | 1438 (104) | | |
| 15-5 | 1163 (101) | 221 (105) | | |
| 15-6 | 6215 (98) | 1325 (91) | | |
| 15-7 | | 1773 (113) | | |
| 15-10 | 1625 (100) | 216 (98) | | |
| 17-1 | 2349 (91) | 667 (84) | | |
| 17-2 | 3715 (97) | 439 (97) | | |
| 17-8 | 2280 (93) | 538 (91) | | |
| 17-10 | 501 (94) | 100 (89) | | |
| 17-11 | 3463 (100) | 875 (90) | | |
| 17-12 | 1141 (96) | 295 (88) | | |
| 17-16 | 1530 (99) | 361 (86) | | |
| 17-17 | 2611 (91) | 684 (93) | | |
| 17-18 | 1159 (92) | 186 (98) | | |
| 17-25 | 3652 (98) | 359 (99) | | |
| 17-28 | 2554 (102) | 182 (98) | | |
| 17-39 | 9842 (125) | 2658 (135) | | |
| 19-1 | >10000 | | | |
| 22-2 | 3610 (83) | 2144 (96) | | |
| 22-3 | >10000 | | | |
| 31-1 | 443 (98) | 115 (124) | | |
| 32-1 | 544 (101) | 77 (110) | | |
| 33-1 | 2985 (92) | 510 (98) | | |
| 40-2 | 792 (80) | 146 (93) | | |
| 40-3 | 2454 (90) | 288 (88) | | |
| 44-2 | 1475 (105) | 177 (103) | | |
| 44-3 | 875 (102) | 91 (93) | | |
| 46-1 | | | 27500 (104) | 27500 (105) |
| 46-2 | | | >50000 | >50000 |
| 46-3 | >10000 | >10000 | 30000 (102) | 30000 (103) |
| 46-6 | 957 (105) | 148 (106) | | |
| 46-8 | 8904 (282) | 1421 (96) | | |
| 46-14 | | | >50000 | >50000 |
| 46-21 | >10000 | 537 (75) | | |
| 46-24 | 3139 (51) | 5823 (95) | | |
| 46-26 | 7585 (36) | 6798 (54) | | |
| 46-27 | >10000 | >10000 | | |
| 46-34 | 7451 (87) | 688 (70) | | |
| 46-44 | | | >50000 | >50000 |
| 46-47 | | | >50000 | >50000 |
| 46-48 | | | >50000 | >50000 |
| 46-50 | | | 48765 (102) | >50000 |
| 46-54 | | | >50000 | 10532 (55) |
| 46-55 | | | >50000 | 11009 (66) |
| 46-59 | | | >50000 | >50000 |
| 46-62 | | | >50000 | 6760 (64) |
| 47-1 | | | >50000 | >50000 |
| 48-1 | 3946 (105) | 639 (96) | | |
| 48-4 | 6447 (79) | 1027 (61) | | |
| 48-5 | 1169 (61) | 118 (93) | | |
| 48-15 | >10000 | 455 (60) | | |
| 48-17 | 1347 (102) | 485 (99) | | |
| 48-19 | 1630 (67) | 278 (66) | | |
| 48-23 | 4955 (123) | 408 (91) | | |
| 48-31 | 6705 (128) | 436 (96) | | |
| 48-33 | 5224 (46) | 583 (52) | | |
| 48-35 | 7574 (100) | 317 (38) | | |
| 48-39 | 78 (86) | 9 (112) | | |
| 48-40 | >10000 | 495 (89) | | |
| 48-41 | 421 (83) | 62 (95) | | |
| 48-48 | >10000 | 2695 (52) | | |
| 48-52 | 4773 (89) | 843 (82) | | |
| 48-61 | 870 (56) | 118 (72) | | |
| 48-64 | 4272 (104) | 288 (85) | | |
| 48-66 | 7360 (100) | 824 (81) | | |
| 48-69 | >10000 | | | |
| 48-71 | >10000 | 163 (54) | | |

[a]Measured using the procedure of Biological Test Example 2 in antagonist mode;
[b]Measured using the procedure of Biological Test Example 3 in antagonist mode; % efficacy indicated where determinable.

What is claimed is:

1. A compound represented by the following structural formula:

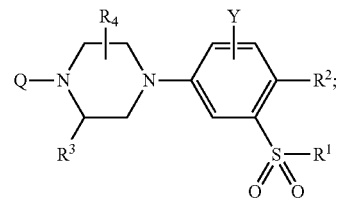

or a pharmaceutically acceptable salt thereof, wherein:

Q is:
1) $R^{10}OC(\!=\!O)\!-\!$;
2) a heteroaryl ring optionally substituted with 1 to 3 groups independently selected from $R^{21}$;
3) a group of formula $R^{30}$-L, wherein $R^{30}$ is optionally substituted with 1 to 3 groups independently selected from $R^{31}$; or
4) a group of formula $R^{40}$-L, wherein $R^{40}$ is optionally substituted with 1 to 3 groups independently selected from $R^{41}$;

$R^1$ is selected from $(C_1\text{-}C_6)$alkyl, $(C_3\text{-}C_6)$cycloalkyl, $(C_3\text{-}C_6)$cycloalkylalkyl$(C_1\text{-}C_3)$alkyl, aryl$(C_1\text{-}C_3)$alkyl, halo$(C_1\text{-}C_6)$alkyl, halo$(C_3\text{-}C_6)$cycloalkyl, halo$(C_3\text{-}C_6)$cycloalkyl$(C_1\text{-}C_3)$alkyl, amino, $(C_1\text{-}C_6)$alkylamino, di$(C_1\text{-}C_6)$alkylamino, aryl$(C_1\text{-}C_3)$alkylamino and {aryl $(C_1\text{-}C_3)$alkyl}{$(C_1\text{-}C_6)$ alkyl}amino, wherein the aryl groups are optionally substituted with 1 to 3 groups independently selected from halogen, cyano, $CONH_2$, $(C_1\text{-}C_3)$alkyl, halo$(C_1\text{-}C_3)$alkyl, $(C_1\text{-}C_3)$alkoxy and halo$(C_1\text{-}C_3)$alkoxy;

$R^2$ is selected from hydrogen, halogen, cyano, $CONH_2$, hydroxy$(C_1\text{-}C_3)$alkyl, amino$(C_1\text{-}C_3)$alkyl, $(C_1\text{-}C_3)$ alkoxy$(C_1\text{-}C_3)$alkyl, $(C_1\text{-}C_3)$alkylcarbonyl$(C_1\text{-}C_3)$alkyl and $(C_1\text{-}C_3)$alkylcarbonylamino$(C_1\text{-}C_3)$alkyl; or $R^2$ is a 5-membered heteroaryl, optionally substituted with 1 or 2 groups independently selected from halogen, cyano, methyl, $CF_3$, methoxy, methoxycarbonyl, ethoxycarbonyl and $CONH_2$;

$R^3$ is (1) $(C_1-C_6)$alkyl, halo$(C_1-C_6)$alkyl, $(C_3-C_6)$cycloalkyl, halo$(C_3-C_6)$cycloalkyl, $(C_1-C_3)$alkoxy$(C_1-C_3)$alkyl, hydroxy$(C_1-C_6)$alkyl, $(C_1-C_6)$alkoxycarbonyl or $(C_1-C_6)$alkoxycarbonyl$(C_1-C_3)$alkyl, or cyano $(C_1-C_6)$alkyl; or (2) aryl, heteroaryl, aryl$(C_1-C_3)$alkyl or heteroaryl$(C_1-C_3)$alkyl, each optionally substituted with 1 to 3 substituents selected from halogen, cyano, $(C_1-C_3)$alkyl, $CF_3$, methoxy and $CONH_2$;

$R^4$ is hydrogen or $(C_1-C_6)$alkyl;

$R^{10}$ is selected from $(C_1-C_8)$alkyl, aryl$(C_1-C_3)$alkyl, halo $(C_1-C_6)$alkyl, $(C_3-C_7)$cycloalkyl, $(C_3-C_6)$cycloalkyl $(C_1-C_3)$alkyl, halo$(C_3-C_7)$cycloalkyl and halo$(C_3-C_6)$ cycloalkyl$(C_1-C_3)$alkyl;

$R^{30}$ is an aryl or a monocyclic 5- or 6-membered heteroaromatic radical containing 1-4 heteroatoms independently selected from N, O, and S;

$R^{40}$ is $(C_4-C_7)$cycloalkyl or heterocyclyl;

$R^{21}$, $R^{31}$, and $R^{41}$ are each independently selected from halogen, hydroxy, amino, nitro, $(C_1-C_6)$alkyl, halo$(C_1-C_6)$alkyl, $(C_3-C_6)$cycloalkyl, $(C_2-C_6)$alkenyl, $(C_1-C_6)$ alkoxy, halo$(C_1-C_6)$alkoxy, hydroxy$(C_1-C_6)$alkyl, hydroxy$(C_1-C_6)$haloalkyl, $(C_1-C_3)$alkoxy$(C_1-C_3)$alkyl, halo$(C_1-C_3)$alkoxy$(C_1-C_3)$alkyl, $(C_1-C_3)$alkoxy$(C_1-C_3)$haloalkyl, $(C_1-C_6)$alkylthio, halo$(C_1-C_6)$alkylthio, $(C_1-C_3)$alkylthio$(C_1-C_3)$alkyl, halo$(C_1-C_3)$alkylthio $(C_1-C_3)$alkyl, cyano$(C_1-C_6)$alkyl, $CO_2H$, $(C_1-C_6)$ alkoxycarbonyl, $(C_1-C_6)$alkylsulfonyl, $(C_1-C_6)$haloalkylsulfonyl, $(C_1-C_3)$alkylsulfonyl$(C_1-C_3)$alkyl, halo$(C_1-C_3)$alkylsulfonyl$(C_1-C_3)$alkyl, heterocyclyl, $R^{22}R^{23}NCO$, $R^{22}R^{23}NCO(C_1-C_3)$alkyl, $R^{22}CONH$, $R^{22}CONH(C_1-C_3)$alkyl, $R^{22}SO_2NH$, $R^{22}SO_2NH(C_1-C_3)$alkyl, $R^{22}R^{23}N$, $R^{22}R^{23}N(C_1-C_3)$alkyl and aryl$(C_1-C_3)$alkyl, wherein aryl$(C_1-C_3)$alkyl is optionally substituted by $R^{25}$;

$R^{22}$ is selected from H, $(C_1-C_6)$alkyl, halo$(C_1-C_6)$alkyl, hydroxy$(C_1-C_6)$alkyl, $(C_1-C_6)$alkoxy$(C_1-C_6)$alkyl, $(C_1-C_6)$alkoxycarbonyl$(C_1-C_6)$alkyl, $(C_1-C_6)$alkoxycarbonylamino$(C_1-C_6)$alkyl and heterocyclyl, wherein the heterocyclyl is optionally substituted with 1 or 2 groups independently selected from $R^{24}$;

$R^{23}$ is hydrogen, $(C_1-C_6)$alkyl, $(C_1-C_6)$alkoxy or halo$(C_1-C_6)$alkyl; or $R^{22}$ and $R^{23}$, together with the nitrogen to which they are attached, form an azetidine, pyrrolidine, piperidine, piperazine or morpholine ring, each optionally substituted by 1 or 2 groups independently selected from $R^{24}$;

$R^{24}$ is selected from halogen, hydroxy, amino $(C_1-C_3)$ alkyl, halo$(C_1-C_3)$alkyl, $(C_1-C_3)$alkoxy and $(C_1-C_6)$ alkoxycarbonyl;

$R^{25}$ is hydroxy$(C_1-C_6)$alkyl or $CO_2H$;

L is $CH_2$, $CHCH_3$ or $C(CH_3)_2$; and

Y is hydrogen, halogen, cyano, $(C_1-C_3)$alkyl, methyl, haloalkyl, or methoxy.

2. The compound of claim 1, wherein

Q is

1) $R^{10}OC(=O)$—;

2) 2-pyridyl, 3-pyridyl, 4-pyridyl, 3-pyridazinyl, 2-pyrimidinyl, 4-pyrimidinyl, 2-pyrazinyl, 2-oxazolyl, 2-thiazolyl, 1,3,4-thiadiazol-2-yl, 2-pyridon-4-yl, 2-benzoxazolyl, 2-benzothiazolyl, thiazolo[4,5-b]pyridin-2-yl, thiazolo[4,5-c]pyridin-2-yl, thiazolo[5,4-c]pyridin-2-yl or thiazolo[5,4-b]pyridin-2-yl, each optionally substituted by one to three groups independently selected from $R^{21}$;

3) phenyl$CH_2$, phenylCHMe, pyridyl$CH_2$, furanyl$CH_2$, each optionally substituted with one to three substituents independently selected from $R^{31}$; or 4) cyclohexyl$CH_2$, bicyclo[3.1.0]hexyl$CH_2$, spiro[2.5]octyl$CH_2$, piperidinyl$CH_2$, pyrrolidinyl$CH_2$ and tetrahydropyranyl$CH_2$, each optionally substituted with one to three substituents independently selected from $R^{41}$;

$R^1$ is selected from Me, $-NH_2$, $-NHMe$, and $-NMe$-4-methoxybenzyl;

$R^2$ is selected from (1) H, F, Cl, CN, $CF_3$, $CH_2OH$, $CH_2NH_2$, $CONH_2$, $CH_2OAc$, $CH_2OMe$, and $CH_2NHAc$ or (2) 2-oxazolyl, 1,3,4-oxadiazol-2-yl, 1,2,4-oxadiazol-5-yl, 2-thiazolyl and 1,3,4-thiadiazol-2-yl each of which is optionally substituted with a group selected from methyl, cyano, ethoxycarbonyl and $CONH_2$;

Y is H, F or Cl;

$R^3$ is selected from i-Pr, i-Bu, t-Bu, $CF_3$, $CF_2Me$, $CH_2CMe_2F$, $CH_2CF_3$, CH(OMe)Me, c-Pr, c-hexyl, phenyl, 2-Cl-phenyl, 2-Br-phenyl, 2-Me-phenyl, 3-Cl-phenyl, 3-Me-phenyl, 4-F-phenyl, 4-Cl-phenyl, 4-Br-phenyl, benzyl, 4-methyl-2-thiazolyl, $CO_2Me$, $CMe_2OH$ and $CH_2CMe_2OH$;

$R^4$ is H or methyl;

$R^{10}$ is selected from i-Pr, t-Bu, i-Bu, t-Bu$CH_2$, benzyl, $CF_3CH_2$, $CF_3CHMe$, $CF_3CMe_2$, and 2,2,3,3-tetrafluorocyclobutyl;

$R^{21}$ is selected from F, Cl, Br, CN, $NO_2$, $NH_2$, OH, Me, i-Pr, c-Pr, $C(=CH_2)$Me, $CHF_2$, $CF_3$, $CF_2Me$, OMe, Oi-Pr, $OCHF_2$, $OCH_2CF_3$, $CH_2OH$, CH(OH)Me, CH(OH)Et, CH(OH)$CF_3$, $CMe_2OH$, CMe(OH)$CF_3$, CH(OMe)$CF_3$, $CMe_2CN$, $C(=O)H$, $C(=O)Me$, $SO_2Me$, $CO_2H$, $CO_2Me$, $CO_2Et$, $CONR^{22}R^{23}$, $CH_2NR^{22}R^{23}$, $CH_2NHAc$, $CH_2SMe$, $CH_2NHSO_2Me$, $CH_2C_6H_4R^{25}$ and 4,4-dimethyl-2-oxazolidinyl;

$R^{22}$ is selected from H, Me, Et, n-Bu, t-Bu, $CH_2CH_2OH$, $CH_2CH_2OMe$, $CH_2CH_2CH_2OH$, $CH_2CH_2CMe_2OH$, $CH_2CH_2CH_2OMe$, $CH_2CO_2Et$, $CH_2CH_2CO_2Et$; $CH_2CH_2CH_2NHCO_2Me$, $CH_2CH_2CH_2NHCO_2t$-Bu, and N-t-BuOC(=O)-3-azetidinyl;

$R^{23}$ is hydrogen, methyl, ethyl or methoxy; or $R^{22}$ and $R^{23}$, together with the nitrogen to which they are attached, form an azetidine or morpholine ring, each optionally substituted by one or two groups independently selected from $R^{24}$;

$R^{24}$ is F, OH, OMe, or $NH_2$;

$R^{25}$ is $CO_2H$ or $CMe_2OH$;

$R^{31}$ is selected from F, Cl, Br, Me, i-Pr, $CF_3$, $OCHF_2$, $OCF_3$, $CMe(OH)CF_3$, $CO_2Me$ and $CMe_2OH$; and $R^{41}$ is selected from F, OH, OMe, Me, i-Pr, $CHF_2$, $CF_3$, $CH_2CF_3$, $CF_2CH_3$, and $CMe_2OH$.

3. The compound of claim 1, wherein

Q is pyridyl or pyrimidinyl, each being substituted with one or two groups independently selected from $R^{21}$;

$R^1$ is selected from methyl, $NH_2$ and NHMe;

$R^2$ is H, F or $CH_2OH$; Y is H;

$R^3$ is i-Pr; and $R^4$ is H.

4. The compound of claim 1, wherein

Q is 2-pyridyl or 2-pyrimidinyl, each being substituted with one $CF_3$ group and optionally substituted with a second group selected from $R^{21}$; and $R^1$ is methyl.

5. The compound of claim 1, wherein at least one $R^{21}$ is a hydroxy$(C_1-C_4)$alkyl group.

6. The compound of claim 1, wherein

Q is phenyl$CH_2$ or pyridyl$CH_2$, each being optionally substituted with one to three substituents independently selected from $R^{31}$;

$R^1$ is methyl, $NH_2$ or NHMe;

$R^2$ is H, F or $CH_2OH$;

Y is H;

$R^3$ is selected from i-Pr, phenyl and halophenyl; and $R^4$ is H.

7. The compound of claim 1, wherein

Q is phenyl$CH_2$ or 3-pyridyl$CH_2$, each being substituted with one $CF_3$ group and optionally substituted with one other group selected from $R^{31}$;

$R^1$ is methyl; and $R^3$ is isopropyl.

8. The compound of claim 1, wherein

Q is cyclohexyl$CH_2$, piperidinyl$CH_2$ or tetrahydropyranyl$CH_2$, each being optionally substituted with one to three substituents independently selected from $R^{41}$;

$R^1$ is methyl, $NH_2$ or NHMe;

$R^2$ is H, F or $CH_2OH$;

Y is H;

$R^3$ is isopropyl, phenyl or halophenyl; and $R^4$ is H.

9. The compound of claim 1, wherein

Q is cyclohexyl$CH_2$, 3-piperidinyl$CH_2$, or 3-tetrahydropyranyl$CH_2$, each being substituted with one $CF_3$ group and optionally substituted with one other group selected from $R^{41}$;

$R^1$ is methyl; and $R^3$ is isopropyl.

10. The compound of claim 1, wherein the compound is of the Formula Ia or Ib:

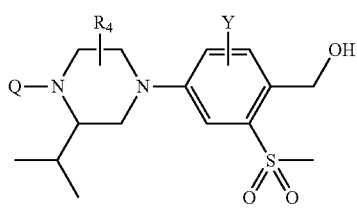

Ia

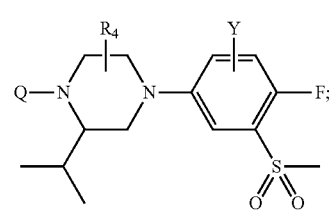

Ib or a pharmaceutically acceptable salt thereof.

11. The compound of claim 1, wherein the compound is represented by structural Formula Ic or Id:

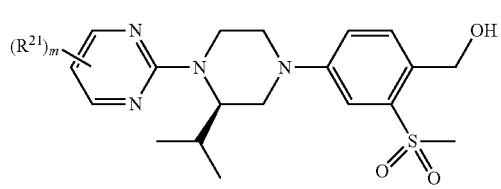

Ic

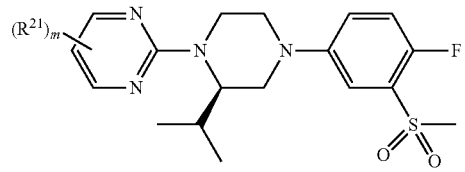

Id or a pharmaceutically acceptable salt thereof, wherein m is 1, 2 or 3.

12. The compound of claim 1, wherein the compound is represented by structural Formula IIc:

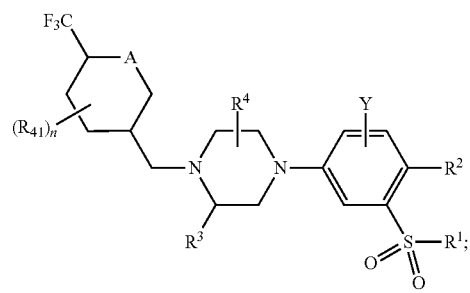

Ik or a pharmaceutically acceptable salt thereof, wherein n is 0, 1 or 2; and A is $CH_2$, NH, NMe or O.

13. A pharmaceutical composition comprising a pharmaceutical carrier or diluent and the compound of claim 1, or a pharmaceutically acceptable salt thereof.

14. The compound of claim 1, wherein the compound is represented by structural Formula Ie or If:

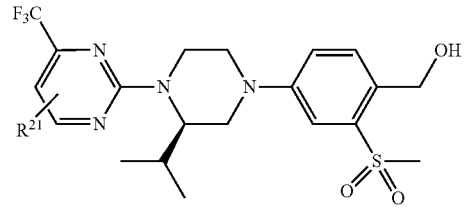

Ie

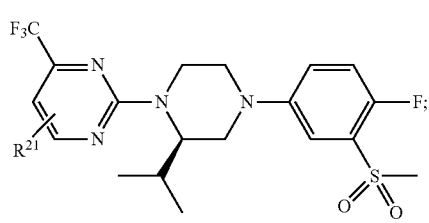

If or a pharmaceutically acceptable salt thereof.

15. The compound of claim 1, wherein the compound is represented by structural Formula Ig:

16. The compound of claim 1, wherein the compound is represented by structural Formula Ih:

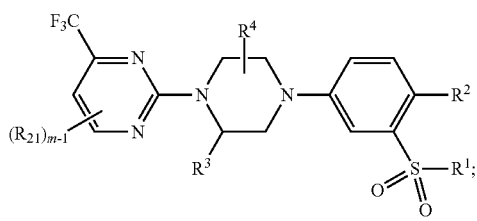

Ig or a pharmaceutically acceptable salt thereof, wherein m is 1, 2 or 3.

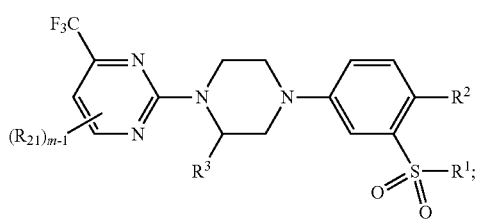

Ih or a pharmaceutically acceptable salt thereof, wherein m is 1, 2 or 3.

17. The compound of claim 1, wherein the compound is represented by structural Formula Ii:

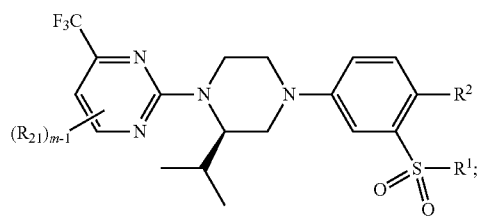

Ii or a pharmaceutically acceptable salt thereof, wherein m is 1, 2 or 3.

18. The compound of claim 1, wherein the compound is represented by structural Formula Ij:

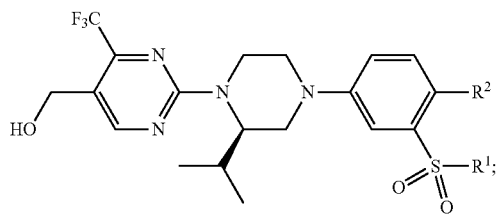

Ij or a pharmaceutically acceptable salt thereof.

19. The compound of claim 1, wherein the compound is represented by structural Formula Il:

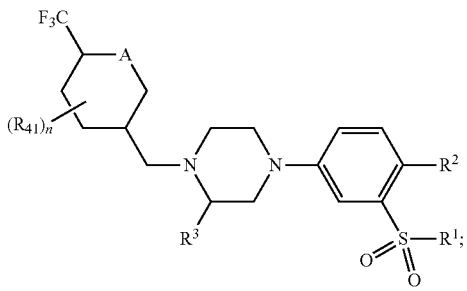

Il or a pharmaceutically acceptable salt thereof, wherein n is 0, 1 or 2; and A is CH$_2$, NH, NMe or O.

20. The compound of claim 1, wherein the compound is represented by structural Formula Im:

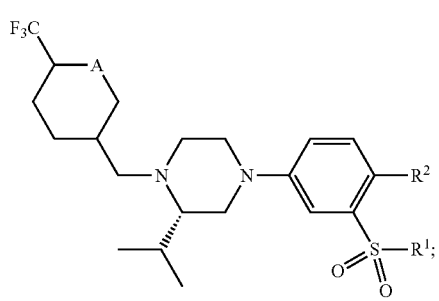

Im or a pharmaceutically acceptable salt thereof, wherein A is CH$_2$, NH, NMe or O.

21. The compound of claim 1, wherein the compound is represented by structural Formula In:

In or a pharmaceutically acceptable salt thereof, wherein A is CH$_2$, NH, NMe or O.

22. The compound of claim 1, wherein the compound is represented by structural Formula Io:

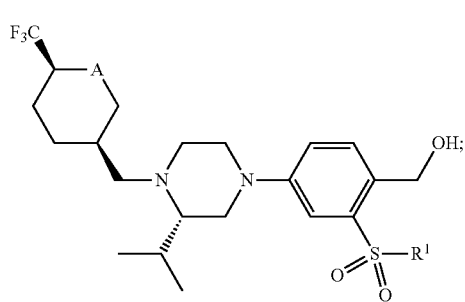
Io
or a pharmaceutically acceptable salt thereof, wherein A is CH$_2$, NH, NMe or O.
23. The compound of claim 1, wherein the compound is represented by structural Formula Ip:
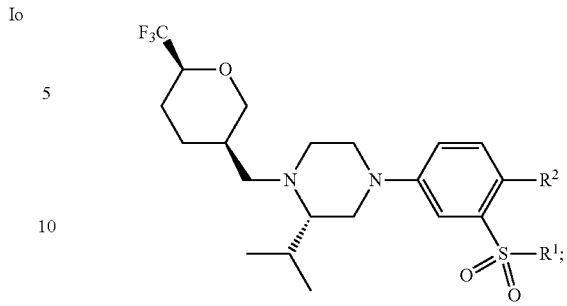
Ip
or a pharmaceutically acceptable salt thereof.
* * * * *

UNITED STATES PATENT AND TRADEMARK OFFICE
CERTIFICATE OF CORRECTION

PATENT NO. : 10,144,715 B2
APPLICATION NO. : 15/502356
DATED : December 4, 2018
INVENTOR(S) : David A. Claremon et al.

Page 1 of 1

It is certified that error appears in the above-identified patent and that said Letters Patent is hereby corrected as shown below:

In the Claims

Column 176, Claim 12, Line 15, replace "Formula IIc:" with --Formula Ik:--.

Column 177, Claim 16, Line 17, replace "Formula III:" with --Formula Ih:--.

Signed and Sealed this
Fifth Day of March, 2019

Andrei Iancu
*Director of the United States Patent and Trademark Office*